(12) United States Patent
Karow et al.

(10) Patent No.: US 12,018,073 B2
(45) Date of Patent: *Jun. 25, 2024

(54) ANTAGONISTS TARGETING THE TGF-β PATHWAY

(71) Applicant: GENSUN BIOPHARMA, INC., Newbury Park, CA (US)

(72) Inventors: Margaret Karow, Santa Rosa Valley, CA (US); Jackie Sheng, Thousand Oaks, CA (US); Wei Zhang, Thousand Oaks, CA (US)

(73) Assignee: GENSUN BIOPHARMA, INC., Newbury Park, CA (US)

( * ) Notice: Subject to any disclaimer, the term of this patent is extended or adjusted under 35 U.S.C. 154(b) by 670 days.

This patent is subject to a terminal disclaimer.

(21) Appl. No.: 16/995,428

(22) Filed: Aug. 17, 2020

(65) Prior Publication Data
US 2021/0002348 A1 Jan. 7, 2021

Related U.S. Application Data

(63) Continuation of application No. 16/706,187, filed on Dec. 6, 2019, now Pat. No. 10,851,157.

(60) Provisional application No. 62/869,111, filed on Jul. 1, 2019.

(51) Int. Cl.
| A61K 38/00 | (2006.01) |
| C07K 14/71 | (2006.01) |
| C07K 16/22 | (2006.01) |
| C07K 16/28 | (2006.01) |

(52) U.S. Cl.
CPC ............. *C07K 16/22* (2013.01); *C07K 14/71* (2013.01); *C07K 16/2818* (2013.01); *C07K 16/2827* (2013.01); *A61K 38/00* (2013.01); *C07K 2317/565* (2013.01); *C07K 2317/567* (2013.01); *C07K 2317/622* (2013.01); *C07K 2317/66* (2013.01); *C07K 2317/75* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,837,243 A | 11/1998 | Deo et al. | |
| 5,869,046 A | 2/1999 | Presta et al. | |
| 5,922,845 A | 7/1999 | Deo et al. | |
| 6,054,297 A | 4/2000 | Carter et al. | |
| 6,111,090 A | 8/2000 | Gorman et al. | |
| 6,121,022 A | 9/2000 | Presta et al. | |
| 6,528,959 B2 | 3/2003 | Kitano et al. | |
| 6,703,020 B1 | 3/2004 | Thorpe et al. | |
| 6,884,879 B1 | 4/2005 | Baca et al. | |
| 7,025,962 B1 | 4/2006 | Gorman et al. | |
| 7,060,269 B1 | 6/2006 | Baca et al. | |
| 7,169,901 B2 | 1/2007 | Baca et al. | |
| 7,227,004 B2 | 6/2007 | Kim | |
| 7,338,660 B2 | 3/2008 | Bedian et al. | |
| 7,365,166 B2 | 4/2008 | Baca et al. | |
| 7,618,632 B2 | 11/2009 | Collins et al. | |
| 7,691,977 B2 | 4/2010 | Fuh et al. | |
| 7,758,859 B2 | 7/2010 | Fuh et al. | |
| 7,811,785 B2 | 10/2010 | Fuh et al. | |
| 7,812,136 B2 | 10/2010 | Mary et al. | |
| 8,367,805 B2 | 2/2013 | Chamberlain et al. | |
| 8,388,967 B2 | 3/2013 | Smith et al. | |
| 8,389,692 B2 | 3/2013 | Takayama et al. | |
| 8,475,798 B2 | 7/2013 | Patti et al. | |
| 8,574,577 B2 | 11/2013 | Barbas, III | |
| 8,586,023 B2 | 11/2013 | Shiku et al. | |
| 8,591,886 B2 | 11/2013 | Ponath et al. | |
| 8,992,913 B2 | 3/2015 | Mader et al. | |
| 9,079,965 B2 | 7/2015 | Zhou et al. | |
| 9,200,079 B2 | 12/2015 | Chamberlain et al. | |
| 9,676,863 B2 | 6/2017 | Lo | |
| 9,764,038 B2 | 9/2017 | Dennler et al. | |
| 9,890,204 B2 | 2/2018 | Brinkmann et al. | |
| 9,987,500 B2 | 6/2018 | Papadopoulos et al. | |
| 9,994,632 B2 | 6/2018 | Kim et al. | |
| 10,112,997 B2 | 10/2018 | Gurney et al. | |
| 10,189,902 B2 | 1/2019 | Maurer et al. | |
| 11,274,142 B2 * | 3/2022 | Gu ................... | C07K 16/2827 |
| 2003/0206899 A1 | 11/2003 | Ferrara et al. | |
| 2005/0186208 A1 | 8/2005 | Fyfe et al. | |
| 2006/0099160 A1 | 5/2006 | Houston et al. | |
| 2014/0308285 A1 | 10/2014 | Yan et al. | |

(Continued)

FOREIGN PATENT DOCUMENTS

| EP | 0090505 | 2/1984 |
| EP | 1947183 | 7/2008 |

(Continued)

OTHER PUBLICATIONS

U.S. Appl. No. 16/706,187, filed Dec. 6, 2019, Pending.
U.S. Appl. No. 16/995,428, filed Aug. 17, 2020, Pending.
Ahmadzadeh, M. et al., "Tumor antigen-specific CD8 T cells infiltrating the tumor express high levels of PD-1 and are functionally impaired", Blood, Aug. 20, 2009, 114(8):1537.
Dall'Acqua, et al., "Increasing the Affinity of a Human IgG1 for the Neonatal Fc Receptor: Biological Consequences", The Journal of Immunology, 2002, 169:5171-5180.
Dall'Acqua, et al., "Properties of Human IgG1s Engineered for Enhanced Binding to the Neonatal Fc Receptor (FcRn)". Journal of Biological Chemistry, 2006, 281:23514-23524.

(Continued)

*Primary Examiner* — Laura B Goddard
(74) *Attorney, Agent, or Firm* — Michael Ye; kalos Athena Wang PLLC

(57) ABSTRACT

Antitumor antagonists that bind specifically to immune checkpoint regulators, angiogenesis pathway regulators and/or TGF pathway regulators are disclosed. Also disclosed are methods for treating proliferative disorders, infections, and immunological disorders with the antitumor antagonists described herein.

22 Claims, 73 Drawing Sheets

Specification includes a Sequence Listing.

(56) References Cited

U.S. PATENT DOCUMENTS

| | | |
|---|---|---|
| 2016/0355589 A1 | 12/2016 | Williams et al. |
| 2017/0044256 A1 | 2/2017 | Grogan et al. |
| 2017/0275353 A1 | 9/2017 | Sheng et al. |
| 2018/0185482 A1 | 7/2018 | Sheng et al. |
| 2022/0213195 A1* | 7/2022 | Song ..................... C07K 14/71 |

FOREIGN PATENT DOCUMENTS

| | | |
|---|---|---|
| EP | 1866339 | 5/2013 |
| WO | 9920758 | 4/1999 |
| WO | 9940196 | 8/1999 |
| WO | 200103720 | 1/2001 |
| WO | 2005007190 | 1/2005 |
| WO | 2005055808 | 6/2005 |
| WO | 2006083289 | 8/2006 |
| WO | 2007133822 | 11/2007 |
| WO | 2010003118 | 1/2010 |
| WO | 2011028683 | 3/2011 |
| WO | 2005115461 | 5/2011 |
| WO | 2011051726 | 5/2011 |
| WO | 2011090754 | 7/2011 |
| WO | 2011/109789 | 9/2011 |
| WO | 2013039954 | 3/2013 |
| WO | 2014062659 | 4/2014 |
| WO | 2015/027082 | 2/2015 |
| WO | 2015/118175 | 8/2015 |
| WO | 2016187594 | 11/2016 |
| WO | 2017218707 | 6/2017 |
| WO | 2017161976 | 9/2017 |
| WO | 2018/029367 | 2/2018 |
| WO | 2018029367 | 2/2018 |
| WS | 20181283939 | 7/2018 |

OTHER PUBLICATIONS

Dranoff, G. et al., "Vaccination with irradiated tumor cells engineered to secrete murine granulocyte-macrophage colony-stimulating factor stimulates potent, specific, and long-lasting antitumor immunity", Proc. Natl. Acad. Sci. U.S. A., Apr. 15, 1993, 90(8):3539-3643.

Greenberg. P.D. et al., "Deficient Cellular Immunit-Finding and Fixing the Defects", Science Jul. 23, 1999, 23:285 (546-551).

Harlow, E. et al., "Antibodies, A Laboratory Manual", (1988), Cold Spring Harbor Publications, New York.

He, Y. et al., "Blocking Programmed Death-1 Ligand-PD-1 Interactions by Local Gene Therapy Results in Enhancement of Antitumor Effect of Secondary Lymphold Tissue Chemokine", The Journal of Immunology, 2004. 173:4919-4928.

Hinton, et al., "An Engineered Human IgG1 Antibody with Longer Serum Half-Life", Journal of Immunology, 2006, 176:346-356.

Hinton, et al., "Engineered Human IgG Antibodies with Longer Serum Half-lives in Primates", Journal of Biological Chemistry, 2004, 279(8): 6213-6216.

Hutloff, A et al., "ICOS is an inducible T-cell co-stimulator structurally and functionally related to CD28", Nature, Jan. 21, 1999. 397:263-266.

International Search Report and Written Opinion of the International Searching Authority dated May 10, 2018 in PCT Application No. PCT/US17/69072.

Karyampudi, L. et al., "Accumulation of memory precursor CD8 T cells in regressing tumors following combination therapy with vaccine and anti-PD-1 antibody", Jun. 2014, 74:2974-2985.

Kim, N.W., et al., "Specific Association of Human Telomerase Activity with Immortal Cells and Cancer", Dec. 1994, vol. 266, pp. 2011-2013.

Kugler, A. et al., "Regression of human metastatic renal cell carcinoma after vaccination with tumor cell-dendritic cell hybrids", Nature Medicine, Mar. 6, 2000, 3:332-336.

Kyi, C. et al., "Checkpoint blocking antibodies in cancer immunotherapy", FEBS Letters, 2014. 588:368-378.

Le Mercier, I. et al., "Beyond CTLA-4 and PD-1, the Generation Z of Negative Checkpoint Regulators", Front. Immunol., Aug. 2015, (6). Article 418.

Lo, B.K.C., "Antibody engineering: Methods and Protocols, Methods in molecular biology", (2004) vol. 248. Humana Press, Clifton, N.J.

Melero, I et al., "Monoclonal antibodies against the 4-1BB T-cell activation molecule eradicate established tumors", Nature Medicine, Jun. 1997, 3(6):682-685.

Mokyr. M.B. et al., "Relization of the Therapeutic Potential of CTLA-4 Blockage in Low-Dose Chemotherpahy-treated Tumor-bearing Mice", Cancer Research (1998), 58:5301-5304.

Nestle, F.O. et al., "Vaccination of melanoma patients with peptide-or tumor lysate-pulsed dendritic cells", Nature Medicine, Mar. 1998, 4(3) 328-332.

Petkova, S.B. et al., "Enhanced half-life of genetically engineered human IgG1 antibodies in a humanized FcRn mouse model: potential application in humorally mediated autoimmune disease", Int. Immunol., Dec. 2006, 16(12):1759-1769.

Ridge, J.P. et al., "A conditioned dendritic cell can be a temporal bridge between a CD4+ T-helper and a T-killer cell", Nature, Jun. 4, 1998, 393:474-478.

Rosenberg, S.A. et al., "A New Era for Cancer Immunotherapy Based on the Genes that Encode Cancer Antigens", Immunity, Mar. 1999, vol. 10, pp. 281-287.

Shields, et al., "High Resolution Mapping of the Binding Site on Human IgG1 for FcγRI, FcγRII, FcγRIII, and FcRn and Design of IgG1 Variants with Improved Binding to the FcγR", Journal of Biological Chemistry, 2001, 276(9):6591-6604.

Tansey, M.G. et al., "The TNF superfamily in 2009: new pathways, new indications, and new drugs", Drug Discovery Today, Dec. 2009, 14(23-24):1082-1088.

Thompson, R.H. et al., "Tumor B7-H1 is Associated with Poor Prognosis in Renal Cell Carcinoma Patients with Long-term Follow-up". (2006), 66(7):3381.

Weinberg, A. D. et al., "Engagement of the OX-40 receptor in vivo enhances antitumor immunity", Journal of Immunology, Feb. 15, 2000, 15:164(4):2160-2169.

Wranik, et al., "Luz-Y, a Novel Platform for the Mammalian Cell Production of Full-length IgG-bispecific Antibodies", Journal of Biological Chemistry, 2012. 287(52):43331-43339.

Yeung et al., "Engineering Human IgG1 Affinity to Human Neonatal Fc Receptor: Impact of Affinity Improvement of Pharmacokinetics in Primates", The Journal of Immunology, 2009, 182:7663.

Zalevsky, J. et al., "Enhanced antibody half-life improves in vivo activity", Nat. Biotechnol., Feb. 2010, 28(2):157-159.

International Search Report and the Written Opinion of the International Searching Authority issued in International Application No. PCT/US19/39979, dated Nov. 12, 2019.

International Search Report and the Written Opinion of the International Searching Authority issued in International Application No. PCT/US19/39982, dated Dec. 3, 2019.

International Search Report and the Written Opinion of the International Searching Authority issued in International Application No. PCT/US19/39994, dated Nov. 21, 2019.

International Search Report and The Written Opinion of the International Searching Authority for International Patent Application No. PCT/US2018/065022, dated Feb. 28, 2020.

* cited by examiner

Anti-PD1 mab sequences

| Mab | Heavy Chain CDR1 | | Heavy Chain CDR2 | | Heavy Chain CDR3 | |
|---|---|---|---|---|---|---|
| PD-01 | NFLMS | (SEQ ID:1) | TISGGGRDTYYVDSVKG | (SEQ ID:2) | RTTYSMDY | (SEQ ID:3) |
| PD-02 | NSYLY | (SEQ ID:4) | GINPSNGGTNFNEKFKT | (SEQ ID:5) | RDYNYDGGFDS | (SEQ ID:6) |
| PD-03 | NSYIY | (SEQ ID:7) | GINPSNGGTNFNEKFKT | (5) | RRDYRYDGGFDS | (SEQ ID:8) |
| PD-04 | NSYIY | (7) | GINPSNGGTNFNEKFKT | (5) | RDYNYDGGFDS | (6) |
| PD-05 | TYYIY | (SEQ ID:9) | GINPGNGGTNFNEKFKI | (SEQ ID:10) | RYHGYDGGLDY | (SEQ ID:11) |
| PD-06 | SYYIH | (SEQ ID:12) | WIFPGSGNSKYNENFKG | (SEQ ID:13) | SETYDYGDY | (SEQ ID:14) |

| Mab | Light Chain CDR1 | | Light Chain CDR2 | | Light Chain CDR3 | |
|---|---|---|---|---|---|---|
| PD-01 | LASQTIGTWLA | (SEQ ID:15) | AATSLAD | (SEQ ID:16) | QQFYSIPWT | (SEQ ID:17) |
| PD-02 | RASSTLYSNYLH | (SEQ ID:18) | RASFLAS | (SEQ ID:19) | QQGSSIPLT | (SEQ ID:20) |
| PD-03 | SASSSLYSSYLH | (SEQ ID:21) | RASFLAS | (19) | QQGSSIPLT | (20) |
| PD-04 | RASSLYSNYLH | (SEQ ID:22) | RASFLAS | (19) | QQGSSIPLT | (20) |
| PD-05 | RASKSVSTSGFSYIH | (SEQ ID:23) | LASNLES | (SEQ ID:24) | QHTWELPNT | (SEQ ID:25) |
| PD-06 | KASQNVGTNVA | (SEQ ID:26) | SASYRYS | (SEQ ID:27) | QQYYSYPYT | (SEQ ID:28) |

FIG. 1 anti-PD-1 Antibody Variable Domain Sequences

PD-01
VH (SEQ ID NO: 29):
EVQLVESGGGLVQPGGSLRLSCAASGFTFSNFLMSWVRQAPGKGLEWVSTISGGGR
DTYYVDSVKGRFTISRDNSKNTLYLQMNSLRAEDTAVYYCAKRTTYSMDYWGQGT
SVTVSS

VL (SEQ ID NO: 30):
DIQMTQSPSSVSASVGDRVTITCLASQTIGTWLAWYQQKPGKAPKLLIYAATSLADG
VPSRFSGSGSGTDFTLTISSLQPEDFATYYCQQFYSIPWTFGGGTKLEIK

PD-02
VH (SEQ ID NO: 31):
QVQLVQSGAEVKKPGASVKVSCKASDYTFTNSYLYWLRQAPGQGLEWMGGINPSN
GGTNFNEKFKTRTTSTRDTSISTAYMELSRLRSDDTVVYYCTRRDYNYDGGFDSWG
QGTLVTVSS

VL (SEQ ID NO: 32):
DIQMTQSPSSLSASVGDRVTFTCRASSTLYSNYLHWYQQKPGKAPKLLIYRASFLAS
GVPSRFSGSGSGTDFTLTISSLQPEDFATYYCQQGSSIPLTFGGGTKVEIK

PD-03
VH (SEQ ID NO: 33)
QVQLVQSGAEVKKPGASVKVSCKASDYTFTNSYIYWVRQAPGQGLEWMGGINPSN
GGTNFNEKFKTRVTSTRDTSISTAYMELSRLRSDDTVVYYCARRDYRYDGGFDSWG
QGTTLTVSS

VL (SEQ ID NO: 34)
DIQMTQSPSSLSASVGDRVTITCSASSSLYSSYLHWYQQKPGKAPKLLIYRASFLASG
VPSRFSGSGSGTDFTLTISSLQPEDFATYYCQQGSSIPLTFGAGTKLDLK

*FIG. 2A*

PD-04
VH (SEQ ID NO: 35):
QVQLVQSGAEVKKPGASVKVSCKASDYTFTNSYIYWVRQAPGQGLEWMGGINPSN
GGTNFNEKFKTRVTSTRDTSISTAYMELSRLRSDDTVVYYCARRDYNYDGGFDSWG
QGTLVTVSS

VL (SEQ ID NO: 36):
DIQMTQSPSSLSASVGDRVTFTCRASSSLYSNYLHWYQQKPGKAPKLLIYRASFLAS
GVPSRFSGSGSGTDFTLTISSLQPEDFATYYCQQGSSIPLTFGGGTKVEIK

PD-05 (2P16)
VH (SEQ ID NO: 37):
QVQLVQSGAEVKKPGASVKVSCKASGYTFTTYYIYWVRQAPGQGLEWMGGINPGN
GGTNFNEKFKIRVTMTRDTSISTAYMELSSLRSEDTAVYYCARRYHGYDGGLDYWG
QGTLVTVSS

VL (SEQ ID NO: 38):
DIVLTQSPASLAVSPGQRATITCRASKSVSTSGFSYIHWYQQKPGQPPKLLIYLASNLE
SGVPARFSGSGSGTDFTLTINPVEANDTANYYCQHTWELPNTFGGGTKVEIK

PD-06 (2P17)
VH (SEQ ID NO: 39):
QVQLVQSGAEVKKPGASVKVSCKASGYTFTSYYIHWVRQAPGQGLEWMGWIFPGS
GNSKYNENFKGRVTLTADTSTSTVYMELSSLRSEDTAVYYCASETYDYGDYWGQGT
LVTVSS

VL (SEQ ID NO: 40):
DIQMTQSPSFLSASVGDRVTITCKASQNVGTNVAWYQQKPGKAPKALIYSASYRYSG
VPSRFSGSGSGTEFTLTISSLQPEDFATYYCQQYYSYPYTFGQGTKLEIK

FIG. 2B

Anti-PD-L1 mab sequences

| Mab   | Heavy Chain CDR1 |             | Heavy Chain CDR2    |             | Heavy Chain CDR3 |             |
|-------|------------------|-------------|---------------------|-------------|------------------|-------------|
| PL-01 | NYWMH            | (SEQ ID:41) | MIHPNTNNYNYNEKFKS   | (SEQ ID:42) | SDYGSSPYYFDY     | (SEQ ID:43) |
| PL-02 | SYWMH            | (SEQ ID:44) | MIHPNVGSTNYNEKFKS   | (SEQ ID:45) | SRYGSSPYYFDY     | (SEQ ID:46) |
| PL-03 | SYWMH            | (44)        | MIHPNSGGNNYNEKFKS   | (SEQ ID:47) | SWYGSSPYYFDY     | (SEQ ID:48) |
| PL-04 | SYWMH            | (44)        | MIHPTGVSTDYNEKFKS   | (SEQ ID:49) | SDYGSSPYYFDY     | (43)        |
| PL-05 | SDYAWN           | (SEQ ID:50) | YISDSGSTSYNPSLKS    | (SEQ ID:51) | SFLRLRSYFDH      | (SEQ ID:52) |
| PL-06 | SYGIN            | (SEQ ID:53) | CIYIGNDYTNYNEKFKG   | (SEQ ID:54) | AYYGSRVDY        | (SEQ ID:55) |
| PL-07 | SYGIN            | (53)        | CIYIGNDYTNYNEKFKG   | (54)        | AYYGSRVDY        | (55)        |
| PL-08 | SYWMH            | (44)        | MIHPNSGGNNYNEKFKS   | (47)        | SWYGSSPYYFDY     | (48)        |

| Mab   | Light Chain CDR1 |             | Light Chain CDR2 |             | Light Chain CDR3 |             |
|-------|------------------|-------------|------------------|-------------|------------------|-------------|
| PL-01 | RASQDIDNYLN      | (SEQ ID:56) | YTSRLHS          | (SEQ ID:57) | QQGYTLPWT        | (SEQ ID:58) |
| PL-02 | RASQDISNYLN      | (SEQ ID:59) | YTSRLQS          | (SEQ ID:60) | QQGNTLPWT        | (SEQ ID:61) |
| PL-03 | RASQDISNYLN      | (59)        | YTSRLHS          | (57)        | QQGNTLPWT        | (61)        |
| PL-04 | RASQDISNYLN      | (59)        | YTSRLHS          | (57)        | QQGDTLPWT        | (SEQ ID:62) |
| PL-05 | KASQDVNVAVA      | (SEQ ID:63) | WASTRHI          | (SEQ ID:64) | QQHYSTPYT        | (SEQ ID:65) |
| PL-06 | KASQDINKYIA      | (SEQ ID:66) | YTSTLQP          | (SEQ ID:67) | LQYDNLYT         | (SEQ ID:68) |
| PL-07 | QSISDYLH         | (SEQ ID:69) | CASQSISG         | (SEQ ID:70) | QNGHSFPYT        | (SEQ ID:71) |
| PL-08 | RASQDIDNYLN      | (56)        | YTSRLHS          | (57)        | QQGYTLPWT        | (58)        |

FIG. 3 anti-PD-L1 Antibody Variable Domain Sequences

PL-01
VH (SEQ ID NO: 72):
QVQLVQSGAEVKKPGASVKVSCKASGYTFTNYWMHWMKQAPGQGLEWMGMIHPNT
NNYNYNEKFKSRVTSTRDTSISTAYMELSRLRSDDTVVYYCARSDYGSSPYYFDYWGQ
GTLVTVSS

VL (SEQ ID NO: 73):
DIQMTQSPSSLSASVGDRVTISCRASQDIDNYLNWYQQKPGKAPKLLIKYTSRLHSGVPS
RFSGSGSGTDFTLTISSLQPEDFATYFCQQGYTLPWTFGGGTKVEIK

PL-02
VH (SEQ ID NO: 74):
QVQLVQSGAEVKKPGASVKVSCKASGYTFTSYWMHWVRQAPGQGLEWMGMIHPNVG
STNYNEKFKSKATMTRDKSSSTVYMELSSLRSEDTAVYYCARSRYGSSPYYFDYWGQG
TLVTVSS

VL (SEQ ID NO: 75):
DIQMTQSPSSLSASVGDRVTISCRASQDISNYLNWYQQKPGKAPKLLIYYTSRLQSGVPS
RFSGSGSGTDFTFTISSLQPEDIATYFCQQGNTLPWTFGQGTKVEIK

PL-03
VH (SEQ ID NO: 76):
QVQLVQSGAEVKKPGASVKVSCKASGYTFTSYWMHWVRQAPGQGLEWMGMIHPNSG
GNNYNEKFKSRVTMTRDTSISTAYMELSRLRSDDTAVYYCARSWYGSSPYYFDYWGQ
GTLVTVSS

VL (SEQ ID NO: 77):
DIQMTQSPSSLSASVGDRVTISCRASQDISNYLNWYQQKPGKAPKLLIYYTSRLHSGVPS
RFSGSGSGTDFTFTISSLQPEDIATYFCQQGNTLPWTFGQGTKVEIK

*FIG. 4A*

PL-04
VH (SEQ ID NO: 78):
QVQLVQSGAEVKKPGASVKVSCKASGYTFTSYWMHWVRQAPGQGLEWMGMIHPTGV
STDYNEKFKSRVTMTRDTSTSTVYMELSSLRSEDTAVYYCARSDYGSSPYYFDYWGQG
TLVTVSS

VL (SEQ ID NO: 79):
DIQMTQSPSSLSASVGDRVTISCRASQDISNYLNWYQQKPGKAPKLLIKYTSRLHSGVPS
RFSGSGSGTDFTLTISSLQPEDFATYFCQQGDTLPWTFGGGTKVEIK

PL-05
VH (SEQ ID NO: 80):
DVQLQESGPGLVKPSQSLSLTCTVTGYSITSDYAWNWIRQFPGNKLEWMGYISDSGSTS
YNPSLKSRISITRDTSKNQFFLQLNSVTTEDTATYYCANSFLRLRSYFDHWGQGTTLTVS
S

VL (SEQ ID NO: 81):
DIVMTQSHKFMSTSVGDRVSITCKASQDVNVAVAWYQQKPGQSPKLLIFWASTRHIGV
PDRFTGSGSGTDYTLTISSVQAEDLALYYCQQHYSTPYTFGGGTKLEIK

PL-06
VH (SEQ ID NO: 82):
QVQLVQSGAEVKKPGASVKVSCKASGYTFTSYGINWVRQAPGQRLEWMGWCIYIGND
YTNYNEKFKGRVTITRDTSASTAYMELSSLRSEDTAVYYCARAYYGSRVDYWGQGTLV
TVSS

VL (SEQ ID NO: 83):
DIQMTQSPSSLSAFVGDRVTITCKASQDINKYIAWYQQKPGKAPKLLIHYTSTLQPGVPS
RFSGSGSGRDFTFTISSLQPEDIATYYCLQYDNLYTFGGGTKVEIK

PL-07
VH (SEQ ID NO: 84):
QVQLVQSGAEVKKPGASVKVSCKASGYTFTSYGINWVRQAPGQRLEWMGWCIYIGND
YTNYNEKFKGRVTITRDTSASTAYMELSSLRSEDTAVYYCARAYYGSRVDYWGQGTLV
TVSS

VL (SEQ ID NO: 85):
EIVLTQSPVTLSLSPGERATLSCQSISDYLHWYLQKPGQAPRLLIKCASQSISGIPARFSGS
GSGSDFTLTISSLEPEDFAVYYCQNGHSFPYTFGGGTKVEIK

FIG. 4B

PL-08
VH (SEQ ID NO: 86):
QVQLVQSGAEVKKPGASVKVSCKASGYTFTSYWMHWVRQAPGQGLEWMGMIHPNSG
GNNYNEKFKSRVTMTRDTSISTAYMELSRLRSDDTAVYYCARSWYGSSPYYFDYWGQ
GTLVTVSS

VL (SEQ ID NO: 87):
DIQMTQSPSSLSASVGDRVTISCRASQDIDNYLNWYQQKPGKAPKLLIKYTSRLHSGVPS
RFSGSGSGTDFTLTISSLQPEDFATYFCQQGYTLPWTFGGGTKVEIK

*FIG. 4C*

Anti-PD-1 VR or Anti-PD-L1 VR

TGF-β RII ECD

Exemplary Functional Domain Sequences in FIG. 5

| VH/VL or Fusion Protein Domain | Amino Acid Sequences of Functional Domains |
|---|---|
| Anti-PD-1 HCVR (2P17) | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSS (SEQ ID NO: 39) |
| Anti-PD-1 LCVR (2P17) | DIQMTQSPSFLSASVGDRVTITCKASQNVGTNVAWYQQKPGKAPKALIYSASYRYSGVPSRFSGSGSGTEFTLTISSLQPEDFATYYCQQYYSYPYTFGQGTKLEIK (SEQ ID NO: 40) |
| Anti-PD-L1 HCVR (PL-08) | QVQLVQSGAEVKKPGASVKVSCKASGYTFTSYWMHWVRQAPGQGLEWMGMIHPNSGGNNYNEKFKSRVTMTRDTSISTAYMELSRLRSDDTAVYYCARSWYGSSPYYFDYWGQGTLVTVSS (SEQ ID NO: 86) |
| Anti-PD-L1 LCVR (PL-08) | DIQMTQSPSSLSASVGDRVTISCRASQDIDNYLNWYQQKPGKAPKLLIKYTSRLHSGVPSRFSGSGSGTDFTLTISSLQPEDFATYFCQQGYTLPWTFGGGTKVEIK (SEQ ID NO: 87) |
| TGF-β RII-ECD | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 89) |

*FIG. 6*

Exemplary heavy chain (HC) and light chain (LC) sequences in FIG. 5

| Bispecific Antagonist Name | Amino acid sequence | Functional Domains |
|---|---|---|
| Bi-PB-1.1 HC | QVQLVQSGAEVKKPGASVKVSCKASGYTFTSYYIHWVRQAPGQGLEWMGW IFPGSGNSKYNENFKGRVTLTADTSTSTVYMELSSLRSEDTAVYYCASETYDYG DYWGQGTLVTVSSASTKGPSVFPLAPCSRSTSESTAALGCLVKDYFPEPVTVS WNSGALTSGVHTFPAVLQSSGLYSLSSVVTVPSSSLGTKTYTCNVDHKPSNTK VDKRVESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNGK EYKCKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGNVFS CSVMHEALHNHYTQKSLSLSLGKGGGGSGGGGSGGGGSIPPHVQKSVNND MIVTDNNGAVKFPQLCKFCDVRFSTCDNQKSCMSNCSITSICEKPQEVCVAV WRKNDENITLETVCHDPKLPYHDFILEDAASPKCIMKEKKKPGETFFMCSCSSD ECNDNIIFSEEYNTSNPD (SEQ ID NO: 92) | anti-PD-1 TGF-β-RII ECD |
| Bi-PB-1.1LC | DIQMTQSPSFLSASVGDRVTITCKASQNVGTNVAWYQQKPGKAPKALIYSASY RYSGVPSRFSGSGSGTEFTLTISSLQPEDFATYYCQQYYSYPYTFGQGTKLEIKRT VAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 93) | |
| Bi-PLB-1.1 HC | QVQLVQSGAEVKKPGASVKVSCKASGYTFTSYWMHWVRQAPGQGLEWMG MIHPNSGGNNYNEKFKSRVTMTRDTSISTAYMELSRLRSDDTAVYYCARSWY GSSPYYFDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNVNHK PSNTKVDKRVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLH QDWLNGKEYKCKVSNKALPAPIEKTISKAKGQPREPQVYTLPPSREEMTKNQV SLTCLVKGFYPSDIAVEWESNGQPENNYKTTPPVLDSDGSFFLYSKLTVDKSR WQQGNVFSCSVMHEALHNHYTQKSLSLSPGKGGGGSGGGGSGGGGSIPPH VQKSVNNDMIVTDNNGAVKFPQLCKFCDVRFSTCDNQKSCMSNCSITSICEK PQEVCVAVWRKNDENITLETVCHDPKLPYHDFILEDAASPKCIMKEKKKPGET FFMCSCSSDECNDNIIFSEEYNTSNPD (SEQ ID NO: 94) | anti-PD-L1 TGF-β-RII ECD |
| Bi-PLB-1.1LC | DIQMTQSPSSLSASVGDRVTISCRASQDIDNYLNWYQQKPGKAPKLLIKYTSRL HSGVPSRFSGSGSGTDFTLTISSLQPEDFATYFCQQGYTLPWTFGGGTKVEIKR TVAAPSVFIFPPSDEQLKSGTASVVCLLNNFYPREAKVQWKVDNALQSGNSQ ESVTEQDSKDSTYSLSSTLTLSKADYEKHKVYACEVTHQGLSSPVTKSFNRGEC (SEQ ID NO: 95) | |

FIG. 7

Functional Domain Sequences in FIGs. 8A-8C

| Functional Domain | Amino Acid Sequences of Functional Domains | Antagonist(s) |
|---|---|---|
| Bevacizumab (Avastin) VH (wt) | EVQLVESGGGLVQPGGSLRLCAASGYTFTNYGMNWVRQAPGKGLEWVGWINTYTGEPTYAADFKRRFTFSLDTSKSTAYLQMNSLRAEDTAVYYCAKYPHYGSSHWYFDVWGQGTLVTVSS (SEQ ID NO: 90) | Bi-AB-1 |
| Bevacizumab (Avastin) VH (mt) | EVQLV<u>Q</u>SGGG<u>V</u>VQPGGSLRLCAASGYTFTNYGMNWVRQAPGKGLEWVGWINTYTGEPTYAADFKRRFTFSLDTSKSTAYLQMNSLRAEDTAVYYCAKYPHYGSSHWYFDVWGQGTLVTVSS (SEQ ID NO: 96) | Bi-A1B-1 |
| Bevacizumab (Avastin) VL | DIQMTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIK (SEQ ID NO: 91) | Bi-AB-1<br>Bi-A1B-1 |
| IgG1 CH1-CH2-CH3 (N297A HC) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQY<u>A</u>STYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO:97) | |
| IgG1 CH1-CH2-CH3 (K447A HC) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG<u>A</u> (SEQ ID NO:98) | Bi-AB-1<br>Bi-A1B-1 |
| IgG1 Fc (CH2-CH3) (K447A HC) | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG<u>A</u> (SEQ ID NO:99) | Bi-ZB-1 |

FIG. 9A

Functional Domain Sequences in FIGs. 8A-8C (CONT)

| Functional Domain | Amino Acid Sequences of Functional Domains | Antagonist(s) |
|---|---|---|
| CL (LC) | RTVAAPSVFIFPPSDEQLKSGTASVVCLLNNFYPREAKVQWKVD NALQSGNSQESVTEQDSKDSTYSLSSTLTLSKADYEKHKVYACEV THQGLSSPVTKSFNRGEC (SEQ ID NO:100) | Bi-AB-1 Bi-A1B-1 |
| $(G4S)_4G$ | GGGGSGGGGSGGGGSGGGGSG (SEQ ID NO: 101) | Bi-AB-1 Bi-A1B-1 Bi-ZB-1 |
| TGF-β RII-ECD | IPPHVQKSVNNDMIVTDNNGAVKFPQLCKFCDVRFSTCDNQKS CMSNCSITSICEKPQEVCVAVWRKNDENITLETVCHDPKLPYHD FILEDAASPKCIMKEKKKPGETFFMCSCSSDECNDNIIFSEEYNTS NPD (SEQ ID NO: 89) | Bi-AB-1 Bi-A1B-1 Bi-ZB-1 |
| VEGF binding domain from Aflibercept | SDTGRPFVEMYSEIPEIIHMTEGRELVIPCRVTSPNITVTLKKFPLD TLIPDGKRIIWDSRKGFIISNATYKEIGLLTCEATVNGHLYKTNYLT HRQTNTIIDVVLSPSHGIELSVGEKLVLNCTARTELNVGIDFNWE YPSSKHQHKKLVNRDLKTQSGSEMKKFLSTLTIDGVTRSDQGLYT CAASSGLMTKKNSTFVRVHEK (SEQ ID NO: 88) | Bi-ZB-1 |

*FIG. 9B*

Heavy chain (HC) and light chain (LC) sequences in FIG. 8

| Antibody (HC/LC) in FIGs. 12-13 | HC or LC amino acid sequence | Functional Domains |
|---|---|---|
| Bi-AB-1 HC (FIG. 8A) | EVQLVESGGGLVQPGGSLRLSCAASGYTFTNYGMNWVRQAPGKGLEWVGW INTYTGEPTYAADFKRRFTFSLDTSKSTAYLQMNSLRAEDTAVYYCAKYPHYYG SSHWYFDVWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNVNHK PSNTKVDKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVLTVLHQ DWLNGKEYKCKVSNKALPAPIEKTISKAKGQPREPQVYTLPPSREEMTKNQVS LTCLVKGFYPSDIAVEWESNGQPENNYKTTPPVLDSDGSFFLYSKLTVDKSRW QQGNVFSCSVMHEALHNHYTQKSLSLSPGAGGGGSGGGGSGGGGSGGGGS GIPPHVQKSVNNDMIVTDNNGAVKFPQLCKFCDVRFSTCDNQKSCMSNCSIT SICEKPQEVCVAVWRKNDENITLETVCHDPKLPYHDFILEDAASPKCIMKEKKK PGETFFMCSCSSDECNDNIIFSEEYNTSNPD (SEQ ID NO: 102) | Anti-VEGF (bevacizumab) TGFβRII ECD |
| Bi-AB-1 LC (FIG. 8A) | DIQMTQSPSSLSASVGDRVTITCSASQDISNYLNWYQQKPGKAPKVLIYFTSSL HSGVPSRFSGSGSGTDFTLTISSLQPEDFATYYCQQYSTVPWTFGQGTKVEIKR TVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC (SEQ ID NO: 103) | |
| Bi-A1B-1 HC (FIG. 8B) | EVQLVQSGGGVVQPGGSLRLSCAASGYTFTNYGMNWVRQAPGKGLEWVG WINTYTGEPTYAADFKRRFTFSLDTSKSTAYLQMNSLRAEDTAVYYCAKYPHYY GSSHWYFDVWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNVNH KPSNTKVDKRVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTVLH QDWLNGKEYKCKVSNKALPAPIEKTISKAKGQPREPQVYTLPPSREEMTKNQV SLTCLVKGFYPSDIAVEWESNGQPENNYKTTPPVLDSDGSFFLYSKLTVDKSRW QQGNVFSCSVMHEALHNHYTQKSLSLSPGAGGGGSGGGGSGGGGSGGGGS GIPPHVQKSVNNDMIVTDNNGAVKFPQLCKFCDVRFSTCDNQKSCMSNCSIT SICEKPQEVCVAVWRKNDENITLETVCHDPKLPYHDFILEDAASPKCIMKEKKK PGETFFMCSCSSDECNDNIIFSEEYNTSNPD (SEQ ID NO: 104) | Anti-VEGF (mutant E6Q/L11V bevacizumab) TGFβRII ECD |
| Bi-A1B-1 LC (FIG. 8B) | DIQMTQSPSSLSASVGDRVTITCSASQDISNYLNWYQQKPGKAPKVLIYFTSSL HSGVPSRFSGSGSGTDFTLTISSLQPEDFATYYCQQYSTVPWTFGQGTKVEIKR TVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC (SEQ ID NO: 103) | |
| Bi-ZB-1 HC (FIG. 8C) | SDTGRPFVEMYSEIPEIIHMTEGRELVIPCRVTSPNITVTLKKFPLDTLIPDGKRII WDSRKGFIISNATYKEIGLLTCEATVNGHLYKTNYLTHRQTNTIIDVVLSPSHGIE LSVGEKLVLNCTARTELNVGIDFNWEYPSSKHQHKKLVNRDLKTQSGSEMKKF LSTLTIDGVTRSDQGLYTCAASSGLMTKKNSTFVRVHEKDKTHTCPPCPAPELL GGPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTT PPVLDSDGSFFLYSKLTVDKSRWQQGNVFSCSVMHEALHNHYTQKSLSLSPG AGGGGSGGGGSGGGGSGGGGSGIPPHVQKSVNNDMIVTDNNGAVKFPQLC KFCDVRFSTCDNQKSCMSNCSITSICEKPQEVCVAVWRKNDENITLETVCHDP KLPYHDFILEDAASPKCIMKEKKKPGETFFMCSCSSDECNDNIIFSEEYNTSNPD (SEQ ID NO: 105) | VEGFR-Fc (Zaltrap; aflibercept) TGFβRII ECD |

*FIG. 10*

Antagonist Configurations in FIGs. 10A-10C

| Antagonist construct | IgG | Binding moieties | Antagonist polypeptide chain | Arrangement of functional domains (NH2--COOH) |
|---|---|---|---|---|
| Bi-AB-1 | IgG1 (K447A), IgG1 (N297A), IgG2 or IgG4 | Avastin (wt) TGFβRII ECD | Bi-AB HC | VH-CH1-CH2-CH3-TGFβRII ECD |
| | | | Bi-AB LC | VL-CL |
| Bi-A1B-1 | IgG1 (K447A), IgG1 (N297A), IgG2 or IgG4 | Avastin (mt) TGFβRII ECD | Bi-A1B HC | VH-CH1-CH2-CH3-TGFβRII ECD |
| | | | Bi-A1B LC | VL-CL |
| Bi-ZB-1 | IgG1 (K447A), IgG1 (N297A), IgG2 or IgG4 | Aflibercept (Zaltrap) TGFβRII ECD | Bi-ZB HC | VEGFR-Fc-CH2-CH3-TGFβRII ECD |

*FIG. 11*

* STD: 1.0ug
1. Transfection control
2. Bi-AB-1
3. Bi-A1B-1
4. Mock

| Molecule | Titer |
|---|---|
| Bi-AB-1 | 90ug/ml |
| Bi-A1B-1 | 240ug/ml |

Protein A purified Bi-ZB-1 has low levels of high molecular weight (HMW) and low molecular weight (LMW) species in comparison to dimers

Bi-PB-1.2                    Bi-PLB-1.2
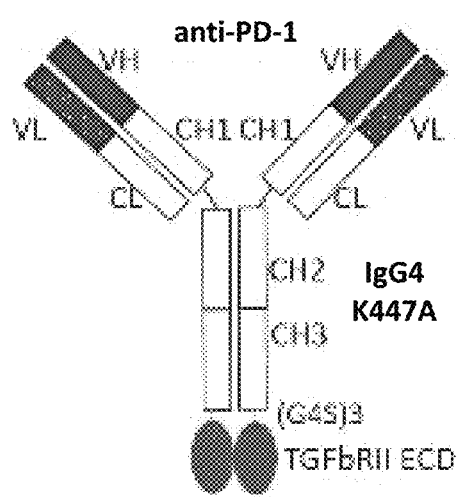 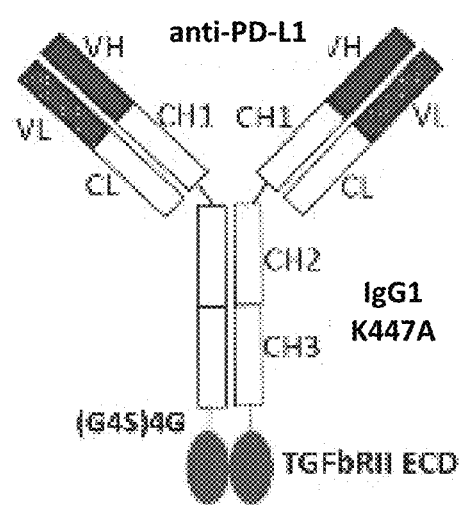
FIG. 20A                     FIG. 20B

Functional Domain Sequences in FIGs. 20A, 20B

| Functional Domain | Amino Acid Sequences of Functional Domains | Antagonist(s) |
|---|---|---|
| Anti-PD-1 VH (2P17) | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSS (SEQ ID NO: 39) | Bi-PB-1.1, -1.2 |
| Anti-PD-L1 VH | QVQLVQSGAEVKKPGASVKVSCKASGYTFTSYWMHWVRQAPGQGLEWMGMIHPNSGGNNYNEKFKSRVTMTRDTSISTAYMELSRLRSDDTAVYYCARSWYGSSPYYFDYWGQGTLVTVSS (SEQ ID NO: 86) | Bi-PLB-1.1, -1.2 |
| IgG4 CH1-CH2-CH3 (K447A) HC | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGA (SEQ ID NO: 174) | Bi-PB-1.2 |
| IgG1 CH1-CH2-CH3 (K447A) HC | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGA (SEQ ID NO: 173) | Bi-PLB-1.2 |
| (G4S)3 | GGGGSGGGGSGGGGS (SEQ ID NO: 156) | Bi-PB-1.1, -1.2 |
| (G4S)4G | GGGGSGGGGSGGGGSGGGGSG (SEQ ID NO: 101) | Bi-PLB-1.1, -1.2 |
| TGF-β RII-ECD | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 89) | Bi-PB-1.1, -1.2 Bi-PLB-1.1, -1.2 |
| Anti-PD-1 VL (2P17) | DIQMTQSPSFLSASVGDRVTITCKASQNVGTNVAWYQQKPGKAPKALIYSASYRYSGVPSRFSGSGSGTEFTLTISSLQPEDFATYYCQQYYSYPYTFGQGTKLEIK (SEQ ID NO: 40) | Bi-PB-1.1, -1.2 |
| Anti-PD-L1 VL | DIQMTQSPSSLSASVGDRVTISCRASQDIDNYLNWYQQKPGKAPKLLIKYTSRLHSGVPSRFSGSGSGTDFTLTISSLQPEDFATYFCQQGYTLPWTFGGGTKVEIK (SEQ ID NO: 87) | Bi-PLB-1.1, -1.2 |
| CL (LC) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 100) | Bi-PB-1.1, -1.2 Bi-PLB-1.1, -1.2 |

*FIG. 21*

Heavy chain (HC) and Light chain (LC) Sequences of Antagonists in FIGs. 20A, 20B

| Antibody (HC/LC) in FIG. 27A/B | Amino acid sequence | Functional Domains |
|---|---|---|
| Bi-PB -1.2 HC | QVQLVQSGAEVKKPGASVKVSCKASGYTFTSYYIHWVRQAPGQGLEWMGW IFPGSGNSKYNENFKGRVTLTADTSTSTVYMELSSLRSEDTAVYYCASETYDYG DYWGQGTLVTVSSASTKGPSVFPLAPCSRSTSESTAALGCLVKDYFPEPVTVS WNSGALTSGVHTFPAVLQSSGLYSLSSVVTVPSSSLGTKTYTCNVDHKPSNTK VDKRVESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNGK EYKCKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGNVF SCSVMHEALHNHYTQKSLSLSLGAGGGGSGGGGSGGGGSIPPHVQKSVNND MIVTDNNGAVKFPQLCKFCDVRFSTCDNQKSCMSNCSITSICEKPQEVCVAV WRKNDENITLETVCHDPKLPYHDFILEDAASPKCIMKEKKKPGETFFMCSCSS DECNDNIIFSEEYNTSNPD (SEQ ID NO: 113) | Anti-PD-1<br><br>TGFβRII ECD |
| Bi-PB-1.2 LC | DIQMTQSPSFLSASVGDRVTITCKASQNVGTNVAWYQQKPGKAPKALIYSAS YRYSGVPSRFSGSGSGTEFTLTISSLQPEDFATYYCQQYYSYPYTFGQGTKLEIK RTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRGE C (SEQ ID NO: 93) | |
| Bi-PLB-1.2 HC | QVQLVQSGAEVKKPGASVKVSCKASGYTFTSYWMHWVRQAPGQGLEWM GMIHPNSGGNNYNEKFKSRVTMTRDTSISTAYMELSRLRSDDTAVYYCARSW YGSSPYYFDYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICNVN HKPSNTKVDKRVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSREEMTKN QVSLTCLVKGFYPSDIAVEWESNGQPENNYKTTPPVLDSDGSFFLYSKLTVDK SRWQQGNVFSCSVMHEALHNHYTQKSLSLSPGAGGGGSGGGGSGGGGSG GGGSGIPPHVQKSVNNDMIVTDNNGAVKFPQLCKFCDVRFSTCDNQKSCM SNCSITSICEKPQEVCVAVWRKNDENITLETVCHDPKLPYHDFILEDAASPKCI MKEKKKPGETFFMCSCSSDECNDNIIFSEEYNTSNPD (SEQ ID NO: 172) | Anti-PD-L1<br><br>TGFβRII ECD |
| Bi-PLB-1.2 LC | DIQMTQSPSSLSASVGDRVTISCRASQDIDNYLNWYQQKPGKAPKLLIKYTSR LHSGVPSRFSGSGSGTDFTLTISSLQPEDFATYFCQQGYTLPWTFGGGTKVEIK RTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRGE C (SEQ ID NO: 95) | |

FIG. 22

Antagonist Configurations in FIGs. 20A, 20B

| Antagonist construct | IgG | Binding moieties | Antagonist polypeptide chain | Arrangement of functional domains (NH2--COOH) |
|---|---|---|---|---|
| Bi-PB-1.2 | IgG1 (K447A), IgG1 (N297A), IgG2 or IgG4 | Anti-PD-1 (2P17) TGF-β1 RII ECD | Bi-PB-1.2 HC TGF-β1 RII ECD | VH-CH1-CH2-CH3-linker-TGF-β1 RII ECD |
| | | | Bi-PB-1.2 LC | VL-CL |
| Bi-PLB-1.2 | IgG1 (K447A), IgG1 (N297A), IgG2 or IgG4 | Anti-PD-L1 (PL-08) TGF-β1 RII ECD | Bi-PLB-1.2 HC TGF-β1 RII ECD | VH-CH1-CH2-CH3-linker-TGF-β1 RII ECD |
| | | | Bi-PLB-1.2 LC | VL-CL |

*FIG. 23*

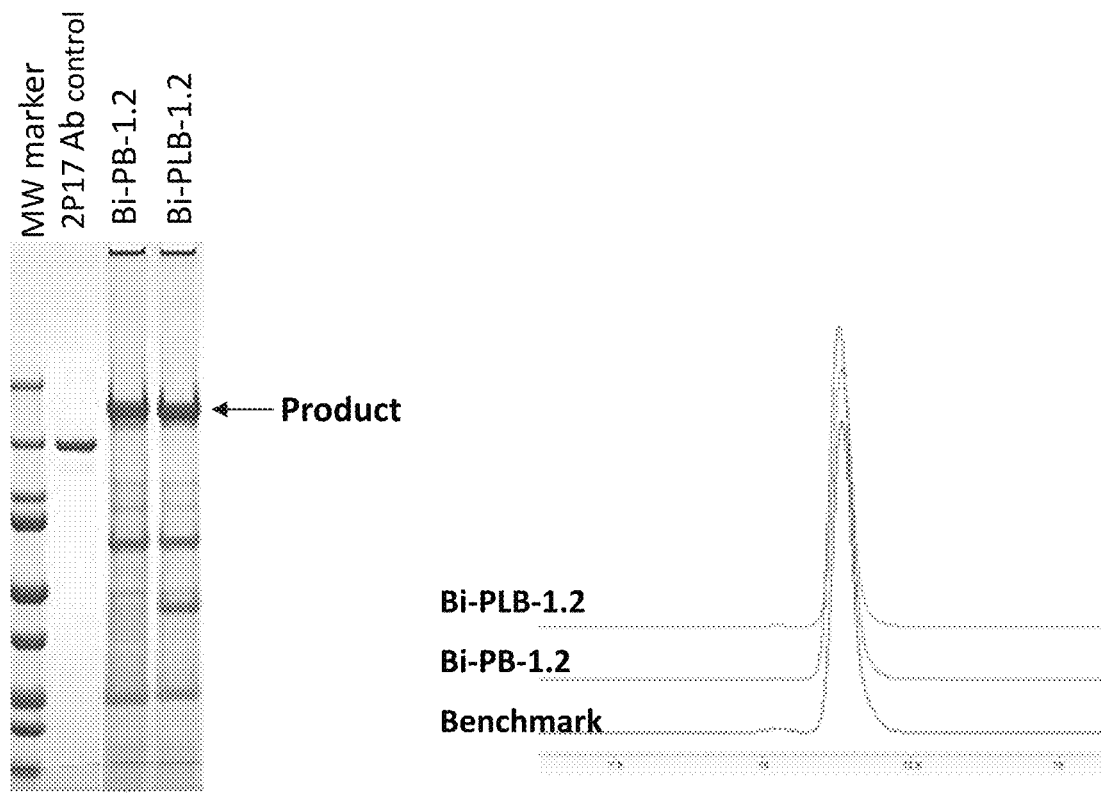
FIG. 24A
FIG. 24B
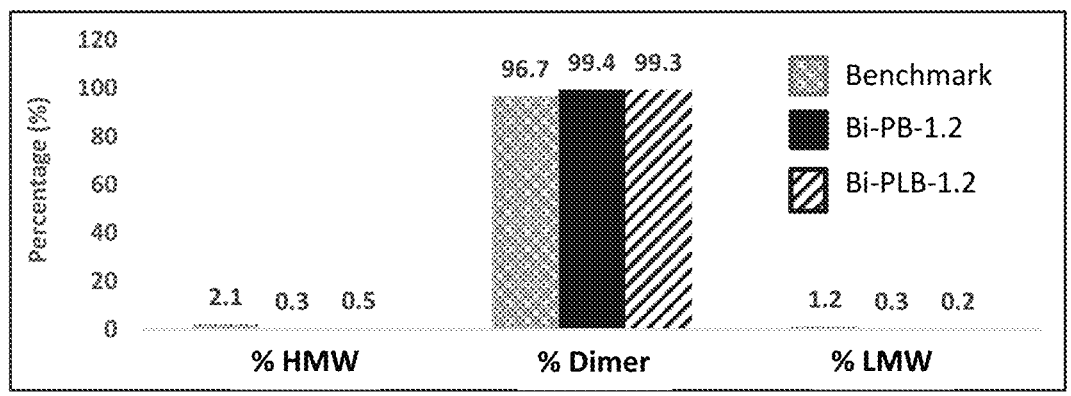
FIG. 24C

PD-L1 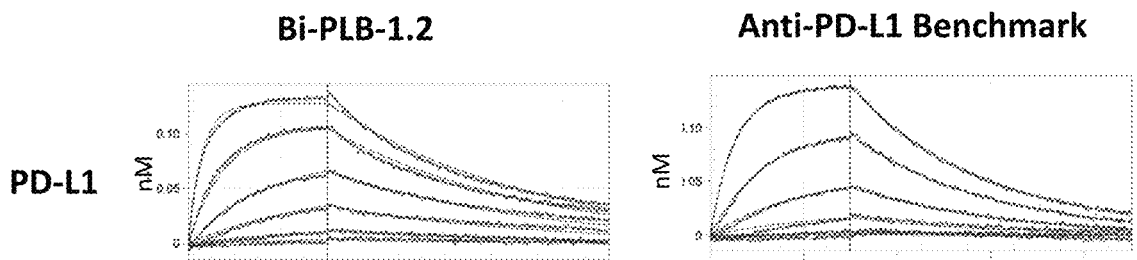
FIG. 27A    FIG. 27C
TGF-β1 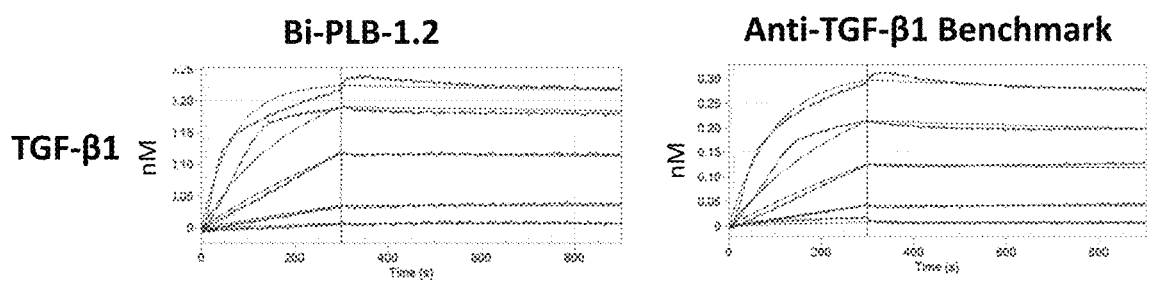
FIG. 27B    FIG. 27D
|  | Soluble Human PD-L1 | | |
|---|---|---|---|
| Antagonist | $K_D$ (nM) | $K_a$ (M$^{-1}$s$^{-1}$) | $K_d$ (s$^{-1}$) |
| Bi-PLB-1.2 | 0.83 | 9.04E+05 | 7.50E-04 |
| Anti-PD-L1 benchmark | 0.75 | 1.71E+06 | 1.28E-03 |
|  | Soluble Human TGF-β1 | | |
| Bi-PLB-1.2 | 0.28 | 2.78E+05 | 7.78E-05 |
| Anti-TGF-β1 benchmark | 0.48 | 2.60E+05 | 1.25E-04 |
FIG. 27E

| Antagonist | Hu PD-1 EC50 (nM) |
|---|---|
| Bi-PB-1.2 | 0.44 |
| anti-PD-1 benchmark | 0.46 |

| Antagonist | Cyno PD-1 EC50 (nM) |
|---|---|
| Bi-PB-1.2 | 0.42 |
| anti-PD-1 benchmark | 0.45 |

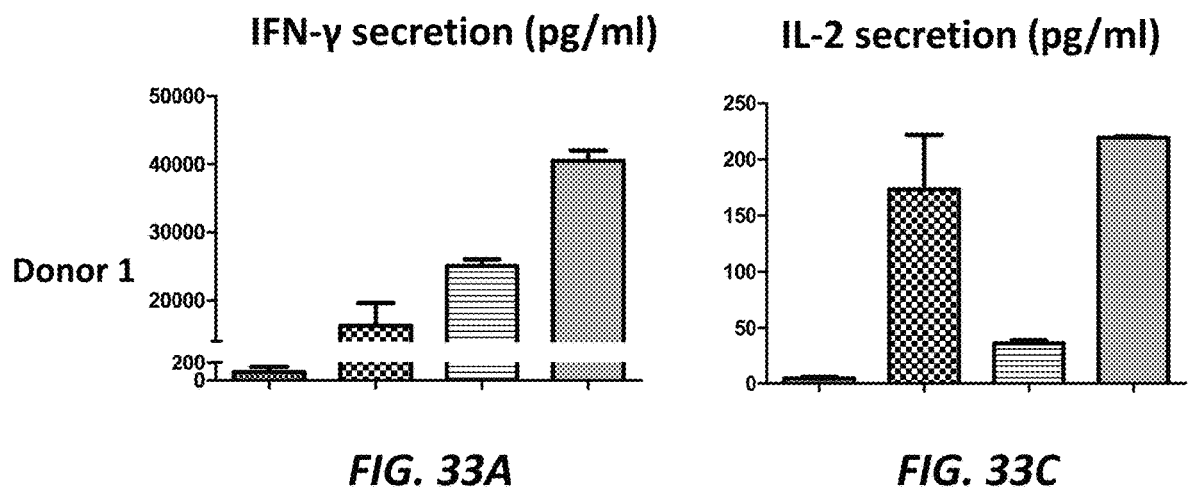
FIG. 33A
FIG. 33C
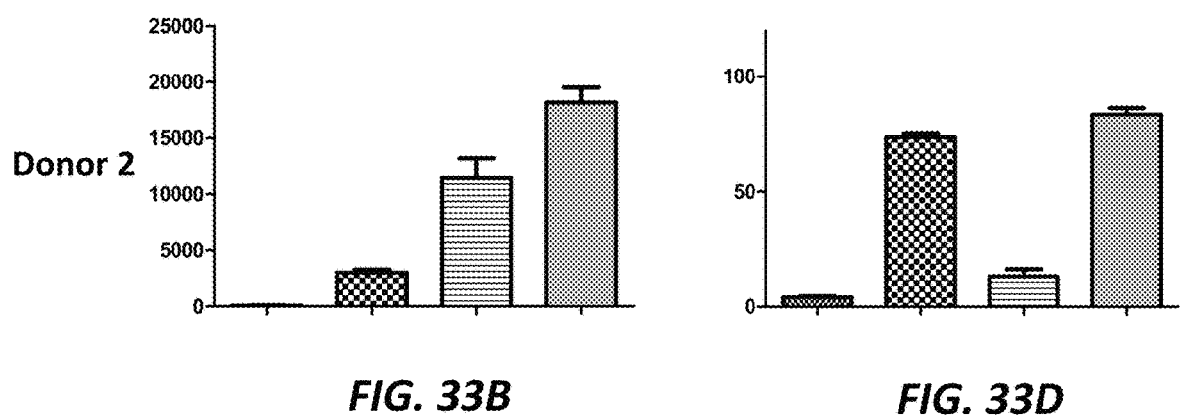
FIG. 33B
FIG. 33D
PBMC with SEB and SHP77 cells and Bi-PB-1.2
PBMC with SEB and SHP77 cells and isotype control
PBMC with SEB stimulation
PBMC with no treatment

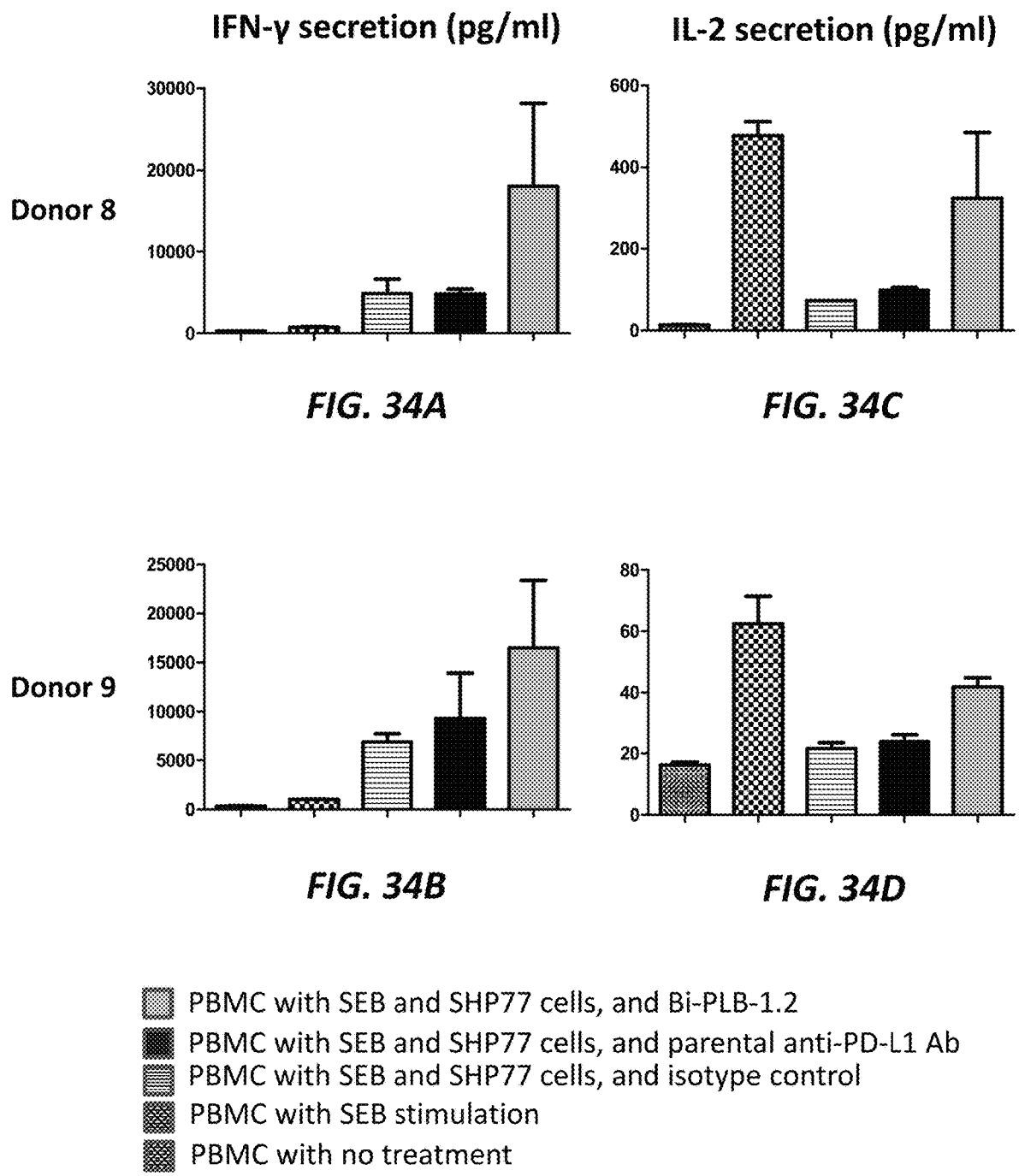

Low molecular weight (LMW) species of Bi-PB-1.2 increase over time stored at 4C, while dimer species decrease over time, consistent with increased clipping

Fractionation of clipped material by cation-exchange chromatography for mass spectrometry analysis to identify the clip site(s)

Bi-AB-1 and Bi-PB-1.2 have similar clipping sites

| Antibody Name | Theoretica Mass (Da) | Observed Mass (Da) | Mass Assignments |
|---|---|---|---|
| Bi-A1B-1 | | 23451.0 | 23450.0 | LC |
| | 66515.8 | 51791.5<br>51920.0<br>66515.0 | HC $^1$EVQ...GIPPHVQ$^{480}$ (SEQ ID NO: 106)<br>HC $^1$EVQ...GIPPHVQK$^{481}$ (SEQ ID NO: 107)<br>HC $^1$EVQ...SNPD$^{610}$ (SEQ ID NO 104;) |
| | C-Terminal Fragments | 13640.0<br>14742.0 | HC $^{491}$DNNG...SNPD$^{610}$ (SEQ ID NO: 108)<br>HC $^{481}$KSVNN...SNPD$^{610}$ (SEQ ID NO: 109) |
| Bi-PB-1.2 | | 23546.2 | 23545.5 | LC |
| | 65129.1 | 50388.5<br>50517.5<br>51045.5<br>51337.0 | HC $^1_{pyro}$QVQLVQ...SIPPHVQ$^{465}$ (SEQ ID NO: 110)<br>HC $^1_{pyro}$QVQLVQ...SIPPHVQK$^{466}$ (SEQ ID NO: 111)<br>HC $^1_{pyro}$QVQLVQ...SIPPHVQ$^{465}$ (SEQ ID NO: 110) + GalNAc-Gal-Sial<br>HC $^1_{pyro}$QVQLVQ...SIPPHVQ$^{465}$ (SEQ ID NO: 110) + GalNAc-Gal-2*Sial |
| | C-Terminal Fragment | 13639.5 | HC $^{476}$DNNG...SNPD$^{595}$ (SEQ ID NO: 108) |

*FIG. 39*

Location of clip sites in the heavy chain sequences of Bi-A1B-1 and Bi-PB-1.2 based on mass spectrometry

Bi-A1B-1 major HC fragments:
(1) $^1$EVQ...PHVQ$^{480}$; (2) $^{491}$DNNG...SNPD$^{610}$ EVQLVQSGGGVVQPGGSLRLSCAASGYTFTNYGMNWVRQAPGKGLEWVGWINTY
TGEPTYAADFKRRFTFSLDTSKSTAYLQMNSLRAEDTAVYYCAKYPHYYGSSHWYFDV
WGQGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSCDKTH
TCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGAGGGGSGGG
GSGGGGSGGGGSGIPPHVQKSVNNDMIVTDNNGAVKFPQLCKFCDVRFSTCDNQK
SCMSNCSITSICEKPQEVCVAVWRKNDENITLETVCHDPKLPYHDFILEDAASPKCIMK
EKKKPGETFFMCSCSSDECNDNIIFSEEYNTSNPD (SEQ ID NO: 112)

*FIG. 40A*

Bi-PB-1.2 major HC fragments:
(1) $^1$QVQL...PHVQ$^{465}$; (2) $^{476}$DNNG...SNPD$^{595}$ QVQLVQSGAEVKKPGASVKVSCKASGYTFTSYYIHWVRQAPGQGLEWMGWIFPGS
GNSKYNENFKGRVTLTADTSTSTVYMELSSLRSEDTAVYYCASETYDYGDYWGQGTLV
TVSSASTKGPSVFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPPCPPCPAPEFLG
GPSVFLFPPKPKDTLMISRTPEVTCVVVDVSQEDPEVQFNWYVDGVEVHNAKTKPRE
EQFNSTYRVVSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDGSFFLYSRLT
VDKSRWQEGNVFSCSVMHEALHNHYTQKSLSLSLGAGGGGSGGGGSGGGGSIPPH
VQKSVNNDMIVTDNNGAVKFPQLCKFCDVRFSTCDNQKSCMSNCSITSICEKPQEVC
VAVWRKNDENITLETVCHDPKLPYHDFILEDAASPKCIMKEKKKPGETFFMCSCSSDEC
NDNIIFSEEYNTSNPD (SEQ ID NO: 113)

*FIG. 40B*

TGFβ RII ECD mutant sequences in Bi-PB-1.2 mutants evaluated for clipping

| TGFβ RII ECD Name | TGFβ RII ECD amino acid sequence |
|---|---|
| TGFβ RII ECD-wt | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 89) |
| TGFβ RII ECD-Δ7 | SVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 114) |
| TGFβ RII ECD-1B | SVNNDMIVTNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 115) |
| TGFβ RII ECD-1C | SVNNDMIVSNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 116) |
| TGFβ RII ECD-1D | IPPHVQQSVNNDMIVTNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 117) |
| TGFβ RII ECD-1E | IPPHVQNSVNNDMIVTNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 118) |
| TGFβ RII ECD-1F | IPPHVQQSVNNDMIVSNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 119) |
| TGFβ RII ECD-1G | IPPHVQNSVNNDMIVSNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 120) |
| TGFβ RII ECD-1H | IPPHVHQSVNNDMIVSNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 121) |
| TGFβ RII ECD-Δ15 | TDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 122) |
| TGFβ RII ECD-Δ20 | AVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 123) |

*FIG. 41A*

Additional TGFβ RII ECD mutant sequences

| Name | Amino Acid Sequence |
|---|---|
| TGFβ RII ECD-1I | SVNNDMIVSANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 251) |
| TGFβ RII ECD-1J | SVNNDMIVAANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 252) |
| TGFβ RII ECD-1K | SVNNDMIVSNNNGAAAFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 253) |
| TGFβ RII ECD-1L | SVNNDMIVAANNGAAAFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 254) |
| TGFβ RII ECD-1M | SVNNDMIVHHNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 255) |
| TGFβ RII ECD-1N | SVNNDMIVPPNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 256) |
| TGFβ RII ECD-1O | SVNNDWIVAANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 257) |
| TGFβ RII ECD-1P | SVNNDWIVAANNWAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 258) |
| TGFβ RII ECD-1Q | MIVSNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 259) |

FIG. 41B

Additional TGFβ RII ECD mutant sequences (cont.)

| Name | amino acid sequence |
|---|---|
| TGFβ RII ECD-1R | MIVSANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 260) |
| TGFβ RII ECD-1S | MIVAANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 261) |
| TGFβ RII ECD-1T | MIVHHNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 262) |
| TGFβ RII ECD-1U | MIVPPNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 263) |
| TGFβ RII ECD-1V | WIVAANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 264) |
| TGFβ RII ECD-1W | WIVAANNWAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 265) |
| TGFβ RII ECD-1X | IVSNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 266) |
| TGFβ RII ECD-1Y | IVSANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 267) |
| TGFβ RII ECD-1Z | IVAANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 268) |
| TGFβ RII ECD-1A1 | IVHHNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 269) |
| TGFβ RII ECD-1B1 | IVPPNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 270) |

*FIG. 41C*

Heavy chain amino acid sequences of Bi-PB-1.2 mutants evaluated for clipping

| Bi-PB1 Name | Heavy chain variable domain amino acid sequence |
|---|---|
| Bi-PB-1.2 HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 113) |
| Bi-PB-1.2Δ7 HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 124) |
| Bi-PB-1.2B HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSSVNNDMIVT<u>N</u>NNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 125) |
| Bi-PB-1.2C HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSSVNNDMIV<u>SN</u>NNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 126) |

FIG. 42A

Heavy chain amino acid sequences of Bi-PB-1 mutants evaluated for clipping (cont)

| Bi-PB1 Name | Heavy chain variable domain amino acid sequence |
|---|---|
| Bi-PB-1.2D HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSIPPHVQQSVNNDMIVTNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 127) |
| Bi-PB-1.2E HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSIPPHVQNSVNNDMIVTNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 128) |
| Bi-PB-1.2F HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSIPPHVQQSVNNDMIVSNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 129) |
| Bi-PB-1.2G HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSIPPHVQNSVNNDMIVSNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 130) |

*FIG. 42B*

Heavy chain amino acid sequences of Bi-PB-1.2 mutants evaluated for clipping (cont)

| Bi-PB1 Name | Heavy chain variable domain amino acid sequence |
|---|---|
| Bi-PB-1.2H HC | QVQLVQSGAEVKKPGASVKVSCKASGYTFTSYYIHWVRQAPGQGLEWMGWIFPGSGNSKYNENFKGR VTLTADTSTSTVYMELSSLRSEDTAVYYCASETYDYGDYWGQGTLVTVSSASTKGPSVFPLAPCSRSTSEST AALGCLVKDYFPEPVTVSWNSGALTSGVHTFPAVLQSSGLYSLSSVVTVPSSSLGTKTYTCNVDHKPSNTK VDKRVESKYGPPCPPCPAPEFLGGPSVFLFPPKPKDTLMISRTPEVTCVVVDVSQEDPEVQFNWYVDGVE VHNAKTKPREEQFNSTYRVVSVLTVLHQDWLNGKEYKCKVSNKGLPSSIEKTISKAKGQPREPQVYTLPPS QEEMTKNQVSLTCLVKGFYPSDIAVEWESNGQPENNYKTTPPVLDSDGSFFLYSRLTVDKSRWQEGNVF SCSVMHEALHNHYTQKSLSLSLGAGGGGSGGGGSGGGGSIPPHVHQSVNNDMIVSNNNGAVKFPQLC KFCDVRFSTCDNQKSCMSNCSITSICEKPQEVCVAVWRKNDENITLETVCHDPKLPYHDFILEDAASPKCI MKEKKKPGETFFMCSCSSDECNDNIIFSEEYNTSNPD (SEQ ID NO: 131) |
| Bi-PB-1.2Δ15 HC | QVQLVQSGAEVKKPGASVKVSCKASGYTFTSYYIHWVRQAPGQGLEWMGWIFPGSGNSKYNENFKGR VTLTADTSTSTVYMELSSLRSEDTAVYYCASETYDYGDYWGQGTLVTVSSASTKGPSVFPLAPCSRSTSEST AALGCLVKDYFPEPVTVSWNSGALTSGVHTFPAVLQSSGLYSLSSVVTVPSSSLGTKTYTCNVDHKPSNTK VDKRVESKYGPPCPPCPAPEFLGGPSVFLFPPKPKDTLMISRTPEVTCVVVDVSQEDPEVQFNWYVDGVE VHNAKTKPREEQFNSTYRVVSVLTVLHQDWLNGKEYKCKVSNKGLPSSIEKTISKAKGQPREPQVYTLPPS QEEMTKNQVSLTCLVKGFYPSDIAVEWESNGQPENNYKTTPPVLDSDGSFFLYSRLTVDKSRWQEGNVF SCSVMHEALHNHYTQKSLSLSLGAGGGGSGGGGSGGGGSGGGGSGTDNNGAVKFPQLCKFCDVRFSTC DNQKSCMSNCSITSICEKPQEVCVAVWRKNDENITLETVCHDPKLPYHDFILEDAASPKCIMKEKKKPGET FFMCSCSSDECNDNIIFSEEYNTSNPD (SEQ ID NO: 132) |
| Bi-PB-1.2Δ20 HC | QVQLVQSGAEVKKPGASVKVSCKASGYTFTSYYIHWVRQAPGQGLEWMGWIFPGSGNSKYNENFKGR VTLTADTSTSTVYMELSSLRSEDTAVYYCASETYDYGDYWGQGTLVTVSSASTKGPSVFPLAPCSRSTSEST AALGCLVKDYFPEPVTVSWNSGALTSGVHTFPAVLQSSGLYSLSSVVTVPSSSLGTKTYTCNVDHKPSNTK VDKRVESKYGPPCPPCPAPEFLGGPSVFLFPPKPKDTLMISRTPEVTCVVVDVSQEDPEVQFNWYVDGVE VHNAKTKPREEQFNSTYRVVSVLTVLHQDWLNGKEYKCKVSNKGLPSSIEKTISKAKGQPREPQVYTLPPS QEEMTKNQVSLTCLVKGFYPSDIAVEWESNGQPENNYKTTPPVLDSDGSFFLYSRLTVDKSRWQEGNVF SCSVMHEALHNHYTQKSLSLSLGAGGGGSGGGGSGGGGSGGGGSGAVKFPQLCKFCDVRFSTCDNQKS CMSNCSITSICEKPQEVCVAVWRKNDENITLETVCHDPKLPYHDFILEDAASPKCIMKEKKKPGETFFMCS CSSDECNDNIIFSEEYNTSNPD (SEQ ID NO: 133) |

FIG. 42C

Heavy chain amino acid sequences of Bi-PB-1.2 mutants evaluated for clipping (cont)

| Bi-PB1 Name | Heavy chain variable domain amino acid sequence |
|---|---|
| Bi-PB-1.2I HC | SQVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSSVNNDMIVSANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 271) |
| Bi-PB-1.2J HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSSVNNDMIVAANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 272) |
| Bi-PB-1.2K HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSSVNNDMIVSNNNGAAAFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 273) |
| Bi-PB-1.2L HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSSVNNDMIVAANNGAAAFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 274) |

FIG. 42D

Heavy chain amino acid sequences of Bi-PB-1.2 mutants evaluated for clipping (cont)

| Bi-PB1 Name | Heavy chain variable domain amino acid sequence |
|---|---|
| Bi-PB-1.2M HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSSVNNDMIVHHNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 275) |
| Bi-PB-1.2N HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSSVNNDMIVPPNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 276) |
| Bi-PB-1.2O HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSSVNNDWIVAANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 277) |
| Bi-PB-1.2P HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSSVNNDWIVAANNWAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 278) |

FIG. 42E

Heavy chain amino acid sequences of Bi-PB-1.2 mutants evaluated for clipping (cont)

| Bi-PB1 Name | Heavy chain variable domain amino acid sequence |
|---|---|
| Bi-PB-1.2Q HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSMIVSNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 279) |
| Bi-PB-1.2R HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSMIVSANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 280) |
| Bi-PB-1.2S HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSMIVAANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 281) |
| Bi-PB-1.2T HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSMIVHHNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 282) |

FIG. 42F

Heavy chain amino acid sequences of Bi-PB-1.2 mutants evaluated for clipping (cont)

| Bi-PB1 Name | Heavy chain variable domain amino acid sequence |
|---|---|
| Bi-PB-1.2U HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSMIVPPNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 283) |
| Bi-PB-1.2V HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSWIVAANNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 284) |
| Bi-PB-1.2W HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSWIVAANNWAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD  (SEQ ID NO: 285) |
| Bi-PB-1.2X HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGAGGGGSGGGGSGGGGSIVSNNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 286) |

FIG. 42G

Heavy chain amino acid sequences of Bi-PB-1.2 mutants evaluated for clipping (cont)

| Bi-PB1 Name | Heavy chain variable domain amino acid sequence |
|---|---|
| Bi-PB-1.2Y HC | QVQLVQSGAEVKKPGASVKVSCKASGYTFTSYYIHWVRQAPGQGLEWMGWIFPGSGNSKYNENFKGRVTL TADTSTSTVYMELSSLRSEDTAVYYCASETYDYGDYWGQGTLVTVSSASTKGPSVFPLAPCSRSTSESTAALGC LVKDYFPEPVTVSWNSGALTSGVHTFPAVLQSSGLYSLSSVVTVPSSSLGTKTYTCNVDHKPSNTKVDKRVESK YGPPCPPCPAPEFLGGPSVFLFPPKPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQEGNVFSCSVMHEALHNHYT QKSLSLSLGAGGGGSGGGGSGGGGSIVSANNGAVKFPQLCKFCDVRFSTCDNQKSCMSNCSITSICEKPQEV CVAVWRKNDENITLETVCHDPKLPYHDFILEDAASPKCIMKEKKKPGETFFMCSCSSDECNDNIIFSEEYNTSN PD (SEQ ID NO: 287) |
| Bi-PB-1.2Z HC | QVQLVQSGAEVKKPGASVKVSCKASGYTFTSYYIHWVRQAPGQGLEWMGWIFPGSGNSKYNENFKGRVTL TADTSTSTVYMELSSLRSEDTAVYYCASETYDYGDYWGQGTLVTVSSASTKGPSVFPLAPCSRSTSESTAALGC LVKDYFPEPVTVSWNSGALTSGVHTFPAVLQSSGLYSLSSVVTVPSSSLGTKTYTCNVDHKPSNTKVDKRVESK YGPPCPPCPAPEFLGGPSVFLFPPKPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQEGNVFSCSVMHEALHNHYT QKSLSLSLGAGGGGSGGGGSGGGGSIVAANNGAVKFPQLCKFCDVRFSTCDNQKSCMSNCSITSICEKPQEV CVAVWRKNDENITLETVCHDPKLPYHDFILEDAASPKCIMKEKKKPGETFFMCSCSSDECNDNIIFSEEYNTSN PD (SEQ ID NO: 288) |
| Bi-PB-1.2A1 HC | QVQLVQSGAEVKKPGASVKVSCKASGYTFTSYYIHWVRQAPGQGLEWMGWIFPGSGNSKYNENFKGRVTL TADTSTSTVYMELSSLRSEDTAVYYCASETYDYGDYWGQGTLVTVSSASTKGPSVFPLAPCSRSTSESTAALGC LVKDYFPEPVTVSWNSGALTSGVHTFPAVLQSSGLYSLSSVVTVPSSSLGTKTYTCNVDHKPSNTKVDKRVESK YGPPCPPCPAPEFLGGPSVFLFPPKPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQEGNVFSCSVMHEALHNHYT QKSLSLSLGAGGGGSGGGGSGGGGSIVHHNNGAVKFPQLCKFCDVRFSTCDNQKSCMSNCSITSICEKPQEV CVAVWRKNDENITLETVCHDPKLPYHDFILEDAASPKCIMKEKKKPGETFFMCSCSSDECNDNIIFSEEYNTSN PD (SEQ ID NO: 289) |
| Bi-PB-1.2B1 HC | QVQLVQSGAEVKKPGASVKVSCKASGYTFTSYYIHWVRQAPGQGLEWMGWIFPGSGNSKYNENFKGRVTL TADTSTSTVYMELSSLRSEDTAVYYCASETYDYGDYWGQGTLVTVSSASTKGPSVFPLAPCSRSTSESTAALGC LVKDYFPEPVTVSWNSGALTSGVHTFPAVLQSSGLYSLSSVVTVPSSSLGTKTYTCNVDHKPSNTKVDKRVESK YGPPCPPCPAPEFLGGPSVFLFPPKPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQEGNVFSCSVMHEALHNHYT QKSLSLSLGAGGGGSGGGGSGGGGSIVPPNNGAVKFPQLCKFCDVRFSTCDNQKSCMSNCSITSICEKPQEV CVAVWRKNDENITLETVCHDPKLPYHDFILEDAASPKCIMKEKKKPGETFFMCSCSSDECNDNIIFSEEYNTSN PD (SEQ ID NO: 290) |

FIG. 42H

Heavy chain (HC) and light chain (LC) aa sequences of Bi-PLB-1.2

| Bi-PB1 Name | Heavy chain variable domain amino acid sequence |
|---|---|
| Bi-PLB-1.2C LC<br>Bi-PLB-1.2D LC<br>Bi-PLB-1.2U LC | DIQMTQSPSSLSASVGDRVTISCRASQDIDNYLNWYQQKPGKAPKLLIKYTSRLHSGVPSRFSGSGSG TDFTLTISSLQPEDFATYFCQQGYTLPWTFGGGTKVEIKRTVAAPSVFIFPPSDEQLKSGTASVVCLLN NFYPREAKVQWKVDNALQSGNSQESVTEQDSKDSTYSLSSTLTLSKADYEKHKVYACEVTHQGLSSP VTKSFNRGEC (SEQ ID NO: 146) |
| Bi-PLB-1.2C HC | QVQLVQSGAEVKKPGASVKVSCKASGYTFTSYWMHWVRQAPGQGLEWMGMIHPNSGGNNYNE KFKSRVTMTRDTSISTAYMELSRLRSDDTAVYYCARSWYGSSPYYFDYWGQGTLVTVSSASTKGPSVF PLAPSSKSTSGGTAALGCLVKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGAGGGGSGGGGSGGGGS GGGGSSVNNDMIVSNNNGAVKFPQLCKFCDVRFSTCDNQKSCMSNCSITSICEKPQEVCVAVWRK NDENITLETVCHDPKLPYHDFILEDAASPKCIMKEKKKPGETFFMCSCSSDECNDNIIFSEEYNTSNPD (SEQ ID NO: 145) |
| Bi-PLB-1.2D HC | QVQLVQSGAEVKKPGASVKVSCKASGYTFTSYWMHWVRQAPGQGLEWMGMIHPNSGGNNYNE KFKSRVTMTRDTSISTAYMELSRLRSDDTAVYYCARSWYGSSPYYFDYWGQGTLVTVSSASTKGPSVF PLAPSSKSTSGGTAALGCLVKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGAGGGGSGGGGSGGGGS GGGGSIPPHVQQSVNNDMIVTNNNGAVKFPQLCKFCDVRFSTCDNQKSCMSNCSITSICEKPQEVC VAVWRKNDENITLETVCHDPKLPYHDFILEDAASPKCIMKEKKKPGETFFMCSCSSDECNDNIIFSEEY NTSNPD (SEQ ID NO: 147) |
| Bi-PLB-1.2U HC | QVQLVQSGAEVKKPGASVKVSCKASGYTFTSYWMHWVRQAPGQGLEWMGMIHPNSGGNNYNE KFKSRVTMTRDTSISTAYMELSRLRSDDTAVYYCARSWYGSSPYYFDYWGQGTLVTVSSASTKGPSVF PLAPSSKSTSGGTAALGCLVKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGAGGGGSGGGGSGGGGS GGGGSMIVPPNNGAVKFPQLCKFCDVRFSTCDNQKSCMSNCSITSICEKPQEVCVAVWRKNDENIT LETVCHDPKLPYHDFILEDAASPKCIMKEKKKPGETFFMCSCSSDECNDNIIFSEEYNTSNPD (SEQ ID NO: 303) |

FIG. 43

Heavy chain (HC) Bi-A1B-1 mutant TGF-β1 ECDs

| Bi-PB1 Name | Heavy chain variable domain amino acid sequence |
|---|---|
| Bi-A1B-1C HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDGS FFLYSKLTVDKSRWQQGNVFSCSVMHEALHNHYTQKSLSLSPGAGGGGSGGGGSGGGGSGGGGSSV NNDMIVSNNNGAVKFPQLCKFCDVRFSTCDNQKSCMSNCSITSICEKPQEVCVAVWRKNDENITLET VCHDPKLPYHDFILEDAASPKCIMKEKKKPGETFFMCSCSSDECNDNIIFSEEYNTSNPD (SEQ ID NO: 148) |
| Bi-A1B-1D HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDGS FFLYSKLTVDKSRWQQGNVFSCSVMHEALHNHYTQKSLSLSPGAGGGGSGGGGSGGGGSGGGGSIP PHVQQSVNNDMIVTNNNGAVKFPQLCKFCDVRFSTCDNQKSCMSNCSITSICEKPQEVCVAVWRKN DENITLETVCHDPKLPYHDFILEDAASPKCIMKEKKKPGETFFMCSCSSDECNDNIIFSEEYNTSNPD (SEQ ID NO: 150) |
| Bi-A1B-1Q HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGS MIVSNNNGAVKFPQLCKFCDVRFSTCDNQKSCMSNCSITSICEKPQEVCVAVWRKNDENITLETVCH DPKLPYHDFILEDAASPKCIMKEKKKPGETFFMCSCSSDECNDNIIFSEEYNTSNPD (SEQ ID NO: 291) |
| Bi-A1B-1R HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGS MIVSANNGAVKFPQLCKFCDVRFSTCDNQKSCMSNCSITSICEKPQEVCVAVWRKNDENITLETVCHD PKLPYHDFILEDAASPKCIMKEKKKPGETFFMCSCSSDECNDNIIFSEEYNTSNPD (SEQ ID NO: 292) |

*FIG. 44A*

Heavy chain (HC) Bi-A1B-1 mutant TGF-β1 ECDs (Cont)

| Bi-PB1 Name | Heavy chain variable domain amino acid sequence |
|---|---|
| Bi-A1B-1S HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGS MIVAANNGAVKFPQLCKFCDVRFSTCDNQKSCMSNCSITSICEKPQEVCVAVWRKNDENITLETVCH DPKLPYHDFILEDAASPKCIMKEKKKPGETFFMCSCSSDECNDNIIFSEEYNTSNPD (SEQ ID NO: 293) |
| Bi-A1B-1T HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGS MIVHHNNGAVKFPQLCKFCDVRFSTCDNQKSCMSNCSITSICEKPQEVCVAVWRKNDENITLETVCH DPKLPYHDFILEDAASPKCIMKEKKKPGETFFMCSCSSDECNDNIIFSEEYNTSNPD (SEQ ID NO: 294) |
| Bi-A1B-1U HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGS MIVPPNNGAVKFPQLCKFCDVRFSTCDNQKSCMSNCSITSICEKPQEVCVAVWRKNDENITLETVCHD PKLPYHDFILEDAASPKCIMKEKKKPGETFFMCSCSSDECNDNIIFSEEYNTSNPD (SEQ ID NO: 295) |
| Bi-A1B-1V HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGS WIVAANNGAVKFPQLCKFCDVRFSTCDNQKSCMSNCSITSICEKPQEVCVAVWRKNDENITLETVCH DPKLPYHDFILEDAASPKCIMKEKKKPGETFFMCSCSSDECNDNIIFSEEYNTSNPD (SEQ ID NO: 296) |

FIG. 44B

Heavy chain (HC) Bi-A1B-1 mutant TGF-β1 ECDs (Cont)

| Bi-PB1 Name | Heavy chain variable domain amino acid sequence |
|---|---|
| Bi-A1B-1W HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGS WIVAANNWAVKFPQLCKFCDVRFSTCDNQKSCMSNCSITSICEKPQEVCVAVWRKNDENITLETVCH DPKLPYHDFILEDAASPKCIMKEKKKPGETFFMCSCSSDECNDNIIFSEEYNTSNPD (SEQ ID NO: 297) |
| Bi-A1B-1X HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGSI VSNNNGAVKFPQLCKFCDVRFSTCDNQKSCMSNCSITSICEKPQEVCVAVWRKNDENITLETVCHDPK LPYHDFILEDAASPKCIMKEKKKPGETFFMCSCSSDECNDNIIFSEEYNTSNPD (SEQ ID NO: 298) |
| Bi-A1B-1Y HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGSI VSANNGAVKFPQLCKFCDVRFSTCDNQKSCMSNCSITSICEKPQEVCVAVWRKNDENITLETVCHDPK LPYHDFILEDAASPKCIMKEKKKPGETFFMCSCSSDECNDNIIFSEEYNTSNPD (SEQ ID NO: 299) |
| Bi-A1B-1Z HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGSI VAANNGAVKFPQLCKFCDVRFSTCDNQKSCMSNCSITSICEKPQEVCVAVWRKNDENITLETVCHDPK LPYHDFILEDAASPKCIMKEKKKPGETFFMCSCSSDECNDNIIFSEEYNTSNPD (SEQ ID NO: 300) |

FIG. 44C

Heavy chain (HC) Bi-A1B-1 mutant TGF-β1 ECDs (Cont)

| Bi-PB1 Name | Heavy chain variable domain amino acid sequence |
|---|---|
| Bi-A1B-1A1 HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGSI VHHNNGAVKFPQLCKFCDVRFSTCDNQKSCMSNCSITSICEKPQEVCVAVWRKNDENITLETVCHDP KLPYHDFILEDAASPKCIMKEKKKPGETFFMCSCSSDECNDNIIFSEEYNTSNPD (SEQ ID NO: 301) |
| Bi-A1B-1B1 HC | EVQLVQSGGGVVQPGGSLRLSCAASGYTFTNYGMNWVRQAPGKGLEWVGWINTYTGEPTYAADFK RRFTFSLDTSKSTAYLQMNSLRAEDTAVYYCAKYPHYYGSSHWYFDVWGQGTLVTVSSASTKGPSVFP LAPSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPGAGGGGSGGGGSGGGGSGGGGSI VHHNNGAVKFPQLCKFCDVRFSTCDNQKSCMSNCSITSICEKPQEVCVAVWRKNDENITLETVCHDP KLPYHDFILEDAASPKCIMKEKKKPGETFFMCSCSSDECNDNIIFSEEYNTSNPD (SEQ ID NO: 302) |

FIG. 44D

Generation of mutants to modify and/or reduce clipping

N-terminus of TGFβ RII ECD:

| | | |
|---|---|---|
| WT: | IPPHVQKSVNNDMIVTDNNGAVKFP... | (SEQ ID NO:134) |
| Δ7: | SVNNDMIVTDNNGAVKFP... | (SEQ ID NO:135) |
| B: | SVNNDMIVTNNNGAVKFP... | (SEQ ID NO:136) |
| C: | SVNNDMIVSNNNGAVKFP... | (SEQ ID NO:137) |
| D: | IPPHVQQSVNNDMIVTNNNGAVKFP... | (SEQ ID NO:138) |
| E: | IPPHVQNSVNNDMIVTNNNGAVKFP... | (SEQ ID NO:139) |
| F: | IPPHVQQSVNNDMIVSNNNGAVKFP... | (SEQ ID NO:140) |
| G: | IPPHVQNSVNNDMIVSNNNGAVKFP... | (SEQ ID NO:141) |
| H: | IPPHVHQSVNNDMIVSNNNGAVKFP... | (SEQ ID NO:142) |
| Δ15: | TDNNGAVKFP... | (SEQ ID NO:143) |
| Δ20: | AVKFP... | (SEQ ID NO:144) |
| I: | SVNNDMIVSANNGAVKFP... | (SEQ ID NO:230) |
| J: | SVNNDMIVAANNGAVKFP... | (SEQ ID NO:231) |
| K: | SVNNDMIVSNNNGAAAFP... | (SEQ ID NO:232) |
| L: | SVNNDMIVAANNGAAAFP... | (SEQ ID NO:233) |
| M: | SVNNDMIVHHNNGAVKFP... | (SEQ ID NO:234) |
| N: | SVNNDMIVPPNNGAVKFP... | (SEQ ID NO:235) |
| O: | SVNNDWIVAANNGAVKFP... | (SEQ ID NO:236) |
| P: | SVNNDWIVAANNWAVKFP... | (SEQ ID NO:237) |
| Q: | MIVSNNNGAVKFP... | (SEQ ID NO:238) |
| R: | MIVSANNGAVKFP... | (SEQ ID NO:239) |
| S: | MIVAANNGAVKFP... | (SEQ ID NO:240) |
| T: | MIVHHNNGAVKFP... | (SEQ ID NO:241) |
| U: | MIVPPNNGAVKFP... | (SEQ ID NO:242) |
| V: | WIVAANNGAVKFP... | (SEQ ID NO:243) |
| W: | WIVAANNWAVKFP... | (SEQ ID NO:244) |
| X: | IVSNNNGAVKFP... | (SEQ ID NO:245) |
| Y: | IVSANNGAVKFP... | (SEQ ID NO:246) |
| Z: | IVAANNGAVKFP... | (SEQ ID NO:247) |
| A1: | IVHHNNGAVKFP... | (SEQ ID NO:248) |
| B1: | IVPPNNGAVKFP... | (SEQ ID NO:249) |

FIG. 45

Transient expression and batch purification of variants indicate they express as well as unmodified fusion molecules

1. 2P17 non reduced
2. 2P17 reduced
3. Bi-PB-1.2B
4. Bi-PB-1.2C
5. Bi-PB-1.2
6. Bi-PB-1.2D
7. Bi-PB-1.2E
8. Bi-PB-1.2F
9. Bi-PB-1.2G
10. Bi-PB-1.2H
11. Bi-PB-1.2

Transient expression and batch purification of variants indicate they express as well as unmodified fusion molecules (Cont)

1. Bi-PB-1.2
2. Bi-PB-1.2C
3. Bi-PB-1.2Δ15
4. Bi-PB-1.2Δ20
5. Bi-PB-1.2I
6. Bi-PB-1.2J
7. Bi-PB-1.2K
8. Bi-PB-1.2L
9. Bi-PB-1.2M
10. Bi-PB-1.2N
11. Bi-PB-1.2O
12. Bi-PB-1.2P

SEC profiles of TGF-β1 ECD mutants (cont)

Variants have low percentages of high molecular weight forms

| Molecule | % HMW | % Dimer | % LMW |
|---|---|---|---|
| Bi-PB-1.2 | 12.1 | 0 | 87.9 |
| Bi-PB-1.2Δ7 | 9.9 | 65.6 | 24.6 |
| Bi-PB-1.2B | 5.6 | 93.3 | 1.2 |
| Bi-PB-1.2C | 4.1 | 94.4 | 1.6 |
| Bi-PB-1.2D | 4.1 | 94.5 | 1.3 |
| Bi-PB-1.2E | 11.6 | 87.2 | 1.2 |
| Bi-PB-1.2F | 3.3 | 95.3 | 1.5 |
| Bi-PB-1.2G | 4.4 | 94.1 | 1.6 |
| Bi-PB-1.2H | 4.4 | 94.2 | 1.3 |
| Bi-PB-1.2Δ15 | 4.6 | 94.3 | 1.1 |
| Bi-PB-1.2Δ20 | 4.6 | 94.7 | 0.6 |

*FIG. 48*

Summary of bioassay IC50s

| Molecule | IC50 (pM) |
|---|---|
| Bi-PB-1.2 | 145.2 |
| Bi-PB-1.2Δ7 | 138.0 |
| Bi-PB-1.2B | 143.9 |
| Bi-PB-1.2C | 124.3 |
| Bi-PB-1.2D | 153.1 |
| Bi-PB-1.2E | 146.4 |
| Bi-PB-1.2F | 129.7 |
| Bi-PB-1.2G | 157.0 |
| Bi-PB-1.2H | 153.7 |
| Bi-PB-1.2Δ15 | 608.9 |
| Bi-PB-1.2Δ20 | 677.5 |

| Molecule | IC50 (nM) |
|---|---|
| Bi-PB-1.2 | 0.26 |
| Bi-PB-1.2I | 0.29 |
| Bi-PB-1.2J | 0.17 |
| Bi-PB-1.2K | 0.38 |
| Bi-PB-1.2L | 0.43 |
| Bi-PB-1.2M | 0.36 |
| Bi-PB-1.2N | 0.26 |
| Bi-PB-1.2O | 0.33 |
| Bi-PB-1.2P | 0.41 |
| Bi-PB-1.2U | 0.22 |
| Bi-PB-1.2A1 | 0.24 |
| Bi-PB-1.2B1 | 0.22 |

| Molecule | IC50 (nM) |
|---|---|
| Bi-A1B-1 | 0.162 |
| Bi-A1B-1C | 0.290 |
| Bi-A1B-1Q | 0.248 |
| Bi-A1B-1R | 0.488 |
| Bi-A1B-1S | 0.175 |
| Bi-A1B-1T | 0.177 |
| Bi-A1B-1U | 0.157 |
| Bi-A1B-1V | 0.209 |
| Bi-A1B-1W | 0.842 |
| Bi-A1B-1X | 0.477 |
| Bi-A1B-1Y | 0.443 |
| Bi-A1B-1Z | 0.320 |
| Bi-A1B-1A1 | 0.312 |
| Bi-A1B-1B1 | 0.228 |

*FIG. 50*

Pharmacokinetics of Bi-PB-1.2C and Bi-PB-1.2D are similar to Bi-PB-1.2

Bi-PB-1.2

Bi-PB-1.2C

Bi-PB-1.2D $t_{1/2}$ is about 5-8 days

Framework regions sequences for anti-PD-1 and anti-PD-L1 CDRs

| SEQ ID NO | Sequence | Description |
|---|---|---|
| 176 | EVQLVESGGGLVQPGGSLRLSCAASGFTFS | PD-01 HFR1 |
| 177 | WVRQAPGKGLEWVS | PD-01 HFR2 |
| 178 | RFTISRDNSKNTLYLQMNSLRAEDTAVYYCAK | PD-01 HFR3 |
| 179 | WGQGTSVTVSS | PD-01 HFR4 |
| 180 | DIQMTQSPSSVSASVGDRVTITC | PD-01 LFR1 |
| 181 | WYQQKPGKAPKLLIY | PD-01, 02, 03, 04; PL-02, 03 LFR2 |
| 182 | GVPSRFSGSGSGTDFTLTISSLQPEDFATYYC | PD-01, 02, 03, 04 LFR3 |
| 183 | FGGGTKLEIK | PD-01; PL-05 LFR4 |
| 184 | QVQLVQSGAEVKKPGASVKVSCKASDYTFT | PD-02, 03, 04 HFR1 |
| 185 | WLRQAPGQGLEWMG | PD-02 HFR2 |
| 186 | RTTSTRDTSISTAYMELSRLRSDDTVVYYCTR | PD-02 HFR3 |
| 187 | WGQGTLVTVSS | PD-02, 04, 05, 06; PL-01, 02, 03, 04, 06, 07, 08 HFR4 |
| 188 | DIQMTQSPSSLSASVGDRVTFTC | PD-02, 04 LFR1 |
| 189 | FGGGTKVEIK | PD-02, 04, 05; PL-01, 04, 06, 07, 08 LFR4 |
| 190 | WVRQAPGQGLEWMG | PD-03, 04, 05, 06; PL-02, 03, 04, 08 HFR2 |
| 191 | RVTSTRDTSISTAYMELSRLRSDDTVVYYCA | PD-03, 04; PL-01 HFR3 |
| 192 | WGQGTTLTVSS | PD-03; PL-05 HFR4 |
| 193 | DIQMTQSPSSLSASVGDRVTITC | PD-03 LFR1 |
| 194 | FGAGTKLDLK | PD-03 LFR4 |
| 195 | FGGGTKVEIK | PD-04, 05; PL-01, 04, 06, 07, 08 LFR4 |
| 196 | QVQLVQSGAEVKKPGASVKVSCKASGYTFT | PD-05, 06; PL-01, 02, 03, 04, 06, 07, 08 HFR1 |
| 197 | RVTMTRDTSISTAYMELSSLRSEDTAVYYCAR | PD-05 HFR3 |
| 198 | DIVLTQSPASLAVSPGQRATITC | PD-05 LFR1 |
| 199 | WYQQKPGQPPKLLIY | PD-05 LFR2 |
| 200 | GVPARFSGSGSGTDFTLTINPVEANDTANYYC | PD-05 LFR3 |
| 201 | RVTLTADTSTSTVYMELSSLRSEDTAVYYCA | PD-06 HFR3 |
| 202 | DIQMTQSPSFLSASVGDRVTITC | PD-06 LFR1 |
| 203 | WYQQKPGKAPKALIY | PD-06 LFR2 |
| 204 | GVPSRFSGSGSGTEFTLTISSLQPEDFATYYC | PD-06 LFR3 |
| 205 | FGQGTKLEIK | PD-06 LFR4 |
| 206 | WMKQAPGQGLEWMG | PL-01 HFR2 |
| 207 | DIQMTQSPSSLSASVGDRVTISC | PL-01, 02, 03, 04, 08 LFR1 |
| 208 | WYQQKPGKAPKLLIK | PL-01, 04, 08 LFR2 |
| 209 | GVPSRFSGSGSGTDFTLTISSLQPEDFATYFC | PL-01, 04, 08 LFR3 |
| 210 | KATMTRDKSSSTVYMELSSLRSEDTAVYYCAR | PL-02 HFR3 |
| 211 | GVPSRFSGSGSGTDFTFTISSLQPEDIATYFC | PL-02, 03 LFR3 |
| 212 | FGQGTKVEIK | PL-02, 03 LFR4 |
| 213 | RVTMTRDTSISTAYMELSRLRSDDTAVYYCAR | PL-03, 08 HFR3 |
| 214 | RVTMTRDTSTSTVYMELSSLRSEDTAVYYCAR | PL-04 HFR3 |
| 215 | QVQLQESGPGLVKPSQSLSLTCTVTGYSIT | PL-05 HFR1 |
| 216 | WIRQFPGNKLEWMG | PL-05 HFR2 |
| 217 | RISITRDTSKNQFFLQLNSVTTEDTATYYCAN | PL-05 HFR3 |
| 218 | DIVMTQSHKFMSTSVGDRVSITC | PL-05 LFR1 |
| 219 | WYQQKPGQSPKLLIF | PL-05 LFR2 |
| 220 | GVPDRFTGSGSGTDYTLTISSVQAEDLALYYC | PL-05 LFR3 |
| 221 | WVRQAPGQRLEWMGW | PL-06, 07 HFR2 |
| 222 | RVTITRDTSASTAYMELSSLRSEDTAVYYCAR | PL-06, 07 HFR3 |
| 223 | DIQMTQSPSSLSAFVGDRVTITC | PL-06 LFR1 |
| 224 | WYQQKPGKAPKLLIH | PL-06 LFR2 |
| 225 | GVPSRFSGSGSGRDFTFTISSLQPEDIATYYC | PL-06 LFR3 |
| 226 | EIVLTQSPVTLSLSPGERATLSC | PL-07 LFR1 |
| 227 | WYLQKPGQAPRLLIK | PL-07 LFR2 |
| 228 | IPARFSGSGSGSDFTLTISSLEPEDFAVYYC | PL-07 LFR3 |

FIG. 53

```
SEQUENCE LISTING

<160> NUMBER OF SEQ ID NOS: 303

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Asn Phe Leu Met Ser
1               5

<210> SEQ ID NO 2
<211> LENGTH: 17
<212> TYPE: PRT
<213> ORGANISM: Artificial Sequence
<220> FEATURE:
```

<223> OTHER INFORMATION: Synthetic

<400> SEQUENCE: 2

Thr Ile Ser Gly Gly Arg Asp Thr Tyr Tyr Val Asp Ser Val Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Arg Thr Thr Tyr Ser Met Asp Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Asn Ser Tyr Leu Tyr
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic

<400> SEQUENCE: 5

Gly Ile Asn Pro Ser Asn Gly Gly Thr Asn Phe Asn Glu Lys Phe Lys
1               5                   10                  15

Thr

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Arg Asp Tyr Asn Tyr Asp Gly Gly Phe Asp Ser
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Asn Ser Tyr Ile Tyr
1               5

<210> SEQ ID NO 8
<211> LENGTH: 12

```
<212> TYPE: PRT
<213> ORGANISM: Artificial Sequence
<220> FEATURE:
<223> OTHER INFORMATION: Synthetic

<400> SEQUENCE: 8

Arg Arg Asp Tyr Arg Tyr Asp Gly Gly Phe Asp Ser
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Thr Tyr Tyr Ile Tyr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic

<400> SEQUENCE: 10

Gly Ile Asn Pro Gly Asn Gly Gly Thr Asn Phe Asn Glu Lys Phe Lys
1               5                   10                  15

Ile

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Arg Tyr His Gly Tyr Asp Gly Gly Leu Asp Tyr
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Ser Tyr Tyr Ile His
1               5

<210> SEQ ID NO 13
<211> LENGTH: 17
<212> TYPE: PRT
<213> ORGANISM: Artificial Sequence
<220> FEATURE:
<223> OTHER INFORMATION: Synthetic

<400> SEQUENCE: 13

Trp Ile Phe Pro Gly Ser Gly Asn Ser Lys Tyr Asn Glu Asn Phe Lys
1               5                   10                  15

Gly
```

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Ser Glu Thr Tyr Asp Tyr Gly Asp Tyr
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Leu Ala Ser Gln Thr Ile Gly Thr Trp Leu Ala
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Ala Ala Thr Ser Leu Ala Asp
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Gln Gln Phe Tyr Ser Ile Pro Trp Thr
1               5

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Arg Ala Ser Ser Thr Leu Tyr Ser Asn Tyr Leu His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Arg Ala Ser Phe Leu Ala Ser
1               5

```
<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

Gln Gln Gly Ser Ser Ile Pro Leu Thr
1               5

<210> SEQ ID NO 21
<211> LENGTH: 12
<212> TYPE: PRT
<213> ORGANISM: Artificial Sequence
<220> FEATURE:
<223> OTHER INFORMATION: Synthetic

<400> SEQUENCE: 21

Ser Ala Ser Ser Ser Leu Tyr Ser Ser Tyr Leu His
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic

<400> SEQUENCE: 22

Arg Ala Ser Ser Ser Leu Tyr Ser Asn Tyr Leu His
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Arg Ala Ser Lys Ser Val Ser Thr Ser Gly Phe Ser Tyr Ile His
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

Leu Ala Ser Asn Leu Glu Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Gln His Thr Trp Glu Leu Pro Asn Thr
1               5

<210> SEQ ID NO 26
```

<211> LENGTH: 11
<212> TYPE: PRT
<213> ORGANISM: Artificial Sequence
<220> FEATURE:
<223> OTHER INFORMATION: Synthetic

<400> SEQUENCE: 26

Lys Ala Ser Gln Asn Val Gly Thr Asn Val Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Ser Ala Ser Tyr Arg Tyr Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Gln Gln Tyr Tyr Ser Tyr Pro Tyr Thr
1               5

<210> SEQ ID NO 29
<211> LENGTH: 117
<212> TYPE: PRT
<213> ORGANISM: Artificial Sequence
<220> FEATURE:
<223> OTHER INFORMATION: Synthetic

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Leu Met Ser Trp Val Arg Gln Ala Pro Gly Lys Gly Leu Glu Trp Val
        35                  40                  45

Ser Thr Ile Ser Gly Gly Gly Arg Asp Thr Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Thr Thr Tyr Ser Met Asp Tyr Trp Gly Gln Gly Thr Ser
            100                 105                 110

Val Thr Val Ser Ser
        115

<210> SEQ ID NO 30
<211> LENGTH: 107
<212> TYPE: PRT
<213> ORGANISM: Artificial Sequence
<220> FEATURE:
<223> OTHER INFORMATION: Synthetic

```
<400> SEQUENCE: 30

Asp Ile Gln Met Thr Gln Ser Pro Ser Val Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Ser Ile Pro Trp
                85                  90                  95

Thr Phe Gly Gly Gly Thr Lys Leu Glu Ile Lys
            100                 105

<210> SEQ ID NO 31
<211> LENGTH: 120
<212> TYPE: PRT
<213> ORGANISM: Artificial Sequence
<220> FEATURE:
<223> OTHER INFORMATION: Synthetic

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Asn Ser
            20                  25                  30

Tyr Leu Tyr Trp Leu Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Thr Arg Thr Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Thr Arg Arg Asp Tyr Asn Tyr Asp Gly Gly Phe Asp Ser Trp Gly Gln
            100                 105                 110

Gly Thr Leu Val Thr Val Ser Ser
        115                 120

<210> SEQ ID NO 32
<211> LENGTH: 108
<212> TYPE: PRT
<213> ORGANISM: Artificial Sequence
<220> FEATURE:
<223> OTHER INFORMATION: Synthetic

<400> SEQUENCE: 32

Asp Ile Gln Met Thr Gln Ser Pro Ser Leu Ser Ala Ser Val Gly
1               5                   10                  15

Asp Arg Val Thr Phe Thr Cys Arg Ala Ser Ser Thr Leu Tyr Ser Asn
            20                  25                  30

Tyr Leu His Trp Tyr Gln Gln Lys Pro Gly Lys Ala Pro Lys Leu Leu
        35                  40                  45

Ile Tyr Arg Ala Ser Phe Leu Ala Ser Gly Val Pro Ser Arg Phe Ser
    50                  55                  60
```

```
Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Gly Ser Ser Ile Pro
                 85                  90                  95

Leu Thr Phe Gly Gly Gly Thr Lys Val Glu Ile Lys
            100                 105
```

<210> SEQ ID NO 33
<211> LENGTH: 120
<212> TYPE: PRT
<213> ORGANISM: Artificial Sequence
<220> FEATURE:
<223> OTHER INFORMATION: Synthetic

<400> SEQUENCE: 33

```
Gln Val Gln Leu Val Gln Ser Gly Ala Glu Val Lys Lys Pro Gly Ala
 1               5                  10                  15

Ser Val Lys Val Ser Cys Lys Ala Ser Asp Tyr Thr Phe Thr Asn Ser
                 20                  25                  30

Tyr Ile Tyr Trp Val Arg Gln Ala Pro Gly Gln Gly Leu Glu Trp Met
             35                  40                  45

Gly Gly Ile Asn Pro Ser Asn Gly Gly Thr Asn Phe Asn Glu Lys Phe
 50                  55                  60

Lys Thr Arg Val Thr Ser Thr Arg Asp Thr Ser Ile Ser Thr Ala Tyr
 65                  70                  75                  80

Met Glu Leu Ser Arg Leu Arg Ser Asp Thr Val Val Tyr Cys
                 85                  90                  95

Ala Arg Arg Asp Tyr Arg Tyr Asp Gly Gly Phe Asp Ser Trp Gly Gln
                100                 105                 110

Gly Thr Thr Leu Thr Val Ser Ser
            115                 120
```

<210> SEQ ID NO 34
<211> LENGTH: 108
<212> TYPE: PRT
<213> ORGANISM: Artificial Sequence
<220> FEATURE:
<223> OTHER INFORMATION: Synthetic

<400> SEQUENCE: 34

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Leu Tyr Ser Ser
                 20                  25                  30

Tyr Leu His Trp Tyr Gln Gln Lys Pro Gly Lys Ala Pro Lys Leu Leu
             35                  40                  45

Ile Tyr Arg Ala Ser Phe Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Gly Ser Ser Ile Pro
                 85                  90                  95

Leu Thr Phe Gly Ala Gly Thr Lys Leu Asp Leu Lys
            100                 105
```

<210> SEQ ID NO 35
<211> LENGTH: 120
<212> TYPE: PRT
<213> ORGANISM: Artificial Sequence

```
<220> FEATURE:
<223> OTHER INFORMATION: Synthetic

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Asn Ser
            20                  25                  30

Tyr Ile Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Thr Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Arg Asp Tyr Asn Tyr Asp Gly Gly Phe Asp Ser Trp Gly Gln
            100                 105                 110

Gly Thr Leu Val Thr Val Ser Ser
        115                 120

<210> SEQ ID NO 36
<211> LENGTH: 108
<212> TYPE: PRT
<213> ORGANISM: Artificial Sequence
<220> FEATURE:
<223> OTHER INFORMATION: Synthetic

<400> SEQUENCE: 36

Asp Ile Gln Met Thr Gln Ser Pro Ser Ser Leu Ser Ala Ser Val Gly
1               5                   10                  15

Asp Arg Val Thr Phe Thr Cys Arg Ala Ser Ser Ser Leu Tyr Ser Asn
            20                  25                  30

Tyr Leu His Trp Tyr Gln Gln Lys Pro Gly Lys Ala Pro Lys Leu Leu
        35                  40                  45

Ile Tyr Arg Ala Ser Phe Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Ser Ser Ile Pro
                85                  90                  95

Leu Thr Phe Gly Gly Gly Thr Lys Val Glu Ile Lys
            100                 105

<210> SEQ ID NO 37
<211> LENGTH: 120
<212> TYPE: PRT
<213> ORGANISM: Artificial Sequence
<220> FEATURE:
<223> OTHER INFORMATION: Synthetic

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Ile Tyr Trp Val Arg Gln Ala Pro Gly Gln Gly Leu Glu Trp Met
        35                  40                  45
```

Gly Gly Ile Asn Pro Gly Asn Gly Gly Thr Asn Phe Asn Glu Lys Phe
        50                  55                  60

Lys Ile Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Tyr His Gly Tyr Asp Gly Gly Leu Asp Tyr Trp Gly Gln
                100                 105                 110

Gly Thr Leu Val Thr Val Ser Ser
            115                 120

<210> SEQ ID NO 38
<211> LENGTH: 111
<212> TYPE: PRT
<213> ORGANISM: Artificial Sequence
<220> FEATURE:
<223> OTHER INFORMATION: Synthetic

<400> SEQUENCE: 38

Asp Ile Val Leu Thr Gln Ser Pro Ala Ser Leu Ala Val Ser Pro Gly
 1               5                  10                  15

Gln Arg Ala Thr Ile Thr Cys Arg Ala Ser Lys Ser Val Ser Thr Ser
             20                  25                  30

Gly Phe Ser Tyr Ile His Trp Tyr Gln Gln Lys Pro Gly Gln Pro Pro
         35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Gln His Thr Trp
                 85                  90                  95

Glu Leu Pro Asn Thr Phe Gly Gly Gly Thr Lys Val Glu Ile Lys
                100                 105                 110

<210> SEQ ID NO 39
<211> LENGTH: 117
<212> TYPE: PRT
<213> ORGANISM: Artificial Sequence
<220> FEATURE:
<223> OTHER INFORMATION: Synthetic

<400> SEQUENCE: 39

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Ile His Trp Val Arg Gln Ala Pro Gly Gln Gly Leu Glu Trp Met
         35                  40                  45

Gly Trp Ile Phe Pro Gly Ser Gly Asn Ser Lys Tyr Asn Glu Asn Phe
 50                  55                  60

Lys Gly Arg Val Thr Leu Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Ser Glu Thr Tyr Asp Tyr Gly Asp Tyr Trp Gly Gln Gly Thr Leu
                100                 105                 110

Val Thr Val Ser Ser
            115

<210> SEQ ID NO 40
<211> LENGTH: 107
<212> TYPE: PRT
<213> ORGANISM: Artificial Sequence
<220> FEATURE:
<223> OTHER INFORMATION: Synthetic

<400> SEQUENCE: 40

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Tyr
                85                  90                  95

Thr Phe Gly Gln Gly Thr Lys Leu Glu Ile Lys
            100                 105

<210> SEQ ID NO 41
<211> LENGTH: 5
<212> TYPE: PRT
<213> ORGANISM: Artificial Sequence
<220> FEATURE:
<223> OTHER INFORMATION: Synthetic

<400> SEQUENCE: 41

Asn Tyr Trp Met His
1               5

<210> SEQ ID NO 42
<211> LENGTH: 17
<212> TYPE: PRT
<213> ORGANISM: Artificial Sequence
<220> FEATURE:
<223> OTHER INFORMATION: Synthetic

<400> SEQUENCE: 42

Met Ile His Pro Asn Thr Asn Tyr Asn Tyr Asn Glu Lys Phe Lys
1               5                   10                  15

Ser

<210> SEQ ID NO 43
<211> LENGTH: 12
<212> TYPE: PRT
<213> ORGANISM: Artificial Sequence
<220> FEATURE:
<223> OTHER INFORMATION: Synthetic

<400> SEQUENCE: 43

Ser Asp Tyr Gly Ser Ser Pro Tyr Tyr Phe Asp Tyr
1               5                   10

<210> SEQ ID NO 44
<211> LENGTH: 5
<212> TYPE: PRT
<213> ORGANISM: Artificial Sequence
<220> FEATURE:

<223> OTHER INFORMATION: Synthetic

<400> SEQUENCE: 44

Ser Tyr Trp Met His
1               5

<210> SEQ ID NO 45
<211> LENGTH: 17
<212> TYPE: PRT
<213> ORGANISM: Artificial Sequence
<220> FEATURE:
<223> OTHER INFORMATION: Synthetic

<400> SEQUENCE: 45

Met Ile His Pro Asn Val Gly Ser Thr Asn Tyr Asn Glu Lys Phe Lys
1               5                   10                  15

Ser

<210> SEQ ID NO 46
<211> LENGTH: 12
<212> TYPE: PRT
<213> ORGANISM: Artificial Sequence
<220> FEATURE:
<223> OTHER INFORMATION: Synthetic

<400> SEQUENCE: 46

Ser Arg Tyr Gly Ser Ser Pro Tyr Tyr Phe Asp Tyr
1               5                   10

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Met Ile His Pro Asn Ser Gly Gly Asn Asn Tyr Asn Glu Lys Phe Lys
1               5                   10                  15

Ser

<210> SEQ ID NO 48
<211> LENGTH: 12
<212> TYPE: PRT
<213> ORGANISM: Artificial Sequence
<220> FEATURE:
<223> OTHER INFORMATION: Synthetic

<400> SEQUENCE: 48

Ser Trp Tyr Gly Ser Ser Pro Tyr Tyr Phe Asp Tyr
1               5                   10

<210> SEQ ID NO 49
<211> LENGTH: 17
<212> TYPE: PRT
<213> ORGANISM: Artificial Sequence
<220> FEATURE:
<223> OTHER INFORMATION: Synthetic

<400> SEQUENCE: 49

Met Ile His Pro Thr Gly Val Ser Thr Asp Tyr Asn Glu Lys Phe Lys
1               5                   10                  15

Ser

```
<210> SEQ ID NO 50
<211> LENGTH: 6
<212> TYPE: PRT
<213> ORGANISM: Artificial Sequence
<220> FEATURE:
<223> OTHER INFORMATION: Synthetic

<400> SEQUENCE: 50

Ser Asp Tyr Ala Trp Asn
1               5

<210> SEQ ID NO 51
<211> LENGTH: 16
<212> TYPE: PRT
<213> ORGANISM: Artificial Sequence
<220> FEATURE:
<223> OTHER INFORMATION: Synthetic

<400> SEQUENCE: 51

Tyr Ile Ser Asp Ser Gly Ser Thr Ser Tyr Asn Pro Ser Leu Lys Ser
1               5                   10                  15

<210> SEQ ID NO 52
<211> LENGTH: 11
<212> TYPE: PRT
<213> ORGANISM: Artificial Sequence
<220> FEATURE:
<223> OTHER INFORMATION: Synthetic

<400> SEQUENCE: 52

Ser Phe Leu Arg Leu Arg Ser Tyr Phe Asp His
1               5                   10

<210> SEQ ID NO 53
<211> LENGTH: 5
<212> TYPE: PRT
<213> ORGANISM: Artificial Sequence
<220> FEATURE:
<223> OTHER INFORMATION: Synthetic

<400> SEQUENCE: 53

Ser Tyr Gly Ile Asn
1               5

<210> SEQ ID NO 54
<211> LENGTH: 17
<212> TYPE: PRT
<213> ORGANISM: Artificial Sequence
<220> FEATURE:
<223> OTHER INFORMATION: Synthetic

<400> SEQUENCE: 54

Cys Ile Tyr Ile Gly Asn Asp Tyr Thr Asn Tyr Asn Glu Lys Phe Lys
1               5                   10                  15

Gly

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Ala Tyr Tyr Gly Ser Arg Val Asp Tyr
1               5
```

<210> SEQ ID NO 56
<211> LENGTH: 11
<212> TYPE: PRT
<213> ORGANISM: Artificial Sequence
<220> FEATURE:
<223> OTHER INFORMATION: Synthetic

<400> SEQUENCE: 56

Arg Ala Ser Gln Asp Ile Asp Asn Tyr Leu Asn
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Synthetic

<400> SEQUENCE: 57

Tyr Thr Ser Arg Leu His Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic

<400> SEQUENCE: 58

Gln Gln Gly Tyr Thr Leu Pro Trp Thr
1               5

<210> SEQ ID NO 59
<211> LENGTH: 11
<212> TYPE: PRT
<213> ORGANISM: Artificial Sequence
<220> FEATURE:
<223> OTHER INFORMATION: Synthetic

<400> SEQUENCE: 59

Arg Ala Ser Gln Asp Ile Ser Asn Tyr Leu Asn
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Synthetic

<400> SEQUENCE: 60

Tyr Thr Ser Arg Leu Gln Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic

<400> SEQUENCE: 61

Gln Gln Gly Asn Thr Leu Pro Trp Thr
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic

<400> SEQUENCE: 62

Gln Gln Gly Asp Thr Leu Pro Trp Thr
1               5

<210> SEQ ID NO 63
<211> LENGTH: 11
<212> TYPE: PRT
<213> ORGANISM: Artificial Sequence
<220> FEATURE:
<223> OTHER INFORMATION: Synthetic

<400> SEQUENCE: 63

Lys Ala Ser Gln Asp Val Asn Val Ala Val Ala
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Synthetic

<400> SEQUENCE: 64

Trp Ala Ser Thr Arg His Ile
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Gln Gln His Tyr Ser Thr Pro Tyr Thr
1               5

<210> SEQ ID NO 66
<211> LENGTH: 11
<212> TYPE: PRT
<213> ORGANISM: Artificial Sequence
<220> FEATURE:
<223> OTHER INFORMATION: Synthetic

<400> SEQUENCE: 66

Lys Ala Ser Gln Asp Ile Asn Lys Tyr Ile Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic

<400> SEQUENCE: 67

Tyr Thr Ser Thr Leu Gln Pro
1               5

<210> SEQ ID NO 68

```
<211> LENGTH: 8
<212> TYPE: PRT
<213> ORGANISM: Artificial Sequence
<220> FEATURE:
<223> OTHER INFORMATION: Synthetic

<400> SEQUENCE: 68

Leu Gln Tyr Asp Asn Leu Tyr Thr
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic

<400> SEQUENCE: 69

Gln Ser Ile Ser Asp Tyr Leu His
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Cys Ala Ser Gln Ser Ile Ser Gly
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic

<400> SEQUENCE: 71

Gln Asn Gly His Ser Phe Pro Tyr Thr
1               5

<210> SEQ ID NO 72
<211> LENGTH: 121
<212> TYPE: PRT
<213> ORGANISM: Artificial Sequence
<220> FEATURE:
<223> OTHER INFORMATION: Synthetic

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Met Lys Gln Ala Pro Gly Gln Gly Leu Glu Trp Met
        35                  40                  45

Gly Met Ile His Pro Asn Thr Asn Tyr Asn Tyr Asn Glu Lys Phe
    50                  55                  60

Lys Ser Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Cys
                85                  90                  95

Ala Arg Ser Asp Tyr Gly Ser Ser Pro Tyr Tyr Phe Asp Tyr Trp Gly
```

```
                    100                 105                 110

Gln Gly Thr Leu Val Thr Val Ser Ser
        115                 120

<210> SEQ ID NO 73
<211> LENGTH: 107
<212> TYPE: PRT
<213> ORGANISM: Artificial Sequence
<220> FEATURE:
<223> OTHER INFORMATION: Synthetic

<400> SEQUENCE: 73

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Lys Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gly Gly Thr Lys Val Glu Ile Lys
            100                 105

<210> SEQ ID NO 74
<211> LENGTH: 121
<212> TYPE: PRT
<213> ORGANISM: Artificial Sequence
<220> FEATURE:
<223> OTHER INFORMATION: Synthetic

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Met Ile His Pro Asn Val Gly Ser Thr Asn Tyr Asn Glu Lys Phe
    50                  55                  60

Lys Ser Lys Ala Thr Met Thr Arg Asp Lys Ser Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Tyr Gly Ser Ser Pro Tyr Tyr Phe Asp Tyr Trp Gly
            100                 105                 110

Gln Gly Thr Leu Val Thr Val Ser Ser
        115                 120

<210> SEQ ID NO 75
<211> LENGTH: 107
<212> TYPE: PRT
<213> ORGANISM: Artificial Sequence
<220> FEATURE:
<223> OTHER INFORMATION: Synthetic

<400> SEQUENCE: 75
```

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asn Thr Leu Pro Trp
                85                  90                  95

Thr Phe Gly Gln Gly Thr Lys Val Glu Ile Lys
            100                 105

<210> SEQ ID NO 76
<211> LENGTH: 121
<212> TYPE: PRT
<213> ORGANISM: Artificial Sequence
<220> FEATURE:
<223> OTHER INFORMATION: Synthetic

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Met Ile His Pro Asn Ser Gly Gly Asn Asn Tyr Asn Glu Lys Phe
50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Trp Tyr Gly Ser Ser Pro Tyr Tyr Phe Asp Tyr Trp Gly
            100                 105                 110

Gln Gly Thr Leu Val Thr Val Ser Ser
        115                 120

<210> SEQ ID NO 77
<211> LENGTH: 107
<212> TYPE: PRT
<213> ORGANISM: Artificial Sequence
<220> FEATURE:
<223> OTHER INFORMATION: Synthetic

<400> SEQUENCE: 77

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro

```
                65                  70                  75                  80
Glu Asp Ile Ala Thr Tyr Phe Cys Gln Gln Gly Asn Thr Leu Pro Trp
                    85                  90                  95

Thr Phe Gly Gln Gly Thr Lys Val Glu Ile Lys
                100                 105
```

<210> SEQ ID NO 78
<211> LENGTH: 121
<212> TYPE: PRT
<213> ORGANISM: Artificial Sequence
<220> FEATURE:
<223> OTHER INFORMATION: Synthetic

<400> SEQUENCE: 78

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Met Ile His Pro Thr Gly Val Ser Thr Asp Tyr Asn Glu Lys Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Gly Ser Ser Pro Tyr Tyr Phe Asp Tyr Trp Gly
                100                 105                 110

Gln Gly Thr Leu Val Thr Val Ser Ser
            115                 120
```

<210> SEQ ID NO 79
<211> LENGTH: 107
<212> TYPE: PRT
<213> ORGANISM: Artificial Sequence
<220> FEATURE:
<223> OTHER INFORMATION: Synthetic

<400> SEQUENCE: 79

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Lys Tyr Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Asp Thr Leu Pro Trp
                85                  90                  95

Thr Phe Gly Gly Gly Thr Lys Val Glu Ile Lys
                100                 105
```

<210> SEQ ID NO 80
<211> LENGTH: 120
<212> TYPE: PRT
<213> ORGANISM: Artificial Sequence
<220> FEATURE:

<223> OTHER INFORMATION: Synthetic

<400> SEQUENCE: 80

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Asp Ser Gly Ser Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Asn Ser Phe Leu Arg Leu Arg Ser Tyr Phe Asp His Trp Gly Gln
            100                 105                 110

Gly Thr Thr Leu Thr Val Ser Ser
            115                 120

<210> SEQ ID NO 81
<211> LENGTH: 107
<212> TYPE: PRT
<213> ORGANISM: Artificial Sequence
<220> FEATURE:
<223> OTHER INFORMATION: Synthetic

<400> SEQUENCE: 81

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Val Ala
            20                  25                  30

Val Ala Trp Tyr Gln Gln Lys Pro Gly Gln Ser Pro Lys Leu Leu Ile
        35                  40                  45

Phe Trp Ala Ser Thr Arg His Ile Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys
            100                 105

<210> SEQ ID NO 82
<211> LENGTH: 119
<212> TYPE: PRT
<213> ORGANISM: Artificial Sequence
<220> FEATURE:
<223> OTHER INFORMATION: Synthetic

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Asn Trp Val Arg Gln Ala Pro Gly Gln Arg Leu Glu Trp Met
        35                  40                  45

Gly Trp Cys Ile Tyr Ile Gly Asn Asp Tyr Thr Asn Tyr Asn Glu Lys

```
                    50                  55                  60
Phe Lys Gly Arg Val Thr Ile Thr Arg Asp Thr Ser Ala Ser Thr Ala
 65                  70                  75                  80

Tyr Met Glu Leu Ser Ser Leu Arg Ser Glu Asp Thr Ala Val Tyr Tyr
                     85                  90                  95

Cys Ala Arg Ala Tyr Tyr Gly Ser Arg Val Asp Tyr Trp Gly Gln Gly
                100                 105                 110

Thr Leu Val Thr Val Ser Ser
            115

<210> SEQ ID NO 83
<211> LENGTH: 106
<212> TYPE: PRT
<213> ORGANISM: Artificial Sequence
<220> FEATURE:
<223> OTHER INFORMATION: Synthetic

<400> SEQUENCE: 83

Asp Ile Gln Met Thr Gln Ser Pro Ser Ser Leu Ser Ala Phe Val Gly
  1               5                  10                  15

Asp Arg Val Thr Ile Thr Cys Lys Ala Ser Gln Asp Ile Asn Lys Tyr
                 20                  25                  30

Ile Ala Trp Tyr Gln Gln Lys Pro Gly Lys Ala Pro Lys Leu Leu Ile
             35                  40                  45

His Tyr Thr Ser Thr Leu Gln Pro Gly Val Pro Ser Arg Phe Ser Gly
 50                  55                  60

Ser Gly Ser Gly Arg Asp Phe Thr Phe Thr Ile Ser Ser Leu Gln Pro
 65                  70                  75                  80

Glu Asp Ile Ala Thr Tyr Tyr Cys Leu Gln Tyr Asp Asn Leu Tyr Thr
                 85                  90                  95

Phe Gly Gly Gly Thr Lys Val Glu Ile Lys
            100                 105

<210> SEQ ID NO 84
<211> LENGTH: 119
<212> TYPE: PRT
<213> ORGANISM: Artificial Sequence
<220> FEATURE:
<223> OTHER INFORMATION: Synthetic

<400> SEQUENCE: 84

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Gly Ile Asn Trp Val Arg Gln Ala Pro Gly Gln Arg Leu Glu Trp Met
             35                  40                  45

Gly Trp Cys Ile Tyr Ile Gly Asn Asp Tyr Thr Asn Tyr Asn Glu Lys
 50                  55                  60

Phe Lys Gly Arg Val Thr Ile Thr Arg Asp Thr Ser Ala Ser Thr Ala
 65                  70                  75                  80

Tyr Met Glu Leu Ser Ser Leu Arg Ser Glu Asp Thr Ala Val Tyr Tyr
                 85                  90                  95

Cys Ala Arg Ala Tyr Tyr Gly Ser Arg Val Asp Tyr Trp Gly Gln Gly
                100                 105                 110

Thr Leu Val Thr Val Ser Ser
            115
```

<210> SEQ ID NO 85
<211> LENGTH: 104
<212> TYPE: PRT
<213> ORGANISM: Artificial Sequence
<220> FEATURE:
<223> OTHER INFORMATION: Synthetic

<400> SEQUENCE: 85

```
Glu Ile Val Leu Thr Gln Ser Pro Val Thr Leu Ser Leu Ser Pro Gly
1               5                   10                  15

Glu Arg Ala Thr Leu Ser Cys Gln Ser Ile Ser Asp Tyr Leu His Trp
            20                  25                  30

Tyr Leu Gln Lys Pro Gly Gln Ala Pro Arg Leu Leu Ile Lys Cys Ala
        35                  40                  45

Ser Gln Ser Ile Ser Gly Ile Pro Ala Arg Phe Ser Gly Ser Gly Ser
    50                  55                  60

Gly Ser Asp Phe Thr Leu Thr Ile Ser Ser Leu Glu Pro Glu Asp Phe
65                  70                  75                  80

Ala Val Tyr Tyr Cys Gln Asn Gly His Ser Phe Pro Tyr Thr Phe Gly
                85                  90                  95

Gly Gly Thr Lys Val Glu Ile Lys
            100
```

<210> SEQ ID NO 86
<211> LENGTH: 121
<212> TYPE: PRT
<213> ORGANISM: Artificial Sequence
<220> FEATURE:
<223> OTHER INFORMATION: Synthetic

<400> SEQUENCE: 86

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Met Ile His Pro Asn Ser Gly Gly Asn Asn Tyr Asn Glu Lys Phe
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Trp Tyr Gly Ser Ser Pro Tyr Tyr Phe Asp Tyr Trp Gly
            100                 105                 110

Gln Gly Thr Leu Val Thr Val Ser Ser
        115                 120
```

<210> SEQ ID NO 87
<211> LENGTH: 107
<212> TYPE: PRT
<213> ORGANISM: Artificial Sequence
<220> FEATURE:
<223> OTHER INFORMATION: Synthetic

<400> SEQUENCE: 87

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
```

```
            20                  25                  30
Leu Asn Trp Tyr Gln Gln Lys Pro Gly Lys Ala Pro Lys Leu Leu Ile
        35                  40                  45

Lys Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gly Gly Thr Lys Val Glu Ile Lys
            100                 105
```

<210> SEQ ID NO 88
<211> LENGTH: 205
<212> TYPE: PRT
<213> ORGANISM: Artificial Sequence
<220> FEATURE:
<223> OTHER INFORMATION: Synthetic

<400> SEQUENCE: 88

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205
```

<210> SEQ ID NO 89
<211> LENGTH: 136
<212> TYPE: PRT
<213> ORGANISM: Artificial Sequence
<220> FEATURE:
<223> OTHER INFORMATION: Synthetic

<400> SEQUENCE: 89

```
Ile Pro Pro His Val Gln Lys Ser Val Asn Asn Asp Met Ile Val Thr
1               5                   10                  15
```

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135

<210> SEQ ID NO 90
<211> LENGTH: 123
<212> TYPE: PRT
<213> ORGANISM: Artificial Sequence
<220> FEATURE:
<223> OTHER INFORMATION: Synthetic

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 91
<211> LENGTH: 107
<212> TYPE: PRT
<213> ORGANISM: Artificial Sequence
<220> FEATURE:
<223> OTHER INFORMATION: Synthetic

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys
                100                 105

<210> SEQ ID NO 92
<211> LENGTH: 595
<212> TYPE: PRT
<213> ORGANISM: Artificial Sequence
<220> FEATURE:
<223> OTHER INFORMATION: Synthetic

<400> SEQUENCE: 92

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Ile His Trp Val Arg Gln Ala Pro Gly Gln Gly Leu Glu Trp Met
             35                  40                  45

Gly Trp Ile Phe Pro Gly Ser Gly Asn Ser Lys Tyr Asn Glu Asn Phe
         50                  55                  60

Lys Gly Arg Val Thr Leu Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Ser Glu Thr Tyr Asp Tyr Gly Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320
```

-continued

Ser Asn Lys Gly Leu Pro Ser Ile Glu Lys Thr Ile Ser Lys Ala
            325                 330                 335

Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Gly Gly Gly Gly
        435                 440                 445

Ser Gly Gly Gly Gly Ser Gly Gly Gly Ser Ile Pro Pro His Val
    450                 455                 460

Gln Lys Ser Val Asn Asn Asp Met Ile Val Thr Asp Asn Asn Gly Ala
465                 470                 475                 480

Val Lys Phe Pro Gln Leu Cys Lys Phe Cys Asp Val Arg Phe Ser Thr
                485                 490                 495

Cys Asp Asn Gln Lys Ser Cys Met Ser Asn Cys Ser Ile Thr Ser Ile
            500                 505                 510

Cys Glu Lys Pro Gln Glu Val Cys Val Ala Val Trp Arg Lys Asn Asp
        515                 520                 525

Glu Asn Ile Thr Leu Glu Thr Val Cys His Asp Pro Lys Leu Pro Tyr
530                 535                 540

His Asp Phe Ile Leu Glu Asp Ala Ala Ser Pro Lys Cys Ile Met Lys
545                 550                 555                 560

Glu Lys Lys Lys Pro Gly Glu Thr Phe Phe Met Cys Ser Cys Ser Ser
                565                 570                 575

Asp Glu Cys Asn Asp Asn Ile Ile Phe Ser Glu Glu Tyr Asn Thr Ser
            580                 585                 590

Asn Pro Asp
        595

<210> SEQ ID NO 93
<211> LENGTH: 214
<212> TYPE: PRT
<213> ORGANISM: Artificial Sequence
<220> FEATURE:
<223> OTHER INFORMATION: Synthetic

<400> SEQUENCE: 93

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 94
<211> LENGTH: 602
<212> TYPE: PRT
<213> ORGANISM: Artificial Sequence
<220> FEATURE:
<223> OTHER INFORMATION: Synthetic

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Met Ile His Pro Asn Ser Gly Asn Asn Tyr Asn Glu Lys Phe
50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Trp Tyr Gly Ser Ser Pro Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Gly Gly Gly Ser Gly Gly Gly Ser Gly Gly Gly
    450                 455                 460

Gly Ser Ile Pro Pro His Val Gln Lys Ser Val Asn Asn Asp Met Ile
465                 470                 475                 480

Val Thr Asp Asn Asn Gly Ala Val Lys Phe Pro Gln Leu Cys Lys Phe
                485                 490                 495

Cys Asp Val Arg Phe Ser Thr Cys Asp Asn Gln Lys Ser Cys Met Ser
            500                 505                 510

Asn Cys Ser Ile Thr Ser Ile Cys Glu Lys Pro Gln Glu Val Cys Val
            515                 520                 525

Ala Val Trp Arg Lys Asn Asp Glu Asn Ile Thr Leu Glu Thr Val Cys
530                 535                 540

His Asp Pro Lys Leu Pro Tyr His Asp Phe Ile Leu Glu Asp Ala Ala
545                 550                 555                 560

Ser Pro Lys Cys Ile Met Lys Glu Lys Lys Pro Gly Glu Thr Phe
                565                 570                 575

Phe Met Cys Ser Cys Ser Ser Asp Glu Cys Asn Asp Asn Ile Ile Phe
            580                 585                 590

Ser Glu Glu Tyr Asn Thr Ser Asn Pro Asp
            595                 600

<210> SEQ ID NO 95
<211> LENGTH: 214
<212> TYPE: PRT
<213> ORGANISM: Artificial Sequence
<220> FEATURE:
```

<223> OTHER INFORMATION: Synthetic

<400> SEQUENCE: 95

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Lys Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 96
<211> LENGTH: 123
<212> TYPE: PRT
<213> ORGANISM: Artificial Sequence
<220> FEATURE:
<223> OTHER INFORMATION: Synthetic

<400> SEQUENCE: 96

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 97
<211> LENGTH: 330
<212> TYPE: PRT
<213> ORGANISM: Artificial Sequence
<220> FEATURE:
<223> OTHER INFORMATION: Synthetic

<400> SEQUENCE: 97

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 98
<211> LENGTH: 330
<212> TYPE: PRT
<213> ORGANISM: Artificial Sequence
<220> FEATURE:
<223> OTHER INFORMATION: Synthetic

<400> SEQUENCE: 98

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Ala
                325                 330

<210> SEQ ID NO 99
<211> LENGTH: 227
<212> TYPE: PRT
<213> ORGANISM: Artificial Sequence
<220> FEATURE:
<223> OTHER INFORMATION: Synthetic

<400> SEQUENCE: 99

Asp Lys Thr His Thr Cys Pro Pro Cys Pro Ala Pro Glu Leu Leu Gly

```
1               5                   10                  15
Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
    210                 215                 220

Pro Gly Ala
225

<210> SEQ ID NO 100
<211> LENGTH: 107
<212> TYPE: PRT
<213> ORGANISM: Artificial Sequence
<220> FEATURE:
<223> OTHER INFORMATION: Synthetic

<400> SEQUENCE: 100

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 101
<211> LENGTH: 21
<212> TYPE: PRT
```

<213> ORGANISM: Artificial Sequence
<220> FEATURE:
<223> OTHER INFORMATION: Synthetic

<400> SEQUENCE: 101

Gly Gly Gly Gly Ser Gly Gly Gly Ser Gly Gly Gly Ser Gly
1               5                   10                  15

Gly Gly Gly Ser Gly
            20

<210> SEQ ID NO 102
<211> LENGTH: 610
<212> TYPE: PRT
<213> ORGANISM: Artificial Sequence
<220> FEATURE:
<223> OTHER INFORMATION: Synthetic

<400> SEQUENCE: 102

Glu Val Gln Leu Val Glu Ser Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Ala Gly Gly Gly Ser Gly Gly Gly Ser Gly
450                 455                 460

Gly Gly Ser Gly Gly Gly Ser Gly Ile Pro Pro His Val Gln
465                 470                 475                 480

Lys Ser Val Asn Asn Asp Met Ile Val Thr Asp Asn Asn Gly Ala Val
                485                 490                 495

Lys Phe Pro Gln Leu Cys Lys Phe Cys Asp Val Arg Phe Ser Thr Cys
            500                 505                 510

Asp Asn Gln Lys Ser Cys Met Ser Asn Cys Ser Ile Thr Ser Ile Cys
            515                 520                 525

Glu Lys Pro Gln Glu Val Cys Val Ala Val Trp Arg Lys Asn Asp Glu
530                 535                 540

Asn Ile Thr Leu Glu Thr Val Cys His Asp Pro Lys Leu Pro Tyr His
545                 550                 555                 560

Asp Phe Ile Leu Glu Asp Ala Ala Ser Pro Lys Cys Ile Met Lys Glu
            565                 570                 575

Lys Lys Lys Pro Gly Glu Thr Phe Phe Met Cys Ser Cys Ser Ser Asp
            580                 585                 590

Glu Cys Asn Asp Asn Ile Ile Phe Ser Glu Glu Tyr Asn Thr Ser Asn
            595                 600                 605

Pro Asp
610

<210> SEQ ID NO 103
<211> LENGTH: 214
<212> TYPE: PRT
<213> ORGANISM: Artificial Sequence
<220> FEATURE:
<223> OTHER INFORMATION: Synthetic

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45
```

```
Tyr Phe Thr Ser Ser Leu His Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 104
<211> LENGTH: 610
<212> TYPE: PRT
<213> ORGANISM: Artificial Sequence
<220> FEATURE:
<223> OTHER INFORMATION: Synthetic

<400> SEQUENCE: 104

Glu Val Gln Leu Val Gln Ser Gly Gly Gly Val Val Gln Pro Gly Gly
 1               5                  10                  15

Ser Leu Arg Leu Ser Cys Ala Ala Ser Gly Tyr Thr Phe Thr Asn Tyr
             20                  25                  30

Gly Met Asn Trp Val Arg Gln Ala Pro Gly Lys Gly Leu Glu Trp Val
         35                  40                  45

Gly Trp Ile Asn Thr Tyr Thr Gly Glu Pro Thr Tyr Ala Ala Asp Phe
     50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
    435                 440                 445

Leu Ser Pro Gly Ala Gly Gly Gly Ser Gly Gly Gly Gly Ser Gly
450                 455                 460

Gly Gly Ser Gly Gly Gly Ser Gly Ile Pro Pro His Val Gln
465                 470                 475                 480

Lys Ser Val Asn Asn Asp Met Ile Val Thr Asp Asn Gly Ala Val
                485                 490                 495

Lys Phe Pro Gln Leu Cys Lys Phe Cys Asp Val Arg Phe Ser Thr Cys
            500                 505                 510

Asp Asn Gln Lys Ser Cys Met Ser Asn Cys Ser Ile Thr Ser Ile Cys
    515                 520                 525

Glu Lys Pro Gln Glu Val Cys Val Ala Val Trp Arg Lys Asn Asp Glu
530                 535                 540

Asn Ile Thr Leu Glu Thr Val Cys His Asp Pro Lys Leu Pro Tyr His
545                 550                 555                 560

Asp Phe Ile Leu Glu Asp Ala Ala Ser Pro Lys Cys Ile Met Lys Glu
                565                 570                 575

Lys Lys Lys Pro Gly Glu Thr Phe Phe Met Cys Ser Cys Ser Ser Asp
            580                 585                 590

Glu Cys Asn Asp Asn Ile Ile Phe Ser Glu Glu Tyr Asn Thr Ser Asn
    595                 600                 605

Pro Asp
```

<210> SEQ ID NO 105
<211> LENGTH: 589
<212> TYPE: PRT
<213> ORGANISM: Artificial Sequence
<220> FEATURE:
<223> OTHER INFORMATION: Synthetic

<400> SEQUENCE: 105

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
```

```
                355                 360                 365
Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Ala
            420                 425                 430

Gly Gly Gly Gly Ser Gly Gly Gly Ser Gly Gly Gly Gly Ser Gly
        435                 440                 445

Gly Gly Ser Gly Ile Pro Pro His Val Gln Lys Ser Val Asn Asn
    450                 455                 460

Asp Met Ile Val Thr Asp Asn Asn Gly Ala Val Lys Phe Pro Gln Leu
465                 470                 475                 480

Cys Lys Phe Cys Asp Val Arg Phe Ser Thr Cys Asp Asn Gln Lys Ser
                485                 490                 495

Cys Met Ser Asn Cys Ser Ile Thr Ser Ile Cys Glu Lys Pro Gln Glu
            500                 505                 510

Val Cys Val Ala Val Trp Arg Lys Asn Asp Glu Asn Ile Thr Leu Glu
        515                 520                 525

Thr Val Cys His Asp Pro Lys Leu Pro Tyr His Asp Phe Ile Leu Glu
    530                 535                 540

Asp Ala Ala Ser Pro Lys Cys Ile Met Lys Glu Lys Lys Pro Gly
545                 550                 555                 560

Glu Thr Phe Phe Met Cys Ser Cys Ser Ser Asp Glu Cys Asn Asp Asn
                565                 570                 575

Ile Ile Phe Ser Glu Glu Tyr Asn Thr Ser Asn Pro Asp
            580                 585

<210> SEQ ID NO 106
<211> LENGTH: 480
<212> TYPE: PRT
<213> ORGANISM: Artificial Sequence
<220> FEATURE:
<223> OTHER INFORMATION: Synthetic

<400> SEQUENCE: 106

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
```

```
                130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Ala Gly Gly Gly Ser Gly Gly Gly Ser Gly
    450                 455                 460

Gly Gly Gly Ser Gly Gly Gly Ser Gly Ile Pro Pro His Val Gln
465                 470                 475                 480

<210> SEQ ID NO 107
<211> LENGTH: 481
<212> TYPE: PRT
<213> ORGANISM: Artificial Sequence
<220> FEATURE:
<223> OTHER INFORMATION: Synthetic

<400> SEQUENCE: 107

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
```

```
                  20                  25                  30
Gly Met Asn Trp Val Arg Gln Ala Pro Gly Lys Gly Leu Glu Trp Val
            35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Arg Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
```

Leu Ser Pro Gly Ala Gly Gly Gly Ser Gly Gly Gly Ser Gly
        450                 455                 460

Gly Gly Gly Ser Gly Gly Gly Ser Gly Ile Pro Pro His Val Gln
465                 470                 475                 480

Lys

<210> SEQ ID NO 108
<211> LENGTH: 120
<212> TYPE: PRT
<213> ORGANISM: Artificial Sequence
<220> FEATURE:
<223> OTHER INFORMATION: Synthetic

<400> SEQUENCE: 108

Asp Asn Asn Gly Ala Val Lys Phe Pro Gln Leu Cys Lys Phe Cys Asp
1               5                   10                  15

Val Arg Phe Ser Thr Cys Asp Asn Gln Lys Ser Cys Met Ser Asn Cys
            20                  25                  30

Ser Ile Thr Ser Ile Cys Glu Lys Pro Gln Glu Val Cys Val Ala Val
        35                  40                  45

Trp Arg Lys Asn Asp Glu Asn Ile Thr Leu Glu Thr Val Cys His Asp
50                  55                  60

Pro Lys Leu Pro Tyr His Asp Phe Ile Leu Glu Asp Ala Ala Ser Pro
65                  70                  75                  80

Lys Cys Ile Met Lys Glu Lys Lys Pro Gly Glu Thr Phe Phe Met
                85                  90                  95

Cys Ser Cys Ser Ser Asp Glu Cys Asn Asp Asn Ile Ile Phe Ser Glu
            100                 105                 110

Glu Tyr Asn Thr Ser Asn Pro Asp
        115                 120

<210> SEQ ID NO 109
<211> LENGTH: 130
<212> TYPE: PRT
<213> ORGANISM: Artificial Sequence
<220> FEATURE:
<223> OTHER INFORMATION: Synthetic

<400> SEQUENCE: 109

Lys Ser Val Asn Asn Asp Met Ile Val Thr Asp Asn Asn Gly Ala Val
1               5                   10                  15

Lys Phe Pro Gln Leu Cys Lys Phe Cys Asp Val Arg Phe Ser Thr Cys
            20                  25                  30

Asp Asn Gln Lys Ser Cys Met Ser Asn Cys Ser Ile Thr Ser Ile Cys
        35                  40                  45

Glu Lys Pro Gln Glu Val Cys Val Ala Val Trp Arg Lys Asn Asp Glu
    50                  55                  60

Asn Ile Thr Leu Glu Thr Val Cys His Asp Pro Lys Leu Pro Tyr His
65                  70                  75                  80

Asp Phe Ile Leu Glu Asp Ala Ala Ser Pro Lys Cys Ile Met Lys Glu
                85                  90                  95

Lys Lys Pro Gly Glu Thr Phe Phe Met Cys Ser Cys Ser Ser Asp
            100                 105                 110

Glu Cys Asn Asp Asn Ile Ile Phe Ser Glu Glu Tyr Asn Thr Ser Asn
        115                 120                 125

Pro Asp
    130

<210> SEQ ID NO 110
<211> LENGTH: 465
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-terminal pyrophosporylation

<400> SEQUENCE: 110

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
```

```
            340                 345                 350
Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Gly Ser Ile Pro Pro His Val
    450                 455                 460

Gln
465

<210> SEQ ID NO 111
<211> LENGTH: 466
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-terminal pyrophosporylation

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205
```

-continued

Thr Lys Val Asp Lys Arg Val Glu Ser Lys Tyr Gly Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Ser Ile Pro Pro His Val
    450                 455                 460

Gln Lys
465

<210> SEQ ID NO 112
<211> LENGTH: 610
<212> TYPE: PRT
<213> ORGANISM: Artificial Sequence
<220> FEATURE:
<223> OTHER INFORMATION: Synthetic

<400> SEQUENCE: 112

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

-continued

```
Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Ala Gly Gly Gly Ser Gly Gly Gly Gly Ser Gly
450                 455                 460

Gly Gly Ser Gly Gly Gly Ser Gly Ile Pro Pro His Val Gln
465                 470                 475                 480

Lys Ser Val Asn Asn Asp Met Ile Val Thr Asp Asn Gly Ala Val
                485                 490                 495

Lys Phe Pro Gln Leu Cys Lys Phe Cys Asp Val Arg Phe Ser Thr Cys
            500                 505                 510

Asp Asn Gln Lys Ser Cys Met Ser Asn Cys Ser Ile Thr Ser Ile Cys
```

```
                515                 520                 525
Glu Lys Pro Gln Glu Val Cys Val Ala Val Trp Arg Lys Asn Asp Glu
        530                 535                 540

Asn Ile Thr Leu Glu Thr Val Cys His Asp Pro Lys Leu Pro Tyr His
545                 550                 555                 560

Asp Phe Ile Leu Glu Asp Ala Ala Ser Pro Lys Cys Ile Met Lys Glu
                565                 570                 575

Lys Lys Lys Pro Gly Glu Thr Phe Phe Met Cys Ser Cys Ser Ser Asp
            580                 585                 590

Glu Cys Asn Asp Asn Ile Ile Phe Ser Glu Glu Tyr Asn Thr Ser Asn
        595                 600                 605

Pro Asp
    610

<210> SEQ ID NO 113
<211> LENGTH: 595
<212> TYPE: PRT
<213> ORGANISM: Artificial Sequence
<220> FEATURE:
<223> OTHER INFORMATION: Synthetic

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Phe Pro Gly Ser Gly Asn Ser Lys Tyr Asn Glu Asn Phe
        50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
```

```
                  260                 265                 270
Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Ser Ile Pro Pro His Val
    450                 455                 460

Gln Lys Ser Val Asn Asn Asp Met Ile Val Thr Asp Asn Asn Gly Ala
465                 470                 475                 480

Val Lys Phe Pro Gln Leu Cys Lys Phe Cys Asp Val Arg Phe Ser Thr
                485                 490                 495

Cys Asp Asn Gln Lys Ser Cys Met Ser Asn Cys Ser Ile Thr Ser Ile
            500                 505                 510

Cys Glu Lys Pro Gln Glu Val Cys Val Ala Val Trp Arg Lys Asn Asp
        515                 520                 525

Glu Asn Ile Thr Leu Glu Thr Val Cys His Asp Pro Lys Leu Pro Tyr
    530                 535                 540

His Asp Phe Ile Leu Glu Asp Ala Ala Ser Pro Lys Cys Ile Met Lys
545                 550                 555                 560

Glu Lys Lys Lys Pro Gly Glu Thr Phe Phe Met Cys Ser Cys Ser Ser
                565                 570                 575

Asp Glu Cys Asn Asp Asn Ile Ile Phe Ser Glu Glu Tyr Asn Thr Ser
            580                 585                 590

Asn Pro Asp
        595

<210> SEQ ID NO 114
<211> LENGTH: 129
<212> TYPE: PRT
<213> ORGANISM: Artificial Sequence
<220> FEATURE:
<223> OTHER INFORMATION: Synthetic

<400> SEQUENCE: 114

Ser Val Asn Asn Asp Met Ile Val Thr Asp Asn Asn Gly Ala Val Lys
1               5                   10                  15

Phe Pro Gln Leu Cys Lys Phe Cys Asp Val Arg Phe Ser Thr Cys Asp
```

```
                    20                  25                  30
Asn Gln Lys Ser Cys Met Ser Asn Cys Ser Ile Thr Ser Ile Cys Glu
                35                  40                  45

Lys Pro Gln Glu Val Cys Val Ala Val Trp Arg Lys Asn Asp Glu Asn
            50                  55                  60

Ile Thr Leu Glu Thr Val Cys His Asp Pro Lys Leu Pro Tyr His Asp
65                  70                  75                  80

Phe Ile Leu Glu Asp Ala Ala Ser Pro Lys Cys Ile Met Lys Glu Lys
                85                  90                  95

Lys Lys Pro Gly Glu Thr Phe Phe Met Cys Ser Cys Ser Ser Asp Glu
            100                 105                 110

Cys Asn Asp Asn Ile Ile Phe Ser Glu Glu Tyr Asn Thr Ser Asn Pro
            115                 120                 125

Asp

<210> SEQ ID NO 115
<211> LENGTH: 129
<212> TYPE: PRT
<213> ORGANISM: Artificial Sequence
<220> FEATURE:
<223> OTHER INFORMATION: Synthetic

<400> SEQUENCE: 115

Ser Val Asn Asn Asp Met Ile Val Thr Asn Asn Gly Ala Val Lys
1               5                   10                  15

Phe Pro Gln Leu Cys Lys Phe Cys Asp Val Arg Phe Ser Thr Cys Asp
                20                  25                  30

Asn Gln Lys Ser Cys Met Ser Asn Cys Ser Ile Thr Ser Ile Cys Glu
                35                  40                  45

Lys Pro Gln Glu Val Cys Val Ala Val Trp Arg Lys Asn Asp Glu Asn
            50                  55                  60

Ile Thr Leu Glu Thr Val Cys His Asp Pro Lys Leu Pro Tyr His Asp
65                  70                  75                  80

Phe Ile Leu Glu Asp Ala Ala Ser Pro Lys Cys Ile Met Lys Glu Lys
                85                  90                  95

Lys Lys Pro Gly Glu Thr Phe Phe Met Cys Ser Cys Ser Ser Asp Glu
            100                 105                 110

Cys Asn Asp Asn Ile Ile Phe Ser Glu Glu Tyr Asn Thr Ser Asn Pro
            115                 120                 125

Asp

<210> SEQ ID NO 116
<211> LENGTH: 129
<212> TYPE: PRT
<213> ORGANISM: Artificial Sequence
<220> FEATURE:
<223> OTHER INFORMATION: Synthetic

<400> SEQUENCE: 116

Ser Val Asn Asn Asp Met Ile Val Ser Asn Asn Gly Ala Val Lys
1               5                   10                  15

Phe Pro Gln Leu Cys Lys Phe Cys Asp Val Arg Phe Ser Thr Cys Asp
                20                  25                  30

Asn Gln Lys Ser Cys Met Ser Asn Cys Ser Ile Thr Ser Ile Cys Glu
                35                  40                  45

Lys Pro Gln Glu Val Cys Val Ala Val Trp Arg Lys Asn Asp Glu Asn
            50                  55                  60
```

```
Ile Thr Leu Glu Thr Val Cys His Asp Pro Lys Leu Pro Tyr His Asp
 65                  70                  75                  80

Phe Ile Leu Glu Asp Ala Ala Ser Pro Lys Cys Ile Met Lys Glu Lys
                 85                  90                  95

Lys Lys Pro Gly Glu Thr Phe Phe Met Cys Ser Cys Ser Ser Asp Glu
            100                 105                 110

Cys Asn Asp Asn Ile Ile Phe Ser Glu Glu Tyr Asn Thr Ser Asn Pro
        115                 120                 125

Asp

<210> SEQ ID NO 117
<211> LENGTH: 136
<212> TYPE: PRT
<213> ORGANISM: Artificial Sequence
<220> FEATURE:
<223> OTHER INFORMATION: Synthetic

<400> SEQUENCE: 117

Ile Pro Pro His Val Gln Gln Ser Val Asn Asn Asp Met Ile Val Thr
 1               5                  10                  15

Asn Asn Asn Gly Ala Val Lys Phe Pro Gln Leu Cys Lys Phe Cys Asp
             20                  25                  30

Val Arg Phe Ser Thr Cys Asp Asn Gln Lys Ser Cys Met Ser Asn Cys
         35                  40                  45

Ser Ile Thr Ser Ile Cys Glu Lys Pro Gln Glu Val Cys Val Ala Val
     50                  55                  60

Trp Arg Lys Asn Asp Glu Asn Ile Thr Leu Glu Thr Val Cys His Asp
 65                  70                  75                  80

Pro Lys Leu Pro Tyr His Asp Phe Ile Leu Glu Asp Ala Ala Ser Pro
                 85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
        130                 135

<210> SEQ ID NO 118
<211> LENGTH: 136
<212> TYPE: PRT
<213> ORGANISM: Artificial Sequence
<220> FEATURE:
<223> OTHER INFORMATION: Synthetic

<400> SEQUENCE: 118

Ile Pro Pro His Val Gln Asn Ser Val Asn Asn Asp Met Ile Val Thr
 1               5                  10                  15

Asn Asn Asn Gly Ala Val Lys Phe Pro Gln Leu Cys Lys Phe Cys Asp
             20                  25                  30

Val Arg Phe Ser Thr Cys Asp Asn Gln Lys Ser Cys Met Ser Asn Cys
         35                  40                  45

Ser Ile Thr Ser Ile Cys Glu Lys Pro Gln Glu Val Cys Val Ala Val
     50                  55                  60

Trp Arg Lys Asn Asp Glu Asn Ile Thr Leu Glu Thr Val Cys His Asp
 65                  70                  75                  80

Pro Lys Leu Pro Tyr His Asp Phe Ile Leu Glu Asp Ala Ala Ser Pro
                 85                  90                  95
```

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp
        130                 135

<210> SEQ ID NO 119
<211> LENGTH: 136
<212> TYPE: PRT
<213> ORGANISM: Artificial Sequence
<220> FEATURE:
<223> OTHER INFORMATION: Synthetic

<400> SEQUENCE: 119

Ile Pro Pro His Val Gln Gln Ser Val Asn Asn Asp Met Ile Val Ser
1               5                   10                  15

Asn Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp
        130                 135

<210> SEQ ID NO 120
<211> LENGTH: 136
<212> TYPE: PRT
<213> ORGANISM: Artificial Sequence
<220> FEATURE:
<223> OTHER INFORMATION: Synthetic

<400> SEQUENCE: 120

Ile Pro Pro His Val Gln Asn Ser Val Asn Asn Asp Met Ile Val Ser
1               5                   10                  15

Asn Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu

Glu Tyr Asn Thr Ser Asn Pro Asp
    130                 135

<210> SEQ ID NO 121
<211> LENGTH: 136
<212> TYPE: PRT
<213> ORGANISM: Artificial Sequence
<220> FEATURE:
<223> OTHER INFORMATION: Synthetic

<400> SEQUENCE: 121

Ile Pro Pro His Val His Gln Ser Val Asn Asn Asp Met Ile Val Ser
1               5                   10                  15

Asn Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135

<210> SEQ ID NO 122
<211> LENGTH: 121
<212> TYPE: PRT
<213> ORGANISM: Artificial Sequence
<220> FEATURE:
<223> OTHER INFORMATION: Synthetic

<400> SEQUENCE: 122

Thr Asp Asn Asn Gly Ala Val Lys Phe Pro Gln Leu Cys Lys Phe Cys
1               5                   10                  15

Asp Val Arg Phe Ser Thr Cys Asp Asn Gln Lys Ser Cys Met Ser Asn
            20                  25                  30

Cys Ser Ile Thr Ser Ile Cys Glu Lys Pro Gln Glu Val Cys Val Ala
        35                  40                  45

Val Trp Arg Lys Asn Asp Glu Asn Ile Thr Leu Glu Thr Val Cys His
    50                  55                  60

Asp Pro Lys Leu Pro Tyr His Asp Phe Ile Leu Glu Asp Ala Ala Ser
65                  70                  75                  80

Pro Lys Cys Ile Met Lys Glu Lys Lys Pro Gly Glu Thr Phe Phe
                85                  90                  95

Met Cys Ser Cys Ser Ser Asp Glu Cys Asn Asp Asn Ile Ile Phe Ser
            100                 105                 110

Glu Glu Tyr Asn Thr Ser Asn Pro Asp
        115                 120

<210> SEQ ID NO 123
<211> LENGTH: 116

-continued

```
<212> TYPE: PRT
<213> ORGANISM: Artificial Sequence
<220> FEATURE:
<223> OTHER INFORMATION: Synthetic

<400> SEQUENCE: 123

Ala Val Lys Phe Pro Gln Leu Cys Lys Phe Cys Asp Val Arg Phe Ser
1               5                   10                  15

Thr Cys Asp Asn Gln Lys Ser Cys Met Ser Asn Cys Ser Ile Thr Ser
            20                  25                  30

Ile Cys Glu Lys Pro Gln Glu Val Cys Val Ala Val Trp Arg Lys Asn
        35                  40                  45

Asp Glu Asn Ile Thr Leu Glu Thr Val Cys His Asp Pro Lys Leu Pro
    50                  55                  60

Tyr His Asp Phe Ile Leu Glu Asp Ala Ala Ser Pro Lys Cys Ile Met
65                  70                  75                  80

Lys Glu Lys Lys Lys Pro Gly Glu Thr Phe Phe Met Cys Ser Cys Ser
                85                  90                  95

Ser Asp Glu Cys Asn Asp Asn Ile Ile Phe Ser Glu Glu Tyr Asn Thr
            100                 105                 110

Ser Asn Pro Asp
        115

<210> SEQ ID NO 124
<211> LENGTH: 588
<212> TYPE: PRT
<213> ORGANISM: Artificial Sequence
<220> FEATURE:
<223> OTHER INFORMATION: Synthetic

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205
```

```
Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Gly Ser Ser Val Asn Asn Asp
450                 455                 460

Met Ile Val Thr Asp Asn Asn Gly Ala Val Lys Phe Pro Gln Leu Cys
465                 470                 475                 480

Lys Phe Cys Asp Val Arg Phe Ser Thr Cys Asp Asn Gln Lys Ser Cys
                485                 490                 495

Met Ser Asn Cys Ser Ile Thr Ser Ile Cys Glu Lys Pro Gln Glu Val
            500                 505                 510

Cys Val Ala Val Trp Arg Lys Asn Asp Glu Asn Ile Thr Leu Glu Thr
        515                 520                 525

Val Cys His Asp Pro Lys Leu Pro Tyr His Asp Phe Ile Leu Glu Asp
    530                 535                 540

Ala Ala Ser Pro Lys Cys Ile Met Lys Glu Lys Lys Pro Gly Glu
545                 550                 555                 560

Thr Phe Phe Met Cys Ser Cys Ser Ser Asp Glu Cys Asn Asp Asn Ile
                565                 570                 575

Ile Phe Ser Glu Glu Tyr Asn Thr Ser Asn Pro Asp
            580                 585
```

<210> SEQ ID NO 125
<211> LENGTH: 588
<212> TYPE: PRT
<213> ORGANISM: Artificial Sequence
<220> FEATURE:

<223> OTHER INFORMATION: Synthetic

<400> SEQUENCE: 125

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Ile His Trp Val Arg Gln Ala Pro Gly Gln Gly Leu Glu Trp Met
        35                  40                  45
Gly Trp Ile Phe Pro Gly Ser Gly Asn Ser Lys Tyr Asn Glu Asn Phe
    50                  55                  60
Lys Gly Arg Val Thr Leu Thr Ala Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Ser Glu Thr Tyr Asp Tyr Gly Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
    210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
```

```
Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
            435                 440                 445

Ser Gly Gly Gly Gly Ser Gly Gly Gly Ser Ser Val Asn Asn Asp
450                 455                 460

Met Ile Val Thr Asn Asn Gly Ala Val Lys Phe Pro Gln Leu Cys
465                 470                 475                 480

Lys Phe Cys Asp Val Arg Phe Ser Thr Cys Asp Asn Gln Lys Ser Cys
                485                 490                 495

Met Ser Asn Cys Ser Ile Thr Ser Ile Cys Glu Lys Pro Gln Glu Val
            500                 505                 510

Cys Val Ala Val Trp Arg Lys Asn Asp Glu Asn Ile Thr Leu Glu Thr
            515                 520                 525

Val Cys His Asp Pro Lys Leu Pro Tyr His Asp Phe Ile Leu Glu Asp
            530                 535                 540

Ala Ala Ser Pro Lys Cys Ile Met Lys Glu Lys Lys Pro Gly Glu
545                 550                 555                 560

Thr Phe Phe Met Cys Ser Cys Ser Ser Asp Glu Cys Asn Asp Asn Ile
                565                 570                 575

Ile Phe Ser Glu Glu Tyr Asn Thr Ser Asn Pro Asp
            580                 585
```

<210> SEQ ID NO 126
<211> LENGTH: 588
<212> TYPE: PRT
<213> ORGANISM: Artificial Sequence
<220> FEATURE:
<223> OTHER INFORMATION: Synthetic

<400> SEQUENCE: 126

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Gly Ser Ser Val Asn Asn Asp
    450                 455                 460

Met Ile Val Ser Asn Asn Gly Ala Val Lys Phe Pro Gln Leu Cys
465                 470                 475                 480

Lys Phe Cys Asp Val Arg Phe Ser Thr Cys Asp Asn Gln Lys Ser Cys
                485                 490                 495

Met Ser Asn Cys Ser Ile Thr Ser Ile Cys Glu Lys Pro Gln Glu Val
            500                 505                 510

Cys Val Ala Val Trp Arg Lys Asn Asp Glu Asn Ile Thr Leu Glu Thr
        515                 520                 525

Val Cys His Asp Pro Lys Leu Pro Tyr His Asp Phe Ile Leu Glu Asp
    530                 535                 540

Ala Ala Ser Pro Lys Cys Ile Met Lys Glu Lys Lys Lys Pro Gly Glu
545                 550                 555                 560

Thr Phe Phe Met Cys Ser Cys Ser Ser Asp Glu Cys Asn Asp Asn Ile
                565                 570                 575

Ile Phe Ser Glu Glu Tyr Asn Thr Ser Asn Pro Asp
            580                 585
```

```
<210> SEQ ID NO 127
<211> LENGTH: 595
<212> TYPE: PRT
<213> ORGANISM: Artificial Sequence
<220> FEATURE:
<223> OTHER INFORMATION: Synthetic

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
50                  55                  60

Lys Gly Arg Val Thr Leu Thr Ala Asp Thr Ser Ser Thr Ser Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
```

```
            370                 375                 380
Glu Asn Asn Tyr Lys Thr Thr Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Ala Gly Gly Gly Gly
            435                 440                 445

Ser Gly Gly Gly Gly Ser Gly Gly Gly Gly Ser Ile Pro Pro His Val
        450                 455                 460

Gln Gln Ser Val Asn Asn Asp Met Ile Val Thr Asn Asn Gly Ala
465                 470                 475                 480

Val Lys Phe Pro Gln Leu Cys Lys Phe Cys Asp Val Arg Phe Ser Thr
                485                 490                 495

Cys Asp Asn Gln Lys Ser Cys Met Ser Asn Cys Ser Ile Thr Ser Ile
                500                 505                 510

Cys Glu Lys Pro Gln Glu Val Cys Val Ala Val Trp Arg Lys Asn Asp
                515                 520                 525

Glu Asn Ile Thr Leu Glu Thr Val Cys His Asp Pro Lys Leu Pro Tyr
            530                 535                 540

His Asp Phe Ile Leu Glu Asp Ala Ala Ser Pro Lys Cys Ile Met Lys
545                 550                 555                 560

Glu Lys Lys Lys Pro Gly Glu Thr Phe Phe Met Cys Ser Cys Ser Ser
                565                 570                 575

Asp Glu Cys Asn Asp Asn Ile Ile Phe Ser Glu Glu Tyr Asn Thr Ser
                580                 585                 590

Asn Pro Asp
        595

<210> SEQ ID NO 128
<211> LENGTH: 595
<212> TYPE: PRT
<213> ORGANISM: Artificial Sequence
<220> FEATURE:
<223> OTHER INFORMATION: Synthetic

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Phe Pro Gly Ser Gly Asn Ser Lys Tyr Asn Glu Asn Phe
50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
```

```
                130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
                195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Ala Gly Gly Gly Gly
                435                 440                 445

Ser Gly Gly Gly Gly Ser Gly Gly Gly Gly Ser Ile Pro Pro His Val
                450                 455                 460

Gln Asn Ser Val Asn Asn Asp Met Ile Val Thr Asn Asn Gly Ala
465                 470                 475                 480

Val Lys Phe Pro Gln Leu Cys Lys Phe Cys Asp Val Arg Phe Ser Thr
                485                 490                 495

Cys Asp Asn Gln Lys Ser Cys Met Ser Asn Cys Ser Ile Thr Ser Ile
                500                 505                 510

Cys Glu Lys Pro Gln Glu Val Cys Val Ala Val Trp Arg Lys Asn Asp
                515                 520                 525

Glu Asn Ile Thr Leu Glu Thr Val Cys His Asp Pro Lys Leu Pro Tyr
530                 535                 540

His Asp Phe Ile Leu Glu Asp Ala Ala Ser Pro Lys Cys Ile Met Lys
545                 550                 555                 560
```

```
Glu Lys Lys Lys Pro Gly Glu Thr Phe Phe Met Cys Ser Cys Ser Ser
                565                 570                 575

Asp Glu Cys Asn Asp Asn Ile Ile Phe Ser Glu Glu Tyr Asn Thr Ser
            580                 585                 590

Asn Pro Asp
        595

<210> SEQ ID NO 129
<211> LENGTH: 595
<212> TYPE: PRT
<213> ORGANISM: Artificial Sequence
<220> FEATURE:
<223> OTHER INFORMATION: Synthetic

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320
```

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Gly Ser Ile Pro Pro His Val
    450                 455                 460

Gln Gln Ser Val Asn Asn Asp Met Ile Val Ser Asn Asn Asn Gly Ala
465                 470                 475                 480

Val Lys Phe Pro Gln Leu Cys Lys Phe Cys Asp Val Arg Phe Ser Thr
                485                 490                 495

Cys Asp Asn Gln Lys Ser Cys Met Ser Asn Cys Ser Ile Thr Ser Ile
            500                 505                 510

Cys Glu Lys Pro Gln Glu Val Cys Val Ala Val Trp Arg Lys Asn Asp
        515                 520                 525

Glu Asn Ile Thr Leu Glu Thr Val Cys His Asp Pro Lys Leu Pro Tyr
    530                 535                 540

His Asp Phe Ile Leu Glu Asp Ala Ala Ser Pro Lys Cys Ile Met Lys
545                 550                 555                 560

Glu Lys Lys Lys Pro Gly Glu Thr Phe Phe Met Cys Ser Cys Ser Ser
                565                 570                 575

Asp Glu Cys Asn Asp Asn Ile Ile Phe Ser Glu Glu Tyr Asn Thr Ser
            580                 585                 590

Asn Pro Asp
        595

<210> SEQ ID NO 130
<211> LENGTH: 595
<212> TYPE: PRT
<213> ORGANISM: Artificial Sequence
<220> FEATURE:
<223> OTHER INFORMATION: Synthetic

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

```
Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Ser Ile Pro Pro His Val
    450                 455                 460

Gln Asn Ser Val Asn Asn Asp Met Ile Val Ser Asn Asn Gly Ala
465                 470                 475                 480

Val Lys Phe Pro Gln Leu Cys Lys Phe Cys Asp Val Arg Phe Ser Thr
                485                 490                 495
```

```
Cys Asp Asn Gln Lys Ser Cys Met Ser Asn Cys Ser Ile Thr Ser Ile
            500                 505                 510

Cys Glu Lys Pro Gln Glu Val Cys Val Ala Val Trp Arg Lys Asn Asp
            515                 520                 525

Glu Asn Ile Thr Leu Glu Thr Val Cys His Asp Pro Lys Leu Pro Tyr
            530                 535                 540

His Asp Phe Ile Leu Glu Asp Ala Ala Ser Pro Lys Cys Ile Met Lys
545                 550                 555                 560

Glu Lys Lys Lys Pro Gly Glu Thr Phe Phe Met Cys Ser Cys Ser Ser
            565                 570                 575

Asp Glu Cys Asn Asp Asn Ile Ile Phe Ser Glu Glu Tyr Asn Thr Ser
            580                 585                 590

Asn Pro Asp
    595

<210> SEQ ID NO 131
<211> LENGTH: 595
<212> TYPE: PRT
<213> ORGANISM: Artificial Sequence
<220> FEATURE:
<223> OTHER INFORMATION: Synthetic

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
            35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
            210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255
```

```
Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Ser Ile Pro Pro His Val
    450                 455                 460

His Gln Ser Val Asn Asn Asp Met Ile Val Ser Asn Asn Gly Ala
465                 470                 475                 480

Val Lys Phe Pro Gln Leu Cys Lys Phe Cys Asp Val Arg Phe Ser Thr
                485                 490                 495

Cys Asp Asn Gln Lys Ser Cys Met Ser Asn Cys Ser Ile Thr Ser Ile
            500                 505                 510

Cys Glu Lys Pro Gln Glu Val Cys Val Ala Val Trp Arg Lys Asn Asp
        515                 520                 525

Glu Asn Ile Thr Leu Glu Thr Val Cys His Asp Pro Lys Leu Pro Tyr
    530                 535                 540

His Asp Phe Ile Leu Glu Asp Ala Ala Ser Pro Lys Cys Ile Met Lys
545                 550                 555                 560

Glu Lys Lys Lys Pro Gly Glu Thr Phe Phe Met Cys Ser Cys Ser Ser
                565                 570                 575

Asp Glu Cys Asn Asp Asn Ile Ile Phe Ser Glu Glu Tyr Asn Thr Ser
            580                 585                 590

Asn Pro Asp
        595

<210> SEQ ID NO 132
<211> LENGTH: 586
<212> TYPE: PRT
<213> ORGANISM: Artificial Sequence
<220> FEATURE:
<223> OTHER INFORMATION: Synthetic

<400> SEQUENCE: 132

Gln Val Gln Leu Val Gln Ser Gly Ala Glu Val Lys Lys Pro Gly Ala
1               5                   10                  15
```

-continued

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
            35                  40                  45

Gly Trp Ile Phe Pro Gly Ser Gly Asn Ser Lys Tyr Asn Glu Asn Phe
50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly

```
                435                 440                 445
Ser Gly Gly Gly Ser Gly Gly Gly Ser Gly Gly Gly Ser
450                 455                 460

Gly Thr Asp Asn Gly Ala Val Lys Phe Pro Gln Leu Cys Lys Phe
465                 470                 475                 480

Cys Asp Val Arg Phe Ser Thr Cys Asp Asn Gln Lys Ser Cys Met Ser
                    485                 490                 495

Asn Cys Ser Ile Thr Ser Ile Cys Glu Lys Pro Gln Glu Val Cys Val
            500                 505                 510

Ala Val Trp Arg Lys Asn Asp Glu Asn Ile Thr Leu Glu Thr Val Cys
            515                 520                 525

His Asp Pro Lys Leu Pro Tyr His Asp Phe Ile Leu Glu Asp Ala Ala
            530                 535                 540

Ser Pro Lys Cys Ile Met Lys Glu Lys Lys Pro Gly Glu Thr Phe
545                 550                 555                 560

Phe Met Cys Ser Cys Ser Ser Asp Glu Cys Asn Asp Asn Ile Ile Phe
                565                 570                 575

Ser Glu Glu Tyr Asn Thr Ser Asn Pro Asp
            580                 585

<210> SEQ ID NO 133
<211> LENGTH: 581
<212> TYPE: PRT
<213> ORGANISM: Artificial Sequence
<220> FEATURE:
<223> OTHER INFORMATION: Synthetic

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Phe Pro Gly Ser Gly Asn Ser Lys Tyr Asn Glu Asn Phe
        50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
```

```
                210                 215                 220
Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Ala Gly Gly Gly Gly
        435                 440                 445

Ser Gly Gly Gly Ser Gly Gly Gly Ser Gly Gly Gly Gly Ser
450                 455                 460

Gly Ala Val Lys Phe Pro Gln Leu Cys Lys Phe Cys Asp Val Arg Phe
465                 470                 475                 480

Ser Thr Cys Asp Asn Gln Lys Ser Cys Met Ser Asn Cys Ser Ile Thr
                485                 490                 495

Ser Ile Cys Glu Lys Pro Gln Glu Val Cys Val Ala Val Trp Arg Lys
                500                 505                 510

Asn Asp Glu Asn Ile Thr Leu Glu Thr Val Cys His Asp Pro Lys Leu
        515                 520                 525

Pro Tyr His Asp Phe Ile Leu Glu Asp Ala Ala Ser Pro Lys Cys Ile
530                 535                 540

Met Lys Glu Lys Lys Pro Gly Glu Thr Phe Phe Met Cys Ser Cys
545                 550                 555                 560

Ser Ser Asp Glu Cys Asn Asp Asn Ile Ile Phe Ser Glu Glu Tyr Asn
                565                 570                 575

Thr Ser Asn Pro Asp
            580

<210> SEQ ID NO 134
<211> LENGTH: 25
<212> TYPE: PRT
<213> ORGANISM: Artificial Sequence
<220> FEATURE:
<223> OTHER INFORMATION: Synthetic
```

```
<400> SEQUENCE: 134

Ile Pro Pro His Val Gln Lys Ser Val Asn Asn Asp Met Ile Val Thr
1               5                   10                  15

Asp Asn Asn Gly Ala Val Lys Phe Pro
            20                  25

<210> SEQ ID NO 135
<211> LENGTH: 18
<212> TYPE: PRT
<213> ORGANISM: Artificial Sequence
<220> FEATURE:
<223> OTHER INFORMATION: Synthetic

<400> SEQUENCE: 135

Ser Val Asn Asn Asp Met Ile Val Thr Asp Asn Asn Gly Ala Val Lys
1               5                   10                  15

Phe Pro

<210> SEQ ID NO 136
<211> LENGTH: 18
<212> TYPE: PRT
<213> ORGANISM: Artificial Sequence
<220> FEATURE:
<223> OTHER INFORMATION: Synthetic

<400> SEQUENCE: 136

Ser Val Asn Asn Asp Met Ile Val Thr Asn Asn Asn Gly Ala Val Lys
1               5                   10                  15

Phe Pro

<210> SEQ ID NO 137
<211> LENGTH: 18
<212> TYPE: PRT
<213> ORGANISM: Artificial Sequence
<220> FEATURE:
<223> OTHER INFORMATION: Synthetic

<400> SEQUENCE: 137

Ser Val Asn Asn Asp Met Ile Val Ser Asn Asn Asn Gly Ala Val Lys
1               5                   10                  15

Phe Pro

<210> SEQ ID NO 138
<211> LENGTH: 25
<212> TYPE: PRT
<213> ORGANISM: Artificial Sequence
<220> FEATURE:
<223> OTHER INFORMATION: Synthetic

<400> SEQUENCE: 138

Ile Pro Pro His Val Gln Gln Ser Val Asn Asn Asp Met Ile Val Thr
1               5                   10                  15

Asn Asn Asn Gly Ala Val Lys Phe Pro
            20                  25

<210> SEQ ID NO 139
<211> LENGTH: 25
<212> TYPE: PRT
<213> ORGANISM: Artificial Sequence
<220> FEATURE:
<223> OTHER INFORMATION: Synthetic

<400> SEQUENCE: 139
```

Ile Pro Pro His Val Gln Asn Ser Val Asn Asn Asp Met Ile Val Thr
1               5                   10                  15

Asn Asn Asn Gly Ala Val Lys Phe Pro
            20                  25

<210> SEQ ID NO 140
<211> LENGTH: 25
<212> TYPE: PRT
<213> ORGANISM: Artificial Sequence
<220> FEATURE:
<223> OTHER INFORMATION: Synthetic

<400> SEQUENCE: 140

Ile Pro Pro His Val Gln Gln Ser Val Asn Asn Asp Met Ile Val Ser
1               5                   10                  15

Asn Asn Asn Gly Ala Val Lys Phe Pro
            20                  25

<210> SEQ ID NO 141
<211> LENGTH: 25
<212> TYPE: PRT
<213> ORGANISM: Artificial Sequence
<220> FEATURE:
<223> OTHER INFORMATION: Synthetic

<400> SEQUENCE: 141

Ile Pro Pro His Val Gln Asn Ser Val Asn Asn Asp Met Ile Val Ser
1               5                   10                  15

Asn Asn Asn Gly Ala Val Lys Phe Pro
            20                  25

<210> SEQ ID NO 142
<211> LENGTH: 25
<212> TYPE: PRT
<213> ORGANISM: Artificial Sequence
<220> FEATURE:
<223> OTHER INFORMATION: Synthetic

<400> SEQUENCE: 142

Ile Pro Pro His Val His Gln Ser Val Asn Asn Asp Met Ile Val Ser
1               5                   10                  15

Asn Asn Asn Gly Ala Val Lys Phe Pro
            20                  25

<210> SEQ ID NO 143
<211> LENGTH: 10
<212> TYPE: PRT
<213> ORGANISM: Artificial Sequence
<220> FEATURE:
<223> OTHER INFORMATION: Synthetic

<400> SEQUENCE: 143

Thr Asp Asn Asn Gly Ala Val Lys Phe Pro
1               5                   10

<210> SEQ ID NO 144
<211> LENGTH: 5
<212> TYPE: PRT
<213> ORGANISM: Artificial Sequence
<220> FEATURE:
<223> OTHER INFORMATION: Synthetic

<400> SEQUENCE: 144

Ala Val Lys Phe Pro
1               5

<210> SEQ ID NO 145
<211> LENGTH: 600
<212> TYPE: PRT
<213> ORGANISM: Artificial Sequence
<220> FEATURE:
<223> OTHER INFORMATION: Synthetic

<400> SEQUENCE: 145

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Met Ile His Pro Asn Ser Gly Gly Asn Asn Tyr Asn Glu Lys Phe
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Trp Tyr Gly Ser Ser Pro Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365
```

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Ala Gly Gly Gly Ser Gly Gly Gly Ser Gly Gly
            450                 455                 460

Gly Ser Gly Gly Gly Ser Ser Val Asn Asn Asp Met Ile Val Ser
465                 470                 475                 480

Asn Asn Asn Gly Ala Val Lys Phe Pro Gln Leu Cys Lys Phe Cys Asp
            485                 490                 495

Val Arg Phe Ser Thr Cys Asp Asn Gln Lys Ser Cys Met Ser Asn Cys
            500                 505                 510

Ser Ile Thr Ser Ile Cys Glu Lys Pro Gln Glu Val Cys Val Ala Val
            515                 520                 525

Trp Arg Lys Asn Asp Glu Asn Ile Thr Leu Glu Thr Val Cys His Asp
            530                 535                 540

Pro Lys Leu Pro Tyr His Asp Phe Ile Leu Glu Asp Ala Ala Ser Pro
545                 550                 555                 560

Lys Cys Ile Met Lys Glu Lys Lys Lys Pro Gly Glu Thr Phe Phe Met
            565                 570                 575

Cys Ser Cys Ser Ser Asp Glu Cys Asn Asp Asn Ile Ile Phe Ser Glu
            580                 585                 590

Glu Tyr Asn Thr Ser Asn Pro Asp
            595                 600

<210> SEQ ID NO 146
<211> LENGTH: 214
<212> TYPE: PRT
<213> ORGANISM: Artificial Sequence
<220> FEATURE:
<223> OTHER INFORMATION: Synthetic

<400> SEQUENCE: 146

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Lys Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
            85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 147
<211> LENGTH: 607
<212> TYPE: PRT
<213> ORGANISM: Artificial Sequence
<220> FEATURE:
<223> OTHER INFORMATION: Synthetic

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Met Ile His Pro Asn Ser Gly Asn Asn Tyr Asn Glu Lys Phe
        50                  55                  60

Lys Ser Arg Val Thr Met Thr Arg Asp Thr Ser Ile Ser Thr Ala Tyr
65              70                  75                  80

Met Glu Leu Ser Arg Leu Arg Ser Asp Asp Thr Ala Val Tyr Tyr Cys
                85                  90                  95

Ala Arg Ser Trp Tyr Gly Ser Ser Pro Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Ala Gly Gly Gly Ser Gly Gly Gly Ser Gly Gly Gly
450                 455                 460

Gly Ser Gly Gly Gly Ser Ile Pro Pro His Val Gln Gln Ser Val
465                 470                 475                 480

Asn Asn Asp Met Ile Val Thr Asn Asn Gly Ala Val Lys Phe Pro
                485                 490                 495

Gln Leu Cys Lys Phe Cys Asp Val Arg Phe Ser Thr Cys Asp Asn Gln
            500                 505                 510

Lys Ser Cys Met Ser Asn Cys Ser Ile Thr Ser Ile Cys Glu Lys Pro
        515                 520                 525

Gln Glu Val Cys Val Ala Val Trp Arg Lys Asn Asp Glu Asn Ile Thr
530                 535                 540

Leu Glu Thr Val Cys His Asp Pro Lys Leu Pro Tyr His Asp Phe Ile
545                 550                 555                 560

Leu Glu Asp Ala Ala Ser Pro Lys Cys Ile Met Lys Glu Lys Lys Lys
                565                 570                 575

Pro Gly Glu Thr Phe Phe Met Cys Ser Cys Ser Ser Asp Glu Cys Asn
            580                 585                 590

Asp Asn Ile Ile Phe Ser Glu Glu Tyr Asn Thr Ser Asn Pro Asp
        595                 600                 605

<210> SEQ ID NO 148
<211> LENGTH: 602
<212> TYPE: PRT
<213> ORGANISM: Artificial Sequence
<220> FEATURE:
<223> OTHER INFORMATION: Synthetic

<400> SEQUENCE: 148

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

```
Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445
```

```
Leu Ser Pro Gly Ala Gly Gly Gly Ser Gly Gly Gly Ser Gly
    450             455             460
Gly Gly Gly Ser Gly Gly Gly Ser Ser Val Asn Asn Asp Met Ile
465             470             475                 480
Val Ser Asn Asn Gly Ala Val Lys Phe Pro Gln Leu Cys Lys Phe
            485             490             495
Cys Asp Val Arg Phe Ser Thr Cys Asp Asn Gln Lys Ser Cys Met Ser
            500             505             510
Asn Cys Ser Ile Thr Ser Ile Cys Glu Lys Pro Gln Glu Val Cys Val
        515             520             525
Ala Val Trp Arg Lys Asn Asp Glu Asn Ile Thr Leu Glu Thr Val Cys
530             535             540
His Asp Pro Lys Leu Pro Tyr His Asp Phe Ile Leu Glu Asp Ala Ala
545             550             555                 560
Ser Pro Lys Cys Ile Met Lys Glu Lys Lys Pro Gly Glu Thr Phe
            565             570             575
Phe Met Cys Ser Cys Ser Ser Asp Glu Cys Asn Asp Asn Ile Ile Phe
            580             585             590
Ser Glu Glu Tyr Asn Thr Ser Asn Pro Asp
        595             600

<210> SEQ ID NO 149
<211> LENGTH: 214
<212> TYPE: PRT
<213> ORGANISM: Artificial Sequence
<220> FEATURE:
<223> OTHER INFORMATION: Synthetic

<400> SEQUENCE: 149

Asp Ile Gln Met Thr Gln Ser Pro Ser Ser Leu Ser Ala Ser Val Gly
1               5                   10                  15
Asp Arg Val Thr Ile Thr Cys Ser Ala Ser Gln Asp Ile Ser Asn Tyr
            20                  25                  30
Leu Asn Trp Tyr Gln Gln Lys Pro Gly Lys Ala Pro Lys Val Leu Ile
        35                  40                  45
Tyr Phe Thr Ser Ser Leu His Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Thr Val Pro Trp
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 150
<211> LENGTH: 609
<212> TYPE: PRT
<213> ORGANISM: Artificial Sequence
<220> FEATURE:
<223> OTHER INFORMATION: Synthetic

<400> SEQUENCE: 150

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
    435                 440                 445

Leu Ser Pro Gly Ala Gly Gly Gly Ser Gly Gly Gly Ser Gly
    450                 455                 460

Gly Gly Gly Ser Gly Gly Gly Ser Ile Pro Pro His Val Gln Gln
465                 470                 475                 480

Ser Val Asn Asn Asp Met Ile Val Thr Asn Asn Gly Ala Val Lys
                485                 490                 495

Phe Pro Gln Leu Cys Lys Phe Cys Asp Val Arg Phe Ser Thr Cys Asp
            500                 505                 510

Asn Gln Lys Ser Cys Met Ser Asn Cys Ser Ile Thr Ser Ile Cys Glu
    515                 520                 525

Lys Pro Gln Glu Val Cys Val Ala Val Trp Arg Lys Asn Asp Glu Asn
530                 535                 540

Ile Thr Leu Glu Thr Val Cys His Asp Pro Lys Leu Pro Tyr His Asp
545                 550                 555                 560

Phe Ile Leu Glu Asp Ala Ala Ser Pro Lys Cys Ile Met Lys Glu Lys
                565                 570                 575

Lys Lys Pro Gly Glu Thr Phe Phe Met Cys Ser Cys Ser Ser Asp Glu
            580                 585                 590

Cys Asn Asp Asn Ile Ile Phe Ser Glu Glu Tyr Asn Thr Ser Asn Pro
    595                 600                 605

Asp

<210> SEQ ID NO 151
<211> LENGTH: 580
<212> TYPE: PRT
<213> ORGANISM: Artificial Sequence
<220> FEATURE:
<223> OTHER INFORMATION: Synthetic

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu

```
            100                 105                 110
Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Ile Pro Pro His Val Gln Lys Ser Val Asn Asn Asp Met
        355                 360                 365

Ile Val Thr Asp Asn Asn Gly Ala Val Lys Phe Pro Gln Leu Cys Lys
    370                 375                 380

Phe Cys Asp Val Arg Phe Ser Thr Cys Asp Asn Gln Lys Ser Cys Met
385                 390                 395                 400

Ser Asn Cys Ser Ile Thr Ser Ile Cys Glu Lys Pro Gln Glu Val Cys
                405                 410                 415

Val Ala Val Trp Arg Lys Asn Asp Glu Asn Ile Thr Leu Glu Thr Val
            420                 425                 430

Cys His Asp Pro Lys Leu Pro Tyr His Asp Phe Ile Leu Glu Asp Ala
        435                 440                 445

Ala Ser Pro Lys Cys Ile Met Lys Glu Lys Lys Pro Gly Glu Thr
    450                 455                 460

Phe Phe Met Cys Ser Cys Ser Ser Asp Glu Cys Asn Asp Asn Ile Ile
465                 470                 475                 480

Phe Ser Glu Glu Tyr Asn Thr Ser Asn Pro Asp Thr Lys Asn Gln Val
                485                 490                 495

Ser Leu Thr Cys Leu Val Lys Gly Phe Tyr Pro Ser Asp Ile Ala Val
            500                 505                 510

Glu Trp Glu Ser Asn Gly Gln Pro Glu Asn Asn Tyr Lys Thr Thr Pro
        515                 520                 525
```

```
Pro Val Leu Asp Ser Asp Gly Ser Phe Phe Leu Tyr Ser Arg Leu Thr
    530                 535                 540

Val Asp Lys Ser Arg Trp Gln Glu Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Leu Gly Lys
            580

<210> SEQ ID NO 152
<211> LENGTH: 214
<212> TYPE: PRT
<213> ORGANISM: Artificial Sequence
<220> FEATURE:
<223> OTHER INFORMATION: Synthetic

<400> SEQUENCE: 152

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln Gln Tyr Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 153
<211> LENGTH: 584
<212> TYPE: PRT
<213> ORGANISM: Artificial Sequence
<220> FEATURE:
<223> OTHER INFORMATION: Synthetic

<400> SEQUENCE: 153

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

-continued

```
                20                  25                  30
Trp Met His Trp Val Arg Gln Ala Pro Gly Gln Gly Leu Glu Trp Met
            35                  40                  45
Gly Met Ile His Pro Asn Ser Gly Asn Asn Tyr Asn Glu Lys Phe
    50                  55                  60
Lys Ser Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                85                  90                  95
Ala Arg Ser Trp Tyr Gly Ser Ser Pro Tyr Tyr Phe Asp Tyr Trp Gly
                100                 105                 110
Gln Gly Thr Leu Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Lys Thr Tyr Thr Cys Asn Val Asp His
            195                 200                 205
Lys Pro Ser Asn Thr Lys Val Asp Lys Arg Val Glu Ser Lys Tyr Gly
            210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
                260                 265                 270
Glu Val Gln Phe Asn Trp Tyr Val Asp Gly Val Glu Val His Asn Ala
            275                 280                 285
Lys Thr Lys Pro Arg Glu Glu Gln Phe Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Ile Pro His Val Gln Lys Ser Val
            355                 360                 365
Asn Asn Asp Met Ile Val Thr Asp Asn Asn Gly Ala Val Lys Phe Pro
        370                 375                 380
Gln Leu Cys Lys Phe Cys Asp Val Arg Phe Ser Thr Cys Asp Asn Gln
385                 390                 395                 400
Lys Ser Cys Met Ser Asn Cys Ser Ile Thr Ser Ile Cys Glu Lys Pro
                405                 410                 415
Gln Glu Val Cys Val Ala Val Trp Arg Lys Asn Asp Glu Asn Ile Thr
            420                 425                 430
Leu Glu Thr Val Cys His Asp Pro Lys Leu Pro Tyr His Asp Phe Ile
        435                 440                 445
```

Leu Glu Asp Ala Ala Ser Pro Lys Cys Ile Met Lys Glu Lys Lys
450                 455                 460

Pro Gly Glu Thr Phe Phe Met Cys Ser Cys Ser Ser Asp Glu Cys Asn
465                 470                 475                 480

Asp Asn Ile Ile Phe Ser Glu Glu Tyr Asn Thr Ser Asn Pro Asp Thr
                485                 490                 495

Lys Asn Gln Val Ser Leu Thr Cys Leu Val Lys Gly Phe Tyr Pro Ser
            500                 505                 510

Asp Ile Ala Val Glu Trp Glu Ser Asn Gly Gln Pro Glu Asn Asn Tyr
        515                 520                 525

Lys Thr Thr Pro Pro Val Leu Asp Ser Asp Gly Ser Phe Phe Leu Tyr
    530                 535                 540

Ser Arg Leu Thr Val Asp Lys Ser Arg Trp Gln Glu Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Leu Gly Lys
            580

<210> SEQ ID NO 154
<211> LENGTH: 214
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Lys Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 155
<211> LENGTH: 15
<212> TYPE: PRT
<213> ORGANISM: Artificial Sequence
<220> FEATURE:
<223> OTHER INFORMATION: Synthetic

<400> SEQUENCE: 155

Lys Arg Ile Trp Phe Ile Pro Arg Ser Ser Trp Tyr Glu Arg Ala
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Synthetic

<400> SEQUENCE: 156

Gly Gly Gly Gly Ser Gly Gly Gly Gly Ser Gly Gly Gly Gly Ser
1               5                   10                  15

<210> SEQ ID NO 157
<211> LENGTH: 54
<212> TYPE: PRT
<213> ORGANISM: Artificial Sequence
<220> FEATURE:
<223> OTHER INFORMATION: Synthetic

<400> SEQUENCE: 157

Ala Gln Gln Glu Glu Cys Glu Trp Asp Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Trp Asp Pro Trp Thr
        35                  40                  45

Cys Glu His Met Leu Glu
    50

<210> SEQ ID NO 158
<211> LENGTH: 285
<212> TYPE: PRT
<213> ORGANISM: Artificial Sequence
<220> FEATURE:
<223> OTHER INFORMATION: Synthetic

<400> SEQUENCE: 158

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
            115                 120                 125

Thr Leu Pro Pro Ser Arg Asp Glu Leu Thr Lys Asn Gln Val Ser Leu
        130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys Gly Gly Gly Gly Ala Gln Gln Glu Glu Cys Glu Trp Asp
225                 230                 235                 240

Pro Trp Thr Cys Glu His Met Gly Ser Gly Ser Ala Thr Gly Gly Ser
                245                 250                 255

Gly Ser Thr Ala Ser Ser Gly Ser Gly Ser Ala Thr His Gln Glu Glu
            260                 265                 270

Cys Glu Trp Asp Pro Trp Thr Cys Glu His Met Leu Glu
        275                 280                 285

<210> SEQ ID NO 159
<211> LENGTH: 330
<212> TYPE: PRT
<213> ORGANISM: Artificial Sequence
<220> FEATURE:
<223> OTHER INFORMATION: Synthetic

<400> SEQUENCE: 159

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 160
<211> LENGTH: 330
<212> TYPE: PRT
<213> ORGANISM: Artificial Sequence
<220> FEATURE:
<223> OTHER INFORMATION: Synthetic

<400> SEQUENCE: 160

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 161
<211> LENGTH: 225
<212> TYPE: PRT
<213> ORGANISM: Artificial Sequence
<220> FEATURE:
<223> OTHER INFORMATION: Synthetic

<400> SEQUENCE: 161

Gly Pro Pro Cys Pro Cys Pro Ala Pro Glu Phe Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser Gln Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Arg Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Leu Gly
    210                 215                 220

Lys
225

<210> SEQ ID NO 162
```

<211> LENGTH: 232
<212> TYPE: PRT
<213> ORGANISM: Artificial Sequence
<220> FEATURE:
<223> OTHER INFORMATION: Synthetic

<400> SEQUENCE: 162

Asp Lys Thr Val Glu Arg Lys Cys Cys Val Glu Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Asn Trp Tyr Val
    50                  55                  60

Asp Gly Val Glu Val His Asn Ala Lys Thr Lys Pro Arg Glu Glu Gln
65                  70                  75                  80

Phe Asn Ser Thr Phe Arg Val Val Ser Val Leu Thr Val Val His Gln
                85                  90                  95

Asp Trp Leu Asn Gly Lys Glu Tyr Lys Cys Lys Val Ser Asn Lys Gly
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 163
<211> LENGTH: 226
<212> TYPE: PRT
<213> ORGANISM: Artificial Sequence
<220> FEATURE:
<223> OTHER INFORMATION: Synthetic

<400> SEQUENCE: 163

Asp Lys Thr His Thr Cys Pro Pro Cys Pro Ala Pro Glu Leu Leu Gly
1               5                   10                  15

Gly Pro Asp Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly

```
            85                  90                  95
Lys Glu Tyr Lys Cys Lys Val Ser Asn Lys Ala Leu Pro Ala Pro Glu
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly
225

<210> SEQ ID NO 164
<211> LENGTH: 226
<212> TYPE: PRT
<213> ORGANISM: Artificial Sequence
<220> FEATURE:
<223> OTHER INFORMATION: Synthetic

<400> SEQUENCE: 164

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
```

<210> SEQ ID NO 165
<211> LENGTH: 224
<212> TYPE: PRT
<213> ORGANISM: Artificial Sequence
<220> FEATURE:
<223> OTHER INFORMATION: Synthetic

<400> SEQUENCE: 165

Gly Pro Pro Cys Pro Cys Pro Ala Pro Glu Phe Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser Gln Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Arg Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Leu Gly
    210                 215                 220

<210> SEQ ID NO 166
<211> LENGTH: 231
<212> TYPE: PRT
<213> ORGANISM: Artificial Sequence
<220> FEATURE:
<223> OTHER INFORMATION: Synthetic

<400> SEQUENCE: 166

Asp Lys Thr Val Glu Arg Lys Cys Cys Val Glu Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Asn Trp Tyr Val
    50                  55                  60

-continued

```
Asp Gly Val Glu Val His Asn Ala Lys Thr Lys Pro Arg Glu Glu Gln
 65                  70                  75                  80

Phe Asn Ser Thr Phe Arg Val Val Ser Val Leu Thr Val His Gln
                 85                  90                  95

Asp Trp Leu Asn Gly Lys Glu Tyr Lys Cys Lys Val Ser Asn Lys Gly
                100                 105                 110

Leu Pro Ala Pro Ile Glu Lys Thr Ile Ser Lys Thr Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 167
<211> LENGTH: 12
<212> TYPE: PRT
<213> ORGANISM: Artificial Sequence
<220> FEATURE:
<223> OTHER INFORMATION: Synthetic

<400> SEQUENCE: 167

Glu Thr Phe Leu Ser Thr Asn Lys Leu Glu Asn Gln
1               5                   10

<210> SEQ ID NO 168
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: acetylated lysine
<220> FEATURE:
<221> NAME/KEY: MOD_RES
<222> LOCATION: (9)..(9)
<223> OTHER INFORMATION: acetylated lysine
<220> FEATURE:
<221> NAME/KEY: MOD_RES
<222> LOCATION: (11)..(12)
<223> OTHER INFORMATION: OP: no PEG unit between peptide and the AZD
      (azetidinone) linker

<400> SEQUENCE: 168

Gln Lys Tyr Gln Pro Leu Asp Glu Lys Asp Lys Thr Leu Tyr Asp Gln
1               5                   10                  15

Phe Met Leu Gln Gln Gly
            20

<210> SEQ ID NO 169
<211> LENGTH: 22
<212> TYPE: PRT
```

```
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 1,5-difluorobenzoyl
<220> FEATURE:
<221> NAME/KEY: MOD_RES
<222> LOCATION: (11)..(12)
<223> OTHER INFORMATION: OP: no PEG unit between peptide and the AZD
      (azetidinone) linker

<400> SEQUENCE: 169

Thr Asn Phe Met Pro Met Asp Asp Leu Glu Lys Arg Leu Tyr Glu Gln
1               5                   10                  15

Phe Ile Leu Gln Gln Gly
            20

<210> SEQ ID NO 170
<211> LENGTH: 18
<212> TYPE: PRT
<213> ORGANISM: Artificial Sequence
<220> FEATURE:
<223> OTHER INFORMATION: Synthetic

<400> SEQUENCE: 170

Ser Val Asn Asn Asp Met Ile Val Thr Asp Asn Asn Gly Ala Val Lys
1               5                   10                  15

Phe Pro

<210> SEQ ID NO 171
<211> LENGTH: 25
<212> TYPE: PRT
<213> ORGANISM: Artificial Sequence
<220> FEATURE:
<223> OTHER INFORMATION: Synthetic

<400> SEQUENCE: 171

Ile Pro Pro His Val Gln Lys Ser Val Asn Asn Asp Met Ile Val Thr
1               5                   10                  15

Asp Asn Asn Gly Ala Val Lys Phe Pro
            20                  25

<210> SEQ ID NO 172
<211> LENGTH: 608
<212> TYPE: PRT
<213> ORGANISM: Artificial Sequence
<220> FEATURE:
<223> OTHER INFORMATION: Synthetic

<400> SEQUENCE: 172

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Met Ile His Pro Asn Ser Gly Gly Asn Asn Tyr Asn Glu Lys Phe
        50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

Ala Arg Ser Trp Tyr Gly Ser Pro Tyr Tyr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Ala Gly Gly Gly Ser Gly Gly Gly Ser Gly Gly Gly
            450                 455                 460

Gly Ser Gly Gly Gly Ser Gly Ile Pro Pro His Val Gln Lys Ser
465                 470                 475                 480

Val Asn Asn Asp Met Ile Val Thr Asp Asn Asn Gly Ala Val Lys Phe
                    485                 490                 495

Pro Gln Leu Cys Lys Phe Cys Asp Val Arg Phe Ser Thr Cys Asp Asn
            500                 505                 510

Gln Lys Ser Cys Met Ser Asn Cys Ser Ile Thr Ser Ile Cys Glu Lys
            515                 520                 525

Pro Gln Glu Val Cys Val Ala Val Trp Arg Lys Asn Asp Glu Asn Ile
530                 535                 540

Thr Leu Glu Thr Val Cys His Asp Pro Lys Leu Pro Tyr His Asp Phe
545                 550                 555                 560

Ile Leu Glu Asp Ala Ala Ser Pro Lys Cys Ile Met Lys Glu Lys Lys
                565                 570                 575

Lys Pro Gly Glu Thr Phe Phe Met Cys Ser Cys Ser Ser Asp Glu Cys
            580                 585                 590

Asn Asp Asn Ile Ile Phe Ser Glu Glu Tyr Asn Thr Ser Asn Pro Asp
            595                 600                 605

<210> SEQ ID NO 173
<211> LENGTH: 330
<212> TYPE: PRT
<213> ORGANISM: Artificial Sequence
<220> FEATURE:
<223> OTHER INFORMATION: Synthetic

<400> SEQUENCE: 173

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Ala
                325                 330

<210> SEQ ID NO 174
<211> LENGTH: 327
<212> TYPE: PRT
<213> ORGANISM: Artificial Sequence
<220> FEATURE:
<223> OTHER INFORMATION: Synthetic

<400> SEQUENCE: 174

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
290                 295                 300

```
Cys Ser Val Met His Glu Ala Leu His Asn His Tyr Thr Gln Lys Ser
305                 310                 315                 320

Leu Ser Leu Ser Leu Gly Ala
            325
```

<210> SEQ ID NO 175
<211> LENGTH: 330
<212> TYPE: PRT
<213> ORGANISM: Artificial Sequence
<220> FEATURE:
<223> OTHER INFORMATION: Synthetic

<400> SEQUENCE: 175

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Ala
                325                 330
```

<210> SEQ ID NO 176
<211> LENGTH: 30
<212> TYPE: PRT
<213> ORGANISM: Artificial Sequence
<220> FEATURE:
<223> OTHER INFORMATION: Synthetic

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 177
<211> LENGTH: 14
<212> TYPE: PRT
<213> ORGANISM: Artificial Sequence
<220> FEATURE:
<223> OTHER INFORMATION: Synthetic

<400> SEQUENCE: 177

Trp Val Arg Gln Ala Pro Gly Lys Gly Leu Glu Trp Val Ser
1               5                   10

<210> SEQ ID NO 178
<211> LENGTH: 32
<212> TYPE: PRT
<213> ORGANISM: Artificial Sequence
<220> FEATURE:
<223> OTHER INFORMATION: Synthetic

<400> SEQUENCE: 178

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 179
<211> LENGTH: 11
<212> TYPE: PRT
<213> ORGANISM: Artificial Sequence
<220> FEATURE:
<223> OTHER INFORMATION: Synthetic

<400> SEQUENCE: 179

Trp Gly Gln Gly Thr Ser Val Thr Val Ser Ser
1               5                   10

<210> SEQ ID NO 180
<211> LENGTH: 23
<212> TYPE: PRT
<213> ORGANISM: Artificial Sequence
<220> FEATURE:
<223> OTHER INFORMATION: Synthetic

<400> SEQUENCE: 180

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 181
<211> LENGTH: 15
<212> TYPE: PRT
<213> ORGANISM: Artificial Sequence

```
<220> FEATURE:
<223> OTHER INFORMATION: Synthetic

<400> SEQUENCE: 181

Trp Tyr Gln Gln Lys Pro Gly Lys Ala Pro Lys Leu Leu Ile Tyr
1               5                   10                  15

<210> SEQ ID NO 182
<211> LENGTH: 32
<212> TYPE: PRT
<213> ORGANISM: Artificial Sequence
<220> FEATURE:
<223> OTHER INFORMATION: Synthetic

<400> SEQUENCE: 182

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 183
<211> LENGTH: 10
<212> TYPE: PRT
<213> ORGANISM: Artificial Sequence
<220> FEATURE:
<223> OTHER INFORMATION: Synthetic

<400> SEQUENCE: 183

Phe Gly Gly Gly Thr Lys Leu Glu Ile Lys
1               5                   10

<210> SEQ ID NO 184
<211> LENGTH: 30
<212> TYPE: PRT
<213> ORGANISM: Artificial Sequence
<220> FEATURE:
<223> OTHER INFORMATION: Synthetic

<400> SEQUENCE: 184

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr
            20                  25                  30

<210> SEQ ID NO 185
<211> LENGTH: 14
<212> TYPE: PRT
<213> ORGANISM: Artificial Sequence
<220> FEATURE:
<223> OTHER INFORMATION: Synthetic

<400> SEQUENCE: 185

Trp Leu Arg Gln Ala Pro Gly Gln Gly Leu Glu Trp Met Gly
1               5                   10

<210> SEQ ID NO 186
<211> LENGTH: 32
<212> TYPE: PRT
<213> ORGANISM: Artificial Sequence
<220> FEATURE:
<223> OTHER INFORMATION: Synthetic

<400> SEQUENCE: 186

Arg Thr Thr Ser Thr Arg Asp Thr Ser Ile Ser Thr Ala Tyr Met Glu
1               5                   10                  15
```

```
Leu Ser Arg Leu Arg Ser Asp Asp Thr Val Val Tyr Tyr Cys Thr Arg
            20                  25                  30
```

<210> SEQ ID NO 187
<211> LENGTH: 11
<212> TYPE: PRT
<213> ORGANISM: Artificial Sequence
<220> FEATURE:
<223> OTHER INFORMATION: Synthetic

<400> SEQUENCE: 187

```
Trp Gly Gln Gly Thr Leu Val Thr Val Ser Ser
1               5                   10
```

<210> SEQ ID NO 188
<211> LENGTH: 23
<212> TYPE: PRT
<213> ORGANISM: Artificial Sequence
<220> FEATURE:
<223> OTHER INFORMATION: Synthetic

<400> SEQUENCE: 188

```
Asp Ile Gln Met Thr Gln Ser Pro Ser Ser Leu Ser Ala Ser Val Gly
1               5                   10                  15

Asp Arg Val Thr Phe Thr Cys
            20
```

<210> SEQ ID NO 189
<211> LENGTH: 10
<212> TYPE: PRT
<213> ORGANISM: Artificial Sequence
<220> FEATURE:
<223> OTHER INFORMATION: Synthetic

<400> SEQUENCE: 189

```
Phe Gly Gly Gly Thr Lys Val Glu Ile Lys
1               5                   10
```

<210> SEQ ID NO 190
<211> LENGTH: 14
<212> TYPE: PRT
<213> ORGANISM: Artificial Sequence
<220> FEATURE:
<223> OTHER INFORMATION: Synthetic

<400> SEQUENCE: 190

```
Trp Val Arg Gln Ala Pro Gly Gln Gly Leu Glu Trp Met Gly
1               5                   10
```

<210> SEQ ID NO 191
<211> LENGTH: 31
<212> TYPE: PRT
<213> ORGANISM: Artificial Sequence
<220> FEATURE:
<223> OTHER INFORMATION: Synthetic

<400> SEQUENCE: 191

```
Arg Val Thr Ser Thr Arg Asp Thr Ser Ile Ser Thr Ala Tyr Met Glu
1               5                   10                  15

Leu Ser Arg Leu Arg Ser Asp Asp Thr Val Val Tyr Tyr Cys Ala
            20                  25                  30
```

<210> SEQ ID NO 192
<211> LENGTH: 11
<212> TYPE: PRT
<213> ORGANISM: Artificial Sequence

```
<220> FEATURE:
<223> OTHER INFORMATION: Synthetic

<400> SEQUENCE: 192

Trp Gly Gln Gly Thr Thr Leu Thr Val Ser Ser
1               5                   10

<210> SEQ ID NO 193
<211> LENGTH: 23
<212> TYPE: PRT
<213> ORGANISM: Artificial Sequence
<220> FEATURE:
<223> OTHER INFORMATION: Synthetic

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 194
<211> LENGTH: 10
<212> TYPE: PRT
<213> ORGANISM: Artificial Sequence
<220> FEATURE:
<223> OTHER INFORMATION: Synthetic

<400> SEQUENCE: 194

Phe Gly Ala Gly Thr Lys Leu Asp Leu Lys
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Synthetic

<400> SEQUENCE: 195

Phe Gly Gly Gly Thr Lys Val Glu Ile Lys
1               5                   10

<210> SEQ ID NO 196
<211> LENGTH: 30
<212> TYPE: PRT
<213> ORGANISM: Artificial Sequence
<220> FEATURE:
<223> OTHER INFORMATION: Synthetic

<400> SEQUENCE: 196

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 197
<211> LENGTH: 32
<212> TYPE: PRT
<213> ORGANISM: Artificial Sequence
<220> FEATURE:
<223> OTHER INFORMATION: Synthetic

<400> SEQUENCE: 197

Arg Val Thr Met Thr Arg Asp Thr Ser Ile Ser Thr Ala Tyr Met Glu
1               5                   10                  15
```

Leu Ser Ser Leu Arg Ser Glu Asp Thr Ala Val Tyr Tyr Cys Ala Arg
            20                  25                  30

<210> SEQ ID NO 198
<211> LENGTH: 23
<212> TYPE: PRT
<213> ORGANISM: Artificial Sequence
<220> FEATURE:
<223> OTHER INFORMATION: Synthetic

<400> SEQUENCE: 198

Asp Ile Val Leu Thr Gln Ser Pro Ala Ser Leu Ala Val Ser Pro Gly
1               5                   10                  15

Gln Arg Ala Thr Ile Thr Cys
            20

<210> SEQ ID NO 199
<211> LENGTH: 15
<212> TYPE: PRT
<213> ORGANISM: Artificial Sequence
<220> FEATURE:
<223> OTHER INFORMATION: Synthetic

<400> SEQUENCE: 199

Trp Tyr Gln Gln Lys Pro Gly Gln Pro Pro Lys Leu Leu Ile Tyr
1               5                   10                  15

<210> SEQ ID NO 200
<211> LENGTH: 32
<212> TYPE: PRT
<213> ORGANISM: Artificial Sequence
<220> FEATURE:
<223> OTHER INFORMATION: Synthetic

<400> SEQUENCE: 200

Gly Val Pro Ala Arg Phe Ser Gly Ser Gly Ser Gly Thr Asp Phe Thr
1               5                   10                  15

Leu Thr Ile Asn Pro Val Glu Ala Asn Asp Thr Ala Asn Tyr Tyr Cys
            20                  25                  30

<210> SEQ ID NO 201
<211> LENGTH: 31
<212> TYPE: PRT
<213> ORGANISM: Artificial Sequence
<220> FEATURE:
<223> OTHER INFORMATION: Synthetic

<400> SEQUENCE: 201

Arg Val Thr Leu Thr Ala Asp Thr Ser Thr Ser Thr Val Tyr Met Glu
1               5                   10                  15

Leu Ser Ser Leu Arg Ser Glu Asp Thr Ala Val Tyr Tyr Cys Ala
            20                  25                  30

<210> SEQ ID NO 202
<211> LENGTH: 23
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Phe Leu Ser Ala Ser Val Gly
1               5                   10                  15

Asp Arg Val Thr Ile Thr Cys
            20

```
<210> SEQ ID NO 203
<211> LENGTH: 15
<212> TYPE: PRT
<213> ORGANISM: Artificial Sequence
<220> FEATURE:
<223> OTHER INFORMATION: Synthetic

<400> SEQUENCE: 203

Trp Tyr Gln Gln Lys Pro Gly Lys Ala Pro Lys Ala Leu Ile Tyr
1               5                   10                  15

<210> SEQ ID NO 204
<211> LENGTH: 32
<212> TYPE: PRT
<213> ORGANISM: Artificial Sequence
<220> FEATURE:
<223> OTHER INFORMATION: Synthetic

<400> SEQUENCE: 204

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 205
<211> LENGTH: 10
<212> TYPE: PRT
<213> ORGANISM: Artificial Sequence
<220> FEATURE:
<223> OTHER INFORMATION: Synthetic

<400> SEQUENCE: 205

Phe Gly Gln Gly Thr Lys Leu Glu Ile Lys
1               5                   10

<210> SEQ ID NO 206
<211> LENGTH: 14
<212> TYPE: PRT
<213> ORGANISM: Artificial Sequence
<220> FEATURE:
<223> OTHER INFORMATION: Synthetic

<400> SEQUENCE: 206

Trp Met Lys Gln Ala Pro Gly Gln Gly Leu Glu Trp Met Gly
1               5                   10

<210> SEQ ID NO 207
<211> LENGTH: 23
<212> TYPE: PRT
<213> ORGANISM: Artificial Sequence
<220> FEATURE:
<223> OTHER INFORMATION: Synthetic

<400> SEQUENCE: 207

Asp Ile Gln Met Thr Gln Ser Pro Ser Ser Leu Ser Ala Ser Val Gly
1               5                   10                  15

Asp Arg Val Thr Ile Ser Cys
            20

<210> SEQ ID NO 208
<211> LENGTH: 15
<212> TYPE: PRT
<213> ORGANISM: Artificial Sequence
<220> FEATURE:
<223> OTHER INFORMATION: Synthetic
```

```
<400> SEQUENCE: 208

Trp Tyr Gln Gln Lys Pro Gly Lys Ala Pro Lys Leu Leu Ile Lys
1               5                   10                  15

<210> SEQ ID NO 209
<211> LENGTH: 32
<212> TYPE: PRT
<213> ORGANISM: Artificial Sequence
<220> FEATURE:
<223> OTHER INFORMATION: Synthetic

<400> SEQUENCE: 209

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Phe Cys
            20                  25                  30

<210> SEQ ID NO 210
<211> LENGTH: 32
<212> TYPE: PRT
<213> ORGANISM: Artificial Sequence
<220> FEATURE:
<223> OTHER INFORMATION: Synthetic

<400> SEQUENCE: 210

Lys Ala Thr Met Thr Arg Asp Lys Ser Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: Synthetic

<400> SEQUENCE: 211

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Phe Cys
            20                  25                  30

<210> SEQ ID NO 212
<211> LENGTH: 10
<212> TYPE: PRT
<213> ORGANISM: Artificial Sequence
<220> FEATURE:
<223> OTHER INFORMATION: Synthetic

<400> SEQUENCE: 212

Phe Gly Gln Gly Thr Lys Val Glu Ile Lys
1               5                   10

<210> SEQ ID NO 213
<211> LENGTH: 32
<212> TYPE: PRT
<213> ORGANISM: Artificial Sequence
<220> FEATURE:
<223> OTHER INFORMATION: Synthetic

<400> SEQUENCE: 213

Arg Val Thr Met Thr Arg Asp Thr Ser Ile Ser Thr Ala Tyr Met Glu
1               5                   10                  15
```

Leu Ser Arg Leu Arg Ser Asp Asp Thr Ala Val Tyr Tyr Cys Ala Arg
            20                  25                  30

<210> SEQ ID NO 214
<211> LENGTH: 32
<212> TYPE: PRT
<213> ORGANISM: Artificial Sequence
<220> FEATURE:
<223> OTHER INFORMATION: Synthetic

<400> SEQUENCE: 214

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 215
<211> LENGTH: 30
<212> TYPE: PRT
<213> ORGANISM: Artificial Sequence
<220> FEATURE:
<223> OTHER INFORMATION: Synthetic

<400> SEQUENCE: 215

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr
            20                  25                  30

<210> SEQ ID NO 216
<211> LENGTH: 14
<212> TYPE: PRT
<213> ORGANISM: Artificial Sequence
<220> FEATURE:
<223> OTHER INFORMATION: Synthetic

<400> SEQUENCE: 216

Trp Ile Arg Gln Phe Pro Gly Asn Lys Leu Glu Trp Met Gly
1               5                   10

<210> SEQ ID NO 217
<211> LENGTH: 32
<212> TYPE: PRT
<213> ORGANISM: Artificial Sequence
<220> FEATURE:
<223> OTHER INFORMATION: Synthetic

<400> SEQUENCE: 217

Arg Ile Ser Ile Thr Arg Asp Thr Ser Lys Asn Gln Phe Phe Leu Gln
1               5                   10                  15

Leu Asn Ser Val Thr Thr Glu Asp Thr Ala Thr Tyr Tyr Cys Ala Asn
            20                  25                  30

<210> SEQ ID NO 218
<211> LENGTH: 23
<212> TYPE: PRT
<213> ORGANISM: Artificial Sequence
<220> FEATURE:
<223> OTHER INFORMATION: Synthetic

<400> SEQUENCE: 218

Asp Ile Val Met Thr Gln Ser His Lys Phe Met Ser Thr Ser Val Gly
1               5                   10                  15

Asp Arg Val Ser Ile Thr Cys

20

<210> SEQ ID NO 219
<211> LENGTH: 15
<212> TYPE: PRT
<213> ORGANISM: Artificial Sequence
<220> FEATURE:
<223> OTHER INFORMATION: Synthetic

<400> SEQUENCE: 219

Trp Tyr Gln Gln Lys Pro Gly Gln Ser Pro Lys Leu Leu Ile Phe
1               5                   10                  15

<210> SEQ ID NO 220
<211> LENGTH: 32
<212> TYPE: PRT
<213> ORGANISM: Artificial Sequence
<220> FEATURE:
<223> OTHER INFORMATION: Synthetic

<400> SEQUENCE: 220

Gly Val Pro Asp Arg Phe Thr Gly Ser Gly Ser Gly Thr Asp Tyr Thr
1               5                   10                  15

Leu Thr Ile Ser Ser Val Gln Ala Glu Asp Leu Ala Leu Tyr Tyr Cys
            20                  25                  30

<210> SEQ ID NO 221
<211> LENGTH: 15
<212> TYPE: PRT
<213> ORGANISM: Artificial Sequence
<220> FEATURE:
<223> OTHER INFORMATION: Synthetic

<400> SEQUENCE: 221

Trp Val Arg Gln Ala Pro Gly Gln Arg Leu Glu Trp Met Gly Trp
1               5                   10                  15

<210> SEQ ID NO 222
<211> LENGTH: 32
<212> TYPE: PRT
<213> ORGANISM: Artificial Sequence
<220> FEATURE:
<223> OTHER INFORMATION: Synthetic

<400> SEQUENCE: 222

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 223
<211> LENGTH: 23
<212> TYPE: PRT
<213> ORGANISM: Artificial Sequence
<220> FEATURE:
<223> OTHER INFORMATION: Synthetic

<400> SEQUENCE: 223

Asp Ile Gln Met Thr Gln Ser Pro Ser Ser Leu Ser Ala Phe Val Gly
1               5                   10                  15

Asp Arg Val Thr Ile Thr Cys
            20

<210> SEQ ID NO 224
<211> LENGTH: 15

<212> TYPE: PRT
<213> ORGANISM: Artificial Sequence
<220> FEATURE:
<223> OTHER INFORMATION: Synthetic

<400> SEQUENCE: 224

Trp Tyr Gln Gln Lys Pro Gly Lys Ala Pro Lys Leu Leu Ile His
1               5                   10                  15

<210> SEQ ID NO 225
<211> LENGTH: 32
<212> TYPE: PRT
<213> ORGANISM: Artificial Sequence
<220> FEATURE:
<223> OTHER INFORMATION: Synthetic

<400> SEQUENCE: 225

Gly Val Pro Ser Arg Phe Ser Gly Ser Gly Ser Gly Arg Asp Phe Thr
1               5                   10                  15

Phe Thr Ile Ser Ser Leu Gln Pro Glu Asp Ile Ala Thr Tyr Tyr Cys
                20                  25                  30

<210> SEQ ID NO 226
<211> LENGTH: 23
<212> TYPE: PRT
<213> ORGANISM: Artificial Sequence
<220> FEATURE:
<223> OTHER INFORMATION: Synthetic

<400> SEQUENCE: 226

Glu Ile Val Leu Thr Gln Ser Pro Val Thr Leu Ser Leu Ser Pro Gly
1               5                   10                  15

Glu Arg Ala Thr Leu Ser Cys
                20

<210> SEQ ID NO 227
<211> LENGTH: 15
<212> TYPE: PRT
<213> ORGANISM: Artificial Sequence
<220> FEATURE:
<223> OTHER INFORMATION: Synthetic

<400> SEQUENCE: 227

Trp Tyr Leu Gln Lys Pro Gly Gln Ala Pro Arg Leu Leu Ile Lys
1               5                   10                  15

<210> SEQ ID NO 228
<211> LENGTH: 31
<212> TYPE: PRT
<213> ORGANISM: Artificial Sequence
<220> FEATURE:
<223> OTHER INFORMATION: Synthetic

<400> SEQUENCE: 228

Ile Pro Ala Arg Phe Ser Gly Ser Gly Ser Gly Ser Asp Phe Thr Leu
1               5                   10                  15

Thr Ile Ser Ser Leu Glu Pro Glu Asp Phe Ala Val Tyr Tyr Cys
                20                  25                  30

<210> SEQ ID NO 229
<211> LENGTH: 18
<212> TYPE: PRT
<213> ORGANISM: Artificial Sequence
<220> FEATURE:
<223> OTHER INFORMATION: Synthetic

```
<400> SEQUENCE: 229

Ser Val Asn Asn Asp Met Ile Val Ser Asn Asn Gly Ala Val Lys
1               5                   10                  15

Phe Pro

<210> SEQ ID NO 230
<211> LENGTH: 18
<212> TYPE: PRT
<213> ORGANISM: Artificial Sequence
<220> FEATURE:
<223> OTHER INFORMATION: Synthetic

<400> SEQUENCE: 230

Ser Val Asn Asn Asp Met Ile Val Ser Ala Asn Gly Ala Val Lys
1               5                   10                  15

Phe Pro

<210> SEQ ID NO 231
<211> LENGTH: 18
<212> TYPE: PRT
<213> ORGANISM: Artificial Sequence
<220> FEATURE:
<223> OTHER INFORMATION: Synthetic

<400> SEQUENCE: 231

Ser Val Asn Asn Asp Met Ile Val Ala Ala Asn Gly Ala Val Lys
1               5                   10                  15

Phe Pro

<210> SEQ ID NO 232
<211> LENGTH: 18
<212> TYPE: PRT
<213> ORGANISM: Artificial Sequence
<220> FEATURE:
<223> OTHER INFORMATION: Synthetic

<400> SEQUENCE: 232

Ser Val Asn Asn Asp Met Ile Val Ser Asn Asn Gly Ala Ala Ala
1               5                   10                  15

Phe Pro

<210> SEQ ID NO 233
<211> LENGTH: 18
<212> TYPE: PRT
<213> ORGANISM: Artificial Sequence
<220> FEATURE:
<223> OTHER INFORMATION: Synthetic

<400> SEQUENCE: 233

Ser Val Asn Asn Asp Met Ile Val Ala Ala Asn Gly Ala Ala Ala
1               5                   10                  15

Phe Pro

<210> SEQ ID NO 234
<211> LENGTH: 18
<212> TYPE: PRT
<213> ORGANISM: Artificial Sequence
<220> FEATURE:
<223> OTHER INFORMATION: Synthetic

<400> SEQUENCE: 234

Ser Val Asn Asn Asp Met Ile Val His His Asn Gly Ala Val Lys
1               5                   10                  15
```

Phe Pro

<210> SEQ ID NO 235
<211> LENGTH: 18
<212> TYPE: PRT
<213> ORGANISM: Artificial Sequence
<220> FEATURE:
<223> OTHER INFORMATION: Synthetic

<400> SEQUENCE: 235

Ser Val Asn Asn Asp Met Ile Val Pro Pro Asn Asn Gly Ala Val Lys
1               5                   10                  15

Phe Pro

<210> SEQ ID NO 236
<211> LENGTH: 18
<212> TYPE: PRT
<213> ORGANISM: Artificial Sequence
<220> FEATURE:
<223> OTHER INFORMATION: Synthetic

<400> SEQUENCE: 236

Ser Val Asn Asn Asp Trp Ile Val Ala Ala Asn Asn Gly Ala Val Lys
1               5                   10                  15

Phe Pro

<210> SEQ ID NO 237
<211> LENGTH: 18
<212> TYPE: PRT
<213> ORGANISM: Artificial Sequence
<220> FEATURE:
<223> OTHER INFORMATION: Synthetic

<400> SEQUENCE: 237

Ser Val Asn Asn Asp Trp Ile Val Ala Ala Asn Asn Trp Ala Val Lys
1               5                   10                  15

Phe Pro

<210> SEQ ID NO 238
<211> LENGTH: 13
<212> TYPE: PRT
<213> ORGANISM: Artificial Sequence
<220> FEATURE:
<223> OTHER INFORMATION: Synthetic

<400> SEQUENCE: 238

Met Ile Val Ser Asn Asn Asn Gly Ala Val Lys Phe Pro
1               5                   10

<210> SEQ ID NO 239
<211> LENGTH: 13
<212> TYPE: PRT
<213> ORGANISM: Artificial Sequence
<220> FEATURE:
<223> OTHER INFORMATION: Synthetic

<400> SEQUENCE: 239

Met Ile Val Ser Ala Asn Asn Gly Ala Val Lys Phe Pro
1               5                   10

<210> SEQ ID NO 240
<211> LENGTH: 13
<212> TYPE: PRT
<213> ORGANISM: Artificial Sequence
<220> FEATURE:
<223> OTHER INFORMATION: Synthetic

<400> SEQUENCE: 240

Met Ile Val Ala Ala Asn Asn Gly Ala Val Lys Phe Pro
1               5                   10

<210> SEQ ID NO 241
<211> LENGTH: 13
<212> TYPE: PRT
<213> ORGANISM: Artificial Sequence
<220> FEATURE:
<223> OTHER INFORMATION: Synthetic

<400> SEQUENCE: 241

Met Ile Val His His Asn Asn Gly Ala Val Lys Phe Pro
1               5                   10

<210> SEQ ID NO 242
<211> LENGTH: 13
<212> TYPE: PRT
<213> ORGANISM: Artificial Sequence
<220> FEATURE:
<223> OTHER INFORMATION: Synthetic

<400> SEQUENCE: 242

Met Ile Val Pro Pro Asn Asn Gly Ala Val Lys Phe Pro
1               5                   10

<210> SEQ ID NO 243
<211> LENGTH: 13
<212> TYPE: PRT
<213> ORGANISM: Artificial Sequence
<220> FEATURE:
<223> OTHER INFORMATION: Synthetic

<400> SEQUENCE: 243

Trp Ile Val Ala Ala Asn Asn Gly Ala Val Lys Phe Pro
1               5                   10

<210> SEQ ID NO 244
<211> LENGTH: 13
<212> TYPE: PRT
<213> ORGANISM: Artificial Sequence
<220> FEATURE:
<223> OTHER INFORMATION: Synthetic

<400> SEQUENCE: 244

Trp Ile Val Ala Ala Asn Asn Trp Ala Val Lys Phe Pro
1               5                   10

<210> SEQ ID NO 245
<211> LENGTH: 12
<212> TYPE: PRT
<213> ORGANISM: Artificial Sequence
<220> FEATURE:
<223> OTHER INFORMATION: Synthetic

<400> SEQUENCE: 245

Ile Val Ser Asn Asn Asn Gly Ala Val Lys Phe Pro
1               5                   10

<210> SEQ ID NO 246
<211> LENGTH: 12
<212> TYPE: PRT
<213> ORGANISM: Artificial Sequence
<220> FEATURE:

<223> OTHER INFORMATION: Synthetic

<400> SEQUENCE: 246

Ile Val Ser Ala Asn Asn Gly Ala Val Lys Phe Pro
1               5                   10

<210> SEQ ID NO 247
<211> LENGTH: 12
<212> TYPE: PRT
<213> ORGANISM: Artificial Sequence
<220> FEATURE:
<223> OTHER INFORMATION: Synthetic

<400> SEQUENCE: 247

Ile Val Ala Ala Asn Asn Gly Ala Val Lys Phe Pro
1               5                   10

<210> SEQ ID NO 248
<211> LENGTH: 12
<212> TYPE: PRT
<213> ORGANISM: Artificial Sequence
<220> FEATURE:
<223> OTHER INFORMATION: Synthetic

<400> SEQUENCE: 248

Ile Val His His Asn Asn Gly Ala Val Lys Phe Pro
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Synthetic

<400> SEQUENCE: 249

Ile Val Pro Pro Asn Asn Gly Ala Val Lys Phe Pro
1               5                   10

<210> SEQ ID NO 250
<211> LENGTH: 129
<212> TYPE: PRT
<213> ORGANISM: Artificial Sequence
<220> FEATURE:
<223> OTHER INFORMATION: Synthetic

<400> SEQUENCE: 250

Ser Val Asn Asn Asp Met Ile Val Ser Asn Asn Gly Ala Val Lys
1               5                   10                  15

Phe Pro Gln Leu Cys Lys Phe Cys Asp Val Arg Phe Ser Thr Cys Asp
                20                  25                  30

Asn Gln Lys Ser Cys Met Ser Asn Cys Ser Ile Thr Ser Ile Cys Glu
            35                  40                  45

Lys Pro Gln Glu Val Cys Val Ala Val Trp Arg Lys Asn Asp Glu Asn
        50                  55                  60

Ile Thr Leu Glu Thr Val Cys His Asp Pro Lys Leu Pro Tyr His Asp
65                  70                  75                  80

Phe Ile Leu Glu Asp Ala Ala Ser Pro Lys Cys Ile Met Lys Glu Lys
                85                  90                  95

Lys Lys Pro Gly Glu Thr Phe Phe Met Cys Ser Cys Ser Ser Asp Glu
                100                 105                 110

Cys Asn Asp Asn Ile Ile Phe Ser Glu Glu Tyr Asn Thr Ser Asn Pro
            115                 120                 125

Asp

<210> SEQ ID NO 251
<211> LENGTH: 129
<212> TYPE: PRT
<213> ORGANISM: Artificial Sequence
<220> FEATURE:
<223> OTHER INFORMATION: Synthetic

<400> SEQUENCE: 251

```
Ser Val Asn Asn Asp Met Ile Val Ser Ala Asn Asn Gly Ala Val Lys
1               5                   10                  15

Phe Pro Gln Leu Cys Lys Phe Cys Asp Val Arg Phe Ser Thr Cys Asp
            20                  25                  30

Asn Gln Lys Ser Cys Met Ser Asn Cys Ser Ile Thr Ser Ile Cys Glu
        35                  40                  45

Lys Pro Gln Glu Val Cys Val Ala Val Trp Arg Lys Asn Asp Glu Asn
    50                  55                  60

Ile Thr Leu Glu Thr Val Cys His Asp Pro Lys Leu Pro Tyr His Asp
65                  70                  75                  80

Phe Ile Leu Glu Asp Ala Ala Ser Pro Lys Cys Ile Met Lys Glu Lys
                85                  90                  95

Lys Lys Pro Gly Glu Thr Phe Phe Met Cys Ser Cys Ser Ser Asp Glu
            100                 105                 110

Cys Asn Asp Asn Ile Ile Phe Ser Glu Glu Tyr Asn Thr Ser Asn Pro
        115                 120                 125

Asp
```

<210> SEQ ID NO 252
<211> LENGTH: 129
<212> TYPE: PRT
<213> ORGANISM: Artificial Sequence
<220> FEATURE:
<223> OTHER INFORMATION: Synthetic

<400> SEQUENCE: 252

```
Ser Val Asn Asn Asp Met Ile Val Ala Ala Asn Asn Gly Ala Val Lys
1               5                   10                  15

Phe Pro Gln Leu Cys Lys Phe Cys Asp Val Arg Phe Ser Thr Cys Asp
            20                  25                  30

Asn Gln Lys Ser Cys Met Ser Asn Cys Ser Ile Thr Ser Ile Cys Glu
        35                  40                  45

Lys Pro Gln Glu Val Cys Val Ala Val Trp Arg Lys Asn Asp Glu Asn
    50                  55                  60

Ile Thr Leu Glu Thr Val Cys His Asp Pro Lys Leu Pro Tyr His Asp
65                  70                  75                  80

Phe Ile Leu Glu Asp Ala Ala Ser Pro Lys Cys Ile Met Lys Glu Lys
                85                  90                  95

Lys Lys Pro Gly Glu Thr Phe Phe Met Cys Ser Cys Ser Ser Asp Glu
            100                 105                 110

Cys Asn Asp Asn Ile Ile Phe Ser Glu Glu Tyr Asn Thr Ser Asn Pro
        115                 120                 125

Asp
```

<210> SEQ ID NO 253
<211> LENGTH: 129
<212> TYPE: PRT

<213> ORGANISM: Artificial Sequence
<220> FEATURE:
<223> OTHER INFORMATION: Synthetic

<400> SEQUENCE: 253

Ser Val Asn Asn Asp Met Ile Val Ser Asn Asn Gly Ala Ala Ala
1               5                   10                  15

Phe Pro Gln Leu Cys Lys Phe Cys Asp Val Arg Phe Ser Thr Cys Asp
            20                  25                  30

Asn Gln Lys Ser Cys Met Ser Asn Cys Ser Ile Thr Ser Ile Cys Glu
        35                  40                  45

Lys Pro Gln Glu Val Cys Val Ala Val Trp Arg Lys Asn Asp Glu Asn
    50                  55                  60

Ile Thr Leu Glu Thr Val Cys His Asp Pro Lys Leu Pro Tyr His Asp
65                  70                  75                  80

Phe Ile Leu Glu Asp Ala Ala Ser Pro Lys Cys Ile Met Lys Glu Lys
                85                  90                  95

Lys Lys Pro Gly Glu Thr Phe Phe Met Cys Ser Cys Ser Ser Asp Glu
            100                 105                 110

Cys Asn Asp Asn Ile Ile Phe Ser Glu Glu Tyr Asn Thr Ser Asn Pro
        115                 120                 125

Asp

<210> SEQ ID NO 254
<211> LENGTH: 129
<212> TYPE: PRT
<213> ORGANISM: Artificial Sequence
<220> FEATURE:
<223> OTHER INFORMATION: Synthetic

<400> SEQUENCE: 254

Ser Val Asn Asn Asp Met Ile Val Ala Ala Asn Asn Gly Ala Ala Ala
1               5                   10                  15

Phe Pro Gln Leu Cys Lys Phe Cys Asp Val Arg Phe Ser Thr Cys Asp
            20                  25                  30

Asn Gln Lys Ser Cys Met Ser Asn Cys Ser Ile Thr Ser Ile Cys Glu
        35                  40                  45

Lys Pro Gln Glu Val Cys Val Ala Val Trp Arg Lys Asn Asp Glu Asn
    50                  55                  60

Ile Thr Leu Glu Thr Val Cys His Asp Pro Lys Leu Pro Tyr His Asp
65                  70                  75                  80

Phe Ile Leu Glu Asp Ala Ala Ser Pro Lys Cys Ile Met Lys Glu Lys
                85                  90                  95

Lys Lys Pro Gly Glu Thr Phe Phe Met Cys Ser Cys Ser Ser Asp Glu
            100                 105                 110

Cys Asn Asp Asn Ile Ile Phe Ser Glu Glu Tyr Asn Thr Ser Asn Pro
        115                 120                 125

Asp

<210> SEQ ID NO 255
<211> LENGTH: 129
<212> TYPE: PRT
<213> ORGANISM: Artificial Sequence
<220> FEATURE:
<223> OTHER INFORMATION: Synthetic

<400> SEQUENCE: 255

Ser Val Asn Asn Asp Met Ile Val His His Asn Asn Gly Ala Val Lys

-continued

```
                1               5                  10                  15
            Phe Pro Gln Leu Cys Lys Phe Cys Asp Val Arg Phe Ser Thr Cys Asp
                         20                  25                  30

Asn Gln Lys Ser Cys Met Ser Asn Cys Ser Ile Thr Ser Ile Cys Glu
                         35                  40                  45

Lys Pro Gln Glu Val Cys Val Ala Val Trp Arg Lys Asn Asp Glu Asn
                         50                  55                  60

Ile Thr Leu Glu Thr Val Cys His Asp Pro Lys Leu Pro Tyr His Asp
             65                  70                  75                  80

Phe Ile Leu Glu Asp Ala Ala Ser Pro Lys Cys Ile Met Lys Glu Lys
                                 85                  90                  95

Lys Lys Pro Gly Glu Thr Phe Phe Met Cys Ser Cys Ser Ser Asp Glu
                         100                 105                 110

Cys Asn Asp Asn Ile Ile Phe Ser Glu Glu Tyr Asn Thr Ser Asn Pro
                         115                 120                 125

Asp
```

<210> SEQ ID NO 256
<211> LENGTH: 129
<212> TYPE: PRT
<213> ORGANISM: Artificial Sequence
<220> FEATURE:
<223> OTHER INFORMATION: Synthetic

<400> SEQUENCE: 256

```
            Ser Val Asn Asn Asp Met Ile Val Pro Pro Asn Asn Gly Ala Val Lys
             1               5                  10                  15

Phe Pro Gln Leu Cys Lys Phe Cys Asp Val Arg Phe Ser Thr Cys Asp
                         20                  25                  30

Asn Gln Lys Ser Cys Met Ser Asn Cys Ser Ile Thr Ser Ile Cys Glu
                         35                  40                  45

Lys Pro Gln Glu Val Cys Val Ala Val Trp Arg Lys Asn Asp Glu Asn
                         50                  55                  60

Ile Thr Leu Glu Thr Val Cys His Asp Pro Lys Leu Pro Tyr His Asp
             65                  70                  75                  80

Phe Ile Leu Glu Asp Ala Ala Ser Pro Lys Cys Ile Met Lys Glu Lys
                                 85                  90                  95

Lys Lys Pro Gly Glu Thr Phe Phe Met Cys Ser Cys Ser Ser Asp Glu
                         100                 105                 110

Cys Asn Asp Asn Ile Ile Phe Ser Glu Glu Tyr Asn Thr Ser Asn Pro
                         115                 120                 125

Asp
```

<210> SEQ ID NO 257
<211> LENGTH: 129
<212> TYPE: PRT
<213> ORGANISM: Artificial Sequence
<220> FEATURE:
<223> OTHER INFORMATION: Synthetic

<400> SEQUENCE: 257

```
            Ser Val Asn Asn Asp Trp Ile Val Ala Ala Asn Asn Gly Ala Val Lys
             1               5                  10                  15

Phe Pro Gln Leu Cys Lys Phe Cys Asp Val Arg Phe Ser Thr Cys Asp
                         20                  25                  30

Asn Gln Lys Ser Cys Met Ser Asn Cys Ser Ile Thr Ser Ile Cys Glu
                         35                  40                  45
```

```
Lys Pro Gln Glu Val Cys Val Ala Val Trp Arg Lys Asn Asp Glu Asn
            50                  55                  60

Ile Thr Leu Glu Thr Val Cys His Asp Pro Lys Leu Pro Tyr His Asp
 65                  70                  75                  80

Phe Ile Leu Glu Asp Ala Ala Ser Pro Lys Cys Ile Met Lys Glu Lys
                 85                  90                  95

Lys Lys Pro Gly Glu Thr Phe Phe Met Cys Ser Cys Ser Ser Asp Glu
                100                 105                 110

Cys Asn Asp Asn Ile Ile Phe Ser Glu Glu Tyr Asn Thr Ser Asn Pro
                115                 120                 125

Asp
```

<210> SEQ ID NO 258
<211> LENGTH: 129
<212> TYPE: PRT
<213> ORGANISM: Artificial Sequence
<220> FEATURE:
<223> OTHER INFORMATION: Synthetic

<400> SEQUENCE: 258

```
Ser Val Asn Asn Asp Trp Ile Val Ala Ala Asn Asn Trp Ala Val Lys
 1               5                  10                  15

Phe Pro Gln Leu Cys Lys Phe Cys Asp Val Arg Phe Ser Thr Cys Asp
                20                  25                  30

Asn Gln Lys Ser Cys Met Ser Asn Cys Ser Ile Thr Ser Ile Cys Glu
                35                  40                  45

Lys Pro Gln Glu Val Cys Val Ala Val Trp Arg Lys Asn Asp Glu Asn
            50                  55                  60

Ile Thr Leu Glu Thr Val Cys His Asp Pro Lys Leu Pro Tyr His Asp
 65                  70                  75                  80

Phe Ile Leu Glu Asp Ala Ala Ser Pro Lys Cys Ile Met Lys Glu Lys
                 85                  90                  95

Lys Lys Pro Gly Glu Thr Phe Phe Met Cys Ser Cys Ser Ser Asp Glu
                100                 105                 110

Cys Asn Asp Asn Ile Ile Phe Ser Glu Glu Tyr Asn Thr Ser Asn Pro
                115                 120                 125

Asp
```

<210> SEQ ID NO 259
<211> LENGTH: 124
<212> TYPE: PRT
<213> ORGANISM: Artificial Sequence
<220> FEATURE:
<223> OTHER INFORMATION: Synthetic

<400> SEQUENCE: 259

```
Met Ile Val Ser Asn Asn Gly Ala Val Lys Phe Pro Gln Leu Cys
 1               5                  10                  15

Lys Phe Cys Asp Val Arg Phe Ser Thr Cys Asp Asn Gln Lys Ser Cys
                20                  25                  30

Met Ser Asn Cys Ser Ile Thr Ser Ile Cys Glu Lys Pro Gln Glu Val
                35                  40                  45

Cys Val Ala Val Trp Arg Lys Asn Asp Glu Asn Ile Thr Leu Glu Thr
            50                  55                  60

Val Cys His Asp Pro Lys Leu Pro Tyr His Asp Phe Ile Leu Glu Asp
 65                  70                  75                  80
```

```
Ala Ala Ser Pro Lys Cys Ile Met Lys Glu Lys Lys Pro Gly Glu
            85                  90                  95

Thr Phe Phe Met Cys Ser Cys Ser Asp Glu Cys Asn Asp Asn Ile
           100                 105                 110

Ile Phe Ser Glu Glu Tyr Asn Thr Ser Asn Pro Asp
        115                 120

<210> SEQ ID NO 260
<211> LENGTH: 124
<212> TYPE: PRT
<213> ORGANISM: Artificial Sequence
<220> FEATURE:
<223> OTHER INFORMATION: Synthetic

<400> SEQUENCE: 260

Met Ile Val Ser Ala Asn Asn Gly Ala Val Lys Phe Pro Gln Leu Cys
1               5                   10                  15

Lys Phe Cys Asp Val Arg Phe Ser Thr Cys Asp Asn Gln Lys Ser Cys
            20                  25                  30

Met Ser Asn Cys Ser Ile Thr Ser Ile Cys Glu Lys Pro Gln Glu Val
        35                  40                  45

Cys Val Ala Val Trp Arg Lys Asn Asp Glu Asn Ile Thr Leu Glu Thr
    50                  55                  60

Val Cys His Asp Pro Lys Leu Pro Tyr His Asp Phe Ile Leu Glu Asp
65                  70                  75                  80

Ala Ala Ser Pro Lys Cys Ile Met Lys Glu Lys Lys Pro Gly Glu
            85                  90                  95

Thr Phe Phe Met Cys Ser Cys Ser Asp Glu Cys Asn Asp Asn Ile
           100                 105                 110

Ile Phe Ser Glu Glu Tyr Asn Thr Ser Asn Pro Asp
        115                 120

<210> SEQ ID NO 261
<211> LENGTH: 124
<212> TYPE: PRT
<213> ORGANISM: Artificial Sequence
<220> FEATURE:
<223> OTHER INFORMATION: Synthetic

<400> SEQUENCE: 261

Met Ile Val Ala Ala Asn Asn Gly Ala Val Lys Phe Pro Gln Leu Cys
1               5                   10                  15

Lys Phe Cys Asp Val Arg Phe Ser Thr Cys Asp Asn Gln Lys Ser Cys
            20                  25                  30

Met Ser Asn Cys Ser Ile Thr Ser Ile Cys Glu Lys Pro Gln Glu Val
        35                  40                  45

Cys Val Ala Val Trp Arg Lys Asn Asp Glu Asn Ile Thr Leu Glu Thr
    50                  55                  60

Val Cys His Asp Pro Lys Leu Pro Tyr His Asp Phe Ile Leu Glu Asp
65                  70                  75                  80

Ala Ala Ser Pro Lys Cys Ile Met Lys Glu Lys Lys Pro Gly Glu
            85                  90                  95

Thr Phe Phe Met Cys Ser Cys Ser Asp Glu Cys Asn Asp Asn Ile
           100                 105                 110

Ile Phe Ser Glu Glu Tyr Asn Thr Ser Asn Pro Asp
        115                 120

<210> SEQ ID NO 262
```

-continued

```
<211> LENGTH: 124
<212> TYPE: PRT
<213> ORGANISM: Artificial Sequence
<220> FEATURE:
<223> OTHER INFORMATION: Synthetic

<400> SEQUENCE: 262

Met Ile Val His His Asn Asn Gly Ala Val Lys Phe Pro Gln Leu Cys
1               5                   10                  15

Lys Phe Cys Asp Val Arg Phe Ser Thr Cys Asp Asn Gln Lys Ser Cys
            20                  25                  30

Met Ser Asn Cys Ser Ile Thr Ser Ile Cys Glu Lys Pro Gln Glu Val
        35                  40                  45

Cys Val Ala Val Trp Arg Lys Asn Asp Glu Asn Ile Thr Leu Glu Thr
50                  55                  60

Val Cys His Asp Pro Lys Leu Pro Tyr His Asp Phe Ile Leu Glu Asp
65                  70                  75                  80

Ala Ala Ser Pro Lys Cys Ile Met Lys Glu Lys Lys Pro Gly Glu
                85                  90                  95

Thr Phe Phe Met Cys Ser Cys Ser Ser Asp Glu Cys Asn Asp Asn Ile
            100                 105                 110

Ile Phe Ser Glu Glu Tyr Asn Thr Ser Asn Pro Asp
            115                 120

<210> SEQ ID NO 263
<211> LENGTH: 124
<212> TYPE: PRT
<213> ORGANISM: Artificial Sequence
<220> FEATURE:
<223> OTHER INFORMATION: Synthetic

<400> SEQUENCE: 263

Met Ile Val Pro Pro Asn Asn Gly Ala Val Lys Phe Pro Gln Leu Cys
1               5                   10                  15

Lys Phe Cys Asp Val Arg Phe Ser Thr Cys Asp Asn Gln Lys Ser Cys
            20                  25                  30

Met Ser Asn Cys Ser Ile Thr Ser Ile Cys Glu Lys Pro Gln Glu Val
        35                  40                  45

Cys Val Ala Val Trp Arg Lys Asn Asp Glu Asn Ile Thr Leu Glu Thr
50                  55                  60

Val Cys His Asp Pro Lys Leu Pro Tyr His Asp Phe Ile Leu Glu Asp
65                  70                  75                  80

Ala Ala Ser Pro Lys Cys Ile Met Lys Glu Lys Lys Pro Gly Glu
                85                  90                  95

Thr Phe Phe Met Cys Ser Cys Ser Ser Asp Glu Cys Asn Asp Asn Ile
            100                 105                 110

Ile Phe Ser Glu Glu Tyr Asn Thr Ser Asn Pro Asp
            115                 120

<210> SEQ ID NO 264
<211> LENGTH: 124
<212> TYPE: PRT
<213> ORGANISM: Artificial Sequence
<220> FEATURE:
<223> OTHER INFORMATION: Synthetic

<400> SEQUENCE: 264

Trp Ile Val Ala Ala Asn Asn Gly Ala Val Lys Phe Pro Gln Leu Cys
1               5                   10                  15
```

-continued

Lys Phe Cys Asp Val Arg Phe Ser Thr Cys Asp Asn Gln Lys Ser Cys
            20                  25                  30

Met Ser Asn Cys Ser Ile Thr Ser Ile Cys Glu Lys Pro Gln Glu Val
        35                  40                  45

Cys Val Ala Val Trp Arg Lys Asn Asp Glu Asn Ile Thr Leu Glu Thr
    50                  55                  60

Val Cys His Asp Pro Lys Leu Pro Tyr His Asp Phe Ile Leu Glu Asp
65                  70                  75                  80

Ala Ala Ser Pro Lys Cys Ile Met Lys Glu Lys Lys Lys Pro Gly Glu
                85                  90                  95

Thr Phe Phe Met Cys Ser Cys Ser Ser Asp Glu Cys Asn Asp Asn Ile
            100                 105                 110

Ile Phe Ser Glu Glu Tyr Asn Thr Ser Asn Pro Asp
        115                 120

<210> SEQ ID NO 265
<211> LENGTH: 124
<212> TYPE: PRT
<213> ORGANISM: Artificial Sequence
<220> FEATURE:
<223> OTHER INFORMATION: Synthetic

<400> SEQUENCE: 265

Trp Ile Val Ala Ala Asn Asn Trp Ala Val Lys Phe Pro Gln Leu Cys
1               5                   10                  15

Lys Phe Cys Asp Val Arg Phe Ser Thr Cys Asp Asn Gln Lys Ser Cys
            20                  25                  30

Met Ser Asn Cys Ser Ile Thr Ser Ile Cys Glu Lys Pro Gln Glu Val
        35                  40                  45

Cys Val Ala Val Trp Arg Lys Asn Asp Glu Asn Ile Thr Leu Glu Thr
    50                  55                  60

Val Cys His Asp Pro Lys Leu Pro Tyr His Asp Phe Ile Leu Glu Asp
65                  70                  75                  80

Ala Ala Ser Pro Lys Cys Ile Met Lys Glu Lys Lys Lys Pro Gly Glu
                85                  90                  95

Thr Phe Phe Met Cys Ser Cys Ser Ser Asp Glu Cys Asn Asp Asn Ile
            100                 105                 110

Ile Phe Ser Glu Glu Tyr Asn Thr Ser Asn Pro Asp
        115                 120

<210> SEQ ID NO 266
<211> LENGTH: 123
<212> TYPE: PRT
<213> ORGANISM: Artificial Sequence
<220> FEATURE:
<223> OTHER INFORMATION: Synthetic

<400> SEQUENCE: 266

Ile Val Ser Asn Asn Asn Gly Ala Val Lys Phe Pro Gln Leu Cys Lys
1               5                   10                  15

Phe Cys Asp Val Arg Phe Ser Thr Cys Asp Asn Gln Lys Ser Cys Met
            20                  25                  30

Ser Asn Cys Ser Ile Thr Ser Ile Cys Glu Lys Pro Gln Glu Val Cys
        35                  40                  45

Val Ala Val Trp Arg Lys Asn Asp Glu Asn Ile Thr Leu Glu Thr Val
    50                  55                  60

Cys His Asp Pro Lys Leu Pro Tyr His Asp Phe Ile Leu Glu Asp Ala
65                  70                  75                  80

```
Ala Ser Pro Lys Cys Ile Met Lys Glu Lys Lys Pro Gly Glu Thr
            85                  90                  95

Phe Phe Met Cys Ser Cys Ser Ser Asp Glu Cys Asn Asp Asn Ile Ile
            100                 105                 110

Phe Ser Glu Glu Tyr Asn Thr Ser Asn Pro Asp
        115                 120
```

<210> SEQ ID NO 267
<211> LENGTH: 123
<212> TYPE: PRT
<213> ORGANISM: Artificial Sequence
<220> FEATURE:
<223> OTHER INFORMATION: Synthetic

<400> SEQUENCE: 267

```
Ile Val Ser Ala Asn Asn Gly Ala Val Lys Phe Pro Gln Leu Cys Lys
1               5                   10                  15

Phe Cys Asp Val Arg Phe Ser Thr Cys Asp Asn Gln Lys Ser Cys Met
            20                  25                  30

Ser Asn Cys Ser Ile Thr Ser Ile Cys Glu Lys Pro Gln Glu Val Cys
        35                  40                  45

Val Ala Val Trp Arg Lys Asn Asp Glu Asn Ile Thr Leu Glu Thr Val
    50                  55                  60

Cys His Asp Pro Lys Leu Pro Tyr His Asp Phe Ile Leu Glu Asp Ala
65                  70                  75                  80

Ala Ser Pro Lys Cys Ile Met Lys Glu Lys Lys Pro Gly Glu Thr
            85                  90                  95

Phe Phe Met Cys Ser Cys Ser Ser Asp Glu Cys Asn Asp Asn Ile Ile
            100                 105                 110

Phe Ser Glu Glu Tyr Asn Thr Ser Asn Pro Asp
        115                 120
```

<210> SEQ ID NO 268
<211> LENGTH: 123
<212> TYPE: PRT
<213> ORGANISM: Artificial Sequence
<220> FEATURE:
<223> OTHER INFORMATION: Synthetic

<400> SEQUENCE: 268

```
Ile Val Ala Ala Asn Asn Gly Ala Val Lys Phe Pro Gln Leu Cys Lys
1               5                   10                  15

Phe Cys Asp Val Arg Phe Ser Thr Cys Asp Asn Gln Lys Ser Cys Met
            20                  25                  30

Ser Asn Cys Ser Ile Thr Ser Ile Cys Glu Lys Pro Gln Glu Val Cys
        35                  40                  45

Val Ala Val Trp Arg Lys Asn Asp Glu Asn Ile Thr Leu Glu Thr Val
    50                  55                  60

Cys His Asp Pro Lys Leu Pro Tyr His Asp Phe Ile Leu Glu Asp Ala
65                  70                  75                  80

Ala Ser Pro Lys Cys Ile Met Lys Glu Lys Lys Pro Gly Glu Thr
            85                  90                  95

Phe Phe Met Cys Ser Cys Ser Ser Asp Glu Cys Asn Asp Asn Ile Ile
            100                 105                 110

Phe Ser Glu Glu Tyr Asn Thr Ser Asn Pro Asp
        115                 120
```

```
<210> SEQ ID NO 269
<211> LENGTH: 123
<212> TYPE: PRT
<213> ORGANISM: Artificial Sequence
<220> FEATURE:
<223> OTHER INFORMATION: Synthetic

<400> SEQUENCE: 269

Ile Val His His Asn Asn Gly Ala Val Lys Phe Pro Gln Leu Cys Lys
1               5                   10                  15

Phe Cys Asp Val Arg Phe Ser Thr Cys Asp Asn Gln Lys Ser Cys Met
            20                  25                  30

Ser Asn Cys Ser Ile Thr Ser Ile Cys Glu Lys Pro Gln Glu Val Cys
        35                  40                  45

Val Ala Val Trp Arg Lys Asn Asp Glu Asn Ile Thr Leu Glu Thr Val
    50                  55                  60

Cys His Asp Pro Lys Leu Pro Tyr His Asp Phe Ile Leu Glu Asp Ala
65                  70                  75                  80

Ala Ser Pro Lys Cys Ile Met Lys Glu Lys Lys Pro Gly Glu Thr
                85                  90                  95

Phe Phe Met Cys Ser Cys Ser Ser Asp Glu Cys Asn Asp Asn Ile Ile
                100                 105                 110

Phe Ser Glu Glu Tyr Asn Thr Ser Asn Pro Asp
        115                 120

<210> SEQ ID NO 270
<211> LENGTH: 123
<212> TYPE: PRT
<213> ORGANISM: Artificial Sequence
<220> FEATURE:
<223> OTHER INFORMATION: Synthetic

<400> SEQUENCE: 270

Ile Val Pro Pro Asn Asn Gly Ala Val Lys Phe Pro Gln Leu Cys Lys
1               5                   10                  15

Phe Cys Asp Val Arg Phe Ser Thr Cys Asp Asn Gln Lys Ser Cys Met
            20                  25                  30

Ser Asn Cys Ser Ile Thr Ser Ile Cys Glu Lys Pro Gln Glu Val Cys
        35                  40                  45

Val Ala Val Trp Arg Lys Asn Asp Glu Asn Ile Thr Leu Glu Thr Val
    50                  55                  60

Cys His Asp Pro Lys Leu Pro Tyr His Asp Phe Ile Leu Glu Asp Ala
65                  70                  75                  80

Ala Ser Pro Lys Cys Ile Met Lys Glu Lys Lys Pro Gly Glu Thr
                85                  90                  95

Phe Phe Met Cys Ser Cys Ser Ser Asp Glu Cys Asn Asp Asn Ile Ile
                100                 105                 110

Phe Ser Glu Glu Tyr Asn Thr Ser Asn Pro Asp
        115                 120

<210> SEQ ID NO 271
<211> LENGTH: 588
<212> TYPE: PRT
<213> ORGANISM: Artificial Sequence
<220> FEATURE:
<223> OTHER INFORMATION: Synthetic

<400> SEQUENCE: 271

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
             20                  25                  30

Tyr Ile His Trp Val Arg Gln Ala Pro Gly Gln Gly Leu Glu Trp Met
         35                  40                  45

Gly Trp Ile Phe Pro Gly Ser Gly Asn Ser Lys Tyr Asn Glu Asn Phe
 50                  55                  60

Lys Gly Arg Val Thr Leu Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430
```

Tyr Thr Gln Lys Ser Leu Ser Leu Ser Leu Gly Ala Gly Gly Gly
                435                 440                 445

Ser Gly Gly Gly Gly Ser Gly Gly Gly Ser Val Asn Asn Asp
450                 455                 460

Met Ile Val Ser Ala Asn Asn Gly Ala Val Lys Phe Pro Gln Leu Cys
465                 470                 475                 480

Lys Phe Cys Asp Val Arg Phe Ser Thr Cys Asp Asn Gln Lys Ser Cys
                485                 490                 495

Met Ser Asn Cys Ser Ile Thr Ser Ile Cys Glu Lys Pro Gln Glu Val
                500                 505                 510

Cys Val Ala Val Trp Arg Lys Asn Asp Glu Asn Ile Thr Leu Glu Thr
            515                 520                 525

Val Cys His Asp Pro Lys Leu Pro Tyr His Asp Phe Ile Leu Glu Asp
            530                 535                 540

Ala Ala Ser Pro Lys Cys Ile Met Lys Glu Lys Lys Pro Gly Glu
545                 550                 555                 560

Thr Phe Phe Met Cys Ser Cys Ser Ser Asp Glu Cys Asn Asp Asn Ile
                565                 570                 575

Ile Phe Ser Glu Glu Tyr Asn Thr Ser Asn Pro Asp
                580                 585

<210> SEQ ID NO 272
<211> LENGTH: 588
<212> TYPE: PRT
<213> ORGANISM: Artificial Sequence
<220> FEATURE:
<223> OTHER INFORMATION: Synthetic

<400> SEQUENCE: 272

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Phe Pro Gly Ser Gly Asn Ser Lys Tyr Asn Glu Asn Phe
        50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

-continued

```
Thr Lys Val Asp Lys Arg Val Glu Ser Lys Tyr Gly Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Gly Ser Val Asn Asn Asp
450                 455                 460

Met Ile Val Ala Ala Asn Asn Gly Ala Val Lys Phe Pro Gln Leu Cys
465                 470                 475                 480

Lys Phe Cys Asp Val Arg Phe Ser Thr Cys Asp Asn Gln Lys Ser Cys
                485                 490                 495

Met Ser Asn Cys Ser Ile Thr Ser Ile Cys Glu Lys Pro Gln Glu Val
            500                 505                 510

Cys Val Ala Val Trp Arg Lys Asn Asp Glu Asn Ile Thr Leu Glu Thr
        515                 520                 525

Val Cys His Asp Pro Lys Leu Pro Tyr His Asp Phe Ile Leu Glu Asp
    530                 535                 540

Ala Ala Ser Pro Lys Cys Ile Met Lys Glu Lys Lys Pro Gly Glu
545                 550                 555                 560

Thr Phe Phe Met Cys Ser Cys Ser Ser Asp Glu Cys Asn Asp Asn Ile
                565                 570                 575

Ile Phe Ser Glu Glu Tyr Asn Thr Ser Asn Pro Asp
            580                 585
```

<210> SEQ ID NO 273
<211> LENGTH: 588
<212> TYPE: PRT
<213> ORGANISM: Artificial Sequence
<220> FEATURE:
<223> OTHER INFORMATION: Synthetic

<400> SEQUENCE: 273

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Ile His Trp Val Arg Gln Ala Pro Gly Gln Gly Leu Glu Trp Met
        35                  40                  45
Gly Trp Ile Phe Pro Gly Ser Gly Asn Ser Lys Tyr Asn Glu Asn Phe
    50                  55                  60
Lys Gly Arg Val Thr Leu Thr Ala Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Ser Glu Thr Tyr Asp Tyr Gly Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
    210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
```

```
                    405                 410                 415
Gly Asn Val Phe Ser Cys Ser Val Met His Glu Ala Leu His Asn His
                420                 425                 430

Tyr Thr Gln Lys Ser Leu Ser Leu Ser Leu Gly Ala Gly Gly Gly Gly
            435                 440                 445

Ser Gly Gly Gly Ser Gly Gly Gly Ser Ser Val Asn Asn Asp
    450                 455                 460

Met Ile Val Ser Asn Asn Gly Ala Ala Phe Pro Gln Leu Cys
465                 470                 475                 480

Lys Phe Cys Asp Val Arg Phe Ser Thr Cys Asp Asn Gln Lys Ser Cys
                485                 490                 495

Met Ser Asn Cys Ser Ile Thr Ser Ile Cys Glu Lys Pro Gln Glu Val
                500                 505                 510

Cys Val Ala Val Trp Arg Lys Asn Asp Glu Asn Ile Thr Leu Glu Thr
                515                 520                 525

Val Cys His Asp Pro Lys Leu Pro Tyr His Asp Phe Ile Leu Glu Asp
                530                 535                 540

Ala Ala Ser Pro Lys Cys Ile Met Lys Glu Lys Lys Pro Gly Glu
545                 550                 555                 560

Thr Phe Phe Met Cys Ser Cys Ser Ser Asp Glu Cys Asn Asp Asn Ile
                565                 570                 575

Ile Phe Ser Glu Glu Tyr Asn Thr Ser Asn Pro Asp
                580                 585
```

<210> SEQ ID NO 274
<211> LENGTH: 588
<212> TYPE: PRT
<213> ORGANISM: Artificial Sequence
<220> FEATURE:
<223> OTHER INFORMATION: Synthetic

<400> SEQUENCE: 274

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
```

```
                180             185             190
Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Gly Ser Ser Val Asn Asn Asp
    450                 455                 460

Met Ile Val Ala Ala Asn Asn Gly Ala Ala Phe Pro Gln Leu Cys
465                 470                 475                 480

Lys Phe Cys Asp Val Arg Phe Ser Thr Cys Asp Asn Gln Lys Ser Cys
                485                 490                 495

Met Ser Asn Cys Ser Ile Thr Ser Ile Cys Glu Lys Pro Gln Glu Val
            500                 505                 510

Cys Val Ala Val Trp Arg Lys Asn Asp Glu Asn Ile Thr Leu Glu Thr
        515                 520                 525

Val Cys His Asp Pro Lys Leu Pro Tyr His Asp Phe Ile Leu Glu Asp
    530                 535                 540

Ala Ala Ser Pro Lys Cys Ile Met Lys Glu Lys Lys Pro Gly Glu
545                 550                 555                 560

Thr Phe Phe Met Cys Ser Cys Ser Ser Asp Glu Cys Asn Asp Asn Ile
                565                 570                 575

Ile Phe Ser Glu Glu Tyr Asn Thr Ser Asn Pro Asp
            580                 585

<210> SEQ ID NO 275
```

```
<211> LENGTH: 588
<212> TYPE: PRT
<213> ORGANISM: Artificial Sequence
<220> FEATURE:
<223> OTHER INFORMATION: Synthetic

<400> SEQUENCE: 275
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

-continued

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
        420                 425                 430

Tyr Thr Gln Lys Ser Leu Ser Leu Ser Leu Gly Ala Gly Gly Gly Gly
    435                 440                 445

Ser Gly Gly Gly Ser Gly Gly Gly Ser Ser Val Asn Asn Asp
450                 455                 460

Met Ile Val His His Asn Asn Gly Ala Val Lys Phe Pro Gln Leu Cys
465                 470                 475                 480

Lys Phe Cys Asp Val Arg Phe Ser Thr Cys Asp Asn Gln Lys Ser Cys
            485                 490                 495

Met Ser Asn Cys Ser Ile Thr Ser Ile Cys Glu Lys Pro Gln Glu Val
        500                 505                 510

Cys Val Ala Val Trp Arg Lys Asn Asp Glu Asn Ile Thr Leu Glu Thr
    515                 520                 525

Val Cys His Asp Pro Lys Leu Pro Tyr His Asp Phe Ile Leu Glu Asp
530                 535                 540

Ala Ala Ser Pro Lys Cys Ile Met Lys Glu Lys Lys Pro Gly Glu
545                 550                 555                 560

Thr Phe Phe Met Cys Ser Cys Ser Ser Asp Glu Cys Asn Asp Asn Ile
            565                 570                 575

Ile Phe Ser Glu Glu Tyr Asn Thr Ser Asn Pro Asp
            580                 585

<210> SEQ ID NO 276
<211> LENGTH: 588
<212> TYPE: PRT
<213> ORGANISM: Artificial Sequence
<220> FEATURE:
<223> OTHER INFORMATION: Synthetic

<400> SEQUENCE: 276

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

```
Gly Ala Leu Thr Ser Val His Thr Phe Pro Ala Val Leu Gln Ser
                165             170             175

Ser Gly Leu Tyr Ser Leu Ser Val Val Thr Val Pro Ser Ser Ser
            180             185             190

Leu Gly Thr Lys Thr Tyr Thr Cys Asn Val Asp His Lys Pro Ser Asn
            195                 200             205

Thr Lys Val Asp Lys Arg Val Glu Ser Lys Tyr Gly Pro Pro Cys Pro
210             215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
            435                 440                 445

Ser Gly Gly Gly Gly Ser Gly Gly Gly Ser Ser Val Asn Asn Asp
450                 455                 460

Met Ile Val Pro Pro Asn Asn Gly Ala Val Lys Phe Pro Gln Leu Cys
465                 470                 475                 480

Lys Phe Cys Asp Val Arg Phe Ser Thr Cys Asp Asn Gln Lys Ser Cys
                485                 490                 495

Met Ser Asn Cys Ser Ile Thr Ser Ile Cys Glu Lys Pro Gln Glu Val
                500                 505                 510

Cys Val Ala Val Trp Arg Lys Asn Asp Glu Asn Ile Thr Leu Glu Thr
            515                 520                 525

Val Cys His Asp Pro Lys Leu Pro Tyr His Asp Phe Ile Leu Glu Asp
            530                 535                 540

Ala Ala Ser Pro Lys Cys Ile Met Lys Glu Lys Lys Pro Gly Glu
545                 550                 555                 560

Thr Phe Phe Met Cys Ser Cys Ser Ser Asp Glu Cys Asn Asp Asn Ile
                565                 570                 575
```

-continued

```
Ile Phe Ser Glu Glu Tyr Asn Thr Ser Asn Pro Asp
            580                 585
```

<210> SEQ ID NO 277
<211> LENGTH: 588
<212> TYPE: PRT
<213> ORGANISM: Artificial Sequence
<220> FEATURE:
<223> OTHER INFORMATION: Synthetic

<400> SEQUENCE: 277

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350
```

```
Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Ala Gly Gly Gly Gly
            435                 440                 445

Ser Gly Gly Gly Gly Ser Gly Gly Gly Ser Ser Val Asn Asn Asp
450                 455                 460

Trp Ile Val Ala Ala Asn Asn Gly Ala Val Lys Phe Pro Gln Leu Cys
465                 470                 475                 480

Lys Phe Cys Asp Val Arg Phe Ser Thr Cys Asp Asn Gln Lys Ser Cys
                485                 490                 495

Met Ser Asn Cys Ser Ile Thr Ser Ile Cys Glu Lys Pro Gln Glu Val
            500                 505                 510

Cys Val Ala Val Trp Arg Lys Asn Asp Glu Asn Ile Thr Leu Glu Thr
            515                 520                 525

Val Cys His Asp Pro Lys Leu Pro Tyr His Asp Phe Ile Leu Glu Asp
            530                 535                 540

Ala Ala Ser Pro Lys Cys Ile Met Lys Glu Lys Lys Pro Gly Glu
545                 550                 555                 560

Thr Phe Phe Met Cys Ser Cys Ser Ser Asp Glu Cys Asn Asp Asn Ile
                565                 570                 575

Ile Phe Ser Glu Glu Tyr Asn Thr Ser Asn Pro Asp
                580                 585

<210> SEQ ID NO 278
<211> LENGTH: 588
<212> TYPE: PRT
<213> ORGANISM: Artificial Sequence
<220> FEATURE:
<223> OTHER INFORMATION: Synthetic

<400> SEQUENCE: 278

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125
```

```
Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Gly Ser Ser Val Asn Asn Asp
450                 455                 460

Trp Ile Val Ala Ala Asn Asn Trp Ala Val Lys Phe Pro Gln Leu Cys
465                 470                 475                 480

Lys Phe Cys Asp Val Arg Phe Ser Thr Cys Asp Asn Gln Lys Ser Cys
                485                 490                 495

Met Ser Asn Cys Ser Ile Thr Ser Ile Cys Glu Lys Pro Gln Glu Val
            500                 505                 510

Cys Val Ala Val Trp Arg Lys Asn Asp Glu Asn Ile Thr Leu Glu Thr
        515                 520                 525

Val Cys His Asp Pro Lys Leu Pro Tyr His Asp Phe Ile Leu Glu Asp
530                 535                 540

Ala Ala Ser Pro Lys Cys Ile Met Lys Glu Lys Lys Lys Pro Gly Glu
```

```
545                 550                 555                 560
Thr Phe Phe Met Cys Ser Cys Ser Ser Asp Glu Cys Asn Asp Asn Ile
                565                 570                 575

Ile Phe Ser Glu Glu Tyr Asn Thr Ser Asn Pro Asp
                580                 585

<210> SEQ ID NO 279
<211> LENGTH: 583
<212> TYPE: PRT
<213> ORGANISM: Artificial Sequence
<220> FEATURE:
<223> OTHER INFORMATION: Synthetic

<400> SEQUENCE: 279

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Phe Pro Gly Ser Gly Asn Ser Lys Tyr Asn Glu Asn Phe
        50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
```

```
                    325                 330                 335
Lys Gly Gln Pro Arg Glu Pro Gln Val Tyr Thr Leu Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly
        435                 440                 445

Ser Gly Gly Gly Gly Ser Gly Gly Gly Ser Met Ile Val Ser Asn
    450                 455                 460

Asn Asn Gly Ala Val Lys Phe Pro Gln Leu Cys Lys Phe Cys Asp Val
465                 470                 475                 480

Arg Phe Ser Thr Cys Asp Asn Gln Lys Ser Cys Met Ser Asn Cys Ser
                485                 490                 495

Ile Thr Ser Ile Cys Glu Lys Pro Gln Glu Val Cys Val Ala Val Trp
            500                 505                 510

Arg Lys Asn Asp Glu Asn Ile Thr Leu Glu Thr Val Cys His Asp Pro
        515                 520                 525

Lys Leu Pro Tyr His Asp Phe Ile Leu Glu Asp Ala Ala Ser Pro Lys
        530                 535                 540

Cys Ile Met Lys Glu Lys Lys Pro Gly Glu Thr Phe Phe Met Cys
545                 550                 555                 560

Ser Cys Ser Ser Asp Glu Cys Asn Asp Asn Ile Ile Phe Ser Glu Glu
                565                 570                 575

Tyr Asn Thr Ser Asn Pro Asp
            580

<210> SEQ ID NO 280
<211> LENGTH: 583
<212> TYPE: PRT
<213> ORGANISM: Artificial Sequence
<220> FEATURE:
<223> OTHER INFORMATION: Synthetic

<400> SEQUENCE: 280

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
```

```
            100                 105                 110
Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
            210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Ala Gly Gly Gly Gly
            435                 440                 445

Ser Gly Gly Gly Gly Ser Gly Gly Gly Gly Ser Met Ile Val Ser Ala
            450                 455                 460

Asn Asn Gly Ala Val Lys Phe Pro Gln Leu Cys Lys Phe Cys Asp Val
465                 470                 475                 480

Arg Phe Ser Thr Cys Asp Asn Gln Lys Ser Cys Met Ser Asn Cys Ser
                485                 490                 495

Ile Thr Ser Ile Cys Glu Lys Pro Gln Glu Val Cys Val Ala Val Trp
            500                 505                 510

Arg Lys Asn Asp Glu Asn Ile Thr Leu Glu Thr Val Cys His Asp Pro
            515                 520                 525
```

```
Lys Leu Pro Tyr His Asp Phe Ile Leu Glu Asp Ala Ala Ser Pro Lys
    530                 535                 540

Cys Ile Met Lys Glu Lys Lys Pro Gly Glu Thr Phe Phe Met Cys
545                 550                 555                 560

Ser Cys Ser Ser Asp Glu Cys Asn Asp Asn Ile Ile Phe Ser Glu Glu
                565                 570                 575

Tyr Asn Thr Ser Asn Pro Asp
            580

<210> SEQ ID NO 281
<211> LENGTH: 583
<212> TYPE: PRT
<213> ORGANISM: Artificial Sequence
<220> FEATURE:
<223> OTHER INFORMATION: Synthetic

<400> SEQUENCE: 281

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300
```

```
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Ser Met Ile Val Ala Ala
450                 455                 460

Asn Asn Gly Ala Val Lys Phe Pro Gln Leu Cys Lys Phe Cys Asp Val
465                 470                 475                 480

Arg Phe Ser Thr Cys Asp Asn Gln Lys Ser Cys Met Ser Asn Cys Ser
                485                 490                 495

Ile Thr Ser Ile Cys Glu Lys Pro Gln Glu Val Cys Val Ala Val Trp
            500                 505                 510

Arg Lys Asn Asp Glu Asn Ile Thr Leu Glu Thr Val Cys His Asp Pro
        515                 520                 525

Lys Leu Pro Tyr His Asp Phe Ile Leu Glu Asp Ala Ala Ser Pro Lys
    530                 535                 540

Cys Ile Met Lys Glu Lys Lys Pro Gly Glu Thr Phe Phe Met Cys
545                 550                 555                 560

Ser Cys Ser Ser Asp Glu Cys Asn Asp Asn Ile Ile Phe Ser Glu Glu
                565                 570                 575

Tyr Asn Thr Ser Asn Pro Asp
            580

<210> SEQ ID NO 282
<211> LENGTH: 583
<212> TYPE: PRT
<213> ORGANISM: Artificial Sequence
<220> FEATURE:
<223> OTHER INFORMATION: Synthetic

<400> SEQUENCE: 282

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Gly Ser Met Ile Val His His
    450                 455                 460

Asn Asn Gly Ala Val Lys Phe Pro Gln Leu Cys Lys Phe Cys Asp Val
465                 470                 475                 480

Arg Phe Ser Thr Cys Asp Asn Gln Lys Ser Cys Met Ser Asn Cys Ser
                485                 490                 495
```

-continued

Ile Thr Ser Ile Cys Glu Lys Pro Gln Val Cys Val Ala Val Trp
            500                 505                 510

Arg Lys Asn Asp Glu Asn Ile Thr Leu Glu Thr Val Cys His Asp Pro
        515                 520                 525

Lys Leu Pro Tyr His Asp Phe Ile Leu Glu Asp Ala Ala Ser Pro Lys
    530                 535                 540

Cys Ile Met Lys Glu Lys Lys Pro Gly Glu Thr Phe Phe Met Cys
545                 550                 555                 560

Ser Cys Ser Ser Asp Glu Cys Asn Asp Asn Ile Ile Phe Ser Glu Glu
                565                 570                 575

Tyr Asn Thr Ser Asn Pro Asp
            580

<210> SEQ ID NO 283
<211> LENGTH: 583
<212> TYPE: PRT
<213> ORGANISM: Artificial Sequence
<220> FEATURE:
<223> OTHER INFORMATION: Synthetic

<400> SEQUENCE: 283

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
            435                 440                 445

Ser Gly Gly Gly Gly Ser Gly Gly Gly Gly Ser Met Ile Val Pro Pro
450                 455                 460

Asn Asn Gly Ala Val Lys Phe Pro Gln Leu Cys Lys Phe Cys Asp Val
465                 470                 475                 480

Arg Phe Ser Thr Cys Asp Asn Gln Lys Ser Cys Met Ser Asn Cys Ser
            485                 490                 495

Ile Thr Ser Ile Cys Glu Lys Pro Gln Glu Val Cys Val Ala Val Trp
            500                 505                 510

Arg Lys Asn Asp Glu Asn Ile Thr Leu Glu Thr Val Cys His Asp Pro
            515                 520                 525

Lys Leu Pro Tyr His Asp Phe Ile Leu Glu Asp Ala Ala Ser Pro Lys
            530                 535                 540

Cys Ile Met Lys Glu Lys Lys Pro Gly Glu Thr Phe Phe Met Cys
545                 550                 555                 560

Ser Cys Ser Ser Asp Glu Cys Asn Asp Asn Ile Ile Phe Ser Glu Glu
            565                 570                 575

Tyr Asn Thr Ser Asn Pro Asp
            580

<210> SEQ ID NO 284
<211> LENGTH: 583
<212> TYPE: PRT
<213> ORGANISM: Artificial Sequence
<220> FEATURE:
<223> OTHER INFORMATION: Synthetic

<400> SEQUENCE: 284

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
            35                  40                  45

```
Gly Trp Ile Phe Pro Gly Ser Gly Asn Ser Lys Tyr Asn Glu Asn Phe
    50              55                  60

Lys Gly Arg Val Thr Leu Thr Ala Asp Thr Ser Thr Ser Thr Val Tyr
65              70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100             105             110

Val Thr Val Ser Ser Ala Ser Thr Lys Gly Pro Ser Val Phe Pro Leu
            115             120             125

Ala Pro Cys Ser Arg Ser Thr Ser Glu Ser Thr Ala Ala Leu Gly Cys
130             135             140

Leu Val Lys Asp Tyr Phe Pro Glu Pro Val Thr Val Ser Trp Asn Ser
145             150             155             160

Gly Ala Leu Thr Ser Gly Val His Thr Phe Pro Ala Val Leu Gln Ser
                165             170             175

Ser Gly Leu Tyr Ser Leu Ser Ser Val Val Thr Val Pro Ser Ser Ser
            180             185             190

Leu Gly Thr Lys Thr Tyr Thr Cys Asn Val Asp His Lys Pro Ser Asn
            195             200             205

Thr Lys Val Asp Lys Arg Val Glu Ser Lys Tyr Gly Pro Pro Cys Pro
210             215             220

Pro Cys Pro Ala Pro Glu Phe Leu Gly Gly Pro Ser Val Phe Leu Phe
225             230             235             240

Pro Pro Lys Pro Lys Asp Thr Leu Met Ile Ser Arg Thr Pro Glu Val
            245             250             255

Thr Cys Val Val Val Asp Val Ser Gln Glu Asp Pro Glu Val Gln Phe
            260             265             270

Asn Trp Tyr Val Asp Gly Val Glu Val His Asn Ala Lys Thr Lys Pro
            275             280             285

Arg Glu Glu Gln Phe Asn Ser Thr Tyr Arg Val Val Ser Val Leu Thr
290             295             300

Val Leu His Gln Asp Trp Leu Asn Gly Lys Glu Tyr Lys Cys Lys Val
305             310             315             320

Ser Asn Lys Gly Leu Pro Ser Ser Ile Glu Lys Thr Ile Ser Lys Ala
            325             330             335

Lys Gly Gln Pro Arg Glu Pro Gln Val Tyr Thr Leu Pro Pro Ser Gln
            340             345             350

Glu Glu Met Thr Lys Asn Gln Val Ser Leu Thr Cys Leu Val Lys Gly
            355             360             365

Phe Tyr Pro Ser Asp Ile Ala Val Glu Trp Glu Ser Asn Gly Gln Pro
370             375             380

Glu Asn Asn Tyr Lys Thr Thr Pro Pro Val Leu Asp Ser Asp Gly Ser
385             390             395             400

Phe Phe Leu Tyr Ser Arg Leu Thr Val Asp Lys Ser Arg Trp Gln Glu
            405             410             415

Gly Asn Val Phe Ser Cys Ser Val Met His Glu Ala Leu His Asn His
            420             425             430

Tyr Thr Gln Lys Ser Leu Ser Leu Ser Leu Gly Ala Gly Gly Gly Gly
            435             440             445

Ser Gly Gly Gly Gly Ser Gly Gly Gly Ser Trp Ile Val Ala Ala
450             455             460

Asn Asn Gly Ala Val Lys Phe Pro Gln Leu Cys Lys Phe Cys Asp Val
```

```
                465                 470                 475                 480
Arg Phe Ser Thr Cys Asp Asn Gln Lys Ser Cys Met Ser Asn Cys Ser
                485                 490                 495

Ile Thr Ser Ile Cys Glu Lys Pro Gln Glu Val Cys Val Ala Val Trp
                500                 505                 510

Arg Lys Asn Asp Glu Asn Ile Thr Leu Glu Thr Val Cys His Asp Pro
                515                 520                 525

Lys Leu Pro Tyr His Asp Phe Ile Leu Glu Asp Ala Ala Ser Pro Lys
                530                 535                 540

Cys Ile Met Lys Glu Lys Lys Pro Gly Glu Thr Phe Phe Met Cys
545                 550                 555                 560

Ser Cys Ser Ser Asp Glu Cys Asn Asp Asn Ile Ile Phe Ser Glu Glu
                565                 570                 575

Tyr Asn Thr Ser Asn Pro Asp
                580

<210> SEQ ID NO 285
<211> LENGTH: 583
<212> TYPE: PRT
<213> ORGANISM: Artificial Sequence
<220> FEATURE:
<223> OTHER INFORMATION: Synthetic

<400> SEQUENCE: 285

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Phe Pro Gly Ser Gly Asn Ser Lys Tyr Asn Glu Asn Phe
        50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
```

```
                245                 250                 255
Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
            435                 440                 445

Ser Gly Gly Gly Gly Ser Gly Gly Gly Gly Ser Trp Ile Val Ala Ala
        450                 455                 460

Asn Asn Trp Ala Val Lys Phe Pro Gln Leu Cys Lys Phe Cys Asp Val
465                 470                 475                 480

Arg Phe Ser Thr Cys Asp Asn Gln Lys Ser Cys Met Ser Asn Cys Ser
                485                 490                 495

Ile Thr Ser Ile Cys Glu Lys Pro Gln Glu Val Cys Val Ala Val Trp
            500                 505                 510

Arg Lys Asn Asp Glu Asn Ile Thr Leu Glu Thr Val Cys His Asp Pro
            515                 520                 525

Lys Leu Pro Tyr His Asp Phe Ile Leu Glu Asp Ala Ala Ser Pro Lys
        530                 535                 540

Cys Ile Met Lys Glu Lys Lys Pro Gly Glu Thr Phe Phe Met Cys
545                 550                 555                 560

Ser Cys Ser Ser Asp Glu Cys Asn Asp Asn Ile Ile Phe Ser Glu Glu
                565                 570                 575

Tyr Asn Thr Ser Asn Pro Asp
            580

<210> SEQ ID NO 286
<211> LENGTH: 582
<212> TYPE: PRT
<213> ORGANISM: Artificial Sequence
<220> FEATURE:
<223> OTHER INFORMATION: Synthetic

<400> SEQUENCE: 286

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

-continued

```
            20                  25                  30
Tyr Ile His Trp Val Arg Gln Ala Pro Gly Gln Gly Leu Glu Trp Met
             35                  40                  45
Gly Trp Ile Phe Pro Gly Ser Gly Asn Ser Lys Tyr Asn Glu Asn Phe
 50                  55                  60
Lys Gly Arg Val Thr Leu Thr Ala Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Ser Glu Thr Tyr Asp Tyr Gly Asp Tyr Trp Gly Gln Gly Thr Leu
                100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
            195                 200                 205
Thr Lys Val Asp Lys Arg Val Glu Ser Lys Tyr Gly Pro Pro Cys Pro
210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
            275                 280                 285
Arg Glu Glu Gln Phe Asn Ser Thr Tyr Arg Val Val Ser Val Leu Thr
            290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
            355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly Ala Gly Gly Gly Gly
            435                 440                 445
```

```
Ser Gly Gly Gly Gly Ser Gly Gly Gly Ser Ile Val Ser Asn Asn
            450             455             460

Asn Gly Ala Val Lys Phe Pro Gln Leu Cys Lys Phe Cys Asp Val Arg
465             470             475             480

Phe Ser Thr Cys Asp Asn Gln Lys Ser Cys Met Ser Asn Cys Ser Ile
                485             490             495

Thr Ser Ile Cys Glu Lys Pro Gln Glu Val Cys Val Ala Val Trp Arg
            500             505             510

Lys Asn Asp Glu Asn Ile Thr Leu Glu Thr Val Cys His Asp Pro Lys
        515             520             525

Leu Pro Tyr His Asp Phe Ile Leu Glu Asp Ala Ala Ser Pro Lys Cys
            530             535             540

Ile Met Lys Glu Lys Lys Lys Pro Gly Glu Thr Phe Phe Met Cys Ser
545             550             555             560

Cys Ser Ser Asp Glu Cys Asn Asp Asn Ile Ile Phe Ser Glu Glu Tyr
                565             570             575

Asn Thr Ser Asn Pro Asp
            580

<210> SEQ ID NO 287
<211> LENGTH: 582
<212> TYPE: PRT
<213> ORGANISM: Artificial Sequence
<220> FEATURE:
<223> OTHER INFORMATION: Synthetic

<400> SEQUENCE: 287

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220
```

```
Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Gly Ser Ile Val Ser Ala Asn
    450                 455                 460

Asn Gly Ala Val Lys Phe Pro Gln Leu Cys Lys Phe Cys Asp Val Arg
465                 470                 475                 480

Phe Ser Thr Cys Asp Asn Gln Lys Ser Cys Met Ser Asn Cys Ser Ile
                485                 490                 495

Thr Ser Ile Cys Glu Lys Pro Gln Glu Val Cys Val Ala Val Trp Arg
            500                 505                 510

Lys Asn Asp Glu Asn Ile Thr Leu Glu Thr Val Cys His Asp Pro Lys
            515                 520                 525

Leu Pro Tyr His Asp Phe Ile Leu Glu Asp Ala Ala Ser Pro Lys Cys
        530                 535                 540

Ile Met Lys Glu Lys Lys Lys Pro Gly Glu Thr Phe Phe Met Cys Ser
545                 550                 555                 560

Cys Ser Ser Asp Glu Cys Asn Asp Asn Ile Ile Phe Ser Glu Glu Tyr
                565                 570                 575

Asn Thr Ser Asn Pro Asp
            580

<210> SEQ ID NO 288
<211> LENGTH: 582
<212> TYPE: PRT
<213> ORGANISM: Artificial Sequence
<220> FEATURE:
<223> OTHER INFORMATION: Synthetic

<400> SEQUENCE: 288
```

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly
            435                 440                 445

Ser Gly Gly Gly Ser Gly Gly Gly Ser Ile Val Ala Ala Asn
    450                 455                 460

Asn Gly Ala Val Lys Phe Pro Gln Leu Cys Lys Phe Cys Asp Val Arg
465                 470                 475                 480

Phe Ser Thr Cys Asp Asn Gln Lys Ser Cys Met Ser Asn Cys Ser Ile
                485                 490                 495

Thr Ser Ile Cys Glu Lys Pro Gln Glu Val Cys Val Ala Val Trp Arg
            500                 505                 510

Lys Asn Asp Glu Asn Ile Thr Leu Glu Thr Val Cys His Asp Pro Lys
            515                 520                 525

Leu Pro Tyr His Asp Phe Ile Leu Glu Asp Ala Ala Ser Pro Lys Cys
            530                 535                 540

Ile Met Lys Glu Lys Lys Pro Gly Glu Thr Phe Phe Met Cys Ser
545                 550                 555                 560

Cys Ser Ser Asp Glu Cys Asn Asp Asn Ile Ile Phe Ser Glu Glu Tyr
                565                 570                 575

Asn Thr Ser Asn Pro Asp
            580

<210> SEQ ID NO 289
<211> LENGTH: 582
<212> TYPE: PRT
<213> ORGANISM: Artificial Sequence
<220> FEATURE:
<223> OTHER INFORMATION: Synthetic

<400> SEQUENCE: 289

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
            435                 440                 445

Ser Gly Gly Gly Gly Ser Gly Gly Gly Gly Ser Ile Val His His Asn
450                 455                 460

Asn Gly Ala Val Lys Phe Pro Gln Leu Cys Lys Phe Cys Asp Val Arg
465                 470                 475                 480

Phe Ser Thr Cys Asp Asn Gln Lys Ser Cys Met Ser Asn Cys Ser Ile
                485                 490                 495

Thr Ser Ile Cys Glu Lys Pro Gln Glu Val Cys Val Ala Val Trp Arg
            500                 505                 510

Lys Asn Asp Glu Asn Ile Thr Leu Glu Thr Val Cys His Asp Pro Lys
515                 520                 525

Leu Pro Tyr His Asp Phe Ile Leu Glu Asp Ala Ala Ser Pro Lys Cys
530                 535                 540

Ile Met Lys Glu Lys Lys Pro Gly Glu Thr Phe Phe Met Cys Ser
545                 550                 555                 560

Cys Ser Ser Asp Glu Cys Asn Asp Asn Ile Ile Phe Ser Glu Glu Tyr
                565                 570                 575

Asn Thr Ser Asn Pro Asp
            580

<210> SEQ ID NO 290
<211> LENGTH: 582
<212> TYPE: PRT

<213> ORGANISM: Artificial Sequence
<220> FEATURE:
<223> OTHER INFORMATION: Synthetic

<400> SEQUENCE: 290

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser

```
                385                 390                 395                 400
        Phe Phe Leu Tyr Ser Arg Leu Thr Val Asp Lys Ser Arg Trp Gln Glu
                        405                 410                 415

Gly Asn Val Phe Ser Cys Ser Val Met His Glu Ala Leu His Asn His
                    420                 425                 430

Tyr Thr Gln Lys Ser Leu Ser Leu Ser Leu Gly Ala Gly Gly Gly
                        435                 440                 445

Ser Gly Gly Gly Ser Gly Gly Gly Ser Ile Val Pro Pro Asn
        450                 455                 460

Asn Gly Ala Val Lys Phe Pro Gln Leu Cys Lys Phe Cys Asp Val Arg
        465                 470                 475                 480

Phe Ser Thr Cys Asp Asn Gln Lys Ser Cys Met Ser Asn Cys Ser Ile
                        485                 490                 495

Thr Ser Ile Cys Glu Lys Pro Gln Glu Val Cys Val Ala Val Trp Arg
                    500                 505                 510

Lys Asn Asp Glu Asn Ile Thr Leu Glu Thr Val Cys His Asp Pro Lys
                        515                 520                 525

Leu Pro Tyr His Asp Phe Ile Leu Glu Asp Ala Ala Ser Pro Lys Cys
                    530                 535                 540

Ile Met Lys Glu Lys Lys Pro Gly Glu Thr Phe Phe Met Cys Ser
        545                 550                 555                 560

Cys Ser Ser Asp Glu Cys Asn Asp Asn Ile Ile Phe Ser Glu Glu Tyr
                        565                 570                 575

Asn Thr Ser Asn Pro Asp
                        580

<210> SEQ ID NO 291
<211> LENGTH: 597
<212> TYPE: PRT
<213> ORGANISM: Artificial Sequence
<220> FEATURE:
<223> OTHER INFORMATION: Synthetic

<400> SEQUENCE: 291

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
```

-continued

```
                165                 170                 175
Pro Ala Val Leu Gln Ser Ser Gly Leu Tyr Ser Leu Ser Ser Val Val
                180                 185                 190

Thr Val Pro Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Ala Gly Gly Gly Ser Gly Gly Gly Ser Gly
    450                 455                 460

Gly Gly Ser Gly Gly Gly Ser Met Ile Val Ser Asn Asn
465                 470                 475                 480

Gly Ala Val Lys Phe Pro Gln Leu Cys Lys Phe Cys Asp Val Arg Phe
                485                 490                 495

Ser Thr Cys Asp Asn Gln Lys Ser Cys Met Ser Asn Cys Ser Ile Thr
            500                 505                 510

Ser Ile Cys Glu Lys Pro Gln Glu Val Cys Val Ala Val Trp Arg Lys
        515                 520                 525

Asn Asp Glu Asn Ile Thr Leu Glu Thr Val Cys His Asp Pro Lys Leu
    530                 535                 540

Pro Tyr His Asp Phe Ile Leu Glu Asp Ala Ala Ser Pro Lys Cys Ile
545                 550                 555                 560

Met Lys Glu Lys Lys Lys Pro Gly Glu Thr Phe Phe Met Cys Ser Cys
                565                 570                 575

Ser Ser Asp Glu Cys Asn Asp Asn Ile Ile Phe Ser Glu Glu Tyr Asn
            580                 585                 590
```

Thr Ser Asn Pro Asp
        595

<210> SEQ ID NO 292
<211> LENGTH: 597
<212> TYPE: PRT
<213> ORGANISM: Artificial Sequence
<220> FEATURE:
<223> OTHER INFORMATION: Synthetic

<400> SEQUENCE: 292

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

-continued

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Ala Gly Gly Gly Ser Gly Gly Gly Ser Gly
    450                 455                 460

Gly Gly Gly Ser Gly Gly Gly Ser Met Ile Val Ser Ala Asn Asn
465                 470                 475                 480

Gly Ala Val Lys Phe Pro Gln Leu Cys Lys Phe Cys Asp Val Arg Phe
                485                 490                 495

Ser Thr Cys Asp Asn Gln Lys Ser Cys Met Ser Asn Cys Ser Ile Thr
            500                 505                 510

Ser Ile Cys Glu Lys Pro Gln Glu Val Cys Val Ala Val Trp Arg Lys
        515                 520                 525

Asn Asp Glu Asn Ile Thr Leu Glu Thr Val Cys His Asp Pro Lys Leu
530                 535                 540

Pro Tyr His Asp Phe Ile Leu Glu Asp Ala Ala Ser Pro Lys Cys Ile
545                 550                 555                 560

Met Lys Glu Lys Lys Lys Pro Gly Glu Thr Phe Phe Met Cys Ser Cys
                565                 570                 575

Ser Ser Asp Glu Cys Asn Asp Asn Ile Ile Phe Ser Glu Glu Tyr Asn
            580                 585                 590

Thr Ser Asn Pro Asp
        595

<210> SEQ ID NO 293
<211> LENGTH: 597
<212> TYPE: PRT
<213> ORGANISM: Artificial Sequence
<220> FEATURE:
<223> OTHER INFORMATION: Synthetic

<400> SEQUENCE: 293

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Ala Gly Gly Gly Ser Gly Gly Gly Ser Gly
    450                 455                 460

Gly Gly Gly Ser Gly Gly Gly Ser Met Ile Val Ala Ala Asn Asn
465                 470                 475                 480

Gly Ala Val Lys Phe Pro Gln Leu Cys Lys Phe Cys Asp Val Arg Phe
                485                 490                 495

Ser Thr Cys Asp Asn Gln Lys Ser Cys Met Ser Asn Cys Ser Ile Thr
            500                 505                 510

Ser Ile Cys Glu Lys Pro Gln Glu Val Cys Val Ala Val Trp Arg Lys
        515                 520                 525

```
Asn Asp Glu Asn Ile Thr Leu Glu Thr Val Cys His Asp Pro Lys Leu
    530                 535                 540

Pro Tyr His Asp Phe Ile Leu Glu Asp Ala Ala Ser Pro Lys Cys Ile
545                 550                 555                 560

Met Lys Glu Lys Lys Lys Pro Gly Glu Thr Phe Phe Met Cys Ser Cys
                565                 570                 575

Ser Ser Asp Glu Cys Asn Asp Asn Ile Ile Phe Ser Glu Glu Tyr Asn
            580                 585                 590

Thr Ser Asn Pro Asp
        595

<210> SEQ ID NO 294
<211> LENGTH: 597
<212> TYPE: PRT
<213> ORGANISM: Artificial Sequence
<220> FEATURE:
<223> OTHER INFORMATION: Synthetic

<400> SEQUENCE: 294

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Ala Gly Gly Gly Ser Gly Gly Gly Ser Gly
450                 455                 460

Gly Gly Gly Ser Gly Gly Gly Ser Met Ile Val His Asn Asn
465                 470                 475                 480

Gly Ala Val Lys Phe Pro Gln Leu Cys Lys Phe Cys Asp Val Arg Phe
            485                 490                 495

Ser Thr Cys Asp Asn Gln Lys Ser Cys Met Ser Asn Cys Ser Ile Thr
            500                 505                 510

Ser Ile Cys Glu Lys Pro Gln Glu Val Cys Val Ala Val Trp Arg Lys
            515                 520                 525

Asn Asp Glu Asn Ile Thr Leu Glu Thr Val Cys His Asp Pro Lys Leu
            530                 535                 540

Pro Tyr His Asp Phe Ile Leu Glu Asp Ala Ala Ser Pro Lys Cys Ile
545                 550                 555                 560

Met Lys Glu Lys Lys Lys Pro Gly Glu Thr Phe Phe Met Cys Ser Cys
            565                 570                 575

Ser Ser Asp Glu Cys Asn Asp Asn Ile Ile Phe Ser Glu Glu Tyr Asn
            580                 585                 590

Thr Ser Asn Pro Asp
            595

<210> SEQ ID NO 295
<211> LENGTH: 597
<212> TYPE: PRT
<213> ORGANISM: Artificial Sequence
<220> FEATURE:
<223> OTHER INFORMATION: Synthetic

<400> SEQUENCE: 295

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

-continued

```
Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Ala Gly Gly Gly Ser Gly Gly Gly Ser Gly
    450                 455                 460

Gly Gly Gly Ser Gly Gly Gly Gly Ser Met Ile Val Pro Pro Asn Asn
```

```
                465                 470                 475                 480
Gly Ala Val Lys Phe Pro Gln Leu Cys Lys Phe Cys Asp Val Arg Phe
                    485                 490                 495
Ser Thr Cys Asp Asn Gln Lys Ser Cys Met Ser Asn Cys Ser Ile Thr
                500                 505                 510
Ser Ile Cys Glu Lys Pro Gln Glu Val Cys Val Ala Val Trp Arg Lys
                515                 520                 525
Asn Asp Glu Asn Ile Thr Leu Glu Thr Val Cys His Asp Pro Lys Leu
            530                 535                 540
Pro Tyr His Asp Phe Ile Leu Glu Asp Ala Ala Ser Pro Lys Cys Ile
545                 550                 555                 560
Met Lys Glu Lys Lys Lys Pro Gly Glu Thr Phe Phe Met Cys Ser Cys
                565                 570                 575
Ser Ser Asp Glu Cys Asn Asp Asn Ile Ile Phe Ser Glu Glu Tyr Asn
                580                 585                 590
Thr Ser Asn Pro Asp
            595
```

<210> SEQ ID NO 296
<211> LENGTH: 597
<212> TYPE: PRT
<213> ORGANISM: Artificial Sequence
<220> FEATURE:
<223> OTHER INFORMATION: Synthetic

<400> SEQUENCE: 296

```
Glu Val Gln Leu Val Gln Ser Gly Gly Gly Val Val Gln Pro Gly Gly
1               5                   10                  15
Ser Leu Arg Leu Ser Cys Ala Ala Ser Gly Tyr Thr Phe Thr Asn Tyr
                20                  25                  30
Gly Met Asn Trp Val Arg Gln Ala Pro Gly Lys Gly Leu Glu Trp Val
            35                  40                  45
Gly Trp Ile Asn Thr Tyr Thr Gly Glu Pro Thr Tyr Ala Ala Asp Phe
        50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
                100                 105                 110
Trp Gly Gln Gly Thr Leu Val Thr Val Ser Ser Ala Ser Thr Lys Gly
            115                 120                 125
Pro Ser Val Phe Pro Leu Ala Pro Ser Ser Lys Ser Thr Ser Gly Gly
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
            195                 200                 205
Asn His Lys Pro Ser Asn Thr Lys Val Asp Lys Arg Val Glu Pro Lys
        210                 215                 220
Ser Cys Asp Lys Thr His Thr Cys Pro Pro Cys Pro Ala Pro Glu Leu
```

```
            225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
                275                 280                 285
Glu Val His Asn Ala Lys Thr Lys Pro Arg Glu Gln Tyr Asn Ser
        290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Glu Glu Met Thr Lys Asn Gln
                355                 360                 365
Val Ser Leu Thr Cys Leu Val Lys Gly Phe Tyr Pro Ser Asp Ile Ala
        370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
        435                 440                 445
Leu Ser Pro Gly Ala Gly Gly Gly Ser Gly Gly Gly Ser
        450                 455                 460
Gly Gly Gly Ser Gly Gly Gly Ser Trp Ile Val Ala Ala Asn Asn
465                 470                 475                 480
Gly Ala Val Lys Phe Pro Gln Leu Cys Lys Phe Cys Asp Val Arg Phe
                485                 490                 495
Ser Thr Cys Asp Asn Gln Lys Ser Cys Met Ser Asn Cys Ser Ile Thr
                500                 505                 510
Ser Ile Cys Glu Lys Pro Gln Glu Val Cys Val Ala Val Trp Arg Lys
                515                 520                 525
Asn Asp Glu Asn Ile Thr Leu Glu Thr Val Cys His Asp Pro Lys Leu
        530                 535                 540
Pro Tyr His Asp Phe Ile Leu Glu Asp Ala Ala Ser Pro Lys Cys Ile
545                 550                 555                 560
Met Lys Glu Lys Lys Pro Gly Glu Thr Phe Phe Met Cys Ser Cys
                565                 570                 575
Ser Ser Asp Glu Cys Asn Asp Asn Ile Ile Phe Ser Glu Glu Tyr Asn
        580                 585                 590
Thr Ser Asn Pro Asp
        595

<210> SEQ ID NO 297
<211> LENGTH: 597
<212> TYPE: PRT
<213> ORGANISM: Artificial Sequence
<220> FEATURE:
<223> OTHER INFORMATION: Synthetic
```

<400> SEQUENCE: 297

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

```
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Ala Gly Gly Gly Ser Gly Gly Gly Ser Gly
450                 455                 460

Gly Gly Gly Ser Gly Gly Gly Ser Trp Ile Val Ala Ala Asn Asn
465                 470                 475                 480

Trp Ala Val Lys Phe Pro Gln Leu Cys Lys Phe Cys Asp Val Arg Phe
                485                 490                 495

Ser Thr Cys Asp Asn Gln Lys Ser Cys Met Ser Asn Cys Ser Ile Thr
            500                 505                 510

Ser Ile Cys Glu Lys Pro Gln Glu Val Cys Val Ala Val Trp Arg Lys
        515                 520                 525

Asn Asp Glu Asn Ile Thr Leu Glu Thr Val Cys His Asp Pro Lys Leu
530                 535                 540

Pro Tyr His Asp Phe Ile Leu Glu Asp Ala Ala Ser Pro Lys Cys Ile
545                 550                 555                 560

Met Lys Glu Lys Lys Pro Gly Glu Thr Phe Phe Met Cys Ser Cys
                565                 570                 575

Ser Ser Asp Glu Cys Asn Asp Asn Ile Ile Phe Ser Glu Tyr Asn
            580                 585                 590

Thr Ser Asn Pro Asp
        595

<210> SEQ ID NO 298
<211> LENGTH: 596
<212> TYPE: PRT
<213> ORGANISM: Artificial Sequence
<220> FEATURE:
<223> OTHER INFORMATION: Synthetic

<400> SEQUENCE: 298

Glu Val Gln Leu Val Gln Ser Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
            195                 200                 205
Asn His Lys Pro Ser Asn Thr Lys Val Asp Lys Arg Val Glu Pro Lys
        210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Ala Gly Gly Gly Ser Gly Gly Gly Gly Ser Gly
450                 455                 460
Gly Gly Ser Gly Gly Gly Gly Ser Ile Val Ser Asn Asn Asn Gly
465                 470                 475                 480
Ala Val Lys Phe Pro Gln Leu Cys Lys Phe Cys Asp Val Arg Phe Ser
                485                 490                 495
Thr Cys Asp Asn Gln Lys Ser Cys Met Ser Asn Cys Ser Ile Thr Ser
            500                 505                 510
Ile Cys Glu Lys Pro Gln Glu Val Cys Val Ala Val Trp Arg Lys Asn
        515                 520                 525
Asp Glu Asn Ile Thr Leu Glu Thr Val Cys His Asp Pro Lys Leu Pro
530                 535                 540
Tyr His Asp Phe Ile Leu Glu Asp Ala Ala Ser Pro Lys Cys Ile Met
545                 550                 555                 560
Lys Glu Lys Lys Lys Pro Gly Glu Thr Phe Phe Met Cys Ser Cys Ser
                565                 570                 575
Ser Asp Glu Cys Asn Asp Asn Ile Ile Phe Ser Glu Glu Tyr Asn Thr
            580                 585                 590
```

Ser Asn Pro Asp
        595

<210> SEQ ID NO 299
<211> LENGTH: 596
<212> TYPE: PRT
<213> ORGANISM: Artificial Sequence
<220> FEATURE:
<223> OTHER INFORMATION: Synthetic

<400> SEQUENCE: 299

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Ala Gly Gly Gly Ser Gly Gly Gly Ser Gly
        450                 455                 460

Gly Gly Gly Ser Gly Gly Gly Ser Ile Val Ser Ala Asn Asn Gly
465                 470                 475                 480

Ala Val Lys Phe Pro Gln Leu Cys Lys Phe Cys Asp Val Arg Phe Ser
            485                 490                 495

Thr Cys Asp Asn Gln Lys Ser Cys Met Ser Asn Cys Ser Ile Thr Ser
        500                 505                 510

Ile Cys Glu Lys Pro Gln Glu Val Cys Val Ala Val Trp Arg Lys Asn
        515                 520                 525

Asp Glu Asn Ile Thr Leu Glu Thr Val Cys His Asp Pro Lys Leu Pro
        530                 535                 540

Tyr His Asp Phe Ile Leu Glu Asp Ala Ala Ser Pro Lys Cys Ile Met
545                 550                 555                 560

Lys Glu Lys Lys Lys Pro Gly Glu Thr Phe Phe Met Cys Ser Cys Ser
            565                 570                 575

Ser Asp Glu Cys Asn Asp Asn Ile Ile Phe Ser Glu Glu Tyr Asn Thr
            580                 585                 590

Ser Asn Pro Asp
        595

<210> SEQ ID NO 300
<211> LENGTH: 596
<212> TYPE: PRT
<213> ORGANISM: Artificial Sequence
<220> FEATURE:
<223> OTHER INFORMATION: Synthetic

<400> SEQUENCE: 300

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Gly Ser Ser His Trp Tyr Phe Asp Val
            100                 105                 110

-continued

Trp Gly Gln Gly Thr Leu Val Thr Val Ser Ser Ala Ser Thr Lys Gly
115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Ala Gly Gly Gly Ser Gly Gly Gly Ser Gly
450                 455                 460

Gly Gly Gly Ser Gly Gly Gly Gly Ser Ile Val Ala Ala Asn Gly
465                 470                 475                 480

Ala Val Lys Phe Pro Gln Leu Cys Lys Phe Cys Asp Val Arg Phe Ser
            485                 490                 495

Thr Cys Asp Asn Gln Lys Ser Cys Met Ser Asn Cys Ser Ile Thr Ser
            500                 505                 510

Ile Cys Glu Lys Pro Gln Glu Val Cys Val Ala Val Trp Arg Lys Asn
            515                 520                 525

Asp Glu Asn Ile Thr Leu Glu Thr Val Cys His Asp Pro Lys Leu Pro

```
                530              535              540
Tyr His Asp Phe Ile Leu Glu Asp Ala Ala Ser Pro Lys Cys Ile Met
545                      550                  555                  560

Lys Glu Lys Lys Lys Pro Gly Glu Thr Phe Phe Met Cys Ser Cys Ser
                    565                  570                  575

Ser Asp Glu Cys Asn Asp Asn Ile Ile Phe Ser Glu Glu Tyr Asn Thr
                580                  585                  590

Ser Asn Pro Asp
        595

<210> SEQ ID NO 301
<211> LENGTH: 596
<212> TYPE: PRT
<213> ORGANISM: Artificial Sequence
<220> FEATURE:
<223> OTHER INFORMATION: Synthetic

<400> SEQUENCE: 301

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
```

```
                290                 295                 300
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Ala Gly Gly Gly Ser Gly Gly Gly Ser Gly
    450                 455                 460

Gly Gly Ser Gly Gly Gly Ser Ile Val His Asn Asn Gly
465                 470                 475                 480

Ala Val Lys Phe Pro Gln Leu Cys Lys Phe Cys Asp Val Arg Phe Ser
                485                 490                 495

Thr Cys Asp Asn Gln Lys Ser Cys Met Ser Asn Cys Ser Ile Thr Ser
            500                 505                 510

Ile Cys Glu Lys Pro Gln Glu Val Cys Val Ala Val Trp Arg Lys Asn
        515                 520                 525

Asp Glu Asn Ile Thr Leu Glu Thr Val Cys His Asp Pro Lys Leu Pro
530                 535                 540

Tyr His Asp Phe Ile Leu Glu Asp Ala Ala Ser Pro Lys Cys Ile Met
545                 550                 555                 560

Lys Glu Lys Lys Lys Pro Gly Glu Thr Phe Phe Met Cys Ser Cys Ser
                565                 570                 575

Ser Asp Glu Cys Asn Asp Asn Ile Ile Phe Ser Glu Glu Tyr Asn Thr
            580                 585                 590

Ser Asn Pro Asp
        595

<210> SEQ ID NO 302
<211> LENGTH: 596
<212> TYPE: PRT
<213> ORGANISM: Artificial Sequence
<220> FEATURE:
<223> OTHER INFORMATION: Synthetic

<400> SEQUENCE: 302

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
```

```
                50                  55                  60
Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Ala Gly Gly Gly Ser Gly Gly Gly Ser Gly
                450                 455                 460

Gly Gly Gly Ser Gly Gly Gly Gly Ser Ile Val Pro Pro Asn Asn Gly
465                 470                 475                 480
```

```
Ala Val Lys Phe Pro Gln Leu Cys Lys Phe Cys Asp Val Arg Phe Ser
            485                 490                 495

Thr Cys Asp Asn Gln Lys Ser Cys Met Ser Asn Cys Ser Ile Thr Ser
            500                 505                 510

Ile Cys Glu Lys Pro Gln Glu Val Cys Val Ala Val Trp Arg Lys Asn
            515                 520                 525

Asp Glu Asn Ile Thr Leu Glu Thr Val Cys His Asp Pro Lys Leu Pro
            530                 535                 540

Tyr His Asp Phe Ile Leu Glu Asp Ala Ala Ser Pro Lys Cys Ile Met
545                 550                 555                 560

Lys Glu Lys Lys Lys Pro Gly Glu Thr Phe Phe Met Cys Ser Cys Ser
            565                 570                 575

Ser Asp Glu Cys Asn Asp Asn Ile Ile Phe Ser Glu Glu Tyr Asn Thr
            580                 585                 590

Ser Asn Pro Asp
            595

<210> SEQ ID NO 303
<211> LENGTH: 595
<212> TYPE: PRT
<213> ORGANISM: Artificial Sequence
<220> FEATURE:
<223> OTHER INFORMATION: Synthetic

<400> SEQUENCE: 303

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Met Ile His Pro Asn Ser Gly Asn Asn Tyr Asn Glu Lys Phe
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Ser Trp Tyr Gly Ser Ser Pro Tyr Tyr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Leu Leu Gly
225                 230                 235                 240
```

```
Gly Pro Ser Val Phe Leu Phe Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Ala Gly Gly Gly Ser Gly Gly Gly Ser Gly Gly Gly
    450                 455                 460

Gly Ser Gly Gly Gly Ser Met Ile Val Pro Pro Asn Asn Gly Ala
465                 470                 475                 480

Val Lys Phe Pro Gln Leu Cys Lys Phe Cys Asp Val Arg Phe Ser Thr
                485                 490                 495

Cys Asp Asn Gln Lys Ser Cys Met Ser Asn Cys Ser Ile Thr Ser Ile
            500                 505                 510

Cys Glu Lys Pro Gln Glu Val Cys Val Ala Val Trp Arg Lys Asn Asp
        515                 520                 525

Glu Asn Ile Thr Leu Glu Thr Val Cys His Asp Pro Lys Leu Pro Tyr
    530                 535                 540

His Asp Phe Ile Leu Glu Asp Ala Ala Ser Pro Lys Cys Ile Met Lys
545                 550                 555                 560

Glu Lys Lys Lys Pro Gly Glu Thr Phe Phe Met Cys Ser Cys Ser Ser
                565                 570                 575

Asp Glu Cys Asn Asp Asn Ile Ile Phe Ser Glu Glu Tyr Asn Thr Ser
            580                 585                 590

Asn Pro Asp
    595
```

ANTAGONISTS TARGETING THE TGF-β PATHWAY

This application is a continuation application of Ser. No. 16/706,187, filed Dec. 6, 2019, which claims priority to U.S. Provisional Patent Application Ser. No. 62/869,111, filed on Jul. 1, 2019. The entirety of all the aforementioned application is expressly incorporated herein by reference for all purposes.

FIELD

The present application relates generally to cancer treatment and, in particular, to bispecific inhibitors capable of modulating pathways associated with tumorigenesis, tumor immunity, and angiogenesis.

BACKGROUND

The inability of the host to eliminate cancer cells remains a major problem. Although an increasing number of therapeutic monoclonal antibodies have been approved for treatment of various cancers, emergence of resistance to these antibodies is frequently observed, given the many different molecular pathways underlying cancer growth and progression to metastasis. Although the immune system is the principal mechanism of cancer prevention, cancer cells counteract immunosurveillance. Natural control mechanisms have been identified that limit T-cell activation so as to prevent collateral damage resulting from unrestrained T-cell activity. This process has been exploited by tumor cells to evade immune responses. Restoring the capacity of immune effector cells, especially T cells, to recognize and eliminate cancer is a major objective in immunotherapy.

The need exists for improved therapeutic binding antagonists or antibodies and methods of treating cancer and chronic viral infections with such reagents.

SUMMARY

The inventors of the present application have discovered that antagonists bearing a TGFβ1 RII ECD domain exhibit unacceptable levels of proteolytic degradation or clipping over time. One aspect of the present application relates to antitumor antagonists containing a first targeting domain specifically binding TGFβ1 and a second targeting domain specifically binding PD-1 or PD-L1, wherein the first targeting domain contains a mutated TGF-β1 RII extracellular domain (mutated ECD) that significantly reduces proteolytic cleavage of the antitumor antagonist.

Another aspect of the present application relates to an antitumor antagonist containing a first targeting domain comprising a TGFβ pathway inhibitor, and a second targeting domain that binds specifically to VEGF.

Another aspect of the present application relates to methods for treating a cell proliferative disorder in a subject. The method comprises the step of administering to a subject in need of such treatment an effective amount the antitumor antagonist of the present application.

BRIEF DESCRIPTION OF THE DRAWINGS

FIG. 1 shows complementary determining region (CDR) sequences of certain anti-PD-1 mabs. The corresponding framework region (FR) sequences are listed in FIG. 53 as SEQ ID NOS: 176-205.

FIGS. 2A-2B show several embodiments of anti-PD-1 antibody variable domain sequences.

FIG. 3 shows CDR sequences of certain anti-PD-L1 mabs. The corresponding FR sequences are listed in FIG. 53 as SEQ ID NOS: 206-228.

FIGS. 4A-4C show several embodiments of anti-PD-L1 antibody variable domain sequences.

FIG. 6 shows exemplary functional domain sequences corresponding to the bispecific antibodies in FIG. 5.

FIG. 7 shows exemplary heavy chain (HC) and light chain (LC) sequences corresponding to selected bispecific antibodies in FIG. 5.

FIGS. 9A and 9B show the various functional domain sequences present in the bispecific antagonists depicted in FIG. 8.

FIG. 10 shows the heavy chain (HC) and light chain (LC) amino acid sequences corresponding to the bispecific antagonists depicted in FIG. 8.

FIG. 11 summarizes the arrangement of functional domains in the bispecific antagonists depicted in FIG. 8.

FIGS. 20A-20B depict two bispecific antitumor antagonists, Bi-PB-1.2 (FIG. 20A) and Bi-PLB-1.2 (FIG. 20B), each comprising antibody backbone (IgG4 K447A or IgG1 K447A) with variable region domains from anti-PD-1 and anti-PD-L1, respectively, and additionally including a TGF-β-RII ECD fused to the carboxy-terminal end of each heavy chain CH3 region.

FIG. 21 shows functional domain sequences present in the bispecific antibodies in FIGS. 20A and 20B.

FIG. 22 show the heavy chain (HC) and light chain (LC) amino acid sequences corresponding to the bispecific antagonists depicted in FIGS. 20A and 20B.

FIG. 23 summarizes the arrangement of functional domains in the bispecific antagonists depicted in FIGS. 20A and 20B.

FIG. 24A shows a non-denaturing polyacrylamide gel (PAGE) analysis showing the expression of Bi-PB-1.2 and Bi-PLB-1.2 in a transient expression system in comparison to 1 μg of parental control antibody (2P17). FIG. 24B depicts size exclusion chromatography (SEC) profiles showing of protein A purified Bi-PB-1.2, Bi-PLB-1.2 and an anti-PDL1-TGF-β1 RII ECD benchmark molecule. FIG. 24C shows that Bi-PB-1.2, Bi-PLB-1.2 and the anti-PDL1-TGF-β1 RII ECD benchmark molecule have low levels of high molecular weight (HMW) low molecular weight (LMW) species in comparison to dimers.

FIGS. 27A-27E show the results of PD-L1 and TGF-β1 binding to Bi-PLB-1.2 (27A, 27B, respectively) and the anti-PDL1-TGF-β1 RII ECD benchmark molecule (27C, 27D), along with their resultant binding affinity constants (27E).

FIGS. 33A-33B show increased IFN-γ secretion from human PBMCs (Donor 1, FIG. 33A; Donor 2, FIG. 33B) with Bi-PB-1.2 relative to the negative control treatments. FIGS. 33C-33D show increased IL-2 section from human PBMCs (Donor 1, FIG. 33C; Donor 2, FIG. 33D) with Bi-PB-1.2 relative to the negative control treatments.

FIGS. 34A-34B show increased IFN-γ secretion from human PBMCs (Donor 8, FIG. 34A; Donor 9, FIG. 34B) with Bi-PLB-1.2 relative to the parental anti-PD-L1 antibody and the negative control treatments. FIGS. 34C-34D show increased IL-2 section from human PBMCs (Donor 8, FIG. 34C; Donor 9, FIG. 34D) with Bi-PLB-1.2 relative to the parental anti-PD-L1 antibody and negative control treatments.

FIG. 39 identifies fragments and clipped fragments identified by mass spectrometry showing that Bi-A1B-1 and Bi-PB-1.2 have similar clipping sites.

FIGS. 40A and 40B show the location of clip sites in the heavy chain amino acid sequences of Bi-A1B-1 and Bi-PB-1.2, respectively, based on mass spectrometry.

FIGS. 41A-41C shows various mutant TGF-β1 RII ECD sequences for investigating clipping of the wild-type TGF-β1 RII ECD.

FIGS. 42A-41H show Bi-PB-1.2 heavy chain sequences containing the mutant TGF-β1 RII ECD sequences in FIGS. 41A-41C. Analysis of these mutants is presented in FIGS. 46-52 below.

FIG. 43 shows Bi-PLB-1.2 heavy chain sequences containing selected mutantTGF-β1 RII ECD sequences in FIGS. 41A and 41C. Analysis of these mutants is presented in FIG. 52 below.

FIGS. 44A-44D show Bi-A1B-1 heavy chain sequences containing selected mutant TGF-β1 RII ECD sequences in FIGS. 49, 50 and 52 below.

FIG. 45 shows the amino acids targeted in the mutant TGF-β1 RII ECD sequences represented in FIGS. 41A-41C.

FIG. 48 shows the percentages of high molecular weight (HMW) species, dimers, and low molecular weight (LMW) species reflected in the SEC profiles in FIGS. 47A-47B.

FIG. 50 shows the IC50s of the Bi-PB-1.2 and Bi-A1B-1 variants and parental controls reflecting their ability to block TGF-β1-mediated activation of luciferase expression under the control of a SMAD response element. Bioactivity was determined by a decrease in the amount of luciferase-mediated luminescence.

FIG. 53 shows framework regions (FRs) corresponding to the anti-PD-1 CDRs (SEQ ID NOs: 176-205) and anti-PD-L1 CDRs (SEQ ID NOs: 206-228) in FIGS. 1 and 3.

DETAILED DESCRIPTION

Definitions

Figure 5A:
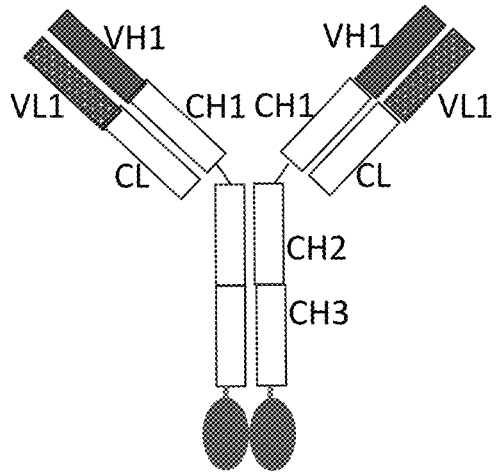
FIGS. 5A-5B show four different bispecific antitumor antagonist configurations, Bi-PB-1, Bi-PLB-1, Bi-PB-2 and Bi-PLB-2, each comprising (1) anti-PD-1 or anti-PD-L1 variable regions and (2) a TGF-β RII ECD domain.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes "one or more" peptides or a "plurality" of such peptides. With respect to the teachings in the present application, any issued patent or patent application publication described in this application is expressly incorporated by reference herein.

As used herein, the term "PD-1" refers to any form of PD-1 and variants thereof that retain at least part of the activity of PD-1. Unless indicated differently, such as by specific reference to human PD-1, PD-1 includes all mammalian species of native sequence PD-1, e.g., human, canine, feline, equine, and bovine.

As used herein, the term "PD-L1" refers to any form of PD-L1 and variants thereof that retain at least part of the activity of PD-L1. Unless indicated differently, such as by specific reference to human PD-L1, PD-L1 includes all mammalian species of native sequence PD-L1, e.g., human, canine, feline, equine, and bovine.

The term "agonist" refers to a substance which promotes (i.e., induces, causes, enhances, or increases) the biological activity or effect of another molecule. The term agonist encompasses substances which bind receptor, such as antibody, and substances which promote receptor function without binding thereto (e.g., by activating an associated protein).

The term "antagonist" or "inhibitor" refers to a substance that prevents, blocks, inhibits, neutralizes, or reduces a biological activity or effect of another molecule, such as a receptor or ligand.

As used herein, the term "antibody" refers to a polypeptide or a polypeptide complex that specifically recognizes and binds to antigen through one or more immunoglobulin variable regions. Antibody can be a whole antibody, antigen binding fragment or a single chain thereof.

The term "antibody" encompasses various broad classes of polypeptides that can be distinguished biochemically. Those skilled in the art will appreciate that heavy chains are classified as alpha, delta, epsilon, gamma, and mu, or α, δ, ε, γ and μ) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are within the scope of the present disclosure, the following discussion will generally be directed to the IgG class of immunoglobulin molecules.

Antibodies or antibody antagonists of the present application may include, but are not limited to polyclonal, monoclonal, multispecific, bispecific, trispecific, human, humanized, primatized, chimeric and, single chain antibodies. Antibodies disclosed herein may be from any animal origin, including birds and mammals. Preferably, the antibodies are human, murine, rat, donkey, rabbit, goat, guinea pig, camel, llama, horse, or chicken antibodies. In some embodiments, the variable region may be condricthoid in origin (e.g., from sharks).

The terms "antibody fragment" or "antigen-binding fragment" are used with reference to a portion of antibody, such as F(ab')2, F(ab)2, Fab', Fab, Fv, single-chain Fvs (scFv), single-chain antibodies, disulfide-linked Fvs (sdFv), fragments comprising either a VL or VH domain, fragments produced by a Fab expression library and anti-idiotypic (anti-Id) antibodies. Regardless of structure, antibody fragment binds with the same antigen that is recognized by the intact antibody. The term "antibody fragment" includes DARTs and diabodies. The term "antibody fragment" also includes any synthetic or genetically engineered proteins comprising immunoglobulin variable regions that act like antibody by binding to a specific antigen to form a complex. A "single-chain fragment variable" or "scFv" refers to a fusion protein of the variable regions of the heavy (VH) and light chains (VL) of immunoglobulins. In some aspects, the regions are connected with a short linker peptide of ten to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. With regard to IgGs, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration where the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains in conventional antibodies increases as they become more distal from the antigen-binding site or amino-terminus of the antibody. In conventional antibodies, the N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains (i.e. HCDR1, HCDR2, HCDR3, LCDR1, LCDR2 and LCDR3). In some instances, e.g., certain immunoglobulin molecules are derived from camelid species or engineered based on camelid immunoglobulins. Alternatively, an immunoglobulin molecule may consist of heavy chains only with no light chains or light chains only with no heavy chains.

In naturally occurring antibodies, the six CDRs present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined.

As used herein, the terms "VH1" and "VH2" refer to immunoglobulin heavy chain variable domains corresponding to two different binding specificities. Likewise, the terms "VL1" and "VL2" refer to light chain variable domains corresponding to two different binding specificities. When used together, it is to be understood that VH1 and VL1 regions define a common binding specificity and that VH2 and VL2 domains define a second binding specificity.

The term "framework region (FR)" as used herein refers to variable domain residues other than the CDR residues. Each variable domain typically has four FRs flanking the corresponding CDRs. For example, a VH domain typically has four HFRs: HFR, HFR2, HFR3 and HFR4 flanking the three HCDRs in the configuration of HFR-HCDR1-HFR2-HCDR2-HFR3-HCDR3-HFR4. Similarly, an LH domain typically has four LFRs flanking the three LCDRs in the configuration of: LFR-LCDR-LFR2-LCDR2-LFR3-LCDR3-LFR4. Exemplary FRs that may be utilized in the antagonists described herein are summarized in FIG. 53.

Light chains are classified as either kappa or lambda (κ, λ). Each heavy chain class may be bound with either a kappa or lambda light chain. In general, the light and heavy chains are covalently bonded to each other, and the "Fc" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

As used herein, the terms "light chain constant region" or "CL" are used interchangeably herein with reference to amino acid sequences derived from an antibody light chain. Preferably, the light chain constant region comprises at least one of a constant kappa domain or constant lambda domain.

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In some embodiments, a polypeptide of the disclosure comprises a polypeptide chain comprising a CH3 domain. Further, antibody for use in the disclosure may lack at least a portion of a CH2 domain (e.g., all or part of a CH2 domain). It should be understood that the heavy chain constant region may be modified such that they vary in amino acid sequence from the naturally occurring immunoglobulin molecule.

For example, as reflected in the disclosure herein below, Applicant has found that the CH3 domain can tolerate or accommodate significant insertions (e.g., greater than 100 aa) in the Fc loop of the CH3 domain (see e.g., Bi-PB-2, Bi-PLB-2 in FIG. 5B). Therefore, in the present application, any of the disclosed inhibitor domains may be similarly inserted in the Fc loop in a manner analogous to the insertion of the TGFβ1 RII ECD domain in the Fc loop as in the heavy chain sequences set forth in SEQ ID NOS: 151-154.

The heavy chain constant region of antibody disclosed herein may be derived from different immunoglobulin molecules. For example, a heavy chain constant region of a polypeptide may comprise a CH1 domain derived from an IgG1 molecule and a hinge region derived from an IgG3 molecule. In another example, a heavy chain constant region can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

A "light chain-heavy chain pair" refers to the collection of a light chain and heavy chain that can form a dimer through a disulfide bond between the CL domain of the light chain and the CH1 domain of the heavy chain.

The subunit structures and three dimensional configurations of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of antibody using conventional numbering schemes (residues 244 to 360, Kabat numbering system; and residues 231-340, EU numbering system). The CH2 domain is unique in that it is not closely paired with another domain. Rather, two N-linked branched carbohydrate chains are interposed between the two CH2 domains of an intact native IgG molecule. The CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains.

As used herein the term "disulfide bond" includes a covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, a "variant" of antibody, antibody fragment or antibody domain refers to antibody, antibody fragment or antibody domain that (1) shares a sequence identity of at least 80%, 85%, 90%, 95%, 96%, 97%, 98% or 99% with the original antibody, antibody fragment or antibody domain, and (2) binds specifically to the same target that the original antibody, antibody fragment or antibody domain binds specifically. It should be understood that where a measure of sequence identity is presented in the form of the phrase "at least x % identical" or "at least x % identity", such an embodiment includes any and all whole number percentages equal to or above the lower limit. Further it should be understood that where an amino acid sequence is presented in the present application, it should be construed as additionally disclosing or embracing amino acid sequences having a sequence identity of at least 80%, at least 85%, at least 90%, at least 95%, at least 96%, at least 97%, at least 98% or at least 99% identity to that amino acid sequence.

It should be understood that where a sequence homology range is presented herein, as in e.g., the phrase "about 80% to about 100%", such an embodiment includes any and all subranges within, wherein the lower number can be any whole number between 80 and 100.

As used herein, the phrase "humanized antibody" refers to antibody derived from a non-human antibody, typically a mouse monoclonal antibody. Alternatively, a humanized antibody may be derived from a chimeric antibody that retains or substantially retains the antigen binding properties of the parental, non-human, antibody but which exhibits diminished immunogenicity as compared to the parental antibody when administered to humans.

As used herein, the phrase "chimeric antibody," refers to antibody where the immunoreactive region or site is obtained or derived from a first species and the constant region (which may be intact, partial or modified in accordance with the instant disclosure) is obtained from a second species. In certain embodiments the target binding region or site will be from a non-human source (e.g., mouse or primate) and the constant region is human.

Included within the scope of the multispecific antibodies of the present application are various compositions and methodologies, including asymmetric IgG-like antibodies (e.g., triomab/quadroma, Trion Pharma/Fresenius Biotech); knobs-into-holes antibodies (Genentech); Cross MAbs (Roche); electrostatically matched antibodies (AMGEN); LUZ-Y (Genentech); strand exchange engineered domain (SEED) body (EMD Serono; Biolonic, Merus); Fab-exchanged antibodies (Genmab), symmetric IgG-like antibodies (e.g. dual targeting (DT)-Ig (GSK/Domantis); two-in-one antibody (Genentech); crosslinked MAbs (Karmanos Cancer Center), mAb2 (F-star); Cov X-body (Cov X/Pfizer); dual variable domain (DVD)-Ig fusions (Abbott); IgG-like bispecific antibodies (Eli Lilly); Ts2Ab (Medimmune/AZ); BsAb (ZymoGenetics); HERCULES (Biogen Idec,TvAb, Roche); scFv/Fc fusions; SCORPION (Emergent BioSolutions/Trubion, ZymoGenetics/BMS); dual affinity retargeting technology (Fc-DART), MacroGenics; dual (scFv)2-Fabs (National Research Center for Antibody Medicine); F(ab)2 fusions (Medarex/AMGEN); dual-action or Bis-Fab (Genentech); Dock-and-Lock (DNL, ImmunoMedics); Fab-Fv (UCB-Celltech); scFv- and diabody-based antibodies (e.g., bispecific T cell engagers (BiTEs, Micromet); tandem diabodies (Tandab, Affimed); DARTs (MacroGenics); single-chain diabodies; TCR-like antibodies (AIT, Receptor Logics); human serum albumin scFv fusion (Merrimack); COMBODIES (Epigen Biotech); and IgG/non-IgG fusions (e.g., immunocytokines (EMDSerono, Philogen, Immun-Gene, ImmunoMedics).

By "specifically binds" or "has specificity to", it is generally meant that antibody binds to an epitope via its antigen-binding domain, and that the binding entails some complementarity between the antigen-binding domain and the epitope. According to this definition, antibody is said to "specifically bind" to an epitope when it binds to that epitope via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D." In some embodiments, antibody or antibody fragment "has specificity to" antigen if the antibody or antibody fragment forms a complex with the antigen with a dissociation constant (Kd) of 10-6M or less, 10-7M or less, 10-8M or less, 10-9M or less, or 10-10M or less.

The phrase "immune checkpoint regulator" refers to a functional class of agents, which inhibit or stimulate signaling through an immune checkpoint. An "immune checkpoint regulator" includes cell surface receptors and their associated ligands, which together provide a means for inhibiting or stimulating signaling pathways associated with T-cell activation. Immune checkpoint regulators that are cell surface receptors are typically members of either the TNF receptor or B7 superfamilies that can induce checkpoint signaling pathways to suppress immune responses, including agents which bind to negative co-stimulatory molecules including without limitation PD-1, TIGIT, LAG-3, TIM-3, BTLA, VISTA, CTLA-4, and their respective ligands.

The phrases "immune checkpoint regulator antagonist", "immune checkpoint binding antagonist" and "immune checkpoint antagonist" are used interchangeably herein with reference to a class of agents that interfere with (or inhibit) the activity of an immune checkpoint regulator so that, as a result of the binding to the checkpoint regulator or its ligand, signaling through the checkpoint regulator receptor is blocked or inhibited. By inhibiting this signaling, immune-suppression can be reversed so that T cell immunity against cancer cells can be re-established or enhanced. Exemplary immune checkpoint antagonists include, but are not limited to PD-1 and its ligands, PD-L1 and PD-L2; TIGIT and its CD155 ligand, PVR; LAG-3 and its ligands, including liver sinusoidal endothelial cell lectin (LSECtin) and Galectin-3; CTLA-4 and its ligands, B7-1 and B7-2; TIM-3 and its ligand, Galectin-9; CD122 and its CD122R ligand; CD70, B7H3, B and T lymphocyte attenuator (BTLA), and VISTA. Immune checkpoint regulator antagonists may include antibody fragments, peptide inhibitors, dominant negative peptides and small molecule drugs, either in isolated forms or as part of a fusion protein or conjugate.

The phrases "immune checkpoint binding agonist" and "immune checkpoint agonist" are used interchangeably herein with reference to a class of agents that stimulate the activity of an immune checkpoint regulator so that, as a result of the binding to the checkpoint regulator or its ligand, signaling through the checkpoint regulator receptor is stimulated. By stimulating this signaling, T cell immunity against cancer cells can be re-established or enhanced. Exemplary immune checkpoint regulator agonists include, but are not limited to members of the tumor necrosis factor (TNF) receptor superfamily, such as CD27, CD40, OX40 (CD 134), glucocorticoid-induced TNFR family-related protein (GITR), and 4-1BB (CD137) and their ligands. Additional checkpoint regulator agonists belong to the B7-CD28 superfamily, including CD28 and ICOS. Immune checkpoint regulator may include antibody fragments, peptide inhibitors, dominant negative peptides and small molecule drugs, either in isolated forms or as part of a fusion protein or conjugate.

The term "antagonist antibody" refers to antibody that binds to a target and prevents or reduces the biological effect of that target. In some embodiments, the term can denote antibody that prevents the target, e.g., PD-1, to which it is bound from performing a biological function.

As used herein, an "anti-PD-1 antagonist antibody" refers to antibody that is able to inhibit PD-1 biological activity and/or downstream events(s) mediated by PD-1. Anti-PD-1 antagonist antibodies encompass antibodies that block, antagonize, suppress or reduce (to any degree including significantly) PD-1 biological activity, including downstream events mediated by PD-1, such as PD-1 binding and downstream signaling, inhibition of T cell proliferation, inhibition of T cell activation, inhibition of IFN secretion, inhibition of IL-2 secretion, inhibition of TNF secretion, induction of IL-10, and inhibition of anti-tumor immune responses. For purposes of the present invention, it will be explicitly understood that the term "anti-PD-1 antagonist antibody" (interchangeably termed "antagonist PD-1 antibody", "antagonist anti-PD-1 antibody" or "PD-1 antagonist antibody") encompasses all the previously identified terms, titles, and functional states and characteristics whereby PD-1 itself, a PD-1 biological activity, or the consequences of the biological activity, are substantially nullified, decreased, or neutralized in any meaningful degree. In some embodiments, anti-PD-1 antagonist antibody binds PD-1 and upregulates anti-tumor immune response.

As used herein, an "anti-PD-L1 antagonist antibody" refers to antibody that is able to inhibit PD-L1 biological activity and/or downstream events(s) mediated by PD-L1. Anti-PD-L1 antagonist antibodies encompass antibodies that block, antagonize, suppress or reduce (to any degree including significantly) PD-L1 biological activity, including downstream events mediated by PD-L1, such as PD-L1 binding and downstream signaling, inhibition of T cell proliferation, inhibition of T cell activation, inhibition of IFN secretion, inhibition of IL-2 secretion, inhibition of TNF secretion, induction of IL-10, and inhibition of anti-tumor immune responses. For purposes of the present invention, it will be explicitly understood that the term "anti-PD-L1 antagonist antibody" (interchangeably termed "antagonist PD-L1 antibody", "antagonist anti-PD-L1 antibody" or "PD-L1 antagonist antibody") encompasses all the previously identified terms, titles, and functional states and characteristics whereby PD-L1 itself, a PD-L1 biological activity, or the consequences of the biological activity, are substantially nullified, decreased, or neutralized in any meaningful degree. The anti-PD-L1 antagonist is designed to bind PD-L1 and upregulate anti-tumor immune responses.

The phrases "dominant-negative protein" or "dominant-negative peptide" refer to a protein or peptide derived from a wild type protein that has been genetically modified by mutation and/or deletion so that the modified protein or peptide interferes with the function of the endogenous wild-type protein from which it is derived.

The phrase "VEGF binding antagonist" refers to a functional class of agents that bind to VEGF-A or its receptor, VEGFR-2, so that, as a result of the binding, activation of VEGFR-2 by VEGF-A is blocked or inhibited. As used herein, the term "VEGF binding antagonists" include antibody fragments, peptide inhibitors, dominant negative peptides and small molecule drugs, either in isolated forms or as part of a fusion protein or conjugate.

The phrase "Tie2 tyrosine kinase receptor binding antagonist" refers to a functional class of agents that bind to a Tie2 tyrosine kinase receptor or one of its ligands so that, as a result of the binding, activation of the Tie2 tyrosine kinase receptor by one or more of its ligands (i.e., Ang1, Ang2, Ang3 and Ang4) is blocked or inhibited. As used herein, the term "Tie2 tyrosine kinase receptor binding antagonist" include antibody fragments, peptide inhibitors, dominant negative peptides and small molecule drugs, either in isolated forms or as part of a fusion protein or conjugate.

The phrase "wherein the one or more mutations reduce proteolytic cleavage of the antitumor antagonist" should be interpreted as relating to an otherwise identical antagonist containing a wild-type ECD.

The phrase "small molecule drug" refers to a molecular entity, often organic or organometallic, that is not a polymer, that has medicinal activity, and that has a molecular weight less than about 2 kDa, less than about 1 kDa, less than about 900 Da, less than about 800 Da or less than about 700 Da. The term encompasses most medicinal compounds termed "drugs" other than protein or nucleic acids, although a small peptide or nucleic acid analog can be considered a small molecule drug. Examples include chemotherapeutic anticancer drugs and enzymatic inhibitors. Small molecules drugs can be derived synthetically, semi-synthetically (i.e., from naturally occurring precursors), or biologically.

When describing polypeptide domain arrangements with hyphens between individual domains (e.g., CH2-CH3), it should be understood that the order of the listed domains is from the amino terminal end to the carboxy terminal end.

The term "immunoconjugate" refers to antibody which is fused by covalent linkage to an inhibitory peptide or small molecule drug. The peptide or small molecule drug can be linked to the C-terminus of a constant heavy chain or to the N-terminus of a variable light and/or heavy chain.

A "linker" may be used to link the peptide or small molecule drug, such as a maytansinoid, to the antitumor antagonists in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include GGGGS, charged linkers, and hydrophilic forms thereof as described herein and know in the art. The immunoconjugate may further include a flexible 3-15 amino acid peptide (or spacer) between an antitumor antagonist and the peptide and/or small molecule drug. In some embodiments, the linker comprises 3, 4, 5, 6, 7 or 8 repeats of GGGGS. In some embodiments, the linker consists of 3 or 4 repeats of GGGGS.

As used herein, the term "scaffold", refers to any polymer of amino acids that exhibits properties desired to support the function of antagonist, including addition of antibody specificity, enhancement of antibody function or support of antibody structure and stability. A scaffold can be grafted with binding domains of a donor polypeptide to confer the binding specificity of the donor polypeptide onto the scaffold.

As used herein, the phrase "multispecific inhibitor" refers to a molecule comprising at least two targeting domains with different binding specificities. In some embodiments, the multispecific inhibitor is a polypeptide comprising a scaffold and two or more immunoglobulin antigen binding domains targeting different antigens or epitopes. In certain embodiments, the multispecific inhibitor is a bispecific antibody or antagonist. In other embodiments, the multispecific inhibitor is a trispecific antibody or antagonist.

As used herein, the phrase "bispecific" refers to a molecule comprising at least two targeting domains with different binding specificities. Each targeting domain is capable of binding specifically to a target molecule and inhibiting a biological function of the target molecule upon binding to the target molecule. In some embodiments, the bispecific checkpoint regulator antagonist is a polymeric molecule having two or more peptides. In some embodiments, the targeting domain comprises antigen binding domain or a CDR of antibody. In some embodiments, the bispecific inhibitor is a bispecific antibody.

The terms "bispecific antibody," and "bispecific antagonist" are used interchangeably herein with reference to antibody that can specifically bind two different antigens (or epitopes). In some embodiments, the bispecific antibody is a full-length antibody that binds one antigen (or epitope) on one of its two binding arms (one pair of HC/LC), and binds a different antigen (or epitope) on its second arm (a different pair of HC/LC). In these embodiments, the bispecific antibody has two distinct antigen binding arms (in both specificity and CDR sequences) and is monovalent for each antigen it binds to.

In other embodiments, the bispecific antibody is a full-length antibody that can bind two different antigens (or epitopes) in each of its two binding arms (two pairs of HC/LC) In these embodiments, the bispecific antibody has two identical antigen binding arms, with identical specificity and identical CDR sequences, and is bivalent for each antigen it binds to.

Exemplary bispecific antibodies may include asymmetric IgG-like antibodies (e.g., triomab/quadroma, Trion Pharma/Fresenius Biotech); knobs-into-holes antibodies (Genentech); Cross MAbs (Roche); electrostatically matched antibodies (AMGEN); LUZ-Y (Genentech); strand exchange engineered domain (SEED) body (EMD Serono; biolonic, Merus); Fab-exchanged antibodies (Genmab), symmetric IgG-like antibodies (e.g. dual targeting (DT)-Ig (GSK/Domantis); two-in-one antibody (Genentech); crosslinked MAbs (Karmanos Cancer Center), mAb[2] (F-star); Cov X-body (Cov X/Pfizer); dual variable domain (DVD)-Ig fusions (Abbott); IgG-like bispecific antibodies (Eli Lilly); Ts2Ab (Medimmune/AZ); BsAb (ZymoGenetics); HERCULES (Biogen Idec,TvAb, Roche); scFv/Fc fusions; SCORPION (Emergent BioSolutions/Trubion, ZymoGenetics/BMS); dual affinity retargeting technology (Fc-DART), MacroGenics; dual (scFv)$_2$-Fabs (National Research Center for Antibody Medicine); F(ab)$_2$ fusions (Medarex/AM- GEN); dual-action or Bis-Fab (Genentech); Dock-and-Lock (DNL, ImmunoMedics); Fab-Fv (UCB-Celltech); scFv- and diabody-based antibodies (e.g., bispecific T cell engagers (BiTEs, Micromet); tandem diabodies (Tandab, Affimed); DARTs (MacroGenics); single-chain diabodies; TCR-like antibodies (AIT, Receptor Logics); human serum albumin scFv fusion (Merrimack); COMBODIES (Epigen Biotech); and IgG/non-IgG fusions (e.g., immunocytokines (EMDSerono, Philogen, ImmunoGene, ImmunoMedics).

The terms "treat" and "treatment" refer to the amelioration of one or more symptoms associated with a cell proliferative disorder; prevention or delay of the onset of one or more symptoms of a cell proliferative disorder; and/or lessening of the severity or frequency of one or more symptoms of cell proliferative disorder.

The phrases "to a patient in need thereof", "to a patient in need of treatment" or "a subject in need of treatment" includes subjects, such as mammalian subjects, that would benefit from administration of the antitumor antagonist of the present disclosure for treatment of a cell proliferative disorder.

The terms "therapeutically effective amount", "pharmacologically effective amount", and "physiologically effective amount" are used interchangeably to mean the amount of antitumor antagonist that is needed to provide a threshold level of active antagonist agents in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein or otherwise available in the relevant literature.

The terms, "improve", "increase" or "reduce", as used in this context, indicate values or parameters relative to a baseline measurement, such as a measurement in the same individual prior to initiation of the treatment described herein, or a measurement in a control individual (or multiple control individuals) in the absence of the treatment described herein.

A "control individual" is an individual afflicted with the same cell proliferative disorder as the individual being treated, who is about the same age as the individual being treated (to ensure that the stages of the disease in the treated individual and the control individual(s) are comparable). The individual (also referred to as "patient" or "subject") being treated may be a fetus, infant, child, adolescent, or adult human with a cell proliferative disorder.

The term "cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is a neoplasm, cancer or tumor.

The term "cancer" or "tumor" refers to any one of a variety of malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Exemplary cancers for treatment with the methods of the instant disclosure include cancer of the brain, bladder, breast, cervix, colon, head and neck, kidney, lung, non-small cell lung, mesothelioma, ovary, prostate, stomach and uterus, leukemia, and medulloblastoma.

The term "leukemia" refers to progressive, malignant diseases of the blood-forming organs and is generally characterized by a distorted proliferation and development of leukocytes and their precursors in the blood and bone marrow. Exemplary leukemias include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to the malignant growth of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, and carcinoma *villosum*.

The term "sarcoma" refers to a tumor made up of a substance like the embryonic connective tissue and is generally composed of closely packed cells embedded in a fibrillar or homogeneous substance. Exemplary sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

I. Bispecific Antagonists Targeting the TGF-β Pathway

TGF-β is considered the primary cytokine mediating immunosuppression through the induction and maintenance of T regulatory cells, as well as the direct suppression of innate and adaptive immune cells such as NK, DC, and T cells. TGF-β also plays roles in neoangiogenesis and stabilizing tumor vessels, as well as directly impacting tumors through epithelial mesenchymal transition leading to cell migration and invasion. As a potent inducer of angiogenesis, TGF-β1 provides a critical support system for solid tumors and plays an important role in tumor cell dissemination. Accordingly, TGF-β status is a strong predictor of anti-PD1/PD-L1 resistance and overall survival for a variety of cancers.

Many cells synthesize TGF-β and almost all of them have specific receptors for these peptides. TGF-β 1, TGF-β2, and TGF-β3 all function through the same receptor signaling system. The active form of TGF-β is a dimer that signals through the formation of a membrane bound heterotetramer composed of the serine threonine type 1 and type 2 receptors, TGF-β RI and TGF RII, respectively. Recently, TGF-β pathway inhibitors have been developed in the form of e.g., antibodies or binding fragments directed against TGF-β1 or TGF-β1 RII, such as dominant negative fusion protein fragments containing the extracellular domain (ECD) of TGF-β1 RII.

However, in the course of developing such binding reagents, the inventors of the present application have discovered that antagonists bearing a TGFβ1 RII ECD domain exhibit unacceptable levels of proteolytic degradation or clipping over time. To address this problem, TGF-β1 RII ECD mutant variants have been developed that reduce clipping within this domain. As further described herein, the TGFβ1 RII ECDs have been further combined with additional binding agents targeting additional checkpoint regulator pathways or angiogenesis pathways to generate bispecific antagonists with significantly reduced level of proteolytic degradation or clipping over time.

In one aspect, the present application provides a bispecific antagonist inhibiting both the TGFβ pathway and the PD-1/PD-L1 checkpoint regulator pathway.

In another aspect, the present application provides a bispecific antagonist inhibiting both the TGFβ pathway and the vascular endothelial growth factor (VEGF) pathway, vascular endothelial growth factor receptor (VEGFR), or both.

A. Bispecific Antagonists Targeting the TGF-β and PD-1/PD-L1 Pathways

In some embodiments, the bispecific antagonists include a first targeting domain specifically inhibiting the TGF-β pathway and a second targeting domain specifically binding PD-1 or PD-L1. In some embodiments, the first targeting domain comprises a TGF-β pathway inhibitor.

TGF-β Pathway Inhibitors

The TGF-β pathway involves a multifunctional set of peptides that control cell proliferation and differentiation, migration and adhesion, extracellular matrix modification including tumor stroma and immunosuppression, angiogenesis and desmoplasia, apoptosis, and other functions in many cell types. TGF-β is considered the primary cytokine mediating immunosuppression through the induction and maintenance of T regulatory cells, as well as the direct suppression of innate and adaptive immune cells such as NK, DC, and T cells. TGFB also plays roles in neoangiogenesis and stabilizing tumor vessels, as well as directly impacting tumors through epithelial mesenchymal transition leading to cell migration and invasion. As a potent inducer of angiogenesis, TGF-β1 provides a critical support system for solid tumors, as well as a mechanism for tumor cell dissemination.

TGF-β status is a strong predictor of anti-PD1/PD-L1 resistance and overall survival for a variety of cancers. For example, high TGF-β1 levels are associated with poor response to PD1/PD-L1 inhibition in metastatic urothelial cancer patients (Nature (2018) 554(7693):544-548), and a high TGFβ signature is associated with poor prognosis across 33 different cancer types (Immunity (2018) 48:812-830). Inhibition of TGFβ with anti-PD1/PD-L1 further releases CD8 effector cells to kill tumor cells, as well as stimulate other cell types to increase tumor killing capacity.

Many cells synthesize TGF-β and almost all of them have specific receptors for these peptides. TGF-β1, TGF-β2, and TGF-β3 all function through the same receptor signaling system. The active form of TGF-β is a dimer that signals through the formation of a membrane bound heterotetramer composed of the serine threonine type 1 and type 2 receptors, TGF-β RI and TGFβ RII, respectively.

As used herein, a TGF-β pathway inhibitor may be in the form of e.g., antibodies or variable domain fragments directed against TGF-β1 or a TGF-β1 RII, a TGF binding peptide, or dominant negative fusion protein fragment, such as the extracellular domain (ECD) of TGF-β1 RII.

TGF-β1 RII ECD and Variants

In some embodiments, the TGF-β pathway inhibitor comprises a TGF-β1 RII ECD. An exemplary human TGF-β1 RII ECD (wild-type) has the amino acid sequence set forth in SEQ ID NO: 89. The inventors of the present application have discovered that antagonists bearing a TGFβ1 RII ECD domain exhibit unacceptable levels of proteolytic degradation or clipping over time upon storage as described in e.g., Example 9. Therefore, in some embodiments, the TGF-β pathway inhibitors of the present application comprises variants of the human TGF-β1 RII ECD (hereinafter "TGFBR variants"), that contain one or more modifications that reduce proteolytic degradation or clipping. In some embodiments, the modifications comprise substitutions of amino acid residues, deletion of amino acid residues, insertion of amino acid residues, or a combination thereof. In some embodiments, the TGFBR variants comprise one or more substitution mutations at positions 6, 7, 13, 16, 17, 20, 22, and/or 23 of SEQ ID NO: 89. In some embodiments, the one or more substitution mutations replace a non-polar amino acid residue with a polar or hydrophobic amino acid residue.

In some embodiments, the TGFBR variants comprise one or more deletions of amino acids relative to the wide type human TGF-β1 RII ECD sequences. In some embodiments, the one or more deletions are directed to a region encompassing amino acid residues 1-20 of SEQ ID NO: 89 and may include any of the residues in therein. In more particular embodiments, the one or more mutations include a deletion of amino acid residues 1-7, 1-12, 1-13, 1-15, 1-20, 7-12, 7-13, 7-15, 7-20, 8-20, 9-20, 10-20, 11-20, 12-20, 13-20, 14-20, 15-20, 16-20 and/or 17-20 of SEQ ID NO: 89. In more particular embodiments, the one or more deletions include amino acid residues 6, 7, 12, 13, 15, 16, 17 or 20 of SEQ ID NO: 89.

In some embodiments, the TGFBR variant comprises (1) a deletion of one or more amino acid residues in the region of amino acid residues 1-20 of SEQ ID NO: 89 and one or more substitutions at amino acid residues 6, 7, 13, 16, 17, 20, 22, and/or 23 of SEQ ID NO: 89. In some embodiments, the TGFBR variant comprises (1) a deletion of amino acid residues 1-7 of SEQ ID NO: 89 and (2) an amino acid substitution at amino acid residue 13, 16, 17, 20, 22, and 23 of SEQ ID NO: 89 or two amino acid substitutions at amino acid residues 16 and 17 of SEQ ID NO: 89. In some embodiments, one or more amino acid residues 6, 7, 13, 16, 17, 20, 22, and/or 23 of SEQ ID NO: 89 are replaced with one or more polar amino acid residues. In some embodiments, one or more amino acid residues 6, 7, 13, 16, 17, 20, 22, and/or 23 of SEQ ID NO: 89 are replaced with one or more hydrophobic amino acid residues.

In some embodiments, the TGFBR variant comprises an amino acid sequence selected from the group consisting of SEQ ID NOS: 114-123 and 251-270 (FIGS. 41A-41C).

In some embodiments, the TGFBR variant comprises an immunoglobulin heavy chain comprising an amino acid sequence selected from the group consisting of SEQ ID NOS: 124-133, 148, 150, and 271-290 (FIGS. 42A-42H, 44A).

In other embodiments, the TGFBR variant comprises an immunoglobulin heavy chain comprising the amino acid sequence of SEQ ID NOS: 145, SEQ ID NO: 147, or SEQ ID NO: 303 (FIG. 43).

In other embodiments, the TGFBR variant comprises an immunoglobulin heavy chain comprising the amino acid sequence of SEQ ID NOS: 148, SEQ ID NO: 150, or SEQ ID NOS: 291-302 (FIGS. 44A-44D).

It should be understood that wherever a TGFBR variant is cited in this application as comprising an immunoglobulin heavy chain comprising an amino acid sequence selected from the group consisting of SEQ ID NOS: 124-133, 145, 147, 148, 150 and 271-303 (herein "the particular amino acid sequence"), the embodiment should be further construed as representing additional heavy chain embodiments characterized by all heavy chain sequence combinations derived therefrom in which one or more of the pre-existing anti-PD1 amino acid sequences, including HCDR1, HCDR2 and HCDR3 sequences as set forth in FIG. 1 or one or more of the pre-existing anti-PD-L1 sequences, including HCDR1, HCDR2 and HCDR3 sequences as set forth in FIG. 3 are substituted in place of the pre-existing anti-PD1 CDR sequences or anti-PD-L1 CDR sequences present in "the particular amino acid sequence."

Similarly, with respect to the preceding paragraph, any of the immunoglobulin light chains described as pairing with the aforementioned heavy chains represented by SEQ ID NOS: 124-133, 145, 147, 148, 150 and 271-303 should be further construed as representing additional light chain embodiments characterized by all light chain sequence combinations derived therefrom in which one or more of the pre-existing anti-PD1 amino acid sequences, including LCDR1, LCDR2 and LCDR3 sequences as set forth in FIG. 1 or one or more of the pre-existing anti-PD-L1 sequences, including LCDR1, LCDR2 and LCDR3 sequences as set forth in FIG. 3 are substituted in place of the pre-existing anti-PD1 CDR sequences or anti-PD-L1 CDR sequences present in "the particular amino acid sequence."

Likewise, it should be understood that wherever a TGFBR variant is cited in this application as comprising an immunoglobulin heavy chain comprising an amino acid sequence selected from the group consisting of SEQ ID NOS: 124-133, 145, 147, 148, 150 and 271-303 ("the particular amino acid sequence"), the embodiment should be further construed as representing additional heavy chain embodiments, including all light chain sequence combinations derived therefrom in which the pre-existing anti-PD1 heavy chain variable region (HCVR) amino acid sequence in the "particular amino acid sequence" is substituted for a different anti-PD1 HCVR selected from the group consisting of SEQ ID NOS: 29, 31, 33, 35, 37 and 39 as shown in FIGS. 2A-2B or in which the pre-existing anti-PD-L1 HCVR amino acid sequence in "the particular amino acid sequence" is substituted for a different anti-PD-L1 HCVR selected from the group consisting of SEQ ID NOS: 72, 74, 76, 78, 80, 82, 84 and 86 as shown in FIGS. 4A-4C.

Similarly, with respect to the preceding paragraph, any of the immunoglobulin light chains described as pairing with the aforementioned heavy chains in "the particular amino acid sequence" should be further construed as representing additional light chain embodiments, including all light chain sequence combinations derived from the aforementioned light chain sequences in which the pre-existing anti-PD1 light chain variable region (LCVR) amino acid sequence in "the particular amino acid sequence" is substituted for a different anti-PD1 LCVR selected from the group consisting of SEQ ID NOS: 30, 32, 34, 36, 38 and 40 as shown in FIGS.

2A-2B or in which the pre-existing anti-PD-L1 LCVR amino acid sequence in "the particular amino acid sequence" is substituted for a different anti-PD-L1 LCVR selected from the group consisting of SEQ ID NOS: 73, 75, 77, 79, 81, 83, 85 and 87 as shown in FIGS. 4A-4C.

In some embodiments, the TGF-β pathway inhibitor is fused to the carboxy-terminus of an IgG in a bispecific antitumor antagonist, as depicted in e.g., FIGS. 5A-5B, 8A-8C and 20A-20B. Alternatively, the TGF-β1 RII ECD may be fused to the amino-terminus of an IgG in a bispecific antitumor antagonist. In yet other embodiments, the TGF-β1 RII ECD is inserted within the IgG Fc receptor (i.e., CH2 or CH3 regions) of an IgG as depicted in e.g., FIG. 5B.

In some embodiments, anti-TGF-β1, anti-TGF-β1 RII antibodies or variable region fragments thereof may be used in place of a TGF-β1 RII ECD. Exemplary anti-TGF-β1 antibodies are described in U.S. Pat. Nos. 7,067,637, 7,494,651, 7,527,791, and 7,619,069. Exemplary anti-TGF-β1 RII antibodies are described in U.S. Pat. No. 7,579,186. Alternatively, a TGF-β1 RII ECD may be substituted with one or more anti-TGF-β1 and/or anti-TGF-β1 RII peptide inhibitors. An exemplary TGF-β1 peptide inhibitor is KRIWFIPRSSWYERA (SEQ ID NO: 155).

Anti-PD-1 Antibody and Anti-PD-1 Antibody Fragments

In some embodiments, the bispecific TGFβ pathway antagonist includes an anti-PD-1 antibody or antibody fragment. In one embodiment, the PD-1 inhibitor for use in the present application is antibody, or antigen-binding portion thereof, comprising: an immunoglobulin heavy chain complementarity determining region 1 (CDR1) sequence selected from the group consisting of SEQ ID NOS: 1, 4, 7, 9, and 12; an immunoglobulin heavy chain CDR2 sequence selected from the group consisting of SEQ ID NOS: 2, 5, 10, and 13; an immunoglobulin heavy chain CDR3 sequence selected from the group consisting of SEQ ID NOS: 3, 6, 8, 11, and 14; an immunoglobulin light chain CDR1 sequence selected from the group consisting of SEQ ID NOS: 15, 18, 21-23, and 26; an immunoglobulin light chain CDR2 sequence selected from the group consisting of SEQ ID NOS: 16, 19, 24, and 27; or an immunoglobulin light chain CDR3 sequence selected from the group consisting of SEQ ID NOS: 17, 20, 25, and 28.

In another embodiment, the PD-1 inhibitor for use in the present application (as e.g., the second targeting domain) is antibody, or antigen-binding portion thereof, comprising: an immunoglobulin heavy chain CDR1 sequence selected from the group consisting of SEQ ID NOS: 1, 4, 7, 9, and 12; an immunoglobulin heavy chain CDR2 sequence selected from the group consisting of SEQ ID NOS: 2, 5, 10, and 13; an immunoglobulin heavy chain CDR3 sequence from the group consisting of SEQ ID NOS: 3, 6, 8, 11, and 14; an immunoglobulin light chain CDR1 sequence selected from the group consisting of SEQ ID NOS: 15, 18, 21-23, and 26; an immunoglobulin light chain CDR2 sequence selected from the group consisting of SEQ ID NOS: 16, 19, 24, and 27; and an immunoglobulin light chain CDR3 sequence selected from the group consisting of SEQ ID NOS: 17, 20, 25, and 28.

In another embodiment, the PD-1 inhibitor for use in the present application includes: an immunoglobulin heavy chain variable region (HCVR) having at least 80%, 85%, 90%, 95%, or 99% identity to an HCVR amino acid sequence selected from the group consisting of SEQ ID NOS: 29, 31, 33, 35, 37, and 39; an immunoglobulin light chain variable region (LCVR) having at least 80%, 85%, 90%, 95%, or 99% identity to an LCVR amino acid sequence selected from the group consisting of SEQ ID NOS: 30, 32, 34, 36, 38, and 40; or both.

In another embodiment, the PD-1 inhibitor for use in the present application includes: an HCVR amino acid sequence selected from the group consisting of SEQ ID NOS: 29, 31, 33, 35, 37, and 39; an LCVR amino acid sequence selected from the group consisting of SEQ ID NOS: 30, 32, 34, 36, 38, and 40; or both.

In one embodiment, the PD-1 inhibitor includes: an HCVR having at least 80%, 85%, 90%, 95%, or 99% identity to the HCVR amino acid sequence of SEQ ID NO: 39; an LCVR having at least 80%, 85%, 90%, 95%, or 99% identity to the LCVR amino acid sequence of SEQ ID NO: 40; or both. In a more particular embodiment, the PD-1 inhibitor has an HCVR sequence of SEQ ID NO: 39; an LCVR amino acid sequence of SEQ ID NO: 40; or both.

In another embodiments, the PD-1 inhibitor has an immunoglobulin heavy chain variable region that comprises (1) an HCDR1 of SEQ ID NO: 12, an HCDR2 of SEQ ID NO: 13 and an HCDR 3 of SEQ ID NO: 14 and (2) an HFR1 having at least 80%, 85% or 90% identity to the amino acid sequence of SEQ ID NO: 196, an HFR2 having at least 80%, 85% or 90% identity to the amino acid sequence of SEQ ID NO: 190, an HFR3 having at least 80%, 85% or 90% identity to the amino acid sequence of SEQ ID NO: 201, an HFR4 having at least 80%, 85% or 90% identity to the amino acid sequence of SEQ ID NO: 187, and an immunoglobulin heavy chain variable region that comprises (1) an LCDR1 of SEQ ID NO: 26, an LCDR2 of SEQ ID NO: 27 and an LCDR 3 of SEQ ID NO: 28 and (2) an LFR1 having at least 80%, 85% or 90% identity to the amino acid sequence of SEQ ID NO: 202, an LFR2 having at least 80%, 85% or 90% identity to the amino acid sequence of SEQ ID NO: 203, an LFR3 having at least 80%, 85% or 90% identity to the amino acid sequence of SEQ ID NO: 204, an LFR4 having at least 80%, 85% or 90% identity to the amino acid sequence of SEQ ID NO: 205.

In another embodiment, the TGF-β1 antitumor antagonist includes a PD-1 inhibitor comprising: an immunoglobulin heavy chain having at least 80%, 85%, 90%, 95%, or 99% identity to the amino acid sequence of SEQ ID NO: 92 or SEQ ID NO: 113; a light chain having at least 80%, 85%, 90%, 95%, or 99% identity to the amino acid sequence of SEQ ID NO: 93; or both. In a more particular embodiment, the TGF-β1 antitumor antagonist includes a PD-1 inhibitor comprising: an immunoglobulin heavy chain having the amino acid sequence of SEQ ID NO: 92 or SEQ ID NO: 113; an immunoglobulin light chain having the amino acid sequence of SEQ ID NO: 93; or both.

In another embodiment, the TGF-β1 antitumor antagonist includes a PD-1 inhibitor comprising: an immunoglobulin heavy chain having at least 80%, 85%, 90%, 95%, or 99% identity to the amino acid sequence of SEQ ID NO: 94 or SEQ ID NO: 172; an immunoglobulin light chain having at least 80%, 85%, 90%, 95%, or 99% identity to the LCVR amino acid sequence of SEQ ID NO: 95; or both. In a more particular embodiment, the TGF-1 antitumor antagonist includes a PD-1 inhibitor comprising: an immunoglobulin heavy chain having the amino acid sequence of SEQ ID NO: 94 or SEQ ID NO: 172; an immunoglobulin light chain having the amino acid sequence of SEQ ID NO: 95; or both. In another embodiment, the PD-1/TGF-β1 antitumor antagonist includes a TGF-β1 RII ECD inserted within a CH3 loop as depicted in FIG. 5B.

In one embodiment, the TGF-β1 antitumor antagonist includes a PD-1 inhibitor comprising: a heavy chain having at least 80%, 85%, 90%, 95%, or 99% identity to the amino acid sequence of SEQ ID NO: 151; a light chain having at least 80%, 85%, 90%, 95%, or 99% identity to the amino acid sequence of SEQ ID NO: 152; or both. In a more particular embodiment, the TGF-β1 antitumor antagonist includes a PD-1 inhibitor comprising: an immunoglobulin heavy chain having the amino acid sequence of SEQ ID NO: 151; immunoglobulin light chain having the amino acid sequence of SEQ ID NO: 152, or both.

Other PD-1 targeted antagonists include anti-PD-1 antibodies, such as nivolumab (BMS-936558, MDX-1106, OPDIVO™), a human immunoglobulin G4 (IgG4) mAb (Bristol-Myers Squibb); pembrolizumab (MK-3475, lambrolizumab, KEYTRUDA™), a humanized immunoglobulin G4 (IgG4) mAb (Merck); pidilizumab (CT-011)(Medivation); and AMP-224 (Merck). Anti-PD-1 antibodies are commercially available, for example from ABCAM (AB137132), BIOLEGEND™ (EH12.2H7, RMP1-14) and AFFYMETRIX EBIOSCIENCE (J105, J116, MIH4). Anti-PD-1 targeted antitumor antagonists may include any of the HCVRs, LCVRs, and/or CDRs derived from any of the anti-PD-1 antibodies described herein, including those described in FIGS. 1-2.

Anti-PD-L1 Antibody and Anti-PD-L1 Antibody Fragments

In some embodiments, the bispecific TGF-β1 pathway antagonist further includes an anti-PD-L1 antibody or antibody fragment. In one embodiment, the PD-L1 inhibitor for use in the present application is antibody, or antigen-binding portion thereof, comprising: an immunoglobulin heavy chain CDR1 sequence selected from the group consisting of SEQ ID NOS: 41, 44, 50, and 53; an immunoglobulin heavy chain CDR2 sequence selected from the group consisting of SEQ ID NOS: 42, 45, 47, 49, 51, and 54; an immunoglobulin heavy chain CDR3 sequence selected from the group consisting of SEQ ID NOS: 43, 46, 48, 52, and 55; an immunoglobulin light chain CDR1 sequence selected from the group consisting of SEQ ID NOS: 56, 59, 63, 66, and 69; an immunoglobulin light chain CDR2 sequence selected from the group consisting of SEQ ID NOS: 57, 60, 64, 67, and 70; or an immunoglobulin light chain CDR3 sequence selected from the group consisting of SEQ ID NOS: 58, 61, 62, 65, 68, and 71.

In another embodiment, the PD-L1 inhibitor for use in the present application (as e.g., the second targeting domain) is antibody, or antigen-binding portion thereof, comprising: an immunoglobulin heavy chain CDR1 sequence selected from the group consisting of SEQ ID NOS: 41, 44, 50, and 53; an immunoglobulin heavy chain CDR2 sequence selected from the group consisting of SEQ ID NOS: 42, 45, 47, 49, 51, and 54; an immunoglobulin heavy chain CDR3 sequence selected from the group consisting of SEQ ID NOS: 43, 46, 48, 52, and 55; an immunoglobulin light chain CDR1 sequence selected from the group consisting of SEQ ID NOS: 56, 59, 63, 66, and 69; an immunoglobulin light chain CDR2 sequence selected from the group consisting of SEQ ID NOS: 57, 60, 64, 67, and 70; and an immunoglobulin light chain CDR3 sequence selected from the group consisting of SEQ ID NOS: 58, 61, 62, 65, 68, and 71.

In another embodiment, the PD-L1 inhibitor for use in the present application includes: an immunoglobulin HCVR having at least 80%, 85%, 90%, 95%, or 99% identity to an HCVR amino acid sequence selected from the group consisting of SEQ ID NOS: 72, 74, 76, 78, 80, 82, 84, and 86; an immunoglobulin LCVR having at least 80%, 85%, 90%, 95%, or 99% identity to an LCVR amino acid sequence selected from the group consisting of SEQ ID NOS: 73, 75, 77, 79, 81, 83, 85, and 87; or both. In another embodiment, the PD-L1 inhibitor for use in the present application includes: an HCVR having an amino acid sequence selected from the group consisting of SEQ ID NOS: 72, 74, 76, 78, 80, 82, 84, and 86; an LCVR having an amino acid sequence selected from the group consisting of SEQ ID NOS: 73, 75, 77, 79, 81, 83, 85, and 87; or both.

In one embodiment, the PD-L1 inhibitor includes: an HCVR having at least 80%, 85%, 90%, 95%, or 99% identity to the HCVR amino acid sequence of SEQ ID NO: 86; an LCVR having at least 80%, 85%, 90%, 95%, or 99% identity to the LCVR amino acid sequence of SEQ ID NO: 87; or both. In a more particular embodiment, the PD-L1 inhibitor includes: an HCVR having the amino acid sequence of SEQ ID NO: 86; an LCVR having the amino acid sequence of SEQ ID NO: 87; or both.

In another embodiment, the TGF-β1 antitumor antagonist includes a PD-L1 inhibitor comprising: an immunoglobulin heavy chain having at least 80%, 85%, 90%, 95%, or 99% identity to the amino acid sequence of SEQ ID NO: 94 or SEQ ID NO: 172; an immunoglobulin light chain having at least 80%, 85%, 90%, 95%, or 99% identity to the amino acid sequence of SEQ ID NO: 95; or both. In a more particular embodiment, the TGF-β1 antitumor antagonist includes a PD-L1 inhibitor comprising: an immunoglobulin heavy chain having the amino acid sequence of SEQ ID NO: 94 or SEQ ID NO: 172; an immunoglobulin light chain having the amino acid sequence of SEQ ID NO: 95; or both.

Figure 5B:
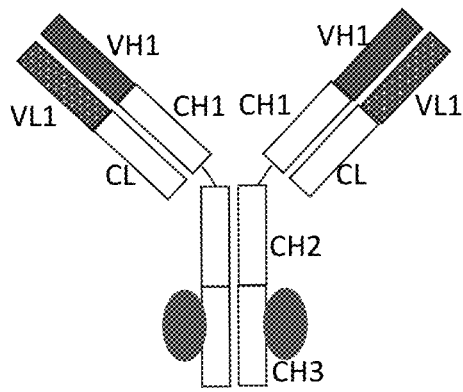

In another embodiment, the PD-L1/TGF-β1 antitumor antagonist includes a TGF-β1 RII ECD inserted within a CH3 loop as depicted in FIG. 5B.

In a particular embodiment, the TGF-β1 antitumor antagonist includes a PD-L1 inhibitor comprising: an immunoglobulin heavy chain having at least 80%, 85%, 90%, 95%, or 99% identity to the amino acid sequence of SEQ ID NO: 153; an immunoglobulin light chain having at least 80%, 85%, 90%, 95%, or 99% identity to the amino acid sequence of SEQ ID NO: 154; or both. In a more particular embodiment, the TGF-β1 antitumor antagonist includes a PD-L1 inhibitor comprising: an immunoglobulin heavy chain having the amino acid sequence of SEQ ID NO: 153; an immunoglobulin light chain having the amino acid sequence of SEQ ID NO: 154, or both.

Other anti-PD-L1 targeted antagonists include anti-PD-L1 antibodies, such as atezolizumab (MPDL3280A, RG7446, Tecentriq), a fully humanized IgG1 mAb (Genentech/Roche); BMS-936559 (MDX-1105), a fully human IgG4 mAb (Bristol-Myers Squibb); durvalumab (MEDI4736, Imfinzi), a human IgG antibody (Medimmune/AstraZeneca); and avelumab (MSB0010718C, Bavencio), a fully human IgG4 monoclonal antibody (Merck, EMD Serono). Anti-PD-L1 targeted antitumor antagonists may include any of the HCVRs, LCVRs, and/or CDRs derived from any of the anti-PD-L1 antibodies described herein, including those described in FIGS. 3-4.

B. Bispecific Antagonists Targeting TGF-β1 and Angiogenesis Pathway(s)

In another aspect, a bispecific antitumor antagonist of the present application includes a first targeting domain specifically binding TGFβ1 or TGFβ1 RII, and a second targeting domain specifically binding VEGF-A, VEGFR, Ang1, Ang2, Tie2R, or a combination thereof. In these embodiments, any of the above described TGFβ1- or TGFβ1 RII-binding fragments may be used in combination with the second targeting domain.

Angiogenesis Pathways

Angiogenesis, the development of new blood vessels from pre-existing vessels, is essential for tumor growth and metastasis. Angiogenesis inhibition presents a potentially valuable strategy for treating diseases, such as cancer, in which progression (e.g., metastasis) is dependent on neovascularization. Inhibition of angiogenesis leads to tumor cell death, which may feed tumor antigen into host antigen presentation pathways. Angiogenesis pathway inhibitors may be in the form of e.g., antibodies, variable domain fragments, or dominant negative fusion protein fragments.

1. VEGF/VEGFR Pathway

The principal VEGF pathway is mediated by the transmembrane tyrosine kinase VEGF-R2. Various isoforms of VEGF, particularly VEGF-A, bind to VEGF-R2, resulting in dimerization and activation through phosphorylation of various downstream tyrosine kinases.

In some embodiments, the antagonist of the present application include a VEGF pathway antagonist that binds to VEGF-A or its receptor VEGFR-2 so that, as a result of the binding, activation of VEGFR-2 by VEGF-A is blocked or inhibited.

In one embodiment, the TGFβ pathway antagonist further includes VEGF pathway antagonist in the form of a dominant negative VEGFR antagonist corresponding to the extracellular domain (ECD) of human VEGF receptor 1 or 2. In a particular embodiment, the TGFβ pathway antagonist includes aflibercept (also known as Zaltrap), a recombinant fusion protein containing VEGF-A binding portions from the extracellular domains of human VEGF receptors 1 and 2 fused to the human IgG1 Fc portion. VEGFR ECDs, such as aflibercept act as soluble receptor decoys for VEGF-A.

In one embodiment, the bispecific antitumor antagonist includes a first targeting domain comprising a TGFβ pathway inhibitor, and a second targeting domain specifically binding VEGF-A, wherein the second targeting domain comprises aflibercept. A suitable source of aflibercept comprises the amino acid sequence set forth in SEQ ID NO: 88. In some embodiments, a bispecific antitumor antagonist includes a modified immunoglobulin heavy chain comprising an amino terminal aflibercept domain linked to a TGF-β1 RII ECD or a TGF-β1 RII ECD variant at the carboxy-terminal end via an IgG1 or IgG4 Fc receptor (Bi-ZB-1) as shown in FIG. 8C. In one embodiment, the modified immunoglobulin heavy chain has the amino acid sequence of SEQ ID NO: 105. Alternatively, the TGF-β1 RII ECD or TGF-β1 RII ECD variant may be positioned at the amino terminal end and the aflibercept domain may be positioned at the carboxy-terminal end.

In another embodiment, the TGFβ pathway antagonist further includes VEGF pathway antagonist comprising anti-VEGFA or anti-VEGFR2 variable region sequences, such as those derived from bevacizumab. Bevacizumab (AVASTIN™) is a humanized antibody comprising a human IgG1 framework regions (FRs) and antigen-binding complementarity-determining regions from the murine anti-hVEGF monoclonal antibody A.4.6.1 that blocks binding of human VEGF-A to VEGFR1 and VEGFR-2. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 Daltons and is glycosylated. In one embodiment, an HCVR of bevacizumab for use in the present application has the amino acid sequence set forth in SEQ ID NO: 90, and an LCVR of bevacizumab has the amino acid sequence set forth in SEQ ID NO: 91.

In some embodiments, amino acid substitutions may be included in a bevacizumab/AVASTIN antibody or fragment thereof as described in U.S. Pat. No. 7,575,893. Exemplary amino acid substitutions include, but are not limited to E1Q, E6Q, L11V, Q13K, L18V, R19K, A23K, or combinations thereof. In one embodiment, a mutant HCVR of bevacizumab for use in the present application has the amino acid sequence set forth in SEQ ID NO: 96, which may be used in conjunction with the LCVR in SEQ ID NO: 91.

In one embodiment, the bispecific antitumor antagonist includes a first targeting domain specifically binding TGFβ1, such as a TGFβ1 RII ECD (or containing anti-TGFβ1- or anti-TGFβ1 RII variable domains), and a second targeting domain specifically binding VEGFA or VEGFR2, such as bevacizumab or any other anti-VEGF or anti-VEGFR2 antibodies, variable region fragments thereof, or functionally active mutant fragments thereof.

In a particular embodiment, a bispecific antitumor TGF-β/VEGF-VEGFR2 antagonist includes an immunoglobulin heavy chain having the amino acid sequence of SEQ ID NO: 102, an immunoglobulin light chain having the amino acid sequence of SEQ ID NO: 103, or both, such as Bi-AB-1 (FIG. 8A), which contains wild-type bevacizumab variable region sequences.

In another embodiment, a bispecific antitumor TGF-β antagonist further includes an immunoglobulin heavy chain having the amino acid sequence of SEQ ID NO: 104, an immunoglobulin light chain having the amino acid sequence of SEQ ID NO: 103, or both, such as Bi-A1B-1 (FIG. 8B), which contains a mutant bevacizumab variable region sequence.

Additional anti-VEGF or anti-VEGFR antibodies or fragments thereof may be based on ranibizumab (trade name Lucentis™), a monoclonal antibody fragment derived from the same parent murine antibody as bevacizumab; the G6 or B20 series antibodies (e.g., G6-23, G6-31, B20-4.1) described in U.S. Patent Publication Nos. 2006/0280747, 2007/0141065 and/or 2007/0020267, as well as the antibodies described in U.S. Pat. Nos. 7,297,334, 7,060,269, 6,884, 879, 6,582,959, 6,703,020; 6,054,297; U.S. Patent Publication Nos. 2007/059312, 2006/009360, 2005/0186208, 2003/0206899, 2003/0190317, and 2003/0203409.

An exemplary anti-VEGFR-2 antibody antagonist is the humanized IgG1 monoclonal antibody, Ramucirumab, which binds to the extracellular domain of VEGFR-2, thereby blocking its interaction with VEGF-A. Additional anti-VEGFR-2 antibodies are described in U.S. Pat. Nos. 7,498,414, 6,448,077 and 6,365,157.

In some embodiments, the antitumor antagonists may further include one or more small molecule antagonists of the VEGF pathway, such as multikinase inhibitors of VEGFR-2, including sunitinib, sorafenib, cediranib, pazonpanib and nintedanib.

2. Ang-Tie2R Pathway

In some embodiments, the bispecific antagonist includes a targeting domain containing at least one Tie2 receptor binding antagonist. A Tie2 tyrosine kinase receptor binding antagonist binds to the Tie2 tyrosine kinase receptor or one of its ligands (i.e., Ang1, Ang2, Ang3 and Ang4) so that, as a result of the binding, activation of the Tie2 tyrosine kinase receptor by one or more of its ligands is blocked or inhibited. Like VEGF, angiopoietin 2 (Ang2) is a critical player in tumor angiogenesis. ANG2 and VEGF also work together to prevent antigen presentation in dendritic cells and macrophages, enhance Treg accumulation, and suppress Teff accumulation. It has been previously shown that inhibiting both VEGF and Ang2 improves survival in a mouse breast cancer model, Tg MMTV-PyMT. Moreover, the addition of anti-PD1 further improves responses.

Tie2 tyrosine kinase receptor binding antagonists for use in the present application may include antibody fragments, peptide inhibitors, dominant negative peptides and small molecule drugs, either in isolated forms or as part of a fusion protein or conjugate. In one embodiment, the Tie2 receptor binding antagonist is an inhibitory peptide from trebananib, TBN-P. In a specific embodiment, the inhibitory peptide comprises the amino acid sequence: AQQEECEWDPWT-CEHMGSGSATGGSGSTASSGSGSATHQEECE-WDPWTCEHMLE (SEQ ID NO: 157). In another embodiment, the Tie2 receptor binding antagonist comprises SEQ ID NO: 158 (TBN-P-IgG).

Other peptide inhibitors of Tie2 activation (including Ang-2 inhibitors) for use in the present application include A-11 (Compugen), which comprises the amino acid sequence ETFLSTNKLENQ (SEQ ID NO: 167); the CVX-060 peptide QK(Ac)YQPLDEK(Ac)DK(OP)TLYDQFMLQQG (SEQ ID NO: 168, Pfizer); the CVX-037 peptide (DFB)TNFMPMDDLEK(OP)RLYEQFILQQG (SEQ ID NO: 169, Pfizer); and CGEN-25017 (Compugen). Additional peptide inhibitors of Tie2 activation are described in U.S. Pat. No. 7,138,370.

Antibody inhibitors of Tie2 activation (and/or angiopoietin-2) for use in the present application include AMG-780 (Amgen), MEDI-3617 (MedImmune/AstraZeneca), DX-2240 (Dyax/Sanofi-Aventis), REGN-910 (Sanofi/Regeneron), RG7594 (Roche), LC06 (Roche), TAvi6 (Roche), AT-006 (Roche/Affitech). Additional Tie2 receptor binding antibody antagonists and antibody binding sequences therefrom are described in U.S. Pat. Nos. 7,521,053, 7,658,924, and 8,030,025, as well as U.S. Patent Publication Nos. 2013/0078248, 2013/0259859, and 2015/0197578.

Tie2 binding antagonists for use in the present application may further include the small molecule inhibitors, CGI-1842 (CGI Pharmaceuticals), LP-590 (Locus Pharmaceuticals), ACTB-1003 (Act Biotech/Bayer AG), CEP-11981 (Cephalon/Teva), MGCD265 (Methylgene), Regorafenib (Bayer), Cabozantinib/XL-184/BMS-907351 (Exelixis), Foretnib (Exelixis), MGCD-265 (MethylGene Inc.).

In certain particular embodiments, the bispecific checkpoint regulator antagonist is a full-length antibody that binds human PD-1 or PD-L1 on one of its two binding arms (one pair of HC/LC), and binds a different antigen (or epitope) on its second arm (a different pair of HC/LC). In these embodiments, the bispecific antibody has two distinct antigen binding arms (in both specificity and CDR sequences), and is monovalent for each antigen it binds to.

In some embodiments, the bispecific checkpoint regulator antagonist is a full-length antibody that can bind human PD-1 and/or PD-L1 in each of its two binding arms (a pair of HC/LC). In these embodiments, the bispecific checkpoint regulator antagonist has two identical antigen binding arms, with identical specificity and identical CDR sequences, and is bivalent for each antigen it binds to.

Immunoglobulin and Non-Immunoglobulin Scaffolds

The bispecific antitumor antagonists of the present application may be constructed with an immunoglobulin backbone or non-immunoglobulin scaffold as described herein. In some embodiments, the bispecific antagonists of the present application are constructed with an immunoglobulin scaffold, such as an IgG1, IgG2 or IgG4 scaffold comprising CH1, CH2 and/or CH3 domains. Use of an IgG1 backbone is preferable for cancer treatment where a target is present on antigen presenting cells that can mediate antibody-dependent cell-mediated cytotoxicity (ADCC). Use of an IgG4 backbone allows targeting of the antigen where antigen binding alone is sufficient to generate the desired therapeutic benefits. IgG4-based antagonists preclude undesirable effector functions associated with e.g., IgG1 antibodies, including FcγR binding and complement activation.

Preferably, the first and second targeting domains are presented in a humanized IgG1 or IgG4 scaffold. Further, the second targeting domain may be fused to the carboxy-terminal end of an IgG1 or IgG4 scaffold. Additionally, the IgG1 or IgG4 scaffold may have a N297A or K447A amino acid substitution. In some embodiments, the first targeting domain may comprise one or more framework regions comprising one or more amino acid substitutions selected from the group consisting of E1Q, E6Q, L11V, Q13K, L18V, R19K, A23K, or any combination thereof. In other embodiments, one or more amino acid residues in the IgG1 or IgG4 scaffold are deglycosylated or mutated to produce a glycosylated variants thereof. Exemplary immunoglobulin scaffolds for use in the bispecific molecules described herein may be selected from the group consisting of SEQ ID NOS: 159-166 and 173-175.

Any one of the antibodies or antagonists can be configured in the form of a monoclonal antibody, chimeric antibody, humanized antibody, scFv, or multi-specific antibody. In addition, any of the antibody antagonists described herein may include multiple binding specificities targeting PD-1, PD-L1, VEGF, VEGFR, Angiopoietin, and/or Tie2R. Moreover, any of the antibody antagonists may be engineered to target multiple epitopes in a given target. Furthermore, in some embodiments, the checkpoint antagonist and/or angiogenesis specificity may be included in the form of a dominant negative fusion protein, such as an extracellular domain (ECD) from a corresponding receptor.

The HCVRs and LCVRs described herein may be linked to a naturally-occurring Fc region or a non-naturally occurring or mutated Fc region, e.g., an effectorless (IgG1 N297A/G) or mostly effectorless Fc (e.g., human IgG2 or IgG4) or, alternatively, an Fc with enhanced binding to one or more activating Fc receptors (FcγRI, FcγRIIa or FcγRIIIa) so as to enhance $T_{reg}$ depletion in the tumor environment. Accordingly, in certain embodiments the anti-PD-1, anti-PD-L1, and/or anti-VEGF HCVRs and LCVRs described herein may be linked to an Fc comprising one or more modifications, typically to alter one or more functional properties of the antibody, such as serum half-life, complement fixation, Fc receptor binding, and/or antigen-dependent cellular cytotoxicity. Furthermore, antibody described herein may be chemically modified (e.g., one or more chemical moieties can be attached to the antibody) or it may be modified to alter its glycosylation, to alter one or more functional properties of the antibody. More specifically, in certain embodiments, the antibodies in the present application may include modifications in the Fc region in order to generate an Fc variant with (a) increased or decreased antibody-dependent cell-mediated cytotoxicity (ADCC), (b) increased or decreased complement mediated cytotoxicity (CDC), (c) increased or decreased affinity for C1q and/or (d) increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g., of the specific Fc region positions identified herein.

For uses where effector function is to be avoided altogether, e.g., when antigen binding alone is sufficient to generate the desired therapeutic benefit, and effector function only leads to (or increases the risk of) undesired side effects, IgG4 antibodies may be used, or antibodies or fragments lacking the Fc region or a substantial portion thereof can be devised, or the Fc may be mutated to eliminate glycosylation altogether (e.g., N297A). Alternatively, a hybrid construct of human IgG2 (CH1 domain and hinge region) and human IgG4 (CH2 and CH3 domains) may be generated that is devoid of effector function, lacking the ability to bind FcγRs (like IgG2) and activate complement (like IgG4). When using an IgG4 constant domain, it is usually preferable to include the substitution S228P, which mimics the hinge sequence in IgG1 and thereby stabilizes IgG4 molecules, reducing Fab-arm exchange between the therapeutic antibody and endogenous IgG4 in the patient being treated.

In certain embodiments, the anti-PD-1-, anti-PD-L1-, anti-VEGF-, anti-angiopoietin-, and/or or anti-Tie2R antibodies or fragments thereof may be modified to increase its biological half-life. Various approaches may be employed, including e.g., those that increase the binding affinity of the Fc region for FcRn. In one embodiment, the antibody is altered within the CH1 or CL region to contain a salvage receptor binding epitope taken from two loops of a CH2 domain of an Fc region of an IgG, as described in U.S. Pat. Nos. 5,869,046 and 6,121,022. The numbering of residues in the Fc region is that of the EU index. Sequence variants disclosed herein are provided with reference to the residue number followed by the amino acid that is substituted in place of the naturally occurring amino acid, optionally preceded by the naturally occurring residue at that position. Where multiple amino acids may be present at a given position, e.g., if sequences differ between naturally occurring isotypes, or if multiple mutations may be substituted at the position, they are separated by slashes (e.g., "X/Y/Z").

Exemplary Fc variants that increase binding to FcRn and/or improve pharmacokinetic properties include substitutions at positions 259, 308, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 305A, 307A, 311A, 312A, 378Q, 380A, 382A, 434A (Shields et al. (2001) J. Biol. Chem., 276(9):6591-6604), 252F, 252Y, 252W, 254T, 256Q, 256E, 256D, 433R, 434F, 434Y, 252Y/254T/256E, 433K/434F/436H (Dall'Acqua et al. (2002) J. Immunol., 169:5171-5180, Dall'Acqua et al. (2006) J. Biol. Chem., 281:23514-23524, and U.S. Pat. No. 8,367,805.

Modification of certain conserved residues in IgG Fc (I253, H310, Q311, H433, N434), such as the N434A variant (Yeung et al. (2009) J. Immunol. 182:7663), have been proposed as a way to increase FcRn affinity, thus increasing the half-life of the antibody in circulation (WO 98/023289). The combination Fc variant comprising M428L and N434S has been shown to increase FcRn binding and increase serum half-life up to five-fold (Zalevsky et al. (2010) Nat. Biotechnol. 28:157). The combination Fc variant comprising T307A, E380A and N434A modifications also extends half-life of IgG1 antibodies (Petkova et al. (2006) Int. Immunol. 18:1759). In addition, combination Fc variants comprising M252Y-M428L, M428L-N434H, M428L-N434F, M428L-N434Y, M428L-N434A, M428L-N434M, and M428L-N434S variants have also been shown to extend half-life (U.S. Patent Publication No. 2006/173170). Further, a combination Fc variant comprising M252Y, S254T and T256E was reported to increase half-life-nearly 4-fold. Dall'Acqua et al. (2006) J. Biol. Chem. 281:23514.

Homodimers and Heterodimers

One of the challenges for efficiently producing bispecific antibody preparations concerns mispairing of heavy and light chains when co-expressing chains of different binding specificities. Table 1 lists several amino acid substitution options for overcoming mispairing between heavy chains of different binding specificities, which "enforce" or preferentially promote correct association between desired heavy chains. Any approach to prevent or reduce mispairing between heavy chains may be used to make the bispecific antitumor antagonists according to the present disclosure.

The "knobs-into-hole" (KiH) approach relies on modifications of the interface between the two CH3 domains where most interactions occur. Typically, a bulky residue is introduced into the CH3 domain of one antibody heavy chain and acts similarly to a key. In the other heavy chain, a "hole" is formed that is able to accommodate this bulky residue, mimicking a lock. The resulting heterodimeric Fc-part can be further stabilized by artificial disulfide bridges.

An alternative approach is based on charged residues with ionic interactions or steric complementarity. This includes altering the charge polarity in the CH3 interface so that co-expression of electrostatically matched Fc domains support favorable attractive interactions and heterodimer formation while retaining the hydrophobic core, whereas unfavorable repulsive charge interactions suppress homodimerization. See Table 1. The amino acid numbering in Table 1 follows the Kabat numbering scheme and can be applied to heavy chain amino acid sequences of the antibodies described herein.

In a further approach, the bispecific molecules of the present application may be constructed with a non-immunoglobulin scaffold containing leucine zipper (LZ) domains. A leucine zipper is a common three-dimensional structural motif in proteins, typically as part of a DNA-binding domain in various transcription factors. A single LZ typically contains 4-5 leucine residues at approximately 7-residue intervals, which forms an amphipathic alpha helix with a hydrophobic region running along one side. In a particular embodiment, a heterodimeric protein scaffold comprises a LZ from the c-jun transcription factor associated with a LZ from the c-fos transcription factor. Although c-jun is known to form jun-jun homodimers and c-fos does not form homodimers, the formation of jun-fos heterodimers is greatly favored over jun-jun homodimers.

A leucine zipper domain may be incorporated in place of CH2-CH3 sequences in the protein scaffold or it may be placed at the carboxy terminal end of the two heavy chains in the bispecific antitumor antagonist. In the case of the latter, a furin cleavage site may be introduced between the carboxy terminal end of CH3 and the amino terminal end of the leucine zipper. This can facilitate furin-mediated cleavage of the leucine zipper following the heterodimerization step when co-expressing the heavy and light chains of the bispecific antitumor antagonist in an appropriate mammalian cell expression system (see Wranik et al., J. Biol. Chem., 287(5):43331-43339, 2012).

TABLE 1

| Type | HC1 | HC2 |
| --- | --- | --- |
| Knobs-into-holes | Y349C, T366S, L368A, Y407V | S354C, T366W |
| Ionic, electrostatic | S183E, E356K, E357K, D399K | S183K, K370E, K409D, K439E |
| Ionic, electrostatic | K392D, K409D | E356K, D399K |
| HA-TF substitutions | S364H, F405A | Y349T, T394F |
| HF-TA substitutions | S364H, T394F | Y349T, F405A |
| Leucine zipper heterodimer | human c-Jun leucine zipper | human c-fos leucine zipper |

The amino acid numbering in Table 1 follows the Kabat numbering scheme and can be applied to heavy chain amino acid sequences of the antibodies described herein. The mutations described in Table 1 may be applied to the sequence (published or otherwise) of any immunoglobulin IgG1 heavy chain, as well as other immunoglobulin classes, and subclasses (or isotypes) therein.

When co-expressing heavy and light chains of bispecific antibodies, the light chains of one binding specificity can also mispair with heavy chains of a different binding specificity. Therefore, in certain embodiments, portions of the heavy chain, light chain or both may be modified relative to the "wild-type" antibody chains from which they are derived to prevent or reduce mispairing of both heavy chain constant regions to one another, as well mispairing of light chain constant regions to their heavy chain counterparts.

The light chain mispairing problem can be addressed in several ways. In some embodiments, sterically complementary mutations and/or disulfide bridges may be incorporated into the two VL/VH interfaces. In other embodiments, mutations can be incorporated based on ionic or electrostatic interactions. In some embodiments, light chain mispairing may be prevented or reduced by employing a first arm with an S183E mutation in the CH1 domain of the heavy chain and an S176K mutation in the CL domain of the light chain. A second arm may include an S183K mutation in the in the CH1 domain of the heavy chain and an S176E mutation in the CL domain of the light chain. In other embodiments, a "CrossMab" approach is employed, where one arm in the bispecific antitumor antagonist (e.g., Fab) is left untouched, but in the other arm containing the other binding specificity, one or more domains in the light chain are swapped with one or more domains in the heavy chain at the heavy chain: light chain interface.

Methods, immunoglobulin domain sequences, including specific mutations for preventing mispairing of heavy and light chains as disclosed above are further described in U.S. Patent Publication Nos. 2014/0243505 and 2013/0022601.

Conjugates

In certain embodiments, the antitumor antagonists of the present application are chemically conjugated to one or more peptides and/or small molecule drugs. The peptides or small molecule drug can be the same or different. The peptides or small molecule drugs can be attached, for example to reduced SH groups and/or to carbohydrate side chains. Methods for making covalent or non-covalent conjugates of peptides or small molecule drugs with antibodies are known in the art and any such known method may be utilized.

In some embodiments the peptide or small molecule drug is attached to the hinge region of a reduced antibody component via disulfide bond formation. Alternatively, such agents can be attached using heterobifunctional cross-linkers, such as N-succinyl 3-(2-pyridyldithio) propionate (SPDP). General techniques for such conjugation are well-known in the art. In some embodiments, the peptide or small molecule drug is conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent. Methods for conjugating peptide inhibitors or small molecule drugs to antibodies via antibody carbohydrate moieties are well-known to those of skill in the art. For example, in one embodiment, the method involves reacting antibody component having an oxidized carbohydrate portion with a carrier polymer that has at least one free amine function. This reaction results in an initial Schiff base (imine) linkage, which can be stabilized by reduction to a secondary amine to form the final conjugate. Exemplary methods for conjugating small molecule drugs and peptides to antibodies are described in U.S. Patent Publication No. 2014/0356385.

Preferably, the antitumor antagonists in the present disclosure retain certain desirable characteristics and pharmacokinetic properties of antibodies, including a desirable in vitro and in vivo stability (e.g., lone half-life and shelf-life stability), efficient delivery into desired target cells, increased affinity for binding partners, desirable antibody-dependent cell-mediated cytotoxicity and complement-dependent cytotoxicity, and reduced renal clearance or excretion. Accordingly, careful attention to size and need for particular constant region effector functions may be considered in the design of the antitumor antagonists.

The bispecific antitumor antagonists described herein may range in size from 50 kD to 300 kD, from 50 kD to 250 kD, from 60 kD to 250 kD, from 80 kDa to 250 kD, from 100 kD to 250 kD, from 125 kD to 250 kD, from 150 kD to 250 kD, from 60 kD to 225 kD, from 75 kD to 225 kD, from 100 kD to 225 kD, from 125 kD to 225 kD, from 150 kD to 225 kD, from 60 kD to 200 kD, from 75 kD to 200 kD, from 100 kD to 125 kD to 200 kD, from 150 kD to 200 kD, from 60 kD to 150 kD, from 75 kD to 150 kD, from 100 kD to 150 kD, from 60 kD to 125 kD, from 75 kD to 125 kD, from 75 kD to 100 kD, or any range encompassed by any combination of whole numbers listed in the above cited ranges or any ranges specified by any combination of whole numbers between any of the above cited ranges.

Kits

The present application further provides a kit comprising a checkpoint regulator antagonist or antitumor antagonist of the present application. In some embodiment, the kit comprises one or more bispecific immune checkpoint regulators containing at least one TGFβ pathway inhibitory domain. In some embodiments, the kit further contains additional reagents, including secondary antibodies for detection, and additional human antibodies described herein (e.g., a human antibody having a complementary activity, which binds to a different epitope in the same antigen, etc.). Kits typically include a label with instructions indicating the intended use of the contents of the kit. The term label includes any writing, or recorded material supplied on or with the kit, or which otherwise accompanies the kit.

II. Methods of Using the Antitumor Antagonists

The antitumor antagonists of the present application have numerous in vitro and in vivo utilities including, for example, enhancement of immune responses and treatment of cancers, infectious diseases or autoimmune diseases.

The antitumor antagonists of the present application may be administered to cells in culture, in vitro or ex vivo, or to human subjects, e.g., in vivo, to enhance immunity in a variety of diseases. Accordingly, provided herein are methods of modifying an immune response in a subject comprising administering to the subject antibody or antigen-binding fragment thereof as described herein such that the immune response in the subject is enhanced, stimulated or up-regulated. Preferred subjects include human patients in whom enhancement of an immune response would be desirable. The methods are particularly suitable for treating human patients having a disorder that can be treated by augmenting an immune response (e.g., the T-cell mediated immune response). The methods are particularly suitable for treatment of cancer or chronic infections in vivo. For example, the antitumor antagonists may be administered together with antigen of interest or the antigen may already be present in the subject to be treated (e.g., a tumor-bearing or virus-bearing subject) to enhance antigen-specific immunity. When antitumor antagonists are administered together with another agent, the two can be administered separately or simultaneously.

In some embodiments, the checkpoint regulator antagonist in the above-described method is an anti-PD-1 antibody, an anti-PD-L1 antibody, a VEGF antibody, a VEGFR antibody, or any fragment thereof in combination with a TGFβRII ECD, a VEGFR ECD, or both.

In any of the antibody embodiments described herein, the antibody is preferably a human or humanized antibody.

Also encompassed within the scope of the present application are methods for detecting and/or measuring the presence of target molecule in a sample comprising contacting the sample, and a control sample, with an antibody, antibody fragment, or bispecific antagonist of the present application, which specifically binds to the target molecule under conditions that allow for formation of a complex between the antagonist and the target molecule. The formation of a complex is then detected, wherein a difference in complex formation between the sample compared to the control sample is indicative the presence of target molecule in the sample.

Given the ability of the antitumor antagonist of the present application to block inhibition or co-inhibition of T cell responses, e.g., antigen-specific T cell responses, provided herein are in vitro and in vivo methods of using the antibodies described herein to stimulate, enhance or upregulate antigen-specific T cell responses, e.g., anti-tumor T cell responses. In certain embodiments, CD3 stimulation is also provided (e.g., by co-incubation with a cell expressing membrane CD3), which stimulation can be provided at the same time, before, or after treatment with a checkpoint regulator antagonist. For example, provided herein are methods of enhancing antigen-specific T cell response comprising contacting said T cell with a checkpoint regulator antagonist described herein, and optionally with CD3, such that antigen-specific T cell response is enhanced, e.g., by removal of a checkpoint regulator mediated inhibitory effect. Any suitable indicator of antigen-specific T cell response can be used to measure the antigen-specific T cell response. Non-limiting examples of such suitable indicators include increased T cell proliferation in the presence of the antibody and/or increase cytokine production in the presence of the antibody. In a preferred embodiment, interleukin-2 and/or interferon-γ production by the antigen-specific T cell is enhanced.

Further encompassed in the present application is a method for enhancing an immune response (e.g., antigen-specific T cell response) in a subject by administering a bispecific antitumor antagonist described herein to the subject such that an immune response (e.g., antigen-specific T cell response) in the subject is enhanced. In a preferred embodiment, the subject is a tumor-bearing subject and an immune response against the tumor is enhanced. A tumor may be a solid tumor or a liquid tumor, e.g., a hematological malignancy. In certain embodiments, a tumor is an immunogenic tumor. In other embodiments, a tumor is non-immunogenic. In certain embodiments, a tumor is PD-L1 positive. In other embodiments a tumor is PD-L1 negative. A subject may also be a virus-bearing subject in which an immune response against the virus is enhanced as a consequence of administering the bispecific antitumor antagonist as described herein.

In one embodiment, a method for inhibiting the growth of tumor cells in a subject comprises administering to the subject a bispecific antitumor antagonist described herein such that growth of the tumor is inhibited in the subject. Also provided are methods of treating chronic viral infection in a subject comprising administering to the subject a bispecific antitumor antagonist as described herein such that the chronic viral infection is treated in the subject.

Also encompassed herein are methods for depleting $T_{reg}$ cells from the tumor microenvironment of a subject with a tumor, e.g., cancerous tumor, comprising administering to the subject a therapeutically effective amount of a bispecific antitumor antagonist described herein that comprises an Fc that stimulates depletion of $T_{reg}$ cells in the tumor microenvironment. An Fc may, e.g., be an Fc with effector function or enhanced effector function, such as binding or having enhanced binding to one or more activating Fc receptors.

In a preferred embodiment, $T_{reg}$ depletion occurs without significant depletion or inhibition of $T_{eff}$ in the tumor microenvironment, and without significant depletion or inhibition of $T_{eff}$ cells and $T_{reg}$ cells outside of the tumor microenvironment. In certain embodiments, the subject has higher levels of checkpoint regulator(s) on $T_{reg}$ cells than on $T_{eff}$ cells, e.g., in the tumor microenvironment. In certain embodiments, the bispecific antagonists may deplete $T_{regs}$ in tumors and/or $T_{regs}$ in tumor infiltrating lymphocytes (TILs). For example, in a CT26 tumor model, an anti-mouse TIGIT antibody formatted as a mouse IgG2a (which exhibits effector function) was found to partially deplete both Treg and CD8$^+$ T cells, but did not deplete CD4$^+$ T cells. An effectorless counterpart antibody or antagonist formatted as a mouse IgG1 D265A, did not deplete T cells.

In certain embodiments, the bispecific antitumor antagonist described herein is given to a subject as an adjunctive therapy. Treatment of cancer patient with a bispecific antitumor antagonist according to the present application may lead to a long-term durable response relative to the current standard of care; long term survival of at least 1, 2, 3, 4, 5, 10 or more years, recurrence free survival of at least 1, 2, 3, 4, 5, or 10 or more years. In certain embodiments, treatment of a cancer patient with bispecific antitumor antagonist prevents recurrence of cancer or delays recurrence of cancer by, e.g., 1, 2, 3, 4, 5, or 10 or more years. Thus, treatment with these antagonists can be used as a primary or secondary line of treatment.

In certain preferred embodiments, the subject has a cell proliferative disease or cancer. Provided herein are methods for treating a subject having cancer, comprising administering to the subject a bispecific antitumor antagonist described herein, such that the subject is treated, e.g., such that growth of cancerous tumors is inhibited or reduced and/or that the tumors regress. The bispecific antitumor antagonists described herein can be used alone to inhibit the growth of cancerous tumors. Alternatively, any of these antitumor antagonists can be used in conjunction with another agent, e.g., other anti-cancer targets, immunogenic agents, standard cancer treatments, or other antibodies, as described below.

Accordingly, provided herein are methods of treating cancer, e.g., by inhibiting growth of tumor cells, in a subject, comprising administering to the subject a therapeutically effective amount of a bispecific antitumor antagonist described herein. Preferably, the antibody contains human or humanized immunoglobulin sequences.

Cancers whose growth may be inhibited using the antibodies of the invention include cancers typically responsive to immunotherapy. Non-limiting examples of cancers for treatment include squamous cell carcinoma, small-cell lung cancer, non-small cell lung cancer, squamous non-small cell lung cancer (NSCLC), non NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NEIL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein may also be used for treatment of metastatic cancers, refractory cancers (e.g., cancers refractory to previous immunotherapy, e.g., with a blocking CTLA-4 or PD-1 antibody), and recurrent cancers.

A bispecific antitumor antagonist of the present application can be administered alone, in combination with another antitumor antagonist, or concurrently with another antitumor antagonist. Alternatively, the bispecific antitumor antagonist can also be administered in combination, or concurrently with, an immunogenic agent, such as cancerous cells, tumor vaccines, purified tumor antigens (including recombinant proteins, peptides, and carbohydrate molecules), cells transfected with genes encoding immune stimulating cytokines, in a cancer vaccine strategy (He et al. (2004) J. Immunol. 173:4919-28), or an oncolytic virus.

Many experimental strategies for vaccination against tumors have been devised. In one of these strategies, a vaccine is prepared using autologous or allogeneic tumor cells. Some of these cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

Cancer vaccines have been shown to enhance effector T-cell infiltration into the tumors in preclinical models. The major types of cancer vaccines include peptide vaccines, vector-based antigen specific vaccines, whole-cell vaccines, and dendritic cell vaccines. All vaccine-based therapies are designed to deliver either single or multiple antigenic epitopes or antigens from the whole cells to the patients and induce tumor-specific effector T cells. Thus, a vaccine-based therapy may be the most efficient way to induce T-cell infiltration into the tumor.

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host.

Inhibition of the checkpoint regulator pathway, TGF-β pathway, and/or angiogenesis pathways may be used in conjunction with a collection of recombinant proteins and/or peptides expressed in a tumor in order to generate an immune response to these proteins. Such proteins may be viewed by the immune system as self-antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) Science 266: 2011-2013). Tumor antigens can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Non-limiting examples of tumor vaccines include sipuleucel-T (Provenge®), an FDA-approved tumor vaccine for metastatic prostate cancer; tumor cells transfected to express the cytokine granulocyte macrophage colony-stimulating factor (GM-CSF), such as the whole cell GM-CSF-secreting irradiated, allogeneic pancreatic cancer vaccine (GVAX; Johns Hopkins); a multi-peptide vaccine consisting of immunogenic peptides derived from breast cancer antigens, neu, legumain, and p-catenin, which prolonged the vaccine-induced progression-free survival of breast tumor-bearing mice when administered in combination with anti-PD-1 antibody (Karyampudi L. et al. (2014) Cancer Res 74:2974-2985); peptides of melanoma antigens, such as peptides of gp100, MAGE antigens, Trp-2, MARTI and/or tyrosinase, or. Other tumor vaccines include proteins from viruses implicated in human cancers such as human papilloma viruses (HPV)(e.g., Gardasil®, Gardasil 9@, and Cervarix®; hepatitis B virus (e.g., Engerix-B and Recombivax HB); hepatitis C virus (HCV), Kaposi's sarcoma associated herpes sarcoma virus (KSHV). Another form of tumor specific antigen that can be used in conjunction with TIGIT inhibition is purified heat shock proteins (HSP) isolated from the tumor tissue itself. These heat shock proteins contain fragments of proteins from the tumor cells and these HSPs are highly efficient at delivery to antigen presenting cells for eliciting tumor immunity. Talimogene laherparepvec (T-VEC, or Imlygic®) is an FDA-approved oncolytic virus for the treatment of some patients with metastatic melanoma that cannot be surgically removed.

Dendritic cells (DC) are potent antigen presenting cells that can be used to prime antigen-specific responses. DC's can be produced ex vivo and loaded with various protein and peptide antigens, as well as tumor cell extracts (Nestle et al. (1998) Nature Medicine 4: 328-332). DCs can also be transduced by genetic means to express these tumor antigens as well. DCs have also been fused directly to tumor cells for the purposes of immunization (Kugler et al. (2000) Nature Medicine 6:332-336). As a method of vaccination, DC immunization may be effectively combined with checkpoint regulator blocking to activate (unleash) more potent anti-tumor responses.

Inhibition of the checkpoint regulator pathway, TGF-β pathway, and/or angiogenesis pathways can also be combined with standard cancer treatments (e.g., surgery, radiation, and chemotherapy). In particular, checkpoint regulator inhibition can be effectively combined with chemotherapeutic regimes. In these instances, it may be possible to reduce the dose of chemotherapeutic reagent administered (Mokyr et al. (1998) Cancer Research 58: 5301-5304). An example of such a combination is antitumor antagonist in combination with decarbazine for the treatment of melanoma. Another example of such a combination is a checkpoint regulator antagonist or antitumor antagonist in combination with interleukin-2 (IL-2) for the treatment of melanoma. For example, the scientific rationale behind the combined use of checkpoint regulator inhibition, TGF-β1/TGF-β1 RII inhibition, and/or angiogenesis inhibition with chemotherapy can promote cell death as a consequence of the cytotoxic action of most chemotherapeutic compounds, thereby resulting in increased levels of tumor antigen in the antigen presentation pathway. Other combination therapies that may result in synergy with checkpoint regulator inhibition, TGF-β1/TGF-β1 RII inhibition, and/or angiogenesis inhibition through cell death are radiation, surgery, and hormone deprivation. Each of these protocols creates a source of tumor antigen in the host.

The bispecific antitumor antagonists described herein may also be constructed to target Fcα or Fcγ receptor-expressing effector cells to tumor cells (see, e.g., U.S. Pat. Nos. 5,922,845 and 5,837,243). For example, anti-Fc receptor/antitumor antigen (e.g., Her-2/neu) bispecific antibodies have been used to target macrophages to sites of tumor. This type of targeting may be adapted to the present embodiments to more effectively activate tumor specific responses. The T cell arm of these responses would be augmented by the inhibition of one or more checkpoint regulator antagonists described herein. Alternatively, antigen may be delivered directly to DCs by the use of bispecific antibodies that bind to tumor antigen and a dendritic cell specific cell surface marker.

Tumors evade host immune surveillance by a large variety of mechanisms. Many of these mechanisms may be overcome by the inactivation of immunosuppressive proteins expressed by the tumors. These include among others TGF-β, IL-10, and Fas ligand. Antibodies to each of these entities can be used in combination with the antitumor antagonists described herein to counteract the effects of the immunosuppressive agent and favor tumor immune responses by the host.

Other antibodies that activate host immune responsiveness can be used in combination with the antitumor antagonists described herein. These include molecules on the surface of dendritic cells that activate DC function and antigen presentation. Anti-CD40 antibodies are able to substitute effectively for T cell helper activity (Ridge et al. (1998) Nature 393: 474-478) and can be used in conjunction with the bispecific antagonists described herein. Activating antibodies to T cell costimulatory molecules, such as OX-40 (Weinberg et al. (2000) Immunol 164: 2160-2169), CD137/

4-1BB (Melero et al. (1997) Nature Medicine 3: 682-685 (1997), and ICOS (Hutloff et al. (1999) Nature 397: 262-266) may also provide for increased levels of T cell activation. In addition, inhibitors of other immune checkpoint regulators may also be used in conjunction with other antitumor antagonists described herein, as further described below.

Bone marrow transplantation is currently being used to treat a variety of tumors of hematopoietic origin. While graft versus host disease is a consequence of this treatment, checkpoint regulator inhibition may be used to increase the effectiveness of the donor engrafted tumor specific T cells by reducing graft vs. tumor responses.

In certain embodiments, antitumor antagonist described herein may be administered to a subject with an infectious disease, especially chronic infections. In this case, similar to its application to cancer, antibody-mediated checkpoint regulator inhibition can be used alone, or as an adjuvant, in combination with vaccines, to enhance immune responsiveness to pathogens, toxins, and self-antigens. Exemplary pathogens for which this therapeutic approach can be applied include, but are not limited to, HIV, Hepatitis (A, B, & C), Influenza, Herpes, Giardia, Malaria, *Leishmania, Staphylococcus aureus*, and *Pseudomonas aeruginosa*. Checkpoint regulator inhibition, TGF-β1/TGF-β1 RII inhibition, and/or angiogenesis inhibition is particularly useful against established infections by agents, such as HIV that present novel or altered antigens over the course of the infections. Administration of bispecific antitumor antagonists can allow for recognition of these antigens as foreign so as to provoke an appropriate T cell response.

Other pathogenic viruses causing infections treatable by the methods described herein include HIV, hepatitis (A, B, or C), herpesvirus infections (e.g., VZV, HSV-1, HAV-6, HSV-II, and CMV, Epstein Barr virus), and infections caused by an adenovirus, influenza virus, flavivirus, echoviruses, rhinoviruses, coxsackie viruses, coronaviruses, respiratory syncytial viruses, mumps viruses, rotavirus, measles virus, rubella virus, parvovirus, vaccinia virus, HTLV virus, dengue virus, papillomavirus, molluscum virus, poliovirus, rabies virus, JC virus, arboviral encephalitis virus, or combination thereof.

Exemplary pathogenic bacteria or diseases caused therefrom which may be treatable by the methods described herein include *Chlamydia, Rickettsia, Mycobacteria, Staphylococci, Streptococci, Pneumonococci, Meningococci* and *Gonococci, Klebsiella, Proteus, Serratia, Pseudomonas, Legionella, Diphtheria, Salmonella, Bacilli, Cholera, Leptospirosis* tetanus, botulism, anthrax, plague, and Lyme disease.

Exemplary pathogenic fungi causing infections treatable by the methods described herein include *Candida* (e.g., *albicans, krusei, glabrata, tropicalis*, etc.), *Cryptococcus neoformans, Aspergillus* (e.g., *fumigatus, niger*, etc.), *Mucorales* (e.g., *mucor, absidia, rhizopus*), *Sporothrix schenkii, Blastomyces dermatitidis, Paracoccidioides brasiliensis, Coccidioides immitis* and *Histoplasma capsulatum*.

Exemplary pathogenic parasites causing infections treatable by the methods described herein include *Entamoeba histolytica, Balantidium coli, Naegleriafowleri, Acanthamoeba* sp., *Giardia Zambia, Cryptosporidium* sp., *Pneumocystis carinii, Plasmodium vivax, Babesia microti, Trypanosoma brucei, Trypanosoma cruzi, Leishmania donovani, Toxoplasma gondii*, and *Nippostrongylus brasiliensis*.

In all of the above methods, checkpoint regulator inhibition, TGF-1/TGF-β1 RII inhibition, and/or angiogenesis inhibition can be combined with other forms of immunotherapy such as cytokine treatment (e.g., interferons, GM-CSF, G-CSF, IL-2), or bispecific antibody therapy using two different binding specificities to provide enhanced presentation of tumor antigens.

The bispecific antitumor antagonists described herein can be used to enhance antigen-specific immune responses by co-administration of one or more of any of these antibodies with antigen of interest (e.g., a vaccine). Accordingly, provided herein are methods of enhancing an immune response to antigen in a subject, comprising administering to the subject: (i) the antigen; and (ii) the bispecific antitumor antagonist, such that an immune response to the antigen in the subject is enhanced. The antigen can be, for example, a tumor antigen, a viral antigen, a bacterial antigen or antigen from a pathogen. Non-limiting examples of such antigens include those discussed in the sections above, such as the tumor antigens (or tumor vaccines) discussed above, or antigens from the viruses, bacteria or other pathogens described above.

In certain embodiments, a peptide or fusion protein comprising the epitope to which the bispecific antitumor antagonist binds may be used as a vaccine instead of, or in addition to, the antitumor antagonist(s).

Suitable routes of administering the antibody compositions (e.g., human monoclonal antibodies, multi-specific antibodies or antagonists and immunoconjugates) described herein in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

Combination Therapies

In another aspect, the present application provides combination therapies for enhancing antigen-specific T cell response in a subject. In one embodiment, the method includes contacting a T cell with bispecific antitumor antagonist in combination with a second antibody, antibody fragment, antagonist or drug such that antigen-specific T cell response or apoptotic pathway is enhanced. For example, in some embodiments, the first bispecific antitumor antagonist specifically binds to a first checkpoint regulator, such PD-1 or PD-L1, and a second bispecific antitumor antagonist specifically binding to a different checkpoint regulator or to a different epitope. In some embodiments, the second antibody or antibody fragment comprises one or more different HCVRs, LCVR, or CDR(s) from PD-1 and/or PD-L1.

In a related aspect, a method of reducing or depleting regulatory T cells in a tumor of a subject in need thereof includes administering an effective amount of antibody or antibody fragment in combination with a second antibody, antibody fragment, antagonist or drug such that the number of regulatory T cells in the subject is reduced.

In some embodiments, the subject has a cell proliferative disease or cancer as described herein.

In other embodiments, the subject has a chronic viral infection, inflammatory disease or autoimmune disease as described herein.

The provision of two distinct signals to T-cells is a widely accepted model for lymphocyte activation of resting T lymphocytes by antigen-presenting cells (APCs). This model further provides for the discrimination of self from non-self and immune tolerance. The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs). This induces T-cells to promote clonal expansion, cytokine secretion, and effector function. In the absence of co-stimulation, T-cells can become refractory to antigen stimulation, which results in a tolerogenic response to either foreign or endogenous antigens.

In the two-signal model, T-cells receive both positive co-stimulatory and negative co-inhibitory signals. The regulation of such positive and negative signals is critical to maximize the host's protective immune responses, while maintaining immune tolerance and preventing autoimmunity. Negative signals seem necessary for induction of T-cell tolerance, while positive signals promote T-cell activation. Both co-stimulatory and co-inhibitory signals are provided to antigen-exposed T cells, and the interplay between co-stimulatory and co-inhibitory signals is essential to controlling the magnitude of an immune response. Further, the signals provided to the T cells change as an infection or immune provocation is cleared, worsens, or persists, and these changes powerfully affect the responding T cells and re-shape the immune response.

The mechanism of co-stimulation is of therapeutic interest because the manipulation of co-stimulatory signals has shown to provide a means to either enhance or terminate cell-based immune response. Recently, it has been discovered that T cell dysfunction or anergy can occur concurrently with an induced and sustained expression of immune checkpoint regulators, such as programmed death 1 polypeptide (PD-1) and its ligands, PD-L1 and PD-L2. PD-L1 is overexpressed in many cancers and is often associated with poor prognosis (Thompson R H et al., Cancer Res 2006, 66(7): 3381). Further, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 114(8):1537). This may be due to exploitation of PD-L1 signaling mediated by PD-L1 expressing tumor cells interacting with PD-1 expressing T cells to result in attenuation of T cell activation and evasion of immune surveillance. Inhibition of the PD-L1/PD-1 interaction provides a means to enhance T cell immunity, including CD8+ T cell-mediated killing of cancer cells and tumors. Similar enhancements to T cell immunity have been observed by inhibiting the binding of PD-L1 to the binding partner B7-1. Consequently, therapeutic targeting of PD-1 and other immune checkpoint regulators are an area of intense interest.

Combining inhibition of TGF-β1 signaling, checkpoint regulator signaling, and/or angiogenesis signaling with other signaling pathways deregulated in tumor cells can provide a means for enhance treatment efficacy. In recent years, a number of immune checkpoint regulators in the form of receptors and their ligands have been identified. One important family of membrane-bound ligands that bind to co-stimulatory or co-inhibitory receptors is the B7 family, which includes CTLA-4 and its ligands, B7-1 and B7-2; PD-1 and its ligands, PD-L1 (B7-H1) and PD-L2 (B7-DC); B7-H2 (ICOS-L), B7-H3, B7-H4, B7-H5 (VISTA), and B7-H6. Additional immune checkpoint antagonists include, but are not limited to TIM-3 and its ligand, Galectin-9; LAG-3 and its ligands, including liver sinusoidal endothelial cell lectin (LSECtin) and Galectin-3; CD122 and its CD122R ligand; CD70, B7H3, B and T lymphocyte attenuator (BTLA), and VISTA (Le Mercier et al. (2015) Front. Immunol., (6), Article 418). In addition, a number of checkpoint regulator antagonists have been identified and tested in various clinical and pre-clinical models and/or approved by the FDA (Kyi et al., FEBS Letters, 588:368-376 (2014). The concept of inhibitory receptor blockade, also known as immune checkpoint blockade, has been validated by virtue of e.g., the FDA approval of the PD-1 inhibitors, nivolumab and pembrolizumab, as well as the anti-CTLA-4 antibody, ipilimumab for metastatic melanoma.

An immune checkpoint antagonist modulates or interferes with the activity of the immune checkpoint regulator so that, as a result of the binding to the checkpoint regulator or its ligand, signaling through the checkpoint regulator receptor is blocked or inhibited. By inhibiting this signaling, immune-suppression can be reversed so that T cell immunity against cancer cells can be re-established or enhanced. In contrast, an immune checkpoint agonist (of e.g., a costimulatory molecule) stimulates the activity of an immune checkpoint regulator so that, as a result of the binding to the checkpoint regulator or its ligand, signaling through the checkpoint regulator receptor is stimulated. By stimulating this signaling, T cell immunity against cancer cells can be re-established or enhanced.

Accordingly, in one embodiment, a method for stimulating an immune response in a subject comprises administering to the subject a bispecific antitumor antagonist described herein in combination with another immune checkpoint regulator described herein above, such that an immune response is stimulated in the subject, for example to inhibit tumor growth or to stimulate anti-viral response. In particular, the bispecific antitumor antagonist(s) can be administered as separate antagonists or as a multi-specific antagonist comprising binding specificities to multiple products.

In some embodiments, the bispecific antitumor antagonist of the present application can be combined to stimulate an immune response with (i) an antagonist of the IgSF family protein, B7 family or TNF family that inhibit T cell activation, or antagonist of a cytokine that inhibits T cell activation (e.g., IL-6, IL-10, TGF-β, VEGF, or other immunosuppressive cytokines) and/or (ii) an agonist of a stimulatory receptors of the IgSF family, B7 family or TNF family or of cytokines to stimulate T cell activation, for stimulating an immune response. In other embodiments, the subject is administered a bispecific antitumor antagonist in combination with anti-CTLA-4 antibody or CTLA-4 antagonist. Exemplary anti-CTLA-4 antibodies for use in accordance with the present application include ipilimumab, trevilizumab and tremelimumab.

In some embodiments, subjects with a cancer exhibiting high expression of a ligand for an immune checkpoint regulator may be administered a bispecific antagonist targeting a different checkpoint regulator antagonist. By way of example, in one embodiment, a subject with a cancer exhibiting high expression of PVR (CD155) and/or Nectin-2 (CD112) and/or low expression PD-L1 may be selected for monotherapy with anti-TIGIT or anti-LAG-3 antibodies or fragments thereof alone, or in a combination therapy with a PD-1 antagonist or other immune checkpoint regulator antagonist. The bispecific antitumor antagonists of the present application may be co-administered with any additional agent(s), e.g., antibodies, antagonists, or drugs in amount(s) effective in stimulating an immune response and/or apoptosis so as to further enhance, stimulate or upregulate an immune response and/or apoptosis in a subject.

In some embodiments, the bispecific antitumor antagonist is administered subsequent to treatment with a different antitumor antagonist. For example, in some embodiments, the bispecific antitumor antagonist of the present application may be administered only after treatment with a monospecific antitumor antagonist has failed, has led to incomplete therapeutic response, or there has been recurrence of the tumor or relapse (such as "PD-1 failure"). In some embodiments, cancers exhibiting such failures may be screened for expression of e.g., PVR and/or Nectin-2 and only those having high level expression are treated with a bispecific antitumor antagonist of the present application.

In certain embodiments, the antitumor antagonist includes a dominant negative protein domain of the immune checkpoint regulator. In particular embodiments, the dominant negative protein comprises an extracellular domain derived from a member selected from the group consisting of PD-L1, PD-L2, PD-1, B7-1, B7-2, B7H3, CTLA-4, LAG-3, TIM-3, TIGIT, BTLA, VISTA, CD70, and combinations thereof. In certain particular embodiments, these extracellular domains are fused to an immunoglobulin constant region or Fc receptor in the presently described antibodies. Such mutants can bind to the endogenous receptor so as to form a complex that is deficient in signaling. In certain embodiments, the extracellular domain is fused to an immunoglobulin constant region or Fc fragment or to a monomer in the oligomeric protein complex.

In certain embodiments, a dominant negative PD-L1 antagonist comprises the extracellular domain of PD-L1, PD-L2, or PD-1. In another embodiment, a dominant-negative PD-1 antagonist is employed, which has a mutation so that it is no longer able to bind PD-L1. An exemplary dominant negative protein is AMP-224 (co-developed by Glaxo Smith Kline and Amplimmune), a recombinant fusion protein comprising the extracellular domain of PD-L2 and the Fc region of human IgG.

Exemplary immune checkpoint regulator agonists include, but are not limited to members of the tumor necrosis factor (TNF) receptor superfamily, such as CD27, CD40, OX40, GITR and 4-1BB (CD137) and their ligands, or members of the B7-CD28 superfamily, including CD28 and ICOS (CD278). Additional checkpoint regulator agonists include CD2, CD5, ICAM-1, LFA-1 (CD11a/CD18), CD30, BAFFR, HVEM, CD7, LIGHT, NKG2C, SLAMF7, NKp80, CD160, B7-H3, CD83 ligand. Immune checkpoint agonists can include antibodies or soluble fusion protein agonists comprising one or more costimulatory domains. Agonist antibodies include, but are not limited to anti-CD40 mAbs, such as CP-870,893, lucatumumab, and dacetuzumab; anti-CD137 mAbs, such as BMS-663513 urelumab, and PF-05082566; anti-OX40 mAbs; anti-GITR mAbs, such as TRX518; anti-CD27 mAbs, such as CDX-1127; and anti-ICOS mAbs.

Exemplary GITR agonists include, e.g., GITR fusion proteins and anti-GITR antibodies (e.g., bivalent anti-GITR antibodies) such as, e.g., a GITR fusion protein described in U.S. Pat. Nos. 6,111,090 and 8,586,023; European Patent No.: 090505B1, PCT Publication Nos.: WO 2010/003118 and WO 2011/090754. Anti-GITR antibodies are described in, e.g., in U.S. Pat. Nos. 7,025,962, 7,618,632, 7,812,135, 8,388,967, and 8,591,886; European Patent Nos.: 1947183B1 and 1866339; PCT Publication Nos.: WO 2011/028683, WO 2013/039954, WO2005/007190, WO 2007/133822, WO 2005/055808, WO 99/40196, WO 2001/03720, WO 99/20758, WO 2006/083289, WO 2005/115451, WO 2011/051726. An exemplary anti-GITR antibody is TRX518.

Another family of membrane bound ligands that bind to co-stimulatory or co-inhibitory receptors is the TNF family of molecules that bind to cognate TNF receptor family members, which include CD40 and CD40L, OX-40, OX-40L, CD70, CD27L, CD30, CD30L, 4-1BBL, CD137/4-1BB, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNF γ, TNFR2, TNFα, LTOR, Lymphotoxin α 1(32, FAS, FASL, RELT, DR6, TROY, NGFR (see, e.g., Tansey, M. G. et al. (2009) Drug Discovery Today, 14(23-24):1082-1088).

Immune checkpoint agonists or costimulatory molecules include cell surface molecules other than antigen receptors or their ligands that are required for an efficient immune response, and include, but are not limited to MHC class I molecules, MHC class II molecules, TNF receptor proteins, immunoglobulin-like proteins, cytokine receptors, integrins, signaling lymphocytic activation molecules (SLAM proteins), activating NK cell receptors, BTLA, Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In one aspect, T cell responses can be stimulated by a combination of the anti-PD-1 or anti-PD-L1 mAbs of the present invention and one or more of (i) antagonist of a protein that inhibits T cell activation (e.g., immune checkpoint inhibitors), such as CTLA-4, PD-1, PD-L1, PD-L2, LAG-3, TIM-3, Galectin 9, CEACAM-1, BTLA, CD69, Galectin-1, CD113, GPR56, VISTA, 2B4, CD48, GARP, PD-1H, LAIR1, TIM-1, CD96 and TIM-4, and (ii) an agonist of a protein that stimulates T cell activation such as B7-1, B7-2, CD28, 4-1BB (CD137), 4-1BBL, ICOS, CD40, ICOS-L, OX40, OX40L, GITR, GITRL, CD70, CD27, CD40, DR3 and CD28H.

Exemplary agents modulating one of the above proteins may be combined with the anti-PD-1 antibodies or anti-PD-L1 antibodies of the present application for treating cancer, include e.g., YERVOY™/ipilimumab or tremelimumab (to CTLA-4), galiximab (to B7.1), OPDIVO™/nivolumab/BMS-936558 (to PD-1), pidilizumab/CT-01 (to PD-1), KEYTRUDA™/pembrolizumab/MK-3475 (to PD-1), AMP224 (to B7-DC/PD-L2), BMS-936559 (to B7-H1), MPDL3280A (to B7-H1), MEDI-570 (to ICOS), AMG557 (to B7H2), MGA271 (to B7H3), IMP321 (to LAG-3), urelumab/BMS-663513 and PF-05082566 (to CD137/4-1BB), CDX-1127 (to CD27), MEDI-6383 and MEDI-6469 (to OX40), RG-7888 (to OX40L), Atacicept (to TACI), CP-870893 (to CD40), lucatumumab (to CD40), dacetuzumab (to CD40), and muromonab-CD3 (to CD3).

Other molecules that can be combined with the antitumor antagonists described herein for the treatment of cancer include antagonists of inhibitory receptors on NK cells or agonists of activating receptors on NK cells. For example, antagonist anti-PD-1, and/or anti-PD-L1 antibodies can be combined with antagonists of KIR (e.g., lirilumab), CSF-1R antagonists, such as RG7155.

Tumors evade host immune surveillance by a large variety of mechanisms. Many of these mechanisms may be overcome by the inactivation of immunosuppressive proteins expressed by the tumors. These include among others TGF-β, IL-10, and Fas ligand. Antibodies to each of these entities can be used in combination with the antitumor antagonists described herein to counteract the effects of the immunosuppressive agent and favor tumor immune responses by the host.

Other antibodies that activate host immune responsiveness can be used in combination with the antitumor antagonists described herein. These include molecules on the surface of dendritic cells that activate DC function and antigen presentation. Anti-CD40 antibodies are able to substitute effectively for T cell helper activity and can be used in conjunction with the antitumor antagonists described herein. Activating antibodies to T cell costimulatory molecules, such as OX-40, CD137/4-1BB, and ICOS may also provide for increased levels of T cell activation.

In certain embodiments, the antitumor antagonists described herein can be co-administered with one or other more therapeutic agents, e.g., anti-cancer agents, radiotoxic agents or an immunosuppressive agent. Such co-administration can solve problems due to development of resistance to drugs, changes in the antigenicity of the tumor cells that would render them unreactive to the antagonist, and toxicities (by administering lower doses of one or more agents).

The antitumor antagonists described herein can be linked to the agent (as an immuno-complex) or can be administered separate from the agent. In the latter case (separate administration), the antibody can be administered before, after or concurrently with the agent or can be co-administered with other known therapies, e.g., anti-cancer therapy, e.g., radiation. The antitumor antagonists described herein may be co-administered with one or more anti-cancer agents so as to provide two anti-cancer agents operating synergistically via different mechanisms to yield a cytotoxic effect in human cancer cells.

The antitumor antagonists described herein may be combined with anti-cancer agent, such an alkylating agent; anthracycline antibiotic; anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; a phosphatidylinositol-3-kinase (PI3K) inhibitor; an Akt inhibitor; a mammalian target of rapamycin (mTOR) inhibitor; a proteasomal inhibitor; a poly(ADP-ribose) polymerase (PARP) inhibitor; a Ras/MAPK pathway inhibitor; a centrosome declustering agent; a multi-kinase inhibitor; a serine/threonine kinase inhibitor; a tyrosine kinase inhibitor; a VEGF/VEGFR inhibitor; a taxane or taxane derivative, an aromatase inhibitor, anthracycline, a microtubule targeting drug, a topoisomerase poison drug, an inhibitor of a molecular target or enzyme (e.g., a kinase or a protein methyltransferase), a cytidine analogue or combination thereof.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary anthracycline antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodinel31 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary histone deacetylase inhibitors include, but are not limited to, vorinostat (Zolinza), valproic acid, romidepsin, entinostat abexinostat, givinostat, and mocetinostat.

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary phosphatidyl-inositol-3 kinase (PI3K) inhibitors include wortmannin an irreversible inhibitor of PI3K, demethoxyviridin a derivative of wortmannin, LY294002, a reversible inhibitor of PI3K; BKM120 (Buparlisib); Idelalisib (a PI3K Delta inhibitor); duvelisib (IPI-145, an inhibitor of PI3K delta and gamma); alpelisib (BYL719), an alpha-specific PI3K inhibitor; TGR 1202 (previously known as RP5264), an oral PI3K delta inhibitor; and copanlisib (BAY 80-6946), an inhibitor PI3Kα,δ isoforms predominantly.

Exemplary Akt inhibitors include, but are not limited to miltefosine, AZD5363, GDC-0068, MK2206, Perifosine, RX-0201, PBI-05204, GSK2141795, and SR13668.

Exemplary MTOR inhibitors include, but are not limited to, everolimus (Afinitor) or temsirolimus (Torisel); rapamune, ridaforolimus; deforolimus (AP23573), AZD8055 (AstraZeneca), OSI-027 (OSI), INK-128, BEZ235, PI-103, Torin1, PP242, PP30, Ku-0063794, WAY-600, WYE-687, WYE-354, and CC-223.

Exemplary proteasomal inhibitors include, but are not limited to, bortezomib (PS-341), ixazomib (MLN 2238), MLN 9708, delanzomib (CEP-18770), carfilzomib (PR-171), YU101, oprozomib (ONX-0912), marizomib (NPI-0052), and disufiram.

Exemplary PARP inhibitors include, but are not limited to, olaparib, iniparib, velaparib, BMN-673, BSI-201, AG014699, ABT-888, GPI21016, MK4827, INO-1001, CEP-9722, PJ-34, Tiq-A, Phen, PF-01367338 and combinations thereof.

Exemplary Ras/MAPK pathway inhibitors include, but are not limited to, trametinib, selumetinib, cobimetinib, CI-1040, PD0325901, AS703026, RO4987655, RO5068760, AZD6244, GSK1120212, TAK-733, U0126, MEK162, and GDC-0973.

Exemplary centrosome declustering agents include, but are not limited to, griseofulvin; noscapine, noscapine derivatives, such as brominated noscapine (e.g., 9-bromonoscapine), reduced bromonoscapine (RBN), N-(3-brormobenzyl) noscapine, aminonoscapine and water-soluble derivatives thereof, CW069; the phenanthridene-derived poly(ADP-ribose) polymerase inhibitor, PJ-34; N2-(3-pyridylmethyl)-5-nitro-2-furamide, N2-(2-thienylmethyl)-5-nitro-2-furamide, and N2-benzyl-5-nitro-2-furamide.

Exemplary multi-kinase inhibitors include, but are not limited to, regorafenib; sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1707 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

In certain embodiments, the antitumor antagonists described herein are administered at a subtherapeutic dose, another anti-immune checkpoint regulator antibody or antagonist is administered at a subtherapeutic dose, the angiogenesis antagonist is administered at a subtherapeutic dose, or any antagonist in a combination thereof is each administered at a subtherapeutic dose.

In certain embodiments, inhibition of the TGFβ/TGFβ RII, checkpoint regulator, and/or angiogenesis pathways may be combined with standard cancer treatments (e.g., surgery, radiation, and chemotherapy) in accordance with conventional chemotherapeutic regimes. In these instances, it may be possible to reduce the dose of chemotherapeutic reagent administered. An example of such a combination is a checkpoint regulator antagonist of the present application in combination with decarbazine for the treatment of melanoma. Another example of such a combination is a checkpoint regulator antagonist of the present application in combination with interleukin-2 (IL-2) for the treatment of melanoma. It is believed that the combined use of checkpoint regulator inhibition and chemotherapy can enhance apoptosis and increase tumor antigen presentation for cytotoxic immunity. Other synergistic combination therapies include checkpoint regulator inhibition through cell death when used in combination with radiation, surgery or hormone deprivation. Each of these protocols creates a source of tumor antigen in the host.

In certain embodiments, the checkpoint regulator antagonists described herein can be used in multi-specific antagonists or in combination with bispecific antibodies targeting Fcα or Fcγ receptor-expressing effector cells to tumor cells (see, e.g., U.S. Pat. Nos. 5,922,845 and 5,837,243). Bispecific antibodies can be used to target two separate antigens. For example anti-Fc receptor/anti-tumor antigen (e.g., Her-2/neu) bispecific antibodies have been used to target macrophages to cancer cells or tumors. This targeting may more effectively activate tumor specific responses. The T cell arm of these responses would be augmented by checkpoint regulator inhibition. Alternatively, antigen may be delivered directly to DCs by the use of bispecific antibodies that bind to tumor antigen and a dendritic cell specific cell surface marker.

III. Nucleic Acids and Host Cells for Expressing the Antitumor Antagonists

In another aspect, the present application provides nucleic acids encoding the antitumor antagonists of the present application, including the heavy and light chains, as well as expression vectors comprising such nucleic acids. In particular, the nucleic acids encode one or more HCDRs, LCDRs, HCVRs and/or LCVRs corresponding to any of the antibodies, antagonists or fragments described herein.

Thus, in one aspect, the present application provides one or more nucleic acids encoding any of the antitumor antagonists, antibodies or antigen-binding portions thereof as described herein.

In another aspect, the present application provides one or more expression vectors comprising the one or more nucleic acids encoding any of the antitumor antagonists, antibodies or antigen-binding portions thereof as described herein.

In another aspect, the present application provides a host cell transformed with the one or more expression vectors comprising the one or more nucleic acids encoding any of the antitumor antagonists, antibodies or antigen-binding portions thereof as described herein.

DNA(s) encoding antigen binding sites can be isolated and sequenced from a monoclonal antibody produced in hybridoma cells using conventional procedures (e.g., by using oligonucleotide probes that are capable of binding specifically to genes encoding the heavy and light chains of the monoclonal antibodies). Alternatively, amino acid sequences from immunoglobulins of interest may be determined by direct protein sequencing, and suitable encoding nucleotide sequences can be designed according to a universal codon table. In other cases, nucleotide and amino acid sequences of antigen binding sites or other immunoglobulin sequences, including constant regions, hinge regions and the like may be obtained from published sources well known in the art.

In one aspect, any of the binding antagonist fragments of the present application may include the use of codon optimized synthetic DNA fragments corresponding to e.g., antibody variable domains etc. For example, the cDNA sequences encoding immunoglobulin VH, VL, HC, LC, CH1, CH2, CH3, and/or framework region can be codon optimized for expression in various human, primate or mammalian cells, such as HEK or CHO cells. The invention also features a nucleic acid molecule that comprise one or both nucleotide sequences that encode heavy and light chain variable regions, CDRs, hypervariable loops, framework regions of the anti-PD-L1 antibody molecules, as described herein.

Expression vectors encoding a particular bispecific antitumor antagonist may be used to synthesize the antitumor antagonists of the present disclosure in cultured cells in vitro or they may be directly administered to a patient to express the antitumor antagonist in vivo or ex vivo. As used herein, an "expression vector" refers to a viral or non-viral vector comprising a polynucleotide encoding one or more polypeptide chains corresponding to the bispecific antitumor antagonists of the present disclosure in a form suitable for expression from the polynucleotide(s) in a host cell for antibody preparation purposes or for direct administration as a therapeutic agent.

A nucleic acid sequence is "operably linked" to another nucleic acid sequence when the former is placed into a functional relationship with the latter. For example, a DNA for a presequence or signal peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a signal peptide, contiguous and in reading phase. However, enhancers do not have to be contiguous. Linking is accomplished by ligation at convenient restriction sites. If such sites do not exist, synthetic oligonucleotide adaptors or linkers may be used in accordance with conventional practice.

Nucleic acid sequences for expressing the antitumor antagonists typically include an amino terminal signal peptide sequence, which is removed from the mature protein. Since the signal peptide sequences can affect the levels of expression, the polynucleotides may encode any one of a variety of different N-terminal signal peptide sequences. It will be appreciated by those skilled in the art that the design of the expression vector can depend on such factors as the choice of the host cell to be transformed, the level of expression of protein desired, and the like.

The above described "regulatory sequences" refer to DNA sequences necessary for the expression of an operably linked coding sequence in one or more host organisms. The term "regulatory sequences" is intended to include promoters, enhancers and other expression control elements (e.g., polyadenylation signals). Regulatory sequences include those which direct constitutive expression of a nucleotide sequence in many types of host cells or those which direct expression of the nucleotide sequence only in certain host cells (e.g., tissue-specific regulatory sequences). Expression vectors generally contain sequences for transcriptional termination, and may additionally contain one or more elements positively affecting mRNA stability.

The expression vector contains one or more transcriptional regulatory elements, including promoters and/or enhancers, for directing the expression of antitumor antagonists. A promoter comprises a DNA sequence that functions to initiate transcription from a relatively fixed location in regard to the transcription start site. A promoter contains core elements required for basic interaction of RNA polymerase and transcription factors, and may operate in conjunction with other upstream elements and response elements.

As used herein, the term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers, and silencers) which regulate activation or repression of genes operably linked thereto in response to developmental and/or external stimuli, and trans-acting regulatory proteins or nucleic acids. A promoter may contain a genomic fragment or it may contain a chimera of one or more TREs combined together.

Preferred promoters are those capable of directing high-level expression in a target cell of interest. The promoters may include constitutive promoters (e.g., HCMV, SV40, elongation factor-1α (EF-1α)) or those exhibiting preferential expression in a particular cell type of interest. Enhancers generally refer to DNA sequences that function away from the transcription start site and can be either 5' or 3' to the transcription unit. Furthermore, enhancers can be within an intron as well as within the coding sequence. They are usually between 10 and 300 bp in length, and they function in cis. Enhancers function to increase and/or regulate transcription from nearby promoters. Preferred enhancers are those directing high-level expression in the antibody producing cell. Cell or tissue-specific transcriptional regulatory elements (TREs) can be incorporated into expression vectors to restrict expression to desired cell types. Pol III promoters (H1 or U6) are particularly useful for expressing shRNAs from which siRNAs are expressed. An expression vector may be designed to facilitate expression of the antitumor antagonist in one or more cell types.

In certain embodiments, one or more expression vectors may be engineered to express both the antitumor antagonist and one or more siRNA targeting the Tie2 pathway, the VEGF pathway or an immune checkpoint regulator.

An siRNA is a double-stranded RNA that can be engineered to induce sequence-specific post-transcriptional gene silencing of mRNAs. Synthetically produced siRNAs structurally mimic the types of siRNAs normally processed in cells by the enzyme Dicer. When expressed from an expression vector, the expression vector is engineered to transcribe a short double-stranded hairpin-like RNA (shRNA) that is processed into a targeted siRNA inside the cell. Synthetic siRNAs and shRNAs may be designed using well known algorithms and synthesized using a conventional DNA/RNA synthesizer.

To co-express the individual chains of the antitumor antagonist, a suitable splice donor and splice acceptor sequences may be incorporated for expressing both products. Alternatively, an internal ribosome binding sequence (IRES) or a 2A peptide sequence, may be employed for expressing multiple products from one promoter. An IRES provides a structure to which the ribosome can bind that does not need to be at the 5' end of the mRNA. It can therefore direct a ribosome to initiate translation at a second initiation codon within an mRNA, allowing more than one polypeptide to be produced from a single mRNA. A 2A peptide contains short sequences mediating co-translational self-cleavage of the peptides upstream and downstream from the 2A site, allowing production of two different proteins from a single transcript in equimolar amounts. CHYSEL is a non-limiting example of a 2A peptide, which causes a translating eukaryotic ribosome to release the growing polypeptide chain that it is synthesizing without dissociating from the mRNA. The ribosome continues translating, thereby producing a second polypeptide.

An expression vector may comprise a viral vector or a non-viral vector. A viral vectors may be derived from an adeno-associated virus (AAV), adenovirus, herpesvirus, vaccinia virus, poliovirus, poxvirus, a retrovirus (including a lentivirus, such as HIV-1 and HIV-2), Sindbis and other RNA viruses, alphavirus, astrovirus, coronavirus, orthomyxovirus, papovavirus, paramyxovirus, parvovirus, picornavirus, togaviruses and the like. A non-viral vector is simply a "naked" expression vector that is not packaged with virally derived components (e.g., capsids and/or envelopes).

In certain cases, these vectors may be engineered to target certain diseases or cell populations by using the targeting characteristics inherent to the virus vector or engineered into the virus vector. Specific cells may be "targeted" for delivery of polynucleotides, as well as expression. Thus, the term "targeting", in this case, may be based on the use of endogenous or heterologous binding agents in the form of capsids, envelope proteins, antibodies for delivery to specific cells, the use of tissue-specific regulatory elements for restricting expression to specific subset(s) of cells, or both.

In some embodiments, expression of the antibody chains is under the control of the regulatory element such as a tissue specific or ubiquitous promoter. In some embodiments, a ubiquitous promoter such as a CMV promoter, CMV-chicken beta-actin hybrid (CAG) promoter, a tissue specific or tumor-specific promoter to control the expression of a particular antibody heavy or light chain or single-chain derivative therefrom.

Non-viral expression vectors can be utilized for non-viral gene transfer, either by direct injection of naked DNA or by encapsulating the antitumor antagonist-encoding polynucleotides in liposomes, microparticles, microcapsules, virus-like particles, or erythrocyte ghosts. Such compositions can be further linked by chemical conjugation to targeting domains to facilitate targeted delivery and/or entry of nucleic acids into desired cells of interest. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin.

Alternatively, naked DNA may be employed. Uptake efficiency of naked DNA may be improved by compaction or by using biodegradable latex beads. Such delivery may be improved further by treating the beads to increase hydrophobicity and thereby facilitate disruption of the endosome and release of the DNA into the cytoplasm.

IV. Methods for Producing the Bispecific Antagonists

In another aspect, the present application provides host cells transformed with the nucleic acids or expression vectors encoding the bispecific antitumor antagonists of the present application. The host cells can be any eukaryotic or prokaryotic cell capable of expressing the bispecific antitumor antagonists of the present application, including immunoglobulin heavy and light chains thereof.

In a further aspect, a method of producing antitumor antagonist comprises culturing a host cell transformed with one or more nucleic acids or expression vectors encoding the bispecific antitumor antagonists of the present application under conditions that allow for production and purification of the antagonists, antibodies or fragments thereof expressed in suitable cells.

In a further aspect, the present application provides a method for producing antibody comprising culturing a cell transiently or stably expressing one or more constructs encoding one or more polypeptide chains in the antibody; and purifying the antibody from the cultured cells. Any cell capable of producing a functional antibody may be used. In preferred embodiments, the antibody-expressing cell is of eukaryotic or mammalian origin, preferably a human cell. Cells from various tissue cell types may be used to express the antibodies. In other embodiments, the cell is a yeast cell, an insect cell or a bacterial cell. Preferably, the antibody-producing cell is stably transformed with a vector expressing the antibody.

One or more expression vectors encoding the antibody heavy or light chains can be introduced into a cell by any conventional method, such as by naked DNA technique, cationic lipid-mediated transfection, polymer-mediated transfection, peptide-mediated transfection, virus-mediated infection, physical or chemical agents or treatments, electroporation, etc. In addition, cells may be transfected with one or more expression vectors for expressing the antibody along with a selectable marker facilitating selection of stably transformed clones expressing the antibody. The antibodies produced by such cells may be collected and/or purified according to techniques known in the art, such as by centrifugation, chromatography, etc.

Examples of suitable selectable markers for mammalian cells include dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR⁻ cells and mouse LTK⁻ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

Exemplary antibody-expressing cells include human Jurkat, human embryonic kidney (HEK) 293, Chinese hamster ovary (CHO) cells, mouse WEHI fibrosarcoma cells, as well as unicellular protozoan species, such as *Leishmania tarentolae*. In addition, stably transformed, antibody producing cell lines may be produced using primary cells immortalized with c-myc or other immortalizing agents.

In one embodiment, the cell line comprises a stably transformed *Leishmania* cell line, such as *Leishmania tarentolae*. *Leishmania* are known to provide a robust, fast-growing unicellular host for high level expression of eukaryotic proteins exhibiting mammalian-type glycosylation patterns. A commercially available *Leishmania* eukaryotic expression kit is available (Jena Bioscience GmbH, Jena, Germany).

In some embodiments, the cell line expresses at least 1 mg, at least 2 mg, at least 5 mg, at least 10 mg, at least 20 mg, at least 50 mg, at least 100 mg, at least 200 mg, at least 300 mg, at least 400 mg, or at least 500 mg of the antibody/liter of culture.

The antibodies in the present application may be isolated from antibody expressing cells following culture and maintenance in any appropriate culture medium, such as RPMI, DMEM, and AIM V©. The antibodies can be purified using conventional protein purification methodologies (e.g., affinity purification, chromatography, etc.), including the use of Protein-A or Protein-G immunoaffinity purification. In some embodiments, antibodies are engineered for secretion into culture supernatants for isolation therefrom.

V. Pharmaceutical Compositions and Methods of Treatment

Another aspect of the present application relates to pharmaceutical compositions and methods for treating a cell proliferative disorder, such as cancer, chronic infections, or immunologically compromised disease states. In one embodiment, the pharmaceutical composition comprises one or more antitumor antagonists of the present application. In some embodiments, the antitumor antagonist(s) comprise: one or more TGF-β1 inhibitors or TGF-β1 RII inhibitors in combination with: (1) a PD-1 inhibitor or a PD-L1 inhibitor; or (2) or one or more angiogenesis inhibitors, such as VEGF inhibitors, VEGFR2 inhibitors, angiopoietin-1/2 inhibitors, and Tie2R inhibitors. The antagonist(s) are formulated together with a pharmaceutically acceptable carrier. Pharmaceutical composition of the present application may include one or more different antibodies, one or more multispecific antibodies, one or more immunoconjugates, or a combination thereof as described herein.

As described above, methods for using the pharmaceutical compositions described herein comprise administering to a subject in need thereof an effective amount of the pharmaceutical composition according to the present disclosure.

Any suitable route or mode of administration can be employed for providing the patient with a therapeutically or prophylactically effective dose of the antibody or antagonist. Exemplary routes or modes of administration include parenteral (e.g., intravenous, intraarterial, intramuscular, subcutaneous, intratumoral), oral, topical (nasal, transdermal, intradermal or intraocular), mucosal (e.g., nasal, sublingual, buccal, rectal, vaginal), inhalation, intralymphatic, intraspinal, intracranial, intraperitoneal, intratracheal, intravesical, intrathecal, enteral, intrapulmonary, intralymphatic, intracavital, intraorbital, intracapsular and transurethral, as well as local delivery by catheter or stent.

A pharmaceutical composition comprising antibody or antagonist in accordance with the present disclosure may be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions may comprise suitable solid or gel phase carriers or excipients. Exemplary carriers or excipients include but are not limited to, calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the therapeutic agents.

The antitumor antagonist can be incorporated into a pharmaceutical composition suitable for parenteral administration. Suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

Therapeutic antitumor antagonist preparations can be lyophilized and stored as sterile powders, preferably under vacuum, and then reconstituted in bacteriostatic water (containing, for example, benzyl alcohol preservative) or in sterile water prior to injection. Pharmaceutical composition may be formulated for parenteral administration by injection e.g., by bolus injection or continuous infusion.

The therapeutic agents in the pharmaceutical compositions may be formulated in a "therapeutically effective amount" or a "prophylactically effective amount". A "therapeutically effective amount" refers to an amount effective, at dosages and for periods of time necessary, to achieve the desired therapeutic result. A therapeutically effective amount of the recombinant vector may vary depending on the condition to be treated, the severity and course of the condition, the mode of administration, whether the antibody or agent is administered for preventive or therapeutic purposes, the bioavailability of the particular agent(s), the ability of the antitumor antagonist to elicit a desired response in the individual, previous therapy, the age, weight and sex of the patient, the patient's clinical history and response to the antibody, the type of the antitumor antagonist used, discretion of the attending physician, etc. A therapeutically effective amount is also one in which any toxic or detrimental effect of the recombinant vector is outweighed by the therapeutically beneficial effects. A "prophylactically effective amount" refers to an amount effective, at dosages and for periods of time necessary, to achieve the desired prophylactic result.

Preferably, the polypeptide domains in the antitumor antagonist are derived from the same host in which they are to be administered in order to reduce inflammatory responses against the administered therapeutic agents.

The antitumor antagonist is suitably administered to the patent at one time or over a series of treatments and may be administered to the patient at any time from diagnosis onwards. The antitumor antagonist may be administered as the sole treatment or in conjunction with other drugs or therapies useful in treating the condition in question.

As a general proposition, a therapeutically effective amount or prophylactically effective amount of the antitumor antagonist will be administered in a range from about 1 ng/kg body weight/day to about 100 mg/kg body weight/day whether by one or more administrations. In a particular embodiment, each antitumor antagonist is administered in the range of from about 1 ng/kg body weight/day to about 10 mg/kg body weight/day, about 1 ng/kg body weight/day to about 1 mg/kg body weight/day, about 1 ng/kg body weight/day to about 100 µg/kg body weight/day, about 1 ng/kg body weight/day to about 10 µg/kg body weight/day, about 1 ng/kg body weight/day to about 1 µg/kg body weight/day, about 1 ng/kg body weight/day to about 100 ng/kg body weight/day, about 1 ng/kg body weight/day to about 10 ng/kg body weight/day, about 10 ng/kg body weight/day to about 100 mg/kg body weight/day, about 10 ng/kg body weight/day to about 10 mg/kg body weight/day, about 10 ng/kg body weight/day to about 1 mg/kg body weight/day, about 10 ng/kg body weight/day to about 100 µg/kg body weight/day, about 10 ng/kg body weight/day to about 10 µg/kg body weight/day, about 10 ng/kg body weight/day to about 1 µg/kg body weight/day, 10 ng/kg body weight/day to about 100 ng/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 µg/kg body weight/day, about 100 ng/kg body weight/day to about 10 µg/kg body weight/day, about 100 ng/kg body weight/day to about 1 µg/kg body weight/day, about 1 µg/kg body weight/day to about 100 mg/kg body weight/day, about 1 µg/kg body weight/day to about 10 mg/kg body weight/day, about 1 µg/kg body weight/day to about 1 mg/kg body weight/day, about 1 µg/kg body weight/day to about 100 µg/kg body weight/day, about 1 µg/kg body weight/day to about 10 µg/kg body weight/day, about 10 µg/kg body weight/day to about 100 mg/kg body weight/day, about 10 µg/kg body weight/day to about 10 mg/kg body weight/day, about 10 µg/kg body weight/day to about 1 mg/kg body weight/day, about 10 µg/kg body weight/day to about 100 µg/kg body weight/day, about 100 µg/kg body weight/day to about 100 mg/kg body weight/day, about 100 µg/kg body weight/day to about 10 mg/kg body weight/day, about 100 µg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In other embodiments, the antitumor antagonist is administered at a dose of 500 g to 20 g every three days, or 25 mg/kg body weight every three days.

In other embodiments, each antitumor antagonist is administered in the range of about 10 ng to about 100 ng per individual administration, about 10 ng to about 1 µg per individual administration, about 10 ng to about 10 µg per individual administration, about 10 ng to about 100 µg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 µg per individual administration, about 100 ng to about 10 µg per individual administration, about 100 ng to about 100 µg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 µg to about 10 µg per individual administration, about 1 µg to about 100 µg per individual administration, about 1 µg to about 1 mg per individual administration, about 1 µg to about 10 mg per individual administration, about 1 µg to about 100 mg per individual administration, about 1 µg to about 1000 mg per injection, about 1 µg to about 10,000 mg per individual administration, about 10 µg to about 100 µg per individual administration, about 10 µg to about 1 mg per individual administration, about 10 µg to about 10 mg per individual administration, about 10 µg to about 100 mg per individual administration, about 10 µg to about 1000 mg per injection, about 10 µg to about 10,000 mg per individual administration, about 100 µg to about 1 mg per individual administration, about 100 µg to about 10 mg per individual administration, about 100 µg to about 100 mg per individual administration, about 100 µg to about 1000 mg per injection, about 100 µg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The antitumor antagonist may be administered daily, every 2, 3, 4, 5, 6 or 7 days, or every 1, 2, 3 or 4 weeks.

In other particular embodiments, the amount of the antitumor antagonist may be administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage will be dependent on the condition, size, age and condition of the patient.

In certain embodiments, the coding sequences for an antitumor antagonist are incorporated into a suitable expression vector (e.g., viral or non-viral vector) for expressing an effective amount of the antitumor antagonist in patient with a cell proliferative disorder. In certain embodiments comprising administration of e.g., one or more recombinant AAV (rAAV) viruses, the pharmaceutical composition may comprise the rAAVs in an amount comprising at least $10^{10}$, at least $10^{11}$, at least $10^{12}$, at least $10^{13}$, or at least $10^{14}$ genome copies (GC) or recombinant viral particles per kg, or any range thereof. In certain embodiments, the pharmaceutical composition comprises an effective amount of the recombinant virus, such as rAAV, in an amount comprising at least $10^{10}$, at least $10^{11}$, at least $10^{12}$, at least $10^{13}$, at least $10^{14}$, at least $10^{15}$ genome copies or recombinant viral particles genome copies per subject, or any range thereof.

Dosages can be tested in several art-accepted animal models suitable for any particular cell proliferative disorder.

Delivery methodologies may also include the use of polycationic condensed DNA linked or unlinked to killed viruses, ligand linked DNA, liposomes, eukaryotic cell delivery vehicles cells, deposition of photopolymerized hydrogel materials, use of a handheld gene transfer particle gun, ionizing radiation, nucleic charge neutralization or fusion with cell membranes, particle mediated gene transfer and the like.

The present invention is further illustrated by the following examples which should not be construed as limiting. The contents of all references, patents and published patent applications cited throughout this application, as well as the Figures and Tables are incorporated herein by reference.

EXAMPLES

Example 1: Generation of Monoclonal Antibodies

Monoclonal antibodies (mAbs) of the present application are generated and screened using techniques well known in the art, see, e.g., Harlow and Lane (1988) *Antibodies, A Laboratory Manual*, Cold Spring Harbor Publications, New York. The antigen specific hybridoma mabs are cloned, sequenced and engineered using techniques well known in the art, see e.g., Lo. B. K. C Methods in Molecular Biology™. Volume 248 2004. Antibody Engineering.

Example 2: Design of Bispecific Antitumor Antagonists

FIGS. 5A and 5B show two bispecific antitumor antagonists, Bi-PB-1 (or Bi-PLB-1) and Bi-PB-1 (or Bi-PLB-2), respectively. These antagonists comprise a checkpoint regulator antibody backbone (anti-PD-1 or anti-PD-L1) along with a TGF-β RII extracellular domain (TGF-β-RII ECD): (i) fused to the carboxy-terminal end of the CH3 region in each of the two heavy chains (FIG. 5A) or (ii) inserted within the CH3 region of the Fc loop (FIG. 5B).

In the embodiments depicted in FIGS. 5A and 5B, the bispecific antibody can have an IgG1 or IgG4 backbone. Furthermore, any one or more of the antibody specificities may be substituted with any other checkpoint regulator antagonist specificity and/or any tumor targeting antibody specificity, such as CD20, EGFR, etc.

FIG. 6 shows exemplary functional domain sequences corresponding to the bispecific antibodies in FIGS. 5A and 5B.

FIGS. 7A-7B show exemplary heavy chain (HC) and light chain (LC) sequences corresponding to the bispecific antibodies depicted in FIGS. 5A and 5B.

Example 3: Design of Additional Bispecific Antagonists

Figure 8A:
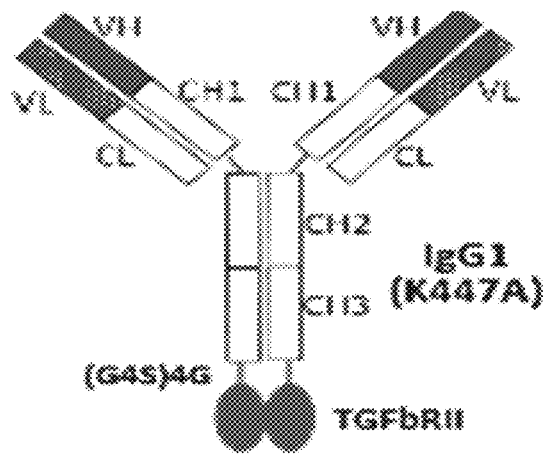
FIGS. 8A-8C depict three different bispecific antagonists, Bi-AB-1, Bi-A1B-1 and Bi-ZB-1, respectively, each comprising a carboxy-terminal TGF-β1 RII extracellular domain (ECD) in a mutant IgG1 (K447A) scaffold. Bi-AB-1 and Bi-A1B-1 both contain amino-terminal anti-VEGF variable regions (VH1, VL1) from Avastin/bevacizumab; Bi-A1B-1 includes two amino acid substitutions in the VH region (E6Q, L11V). Bi-ZB-1 contains an amino terminal aflibercept domain upstream of an IgG1 Fc (K447A) region.
Figure 8B:
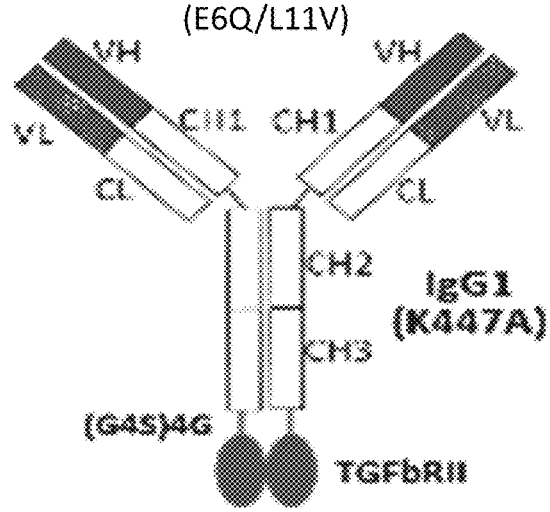
Figure 8C:
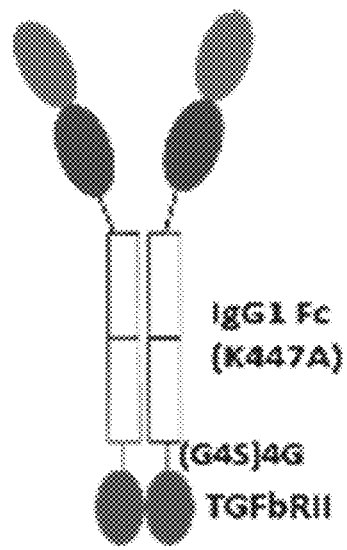

FIGS. 8A-8C show the design of three different bispecific antagonists, Bi-AB-1, Bi-A1B-1 and Bi-ZB-1, respectively, each comprising a carboxy-terminal TGF-β1 RII extracellular domain (ECD) in a mutant IgG1 (K447A) scaffold. Bi-AB-1 and Bi-A1B-1 both contain amino-terminal anti-VEGF variable regions (VH1, VL1) from Avastin/bevacizumab; Bi-A1B-1 includes two amino acid substitutions in the VH region (E6Q, L11V). Bi-ZB-1 contains an amino terminal aflibercept domain upstream of an IgG1 Fc (K447A) region. In other embodiments, instead of a mutant IgG1(K447A) scaffold, the bispecific antagonists comprise a wild-type IgG1 scaffold, a different mutant IgG1 scaffold, an IgG2 scaffold, a mutant IgG2 scaffold, an IgG4 scaffold, or a mutant IgG4 scaffold.

FIGS. 9A and 9B show the various functional domain sequences present the bispecific antagonists depicted in FIGS. 8A-8C.

FIG. 10 shows the heavy chain (HC) and light chain (LC) amino acid sequences corresponding to the bispecific antagonists depicted in FIGS. 8A-8C.

FIG. 11 summarizes the arrangement of functional domains in the bispecific antagonists depicted in FIGS. 8A-8C.

Example 4: Expression and Purification of the Antagonists in FIGS. 10-11

Figure 12:
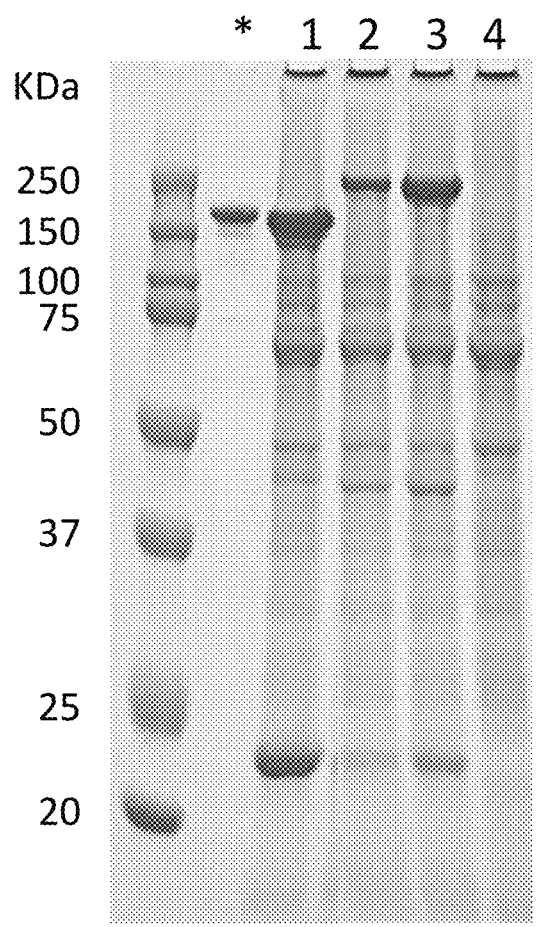
FIG. 12 is a Coomassie blue stained polyacrylamide gel showing improved expression levels of bispecific antibody antagonists Bi-AB-1 and Bi-A1B-1 containing E6Q and L11V mutations when transiently transfected into HEK293 cells as determined by non-reducing polyacrylamide gel electrophoresis (PAGE).

FIG. 12 is a Coomassie blue stained polyacrylamide gel showing improved expression levels of antagonists containing wt VEGF-A or mutant E6Q and L11V mutations (i.e., Bi-AB-1, Bi-A1B-1, respectively) when transiently transfected into HEK293 cells as determined by non-reducing polyacrylamide gel electrophoresis (PAGE). The titers depicted in FIG. 12 were determined by quantifying the cell supernatant using a POROS A column (Applied Biosystems). The results of this analysis showed that the expression level of Bi-A1B-1 was increased by 167% relative to Bi-AB-1.

Figure 13A:
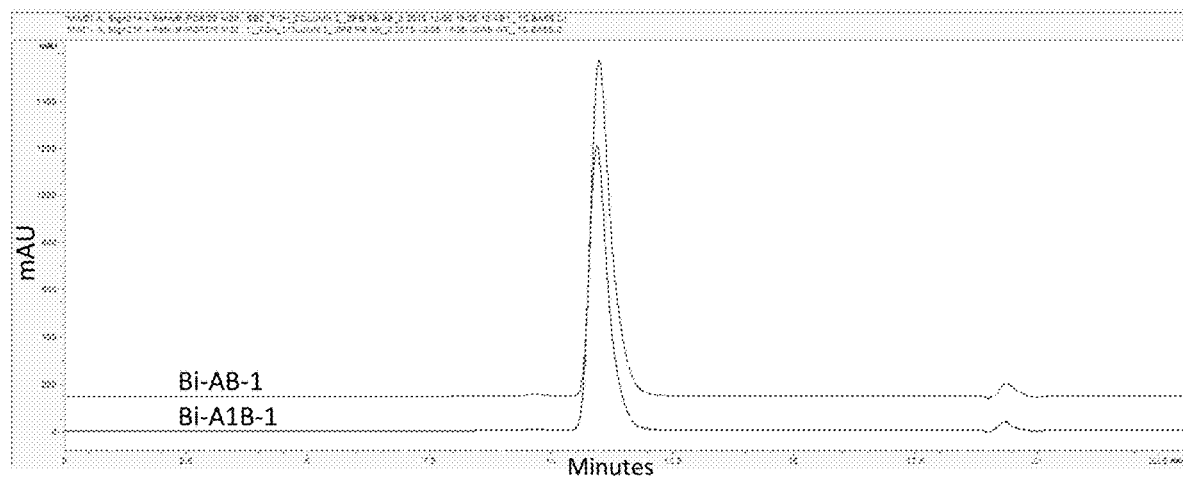
FIG. 13A shows size exclusion chromatography (SEC) profiles of Bi-AB-1 and Bi-A1B-1.
Figure 13B:
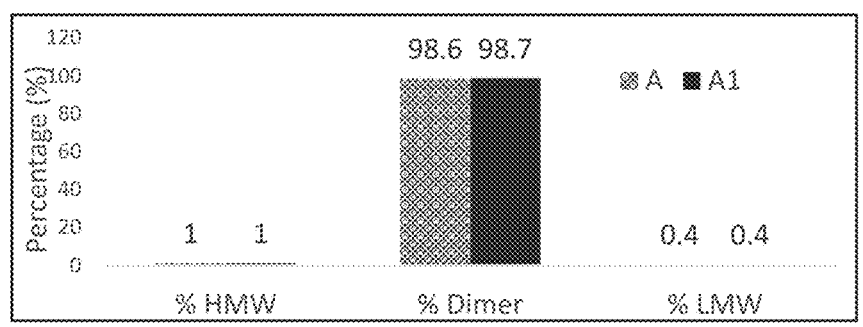
FIG. 13B shows that protein A purified Bi-AB-1 and Bi-A1B-1 have low levels of high molecular weight (HMW, 1%, 1%, respectively) and low molecular weight (LMW, 0.4%, 0.4%, respectively) species in comparison to dimers (98.6%, 98.7%, respectively)

FIG. 13A depicts a size exclusion chromatography (SEC) profile showing relative levels of high molecular weight (HMW), low molecular weight (LMW) species, and dimers resulting from protein A purified Bi-AB-1 and Bi-A1B-1. FIG. 13B shows that the percentage of dimers (98.6% for Bi-AB-1; 98.7% for Bi-A1B-1) greatly outnumber the HMW (1%) and LMW (0.4%) species purified as determined by SE-UPLC using Tosoh TSKgel UP-G3000SWXL columns. These results show that TGF-β1 RII extracellular domain (ECD) fusions to Bi-AB-1 and Bi-A1B-1 did not result in appreciable levels of high molecular weight (HMW) or low molecular weight (LMW) species.

Figures 14A, 14B:
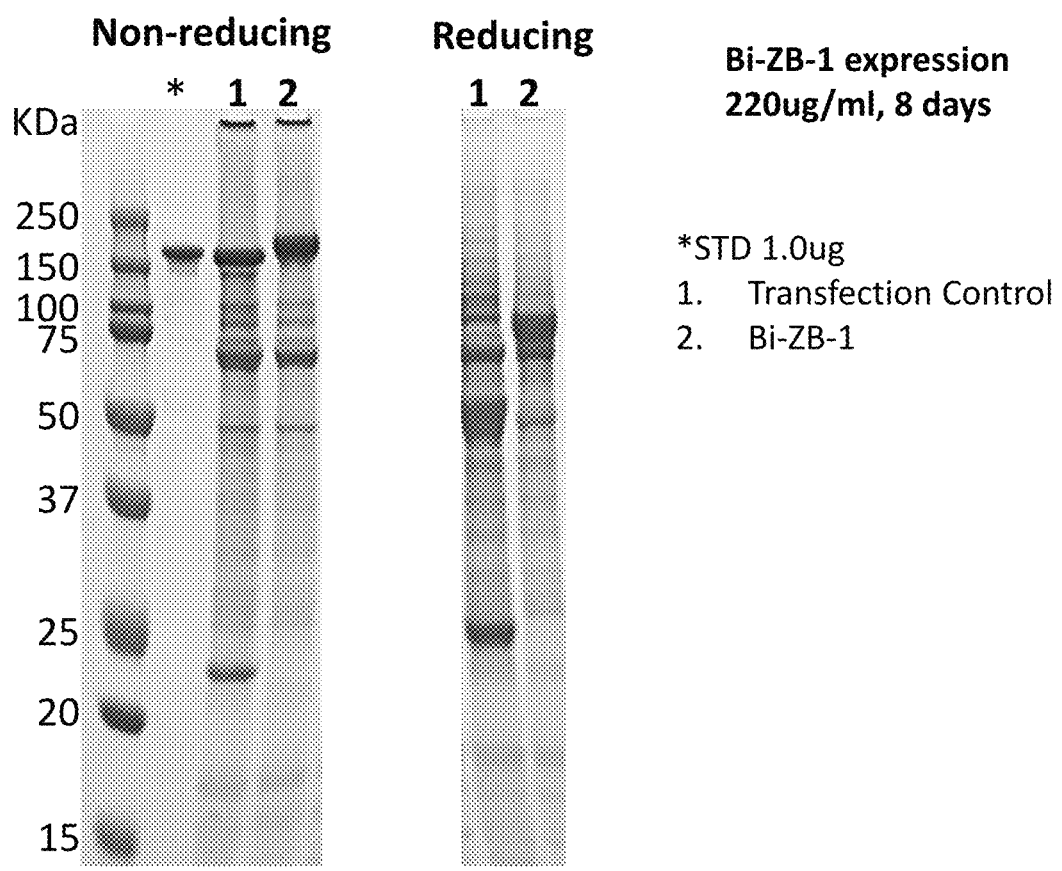
FIGS. 14A and 14B show PAGE gels of transiently expressed Bi-ZB-1 under non-reducing (FIG. 14A) and reducing (FIG. 14B) conditions

FIGS. 14A-164B depict Coomassie blue stained PAGE analyses of under non-reducing and reducing conditions, respectively, from supernatants obtained following transient transfection of Bi-ZB-1. The results of this analysis confirmed good transient expression levels of Bi-ZB-1 (220 µg/ml) after 8 days of growth of cells in vitro.

Figure 15:
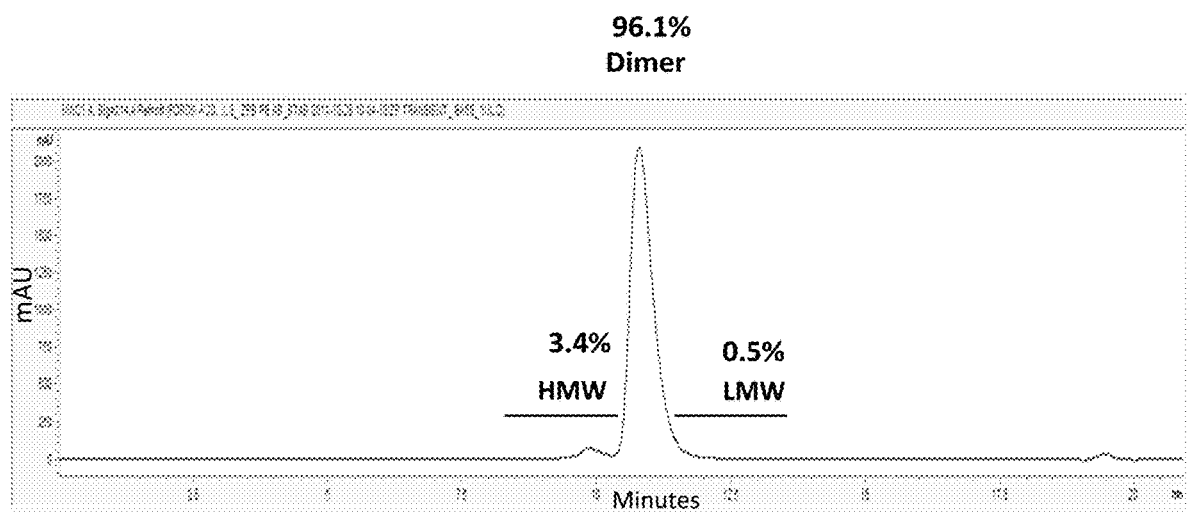
FIG. 15 shows a size exclusion chromatography (SEC) profile showing that protein A purified Bi-ZB-1 has low levels of high molecular weight (HMW, 3.4%) and low molecular weight (LMW, 0.5%) species in comparison to dimers (96.1%).

FIG. 15 depicts a size exclusion chromatography (SEC) profile showing that protein A purified Bi-ZB-1 has low levels of high molecular weight (HMW, 3.4%) and low molecular weight (LMW, 0.5%) species in comparison to dimers (96.1%).

Figure 16:
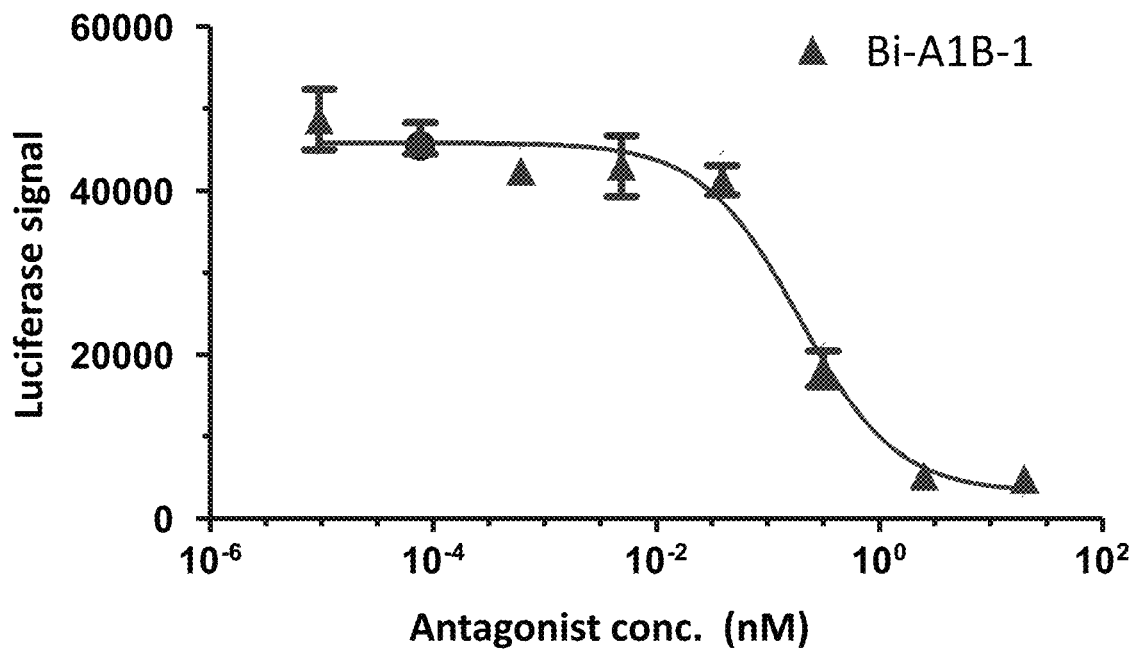
FIG. 16 shows the results of a cell-based assay in which recombinant HEK-293 cells expressing human VEGFR2 and firefly luciferase under the control of NFAT response elements were stimulated with huVEGF165 in the presence of serial dilutions of two anti-VEGF antagonists, Bi-A1B-1 and antibody A. Bioactivity was determined by measuring the decrease in the amount of luciferase-mediated luminescence.

Example 5: Functional Characterization of the Antitumor Antagonists in FIGS. 8A-8C To evaluate the ability of the anti-VEGF antagonist, Bi-A1B-1, to antagonize VEGF-mediated activation of VEGFR2 (i.e., the cognate receptor), a cell-based luciferase assay was conducted. In this experiment, a recombinant HEK-293 cell line expressing human VEGFR2 and a firefly luciferase construct under the control of NFAT response elements was stimulated with huVEGF165 in the presence of serial dilutions of anti-VEGF antagonist (Bi-A1B-1). The results of this assay are shown in FIG. 16. As expected, increasing levels of the anti-VEGF antagonist progressively neutralized the ability of VEGF165 to activate VEGFR2 and induce NFAT-mediated luciferase activity.

Figure 17:
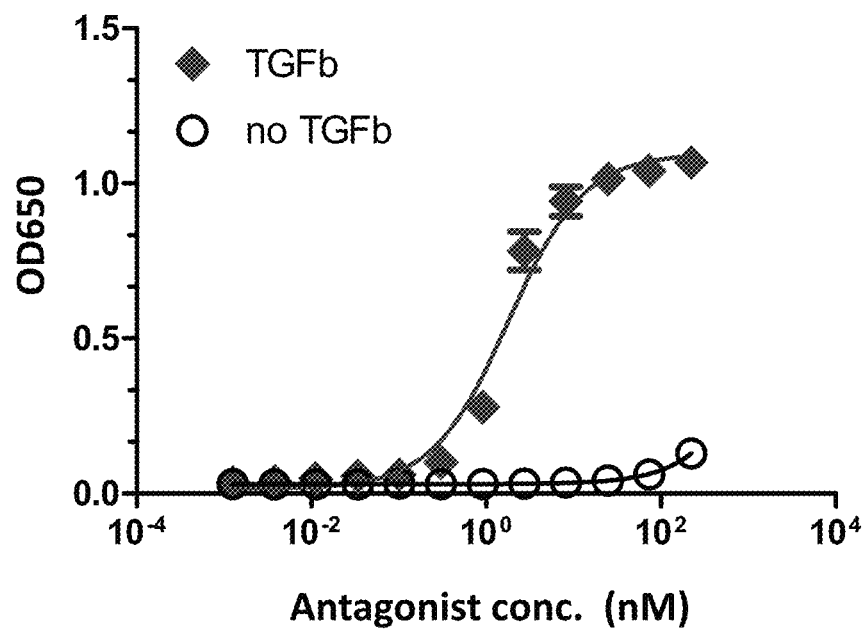
FIG. 17 is an ELISA analysis demonstrating simultaneous binding TGF-β1 and VEGF165 by Bi-A1B-1 in which huTGF-β1 coated 96 well plates incubated with serially diluted samples Bi-A1B-1, followed by biotinylated huVEGF165, whereby bound molecules were detected by Streptavidin-HRP using a TMB substrate.

To evaluate the ability of the bispecific antagonist, Bi-A1B-1 to simultaneously bind TGF-β1 and VEGF165, a sandwich ELISA assay was performed. In this experiment, huTGF-β1 was coated onto 96 well plates and blocked with 5% BSA, followed by addition and incubation of serially diluted samples of Bi-A1B-1, followed by addition of biotinylated huVEGF165. Bound molecules were detected by Streptavidin-HRP using a TMB substrate. The results of this analysis in FIG. 17 show that the bispecific antagonist, Bi-A1B-1 can simultaneously bind both TGF-β1 and VEGF165.

Figure 18:
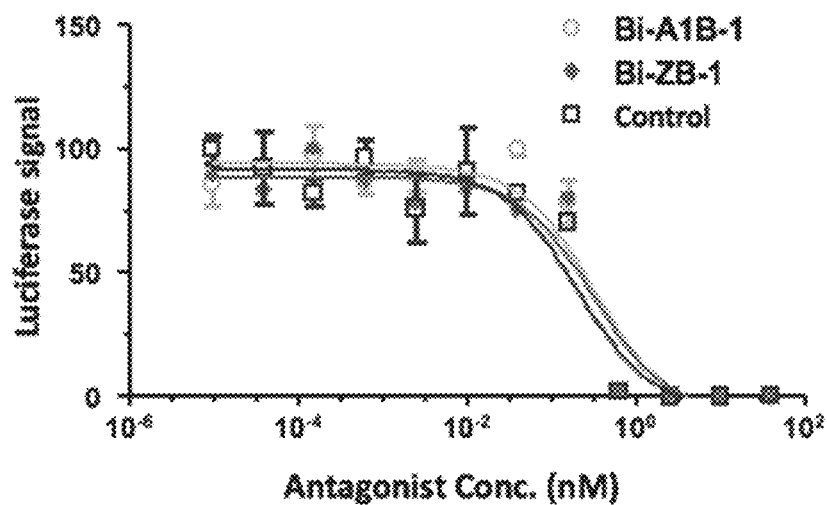
FIG. 18 shows the results of a cell-based assay in which recombinant HEK-293 cells expressing human TGF-β1 RII receptor and firefly luciferase under the control of a SMAD response element and stimulated with huTGF-β1 in the presence of serial dilutions of Bi-A1B-1, Bi-ZB-1, and a control, each containing a TGF-β1 RII extracellular domain (ECD) fusion. Bioactivity was determined by a decrease in the amount of luciferase-mediated luminescence.

To evaluate the ability of the TGF-β1 RII ECD to antagonize TGF-β1-mediated activation of the human TGF-β1 RII (i.e., the cognate receptor), a cell-based luciferase assay was conducted. In this experiment, recombinant HEK-293 cells expressing human TGF-β1 RII receptor and a firefly luciferase construct under the control of a SMAD response element was stimulated with huTGF-β1 in the presence of serial dilutions of antibodies fused to a TGF-β1 RII ECD (Bi-A1B-1, Bi-ZB-1). The results of this analysis are shown in FIG. 18. As expected, increasing levels of antibodies containing a TGF-β1 RII ECD progressively neutralized the ability of TGF-β1 to activate the human TGF-β1 RII and induce NFAT-mediated luciferase activity. In this case, Bi-A1B-1 and Bi-ZB-1 exhibited similar antagonism ability, as reflected in an IC50 of 0.32 nM for Bi-A1B-1 and an IC50 of 0.31 for Bi-ZB-1. These IC50s were comparable to a control TGFBR2 fusion product (IC50=0.20 nM).

Figure 19:
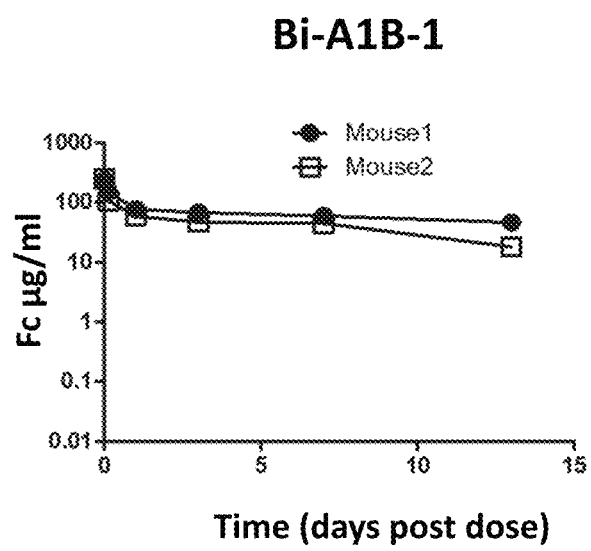
FIG. 19 is a pharmacokinetic profile showing the in vivo half-life ($T_{1/2}$) of the bispecific antagonist Bi-A1B-1 following a tail vein injection into 6-10 week old female CD1 mice. The Bi-A1B-1 antagonist in serum was recovered at various times post-injection and subjected to analysis by ELISA.

To evaluate the pharmacokinetic properties of Bi-A1B-1 in vivo, pharmacokinetic profiles were generated. Briefly, 10 mg/kg of each antagonist was intravenously injected into the tail vein of 6-10 week old female CD1 mice (n=2 mice per molecule). Serum was harvested at 3 minutes, 3 hours, 1 day, 3 days, 7 days and 10 days post injection. To detect the antibodies in the serum, 96 well ELISA plates were coated with 5 µg/ml goat anti-human IgG F(ab')2 fragment and then blocked with 5% milk in PBS. Serially diluted mouse serum in 5% milk and serially diluted purified protein molecule as standard were added to the plates. Following incubation with peroxidase conjugated mouse anti-human IgG and further washes, bispecific antagonist Bi-A1B-1 (FIG. 19) antibodies were detected following incubation with TMB-ELISA substrate. The results of this analysis showed that the half-life (T2) of the bispecific antagonist Bi-A1B-1 is 7.4-16 days.

Example 6: Design of Bispecific PD-1/PD-L1 Antagonists with TGF-β1 ECDs

FIGS. 20A-20B depict two bispecific antitumor antagonists, Bi-PB-1.2 (FIG. 20A) and Bi-PLB-1.2 (FIG. 20B), each comprising an antibody backbone (IgG4 K447A or IgG1 K447A) with variable region domains from anti-PD-1 and anti-PD-L1, respectively, and additionally including a TGF-β-RII ECD fused to the carboxy-terminal end of each heavy chain CH3 region.

FIG. 21 shows functional domain sequences present in the bispecific antibodies in FIGS. 20A and 20B. FIG. 22 show the heavy chain (HC) and light chain (LC) amino acid sequences corresponding to the bispecific antagonists depicted in FIGS. 20A and 20B. FIG. 23 summarizes the arrangement of functional domains in the bispecific antagonists depicted in FIGS. 20A and 20B.

Figure 25A:
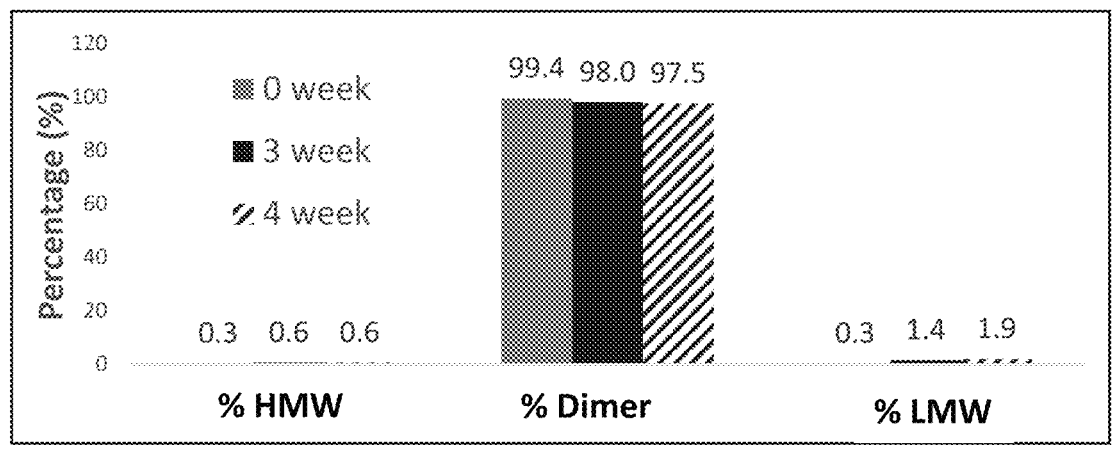
FIGS. 25A-25B show that the Dimer, HMW and LMW forms of Bi-PB-1.2 (FIG. 25A) and Bi-PLB-1.2 (FIG. 25B) exhibit good stability for at least 4 weeks at 4° C.
Figure 25B:
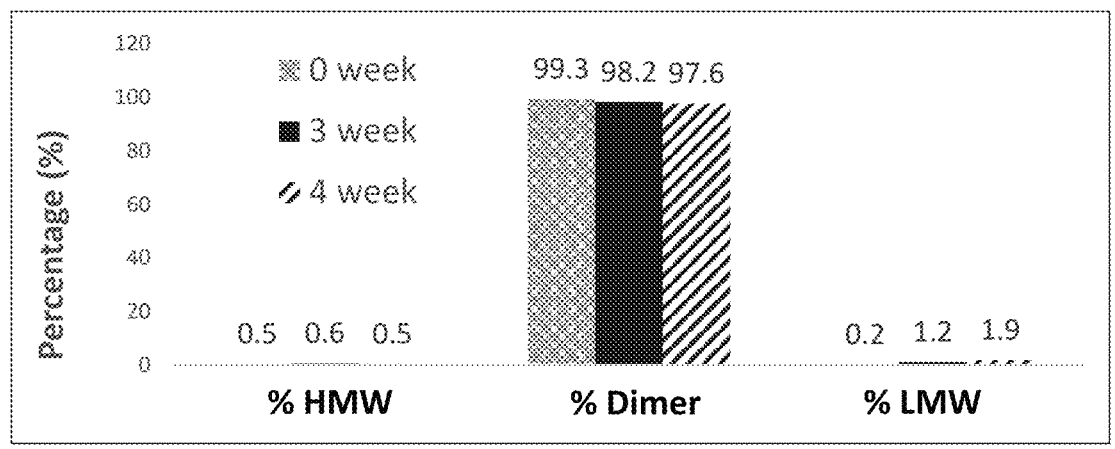

Example 7: Expression and Purification of Bispecific Antagonists in FIGS. 20A-20B FIG. 24A depicts a non-denaturing polyacrylamide gel (PAGE) analysis showing expression of Bi-PB-1.2 and Bi-PLB-1.2 in a transient expression system in comparison to 1 µg of purified a parental control antibody (2P17). FIG. 24B depicts size exclusion chromatography (SEC) profiles showing that protein A purified Bi-PB-1.2, Bi-PLB-1.2 and anti-PDL1 TGF-β-RII ECD fusion antibodies (Benchmark) from transiently transfected HEK293 cells have low levels of high molecular weight (HMW) low molecular weight (LMW) species in comparison to dimerized molecules ("Dimers"), as shown in FIG. 24C. FIGS. 25A-25B show that the Dimer, HMW and LMW forms of Bi-PB-1.2 and Bi-PLB-1.2 exhibit good stability for at least 4 weeks at 4° C.

Example 8: Functional Characterization of Bi-PB-1.2 and Bi-PLB-1.2 Antagonists in FIGS. 20A-20B 1. Binding of Bi-PB-1.2 to PD-1 and TGF-β1 by Bio-Layer Interferometry Bio-light interferometry was carried out using the Octet RED96 system (ForteBio Octet RED96 System) to characterize the binding kinetics of antibodies against His tagged human PD-1 protein or His tagged TGF-β1. 20 nM of antibody was loaded onto the anti-human IgG capture biosensors. Association of analyte (His tagged human PD-1 or TGF-β1 protein) was observed by placing the biosensors in wells containing 2 or 3 fold serial dilution of analytes (72 nM being the highest concentration) for 5 mins. Dissociation was measured after transfer of the biosensors into kinetic buffer alone and monitoring of the interferometry signal for 10 minutes. The observed on and off rates (Ka and Kd) were fit using a 1:1 binding global fit model comprising at least 5 concentrations tested, and the equilibrium binding constant $K_D$ was then calculated.

Figures 26A, 26B, 26C, 26D, 26E:
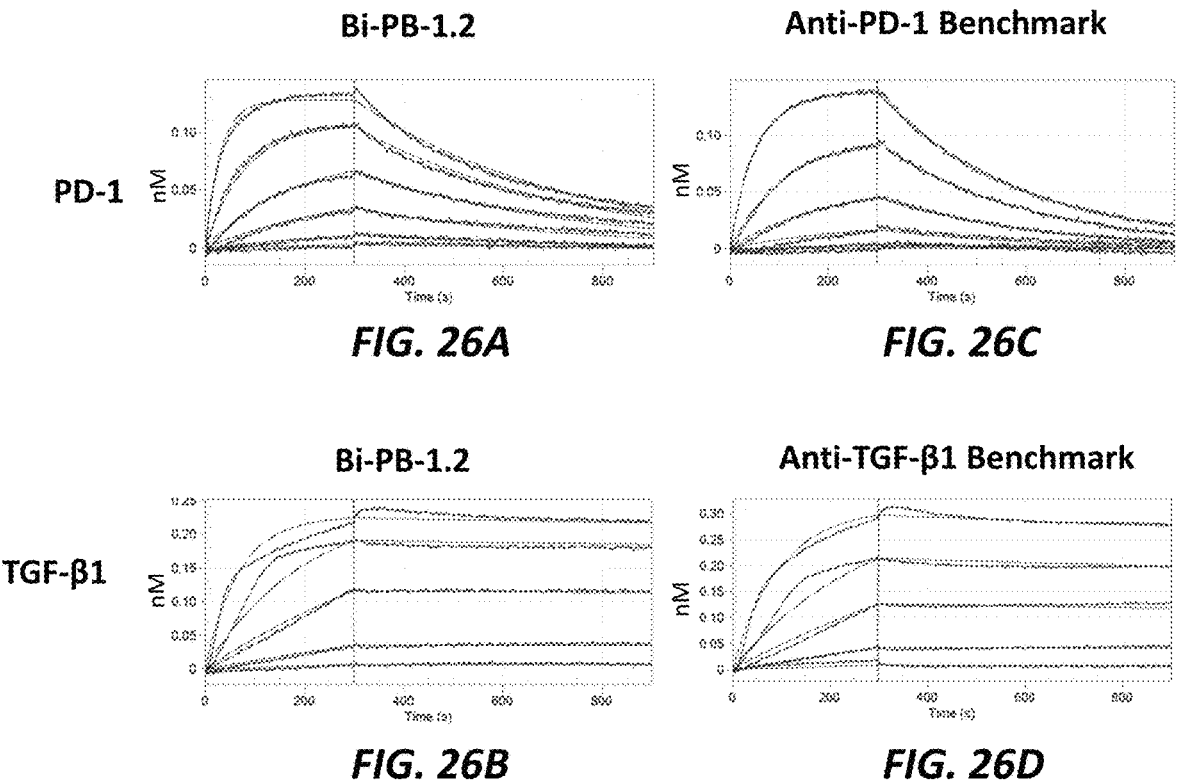
FIGS. 26A-26E show the results of PD-1 and TGF-β1 binding to Bi-PB-1.2 (26A, 26B, respectively) and corresponding anti-PD-1 and anti-PDL1-TGF-β1 RII ECD benchmark molecules (26C, 26D, respectively), along with their resultant binding affinity constants (26E).

FIGS. 26A-26E show the results of PD-1 and TGF-β1 binding to Bi-PB-1.2 (FIGS. 26A, 26B, respectively) and corresponding anti-PD-1 antibody and the benchmark (M7824 from Merck KGA) (FIGS. 26C, 26D, respectively), along with their resultant binding affinity constants (FIG. 26E). The results show that the binding affinities of Bi-PB-1.2 for PD-1 and TGF-1 are better than the anti-PD-1 benchmark and the M7824 benchmark.

2. Binding of Bi-PLB-1.2 to PD-L1 and TGF-β1 by Bio-Layer Interferometry

Binding of Bi-PLB-1.2 to PD-L1 and TGF-β1 by bio-layer interferometry was carried out as described for Bi-PB-1.2 above. FIGS. 27A-27E show the results of PD-1 and TGF-β1 binding to Bi-PB-1.2 (FIGS. 27A, 27B, respectively) and corresponding anti-PD-1 and anti-PDL1 TGF-β-RII ECD fusion antibody (TGF-1 Benchmark) (FIGS. 27C, 27D, respectively), along with their resultant binding affinity constants (FIG. 27E). The results show that the binding affinity of Bi-PLB-1.2 for TGF-1 is better than the TGF-1 ECD benchmark, and the binding affinity of Bi-PLB-1.2 for PD-L1 is comparable to the anti-PD-L1 benchmark.

3. Simultaneous Binding to PD-1/PD-L1 by Bi-PB-1.2 and Bi-PLB-1.2

Figure 28A:
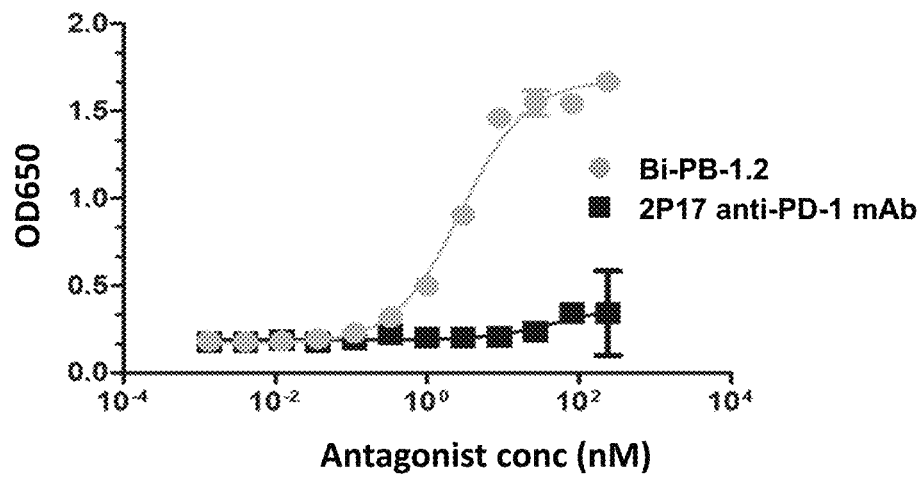
FIG. 28A shows an ELISA assays demonstrating simultaneous binding of TGF-β1 and PD-1 by Bi-PB-1.2 in which huTGF-β1 coated 96 well plates were incubated with serially diluted samples of Bi-PB-1.2, followed by biotinylated hu PD-1, whereby bound molecules were detected by Streptavidin-HRP using a TMB substrate.
Figure 28B:
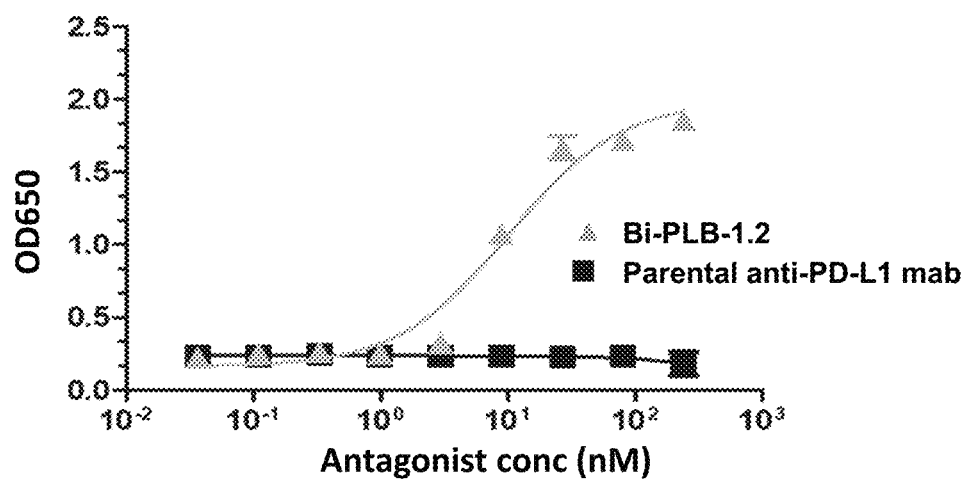
FIG. 28B shows an ELISA assay demonstrating simultaneous binding of TGF-β1 and PD-L1 by Bi-PLB-1.2 in which huTGF-β1 coated 96 well plates were incubated with serially diluted samples of Bi-PLB-1.2, followed by biotinylated hu PD-L1, whereby bound molecules were detected by Streptavidin-HRP using a TMB substrate.

FIG. 28A shows an ELISA assay demonstrating simultaneous binding of TGF-β1 and PD-1 by Bi-PB-1.2 in which huTGF-β1 coated 96 well plates were incubated with serially diluted samples of Bi-PB-1.2, followed by His-tagged huPD-1, whereby bound molecules were detected by anti-His tag-HRP using a TMB substrate. FIG. 28B shows an ELISA assay demonstrating simultaneous binding of TGF-β1 and PD-L1 by Bi-PLB-1.2 in which huTGF-β1 coated 96 well plates were incubated with serially diluted samples of Bi-PLB-1.2, followed by His-tagged huPD-L1, whereby bound molecules were detected by anti-His tag-HRP using a TMB substrate. The EC50 values reflect the half maximal effective concentrations producing a response halfway between the baseline and maximum response with respect to binding human PD-1 or PD-L1.

Figure 29A:
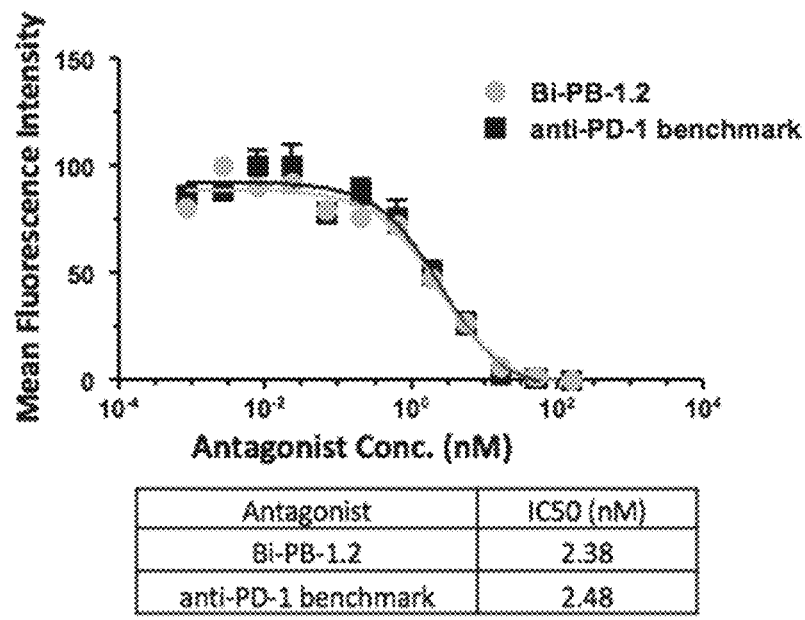
FIG. 29A shows the ability of Bi-PB-1.2 and anti-PD-1 benchmark antibody to block binding of PD-1 to PD-L1.

4. Bi-PB-1.2 Potently Blocks Binding of Both PD-L1 and TGF-β1 to their Receptors In FIG. 29A, a blocking assay was carried out to calculate IC50 values corresponding to ability of Bi-PB-1.2 to block the binding of PD-1 to PD-L1 in comparison to an anti-PD-1 benchmark antibody. Briefly, 2 fold serial dilutions of Bi-PB-1.2 or the benchmark anti-PD-1 antibody (highest Ab concentration: 128 nM; Triplicates for each mAb) were prepared. Human PD-1 transfected CHO-KI cells were washed with FACS buffer (0.5% BSA 2 mM EDTA in PBS) and re-suspended at a concentration of $10^6$ cells/ml. FITC labeled human PD-L1-Fc protein was added to the human PD-1 transfected CHO-KI cells at a final concentration of 7 μg/ml and mixed well. Without incubation, 2,000 of these CHO-KI cells (with PD-L1 Protein) in 20 μl FACS buffer was immediately added to a 96-well round bottom plate and 20 μl or 2 fold serial diluted antibodies were immediately added to the cells and incubated at 4° C. for 30 mins. The cells were then washed and re-suspended in 30 μl 7AAD solution; 35 μl 10% neutral buffered formalin solution was then added and incubated for 15 min. before analysis using the iQue intellicyt system. As expected, the results of this analysis in FIG. 29A showed that increasing levels of Bi-PB-1.2 progressively block the ability of PD-L1 to bind to its receptor. Further, the calculated IC50 of Bi-PB-1.2 for PD-L1 was found to be comparable to the IC50 of the anti-PD-1 benchmark for PD-L1.

Figure 29B:
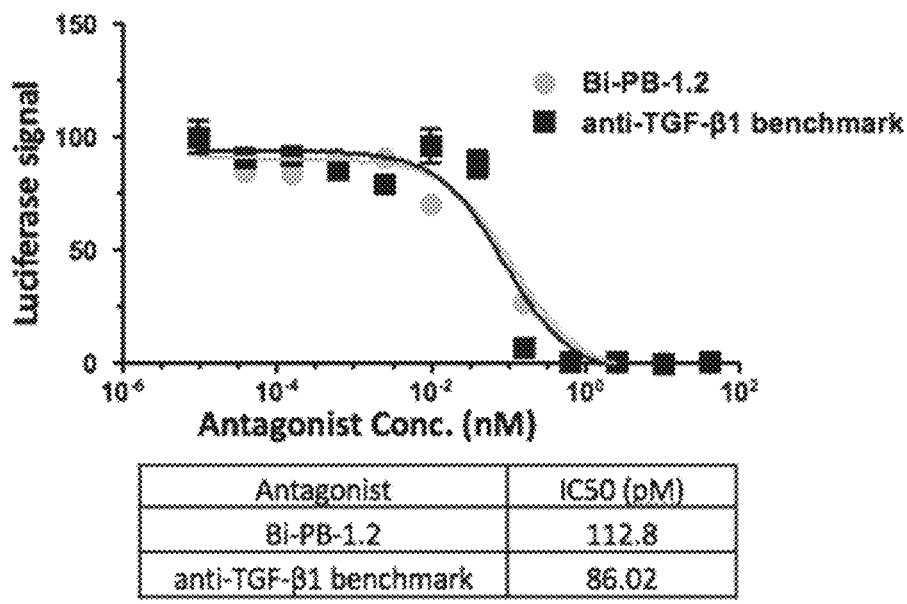
FIG. 29B shows the results of a cell-based assay showing the ability of serial dilutions of Bi-PB-1.2 and anti-PDL1-TGF-β1 RII ECD benchmark molecule to block the ability of TGF-β1 to activate luciferase expression under the control of a SMAD response element. Bioactivity was determined by a decrease in the amount of luciferase-mediated luminescence.

To evaluate the ability of the TGF-β1 RII ECD to antagonize TGF-β1-mediated activation of the human TGF-β1 RII (i.e., the cognate receptor), a cell-based luciferase assay was conducted. In this experiment, recombinant HEK-293 cells expressing human TGF-β1 RII receptor and a firefly luciferase construct under the control of a SMAD response element was stimulated with huTGF-β1 in the presence of serial dilutions of Bi-PB-1.2 containing a TGF-β1 RII ECD. Bioactivity was determined by a decrease in the amount of luciferase-mediated luminescence. The results of this assay are shown in FIG. 29B. As expected, increasing levels of Bi-PB-1.2 and the benchmark anti-PD-L1 TGF-11 RII ECD progressively neutralized the ability of TGF-β1 to activate the human TGF-β1 RII and induce NFAT-mediated luciferase activity. Further, the calculated IC50 Bi-PB-1.2 for TGF-β1 was found to be comparable to the IC50 of the anti-PD-L1 TGF-β1 RII ECD benchmark for TGF-β 1.

5. Bi-PB-1.2 Binds Both Human and Cynomolgus PD-1 with Similar Activity

Figure 30A:
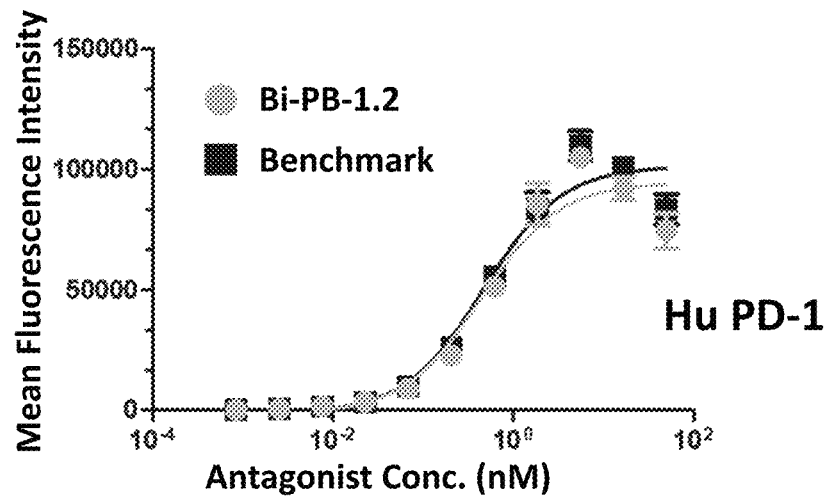
FIGS. 30A-30B show binding of Bi-PB-1.2 and both anti-human PD-1 and anti-cyno PD-1 benchmark antibodies to human PD-1 (FIG. 30A) and cynomolgus PD-1 (FIG. 30B), along with their corresponding EC50 values reflecting the half maximal effective concentrations ($EC_{50}$) producing a response halfway between the baseline and maximum response with respect to binding human PD-1 and cyno PD-1, respectively.
Figure 30B:
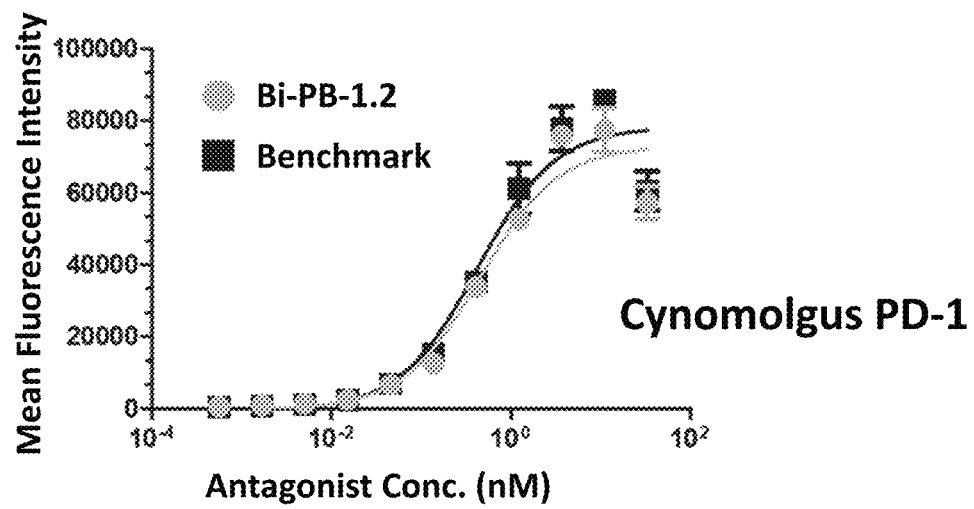

To evaluate the ability of Bi-PB-1.2 to bind both human and cyno PD-1, serial dilutions of Bi-PB-1.2 were added to CHO-K1 cells (20,000 cells/well) overexpressing human or cyno PD-1. The mixtures were incubated at 4° C. for 20 min, washed 3 times, and stained with the secondary antibody, PE labeled F(ab')2-Goat anti-human IgG Fc (Thermo H10104) at 4° C. for 20 min. Cells were washed and resuspended in 7AAD solution and fixed in 10% neutral buffered formalin solution for 15 minutes before analysis with the iQue Intellicyt system. FIGS. 30A-30B show binding of Bi-PB-1.2 to both human PD-1 (FIG. 30A) and cyno PD-1 (FIG. 30B). As expected, the anti-human PD-1 benchmark antibody was similarly found to bind human PD-1 (FIG. 30A) and cynomolgus PD-1 (FIG. 30B). Corresponding EC50 values reflecting the half maximal effective concentrations ($EC_{50}$) producing a response halfway between the baseline and maximum response with respect to binding human PD-1 and cyno PD-1, respectively, were also determined. In this case, the EC50 values show similar binding properties of Bi-PB-1.2 as the benchmark antibody.

Figure 31A:
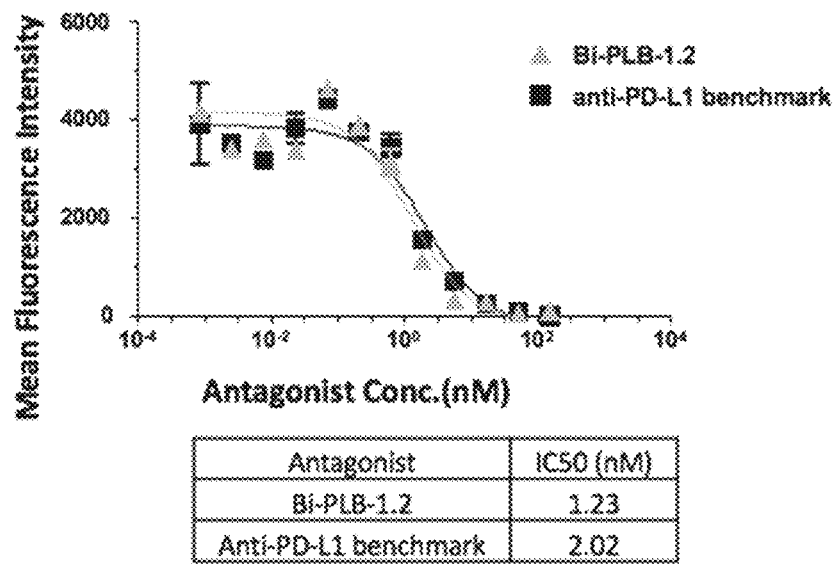
FIG. 31A shows the ability of Bi-PLB-1.2 and anti-PD-L1 benchmark antibody to block binding of PD-L1 to PD-1.

6. Bi-PLB-1.2 Potently Blocks Binding of Both PD-1 and TGF-β1 to their Receptors A blocking assay was carried out to calculate IC50 values corresponding to the binding between Bi-PLB-1.2 and PD-L1 in comparison to anti-PD-L1 benchmark antibody, essentially as described in Example 8, section 4 above. FIG. 31A shows that increasing concentrations of Bi-PLB-1.2 or anti-PD-L1 benchmark antibody progressively blocked binding of PD-1 to PD-L1. As reflected in the IC50 values obtained, the bispecific are comparable to the anti-PD-L1 benchmark.

Figure 31B:
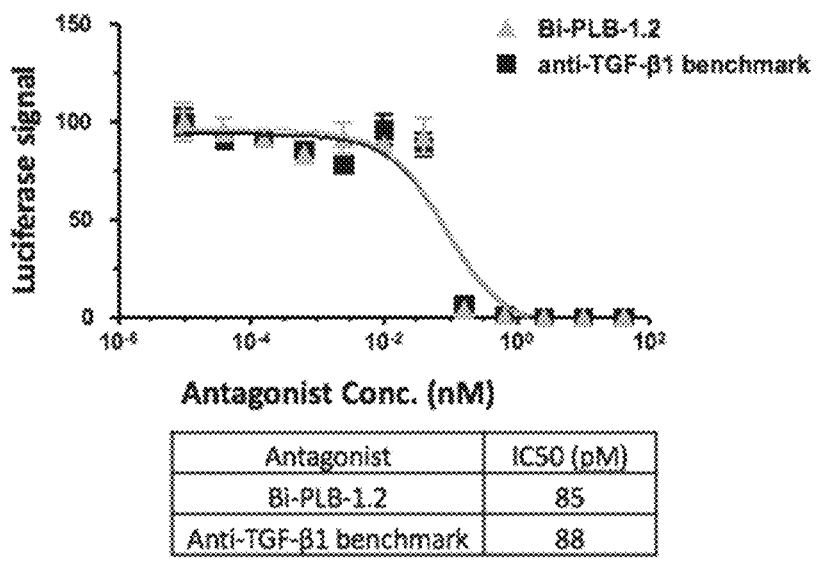
FIG. 31B shows the results of a cell-based assay showing the ability of serial dilutions of Bi-PLB-1.2 and anti-PDL1-TGF-β1 RII ECD benchmark molecule to block the ability of TGF-β1 to activate luciferase expression under the control of a SMAD response element. Bioactivity was determined by a decrease in the amount of luciferase-mediated luminescence.

To calculate IC50 values corresponding to the binding between Bi-PLB-1.2 and TGF-β1 in comparison to anti-TGF-β1 benchmark antibody, the cell-based assay described in Example 8, section 4 was carried out. FIG. 31B shows the ability of serial dilutions of Bi-PLB-1.2 and anti-PDL1-TGF-β1 RII ECD benchmark to block the ability of TGF-β1 to activate luciferase expression under the control of a SMAD response element. As reflected in the IC50 values obtained, the bispecific antibody exhibited similar binding characteristics as the anti-PDL1-TGF-β1 RII ECD benchmark.

7. Bi-PLB-1.2 Binds Both Human and Cynomolgus PD-1 with Similar Activities

Figure 32A:
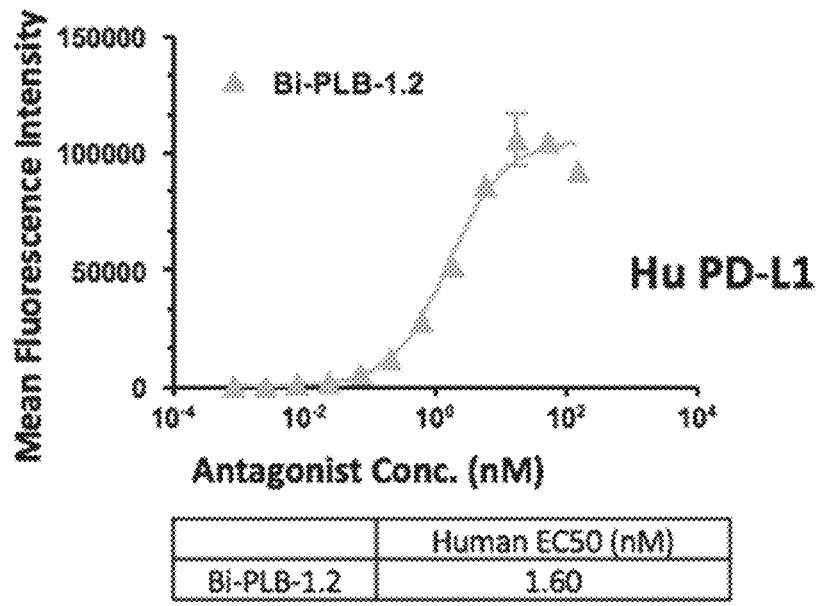
FIGS. 32A-32B show binding of Bi-PLB-1.2 and both anti-human PD-L1 and anti-cyno PD-L1 benchmark antibodies to human PD-L1 (FIG. 32A) and cyno PD-L1 (FIG. 32B), along with their corresponding EC50 values reflecting the half maximal effective concentrations ($EC_{50}$) producing a response halfway between the baseline and maximum response with respect to binding human PD-L1 and cyno PD-L1, respectively.
Figure 32B:
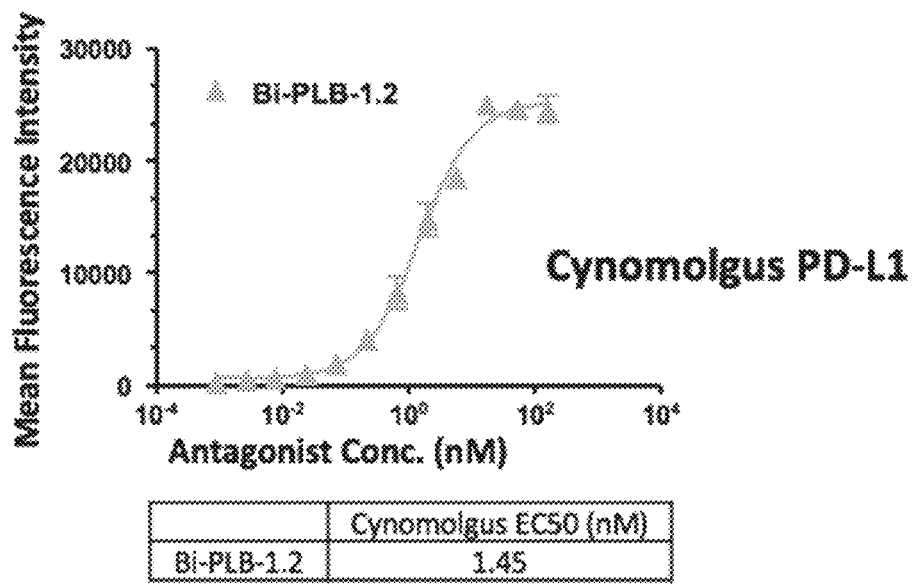

To evaluate the ability of Bi-PLB-1.2 to bind both human and cynomolgus PD-L1, serial dilutions of Bi-PLB-1.2 were added to CHO-K1 cells (20,000 cells/well) overexpressing human or cyno PD-L1, essentially as described in Example 9, section 5. FIGS. 32A-32B show that Bi-PLB-1.2 bound both human PD-L1 (FIG. 32A) and cyno PD-L1 (FIG. 32B). The resulting EC50 values reflect the half maximal effective concentrations ($EC_{50}$) producing a response halfway between the baseline and maximum response with respect to binding human PD-1 and cyno PD-1, respectively, were also determined.

8. Bi-PB-1.2 Enhances T Cell Activation

Human T cell assays were performed to show the functionality of the Bi-PB-1.2 antibodies. Briefly, normal healthy human PBMC collected from Donors 1 and 2 were each activated with SEB (Toxin Technology, Cat#: BT202). To assay for IFN-γ production, 100,000 cells were stimulated with 0.5 ug/ml SEB in a 96 well plate. 25,000 tumor suppressing, SHP77 cells were added to provide inhibitory signals. 66 nM of Bi-PB-1.2 mAbs or isotype control Ab was added. 5 days later, the supernatant was examined for IFN-γ and IL-2 by ELISA. FIGS. 33A-33B show increased IFN-γ (Donor 1, 40A; Donor 2, FIG. 33B) and IL-2 (Donor 1, 40C; Donor 2, FIG. 33D) with Bi-PB-1.2 relative to the negative control treatments.

9. Bi-PLB-1.2 Enhances T Cell Activation and Overcomes T Cell Suppression by Tumor Cells Better than the Parental Anti-PD-L1 Antibody FIGS. 34A-34D and show increased IFN-γ secretion from human PBMCs (Donor 8, FIG. 34A; Donor 9, FIG. 34B) with Bi-PLB-1.2 relative to the negative control treatments and the parental anti-PD-L1 antibody. FIGS. 34C-34D show increased IL-2 section from human PBMCs (Donor 8, FIG. 34C; Donor 9, FIG. 34D) with Bi-PLB-1.2 relative to the negative control treatments and the parental anti-PD-L1 antibody. These results are consistent with the notion that Bi-PLB-1.2 overcomes T cell suppression by tumor cells better than the parental anti-PD-L1 antibody.

10. Improved Pharmacokinetic Profile in Mice for Bi-PB-1.2 and Bi-PLB-1.2 Compared to a Benchmark Antibody To evaluate the pharmacokinetic properties of Bi-PB-1.2, Bi-PLB-1.2 and a benchmark antibody in vivo, pharmacokinetic profiles were generated. Briefly, 10 mg/kg of each antagonist was intravenously injected into the tail vein of 6-10 week old female CD1 mice (n=2 mice per molecule). Serum was harvested at 3 minutes, 3 hours, 1 day, 3 days, 7 days and 10 days post injection. To detect the antibodies in the serum, 96 well ELISA plates were coated with 5 μg/ml goat anti-human IgG F(ab')2 fragment and then blocked with 5% milk in PBS. Serially diluted mouse serum in 5% milk and serially diluted purified protein molecule as standard were added to the plates.

Figures 35A, 35C:
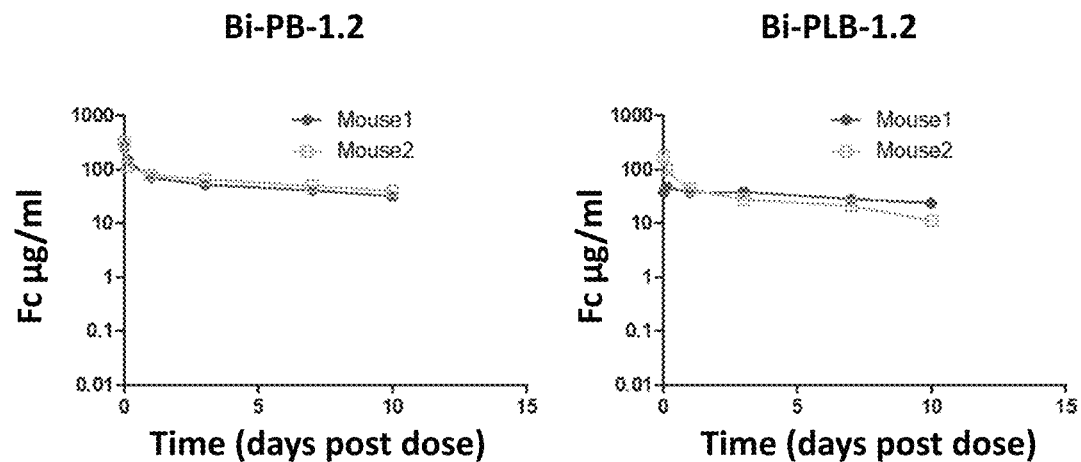
FIGS. 35A-35F show that Bi-PB-1.2 and Bi-PLB-1.2 exhibit improved pharmacokinetic profiles relative to a benchmark antibody following a tail vein injection into 6-10 week old female CD1 mice. The antibody antagonists, Bi-PB-1.2, Bi-PLB-1.2, and Benchmark were recovered from serum at various times post-injection and subjected to analysis by ELISA (FIGS. 35A, 35C, 35E, respectively) and Western blot (FIGS. 35B, 35D, 35F, respectively).
Figures 35B, 35D:
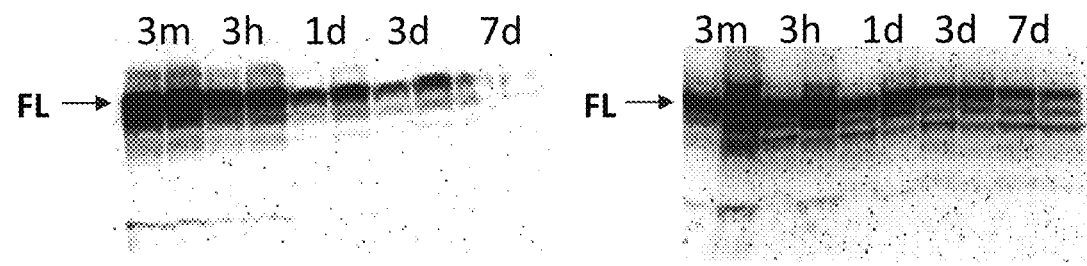
Figures 35E, 35F:
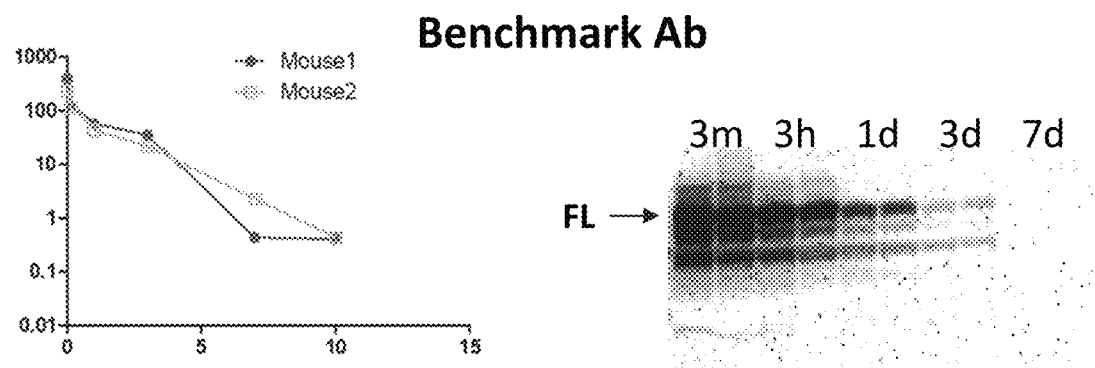

Following incubation with peroxidase conjugated mouse anti-human IgG and further washes, Bi-PB-1.2 (FIG. 35A), Bi-PLB-1.2 (FIG. 35C), and the anti-PDL1-TGF-β1 RII ECD benchmark (M8724) (FIG. 35E) were detected following incubation with TMB-ELISA substrate. The integrity and clipping of the injected antibodies Bi-PB-1.2 (FIG. 35B), Bi-PLB-1.2 (FIG. 35D), and the benchmark (FIG. 35F) in the mouse serum were also analyzed by anti-human Fc Western blot. The results of this analysis show improved pharmacokinetic profiles in mice for Bi-PB-1.2 and Bi-PLB-1.2 compared to the benchmark antibody.

Example 9: Investigation of Proteolytic Cleavage in TGFβ1 RII ECD Domain

Figure 36:
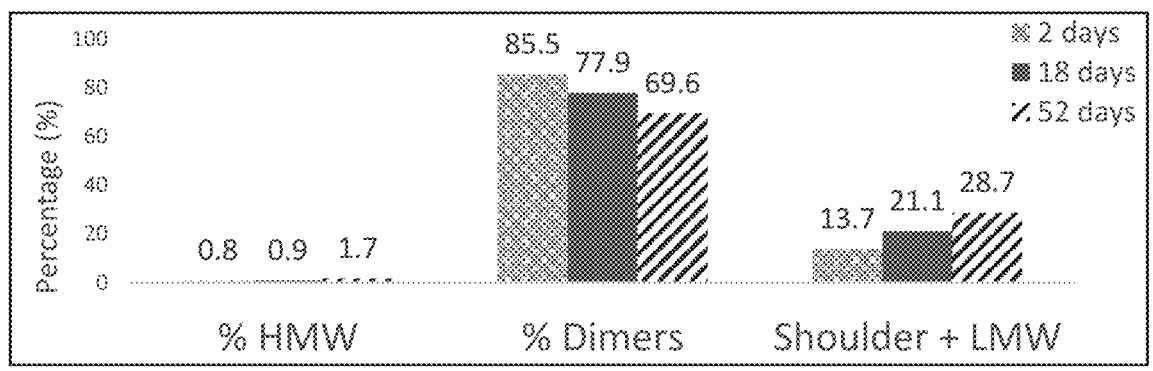
FIG. 36 shows that the percentage of low molecular weight (LMW) species of Bi-PB-1.2 (PD1-TGFβ-ECD) produced by stably transfected CHO cells increases over time stored at 4° C., while the percentage of dimer species decreases over time, consistent with increased clipping over as determined by size-exclusion ultra-high performance liquid chromatography (SE-UHPLC).

The inventors of the present application have unexpectedly discovered that antagonists bearing a TGFβ1 RII ECD domain exhibit unacceptable levels of proteolytic degradation or clipping over time upon storage when they are produced by stably transfected CHO cells. This is illustrated in FIG. 36, which shows that the percentage of low molecular weight (LMW) species of Bi-PB-1.2 (PD1/TGFβ1 RII ECD; see FIG. 20A) increase over time stored at 4° C., while the percentage of dimer species decreases over time as determined by SE-UPLC using Tosoh TSKgel UP-G3000SWXL columns.

Figure 37:
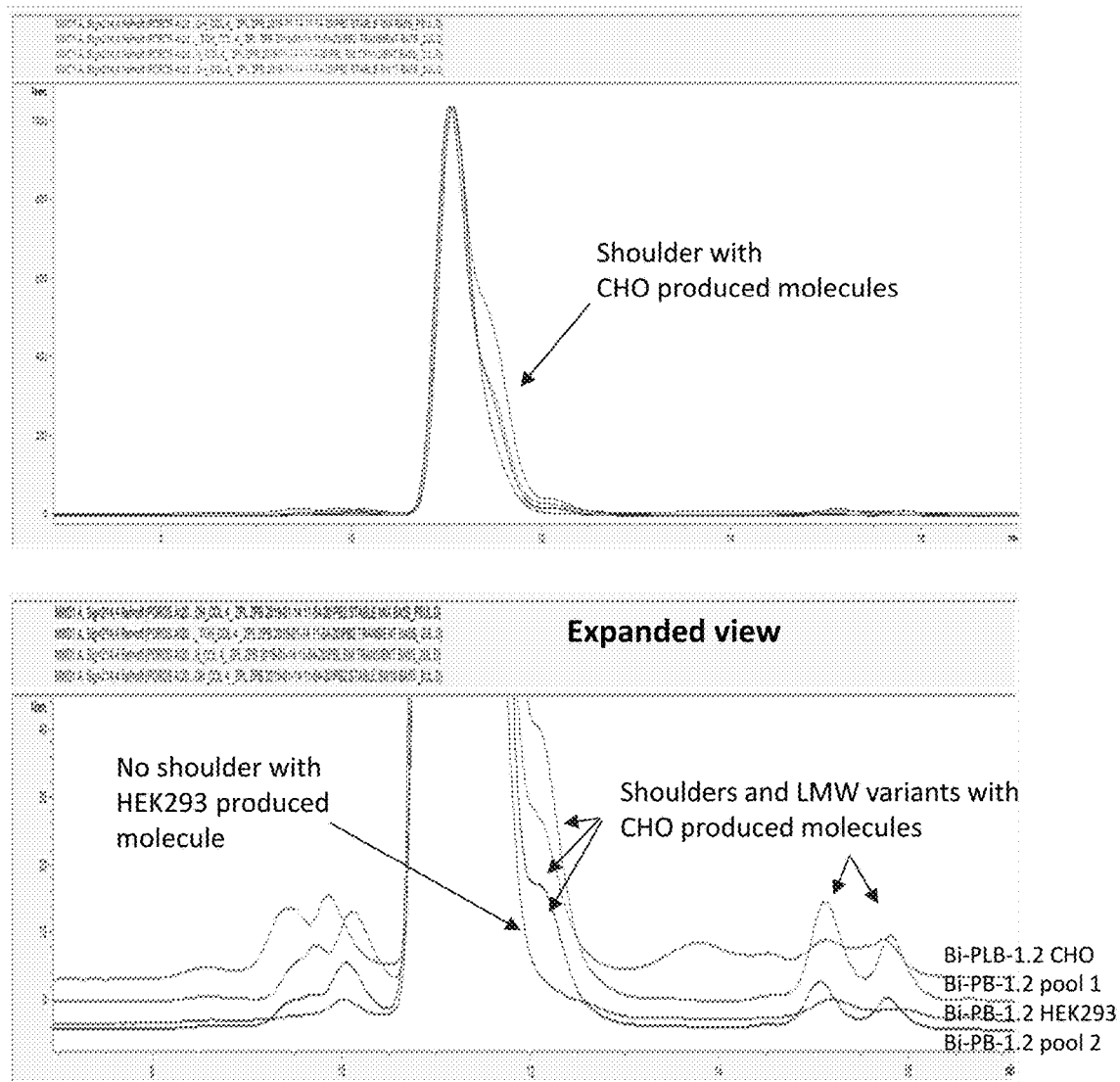
FIG. 37 shows size exclusion chromatograph (SEC) profiles of the bispecific antagonist, Bi-PB-1.2 (PD1-TGF-β1 RII ECD) and a PLB-1 benchmark (BM) antibody expressed in stably transformed CHO cells, which depict a shoulder in the main peak consistent with increased clipping compared to Bi-PD-1.2 produced by HEK293 transiently transfected cells.

Because the LMW forms had not been seen when the PD1/PDL1-TGFB RII ECD molecules were produced by transiently transfected HEK293 cells, SEC analyses were performed to compare stable CHO produced benchmark and Bi-PB-1.2 from 2 different CHO transfection pool to bi_PB1.2 that was produced from HEK293 cells (FIG. 37). As shown in FIG. 37, the SEC profiles illustrate a shoulder near the main peak, along with smaller secondary peaks for the molecules that were produced by CHO cells, but not by HEK293 cells consistent with increased proteolytic cleavage (or clipping) of CHO produced molecules.

Figure 38:
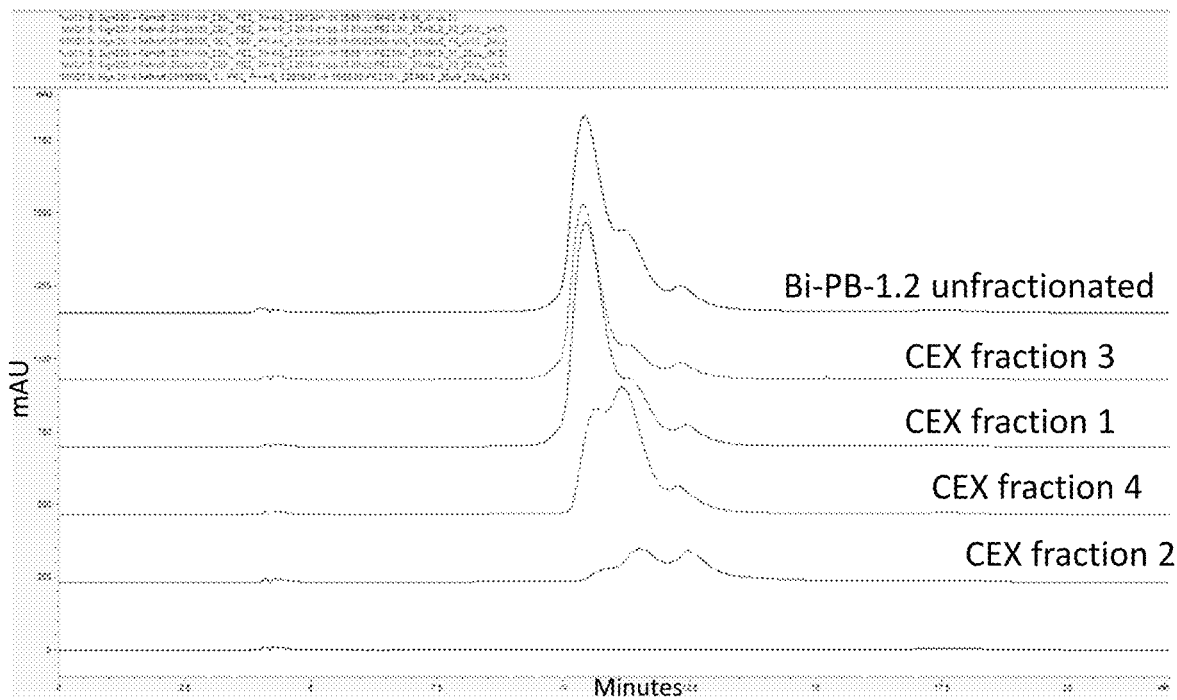
FIG. 38 shows SEC profiles of Bi-PB-1.2 fractions obtained by cation-exchange chromatography (CEX).
Figure 46A:
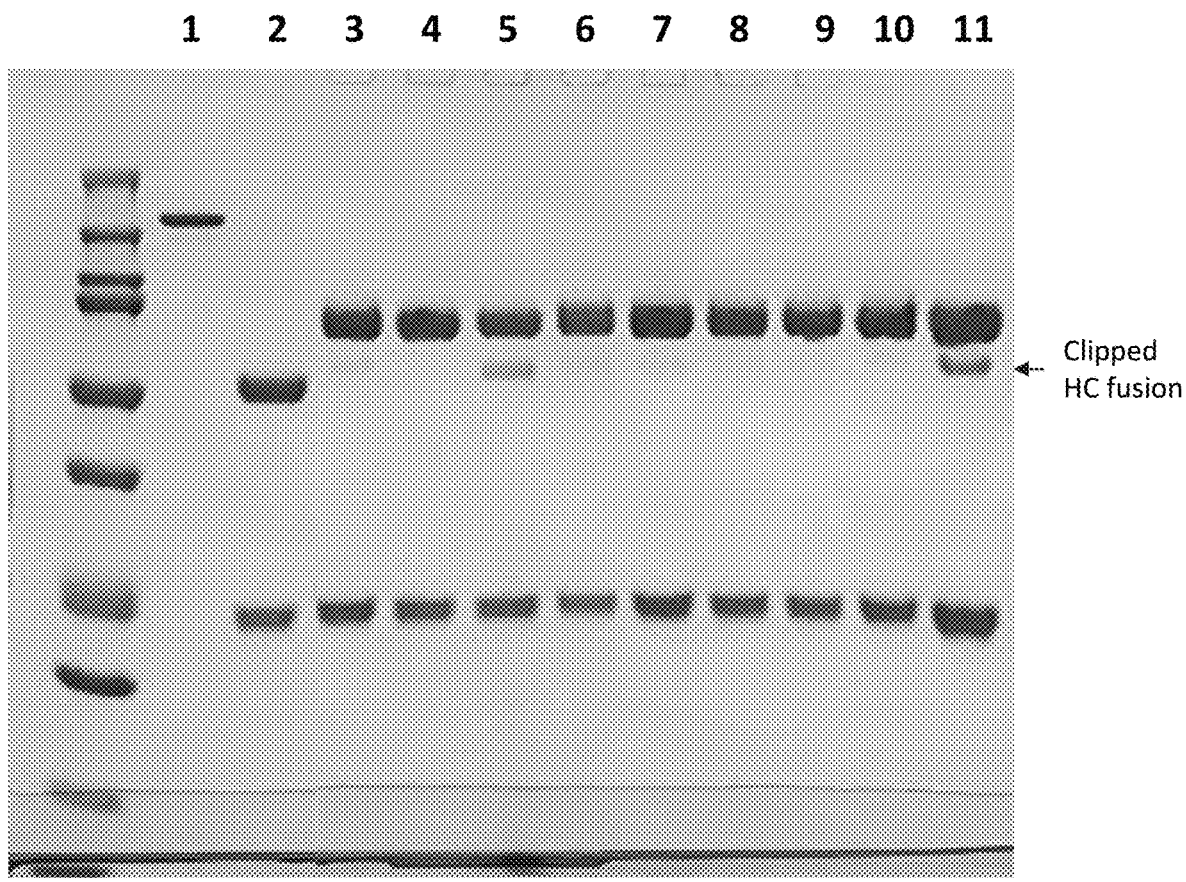
FIG. 46A-46C depict reducing polyacrylamide gel (PAGE) analyses showing similar expression levels and yields from the Bi-PB-1.2 TGFβ1 ECD mutants compared to the parental wild-type Bi-PB-1.2 following protein A-affinity purification of molecules from stable Chinese hamster ovary cell (CHO) transformants.
Figure 46B:
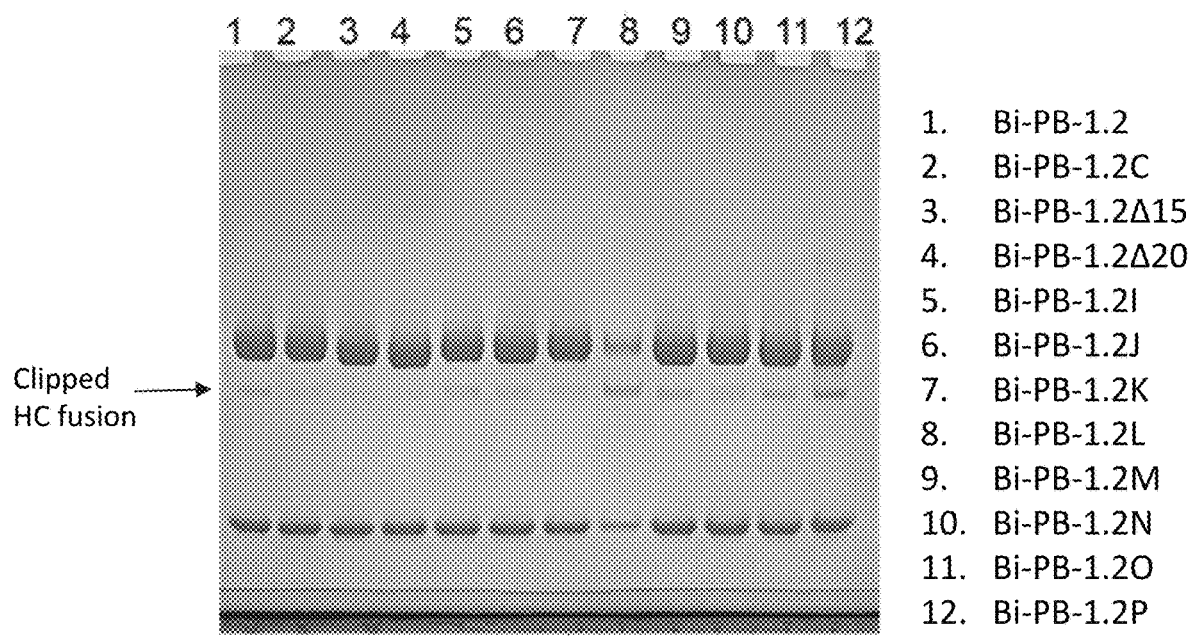
Figure 46C:
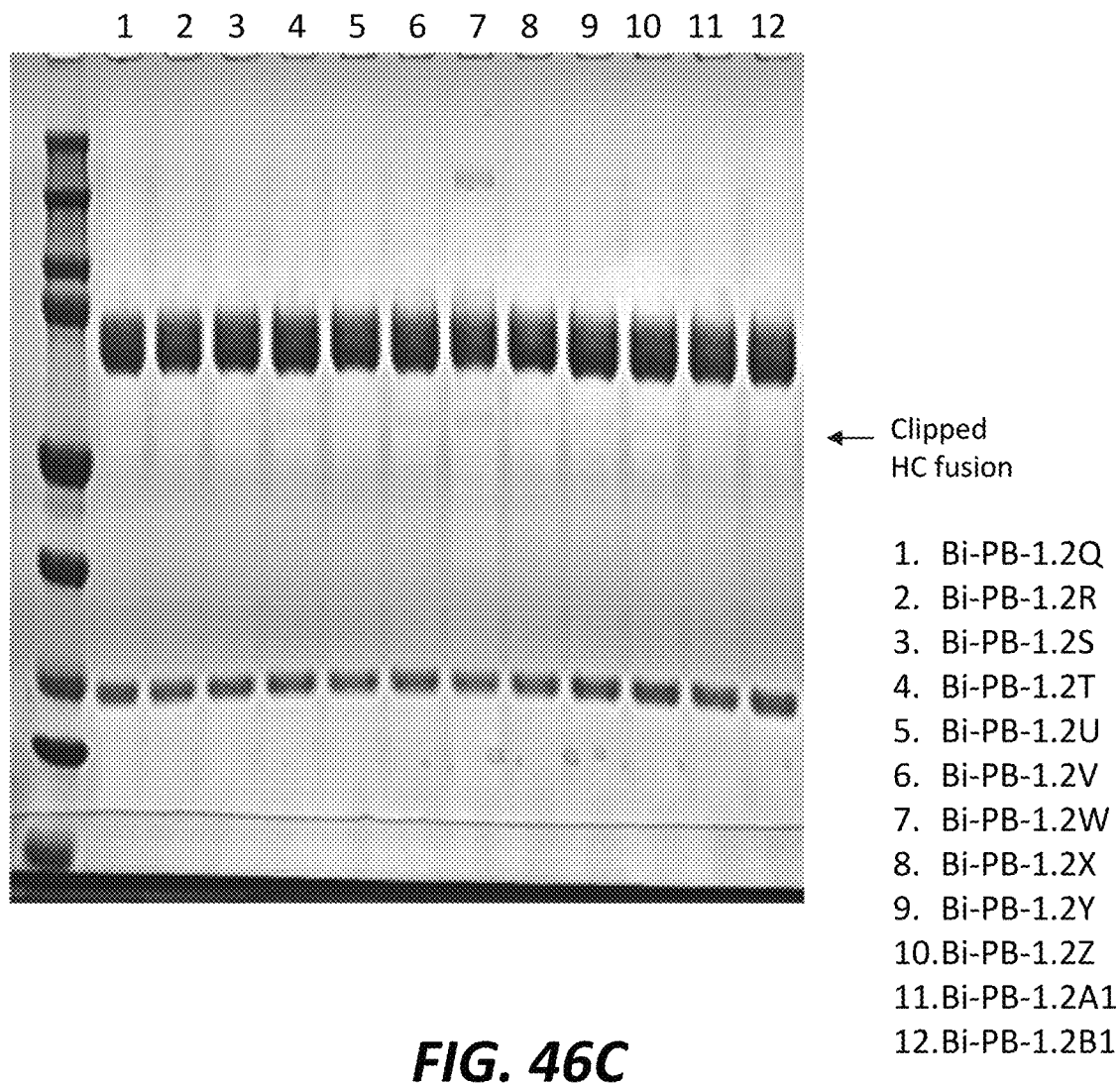
Figure 47A:
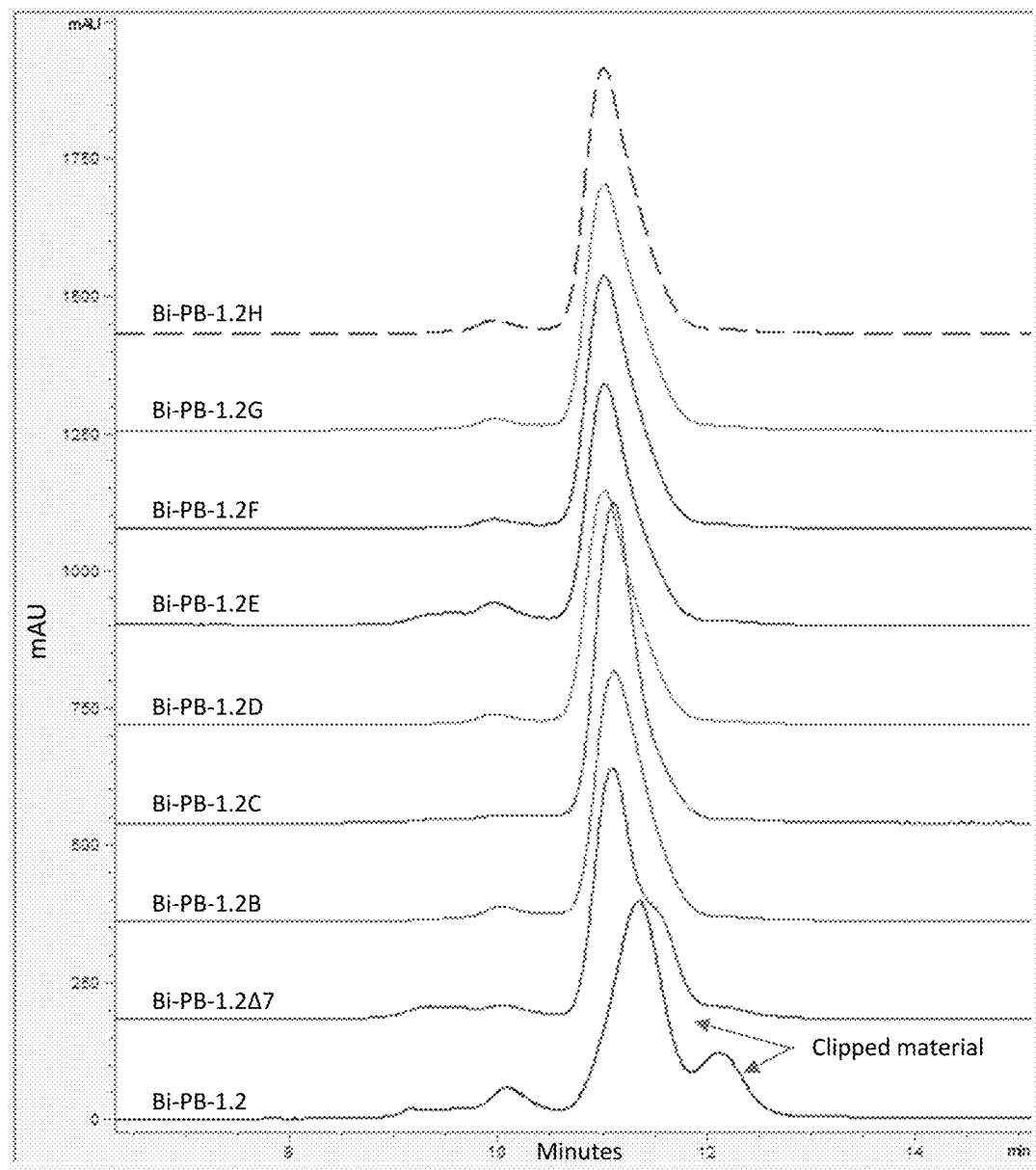
FIG. 47A shows SEC profiles corresponding to Bi-PB-1.2 and the mutants, Bi-PB-1.2-Δ7, Bi-PB-1.2B to Bi-PB-1.2H, which show reduced clipping (no shoulder) of the mutants compared to Bi-PB-1.2.
Figure 47B:
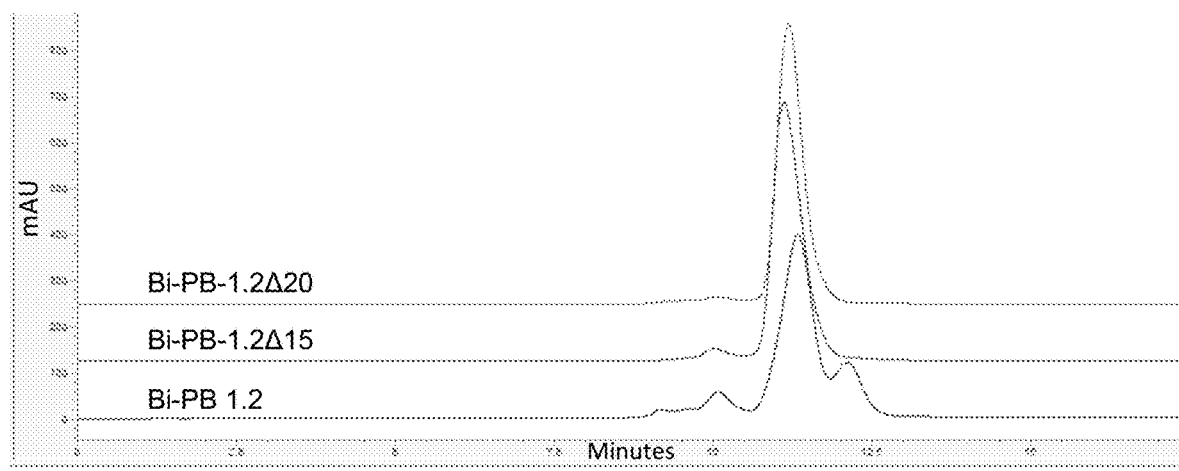
FIG. 47B shows SEC profiles corresponding to Bi-PB-1.2 and the mutants, Bi-PB-1.2-Δ15, and Bi-PB-1.2-Δ20, which show reduced clipping (no shoulder) of the mutants compared to Bi-PB-1.2.
Figure 49:
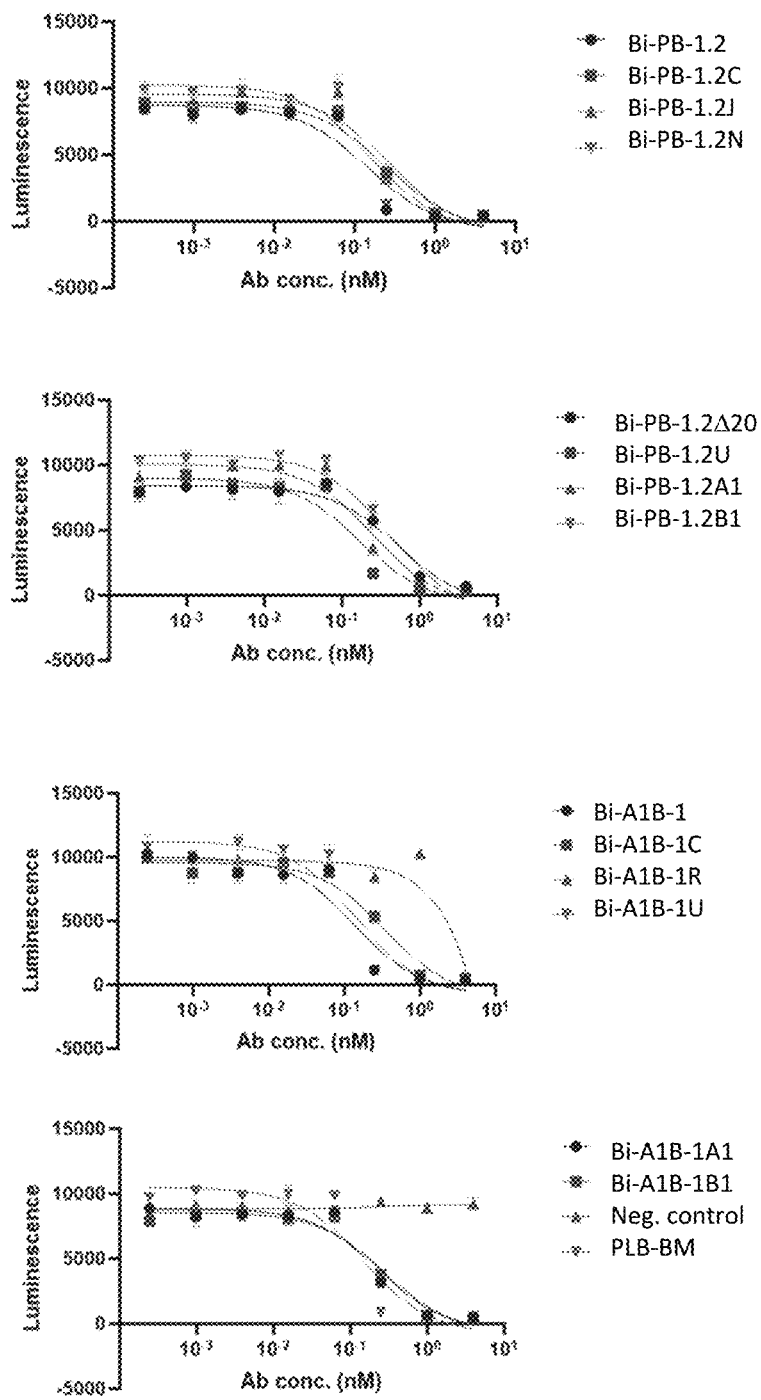
FIG. 49 shows the results of a cell-based assay showing the ability of serial dilutions of the Bi-PB-1.2 and Bi-A1B-1 variants and controls (i.e., parental Bi-PB-1.2, Bi-A1B-1 and PLB-BM (Benchmark) and negative control antibody) produced by HEK293 transient transfection to block the ability of TGF-β1 to activate luciferase expression under the control of a SMAD response element. Bioactivity was determined by a decrease in the amount of luciferase-mediated luminescence.
Figure 51A:
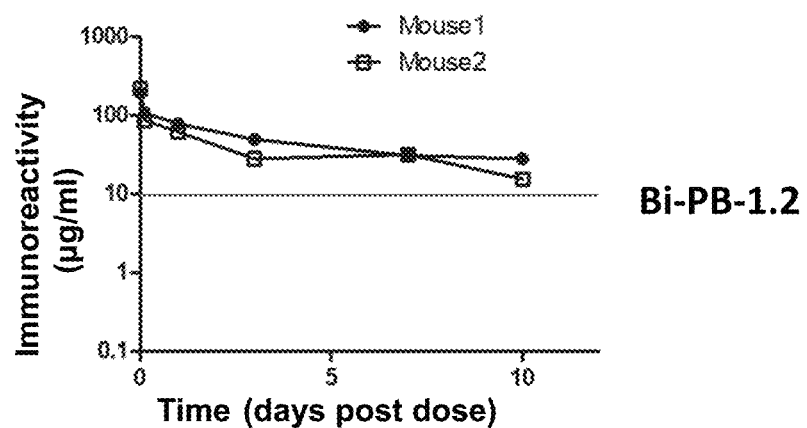
FIGS. 51A-51C show that Bi-PB-1.2 (FIG. 51A), Bi-PB-1.2C (FIG. 51B) and Bi-PB-1.2D (FIG. 51C) have similar pharmacokinetics in paired mice, characterized by a T of about 5-8 days.
Figure 51B:
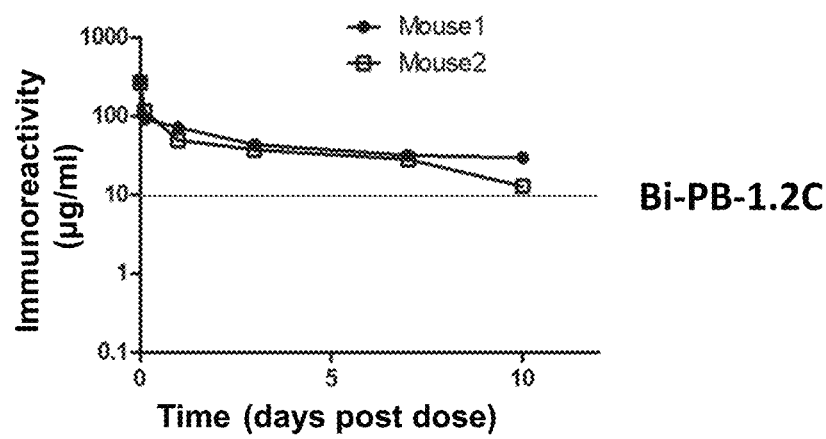
Figure 51C:
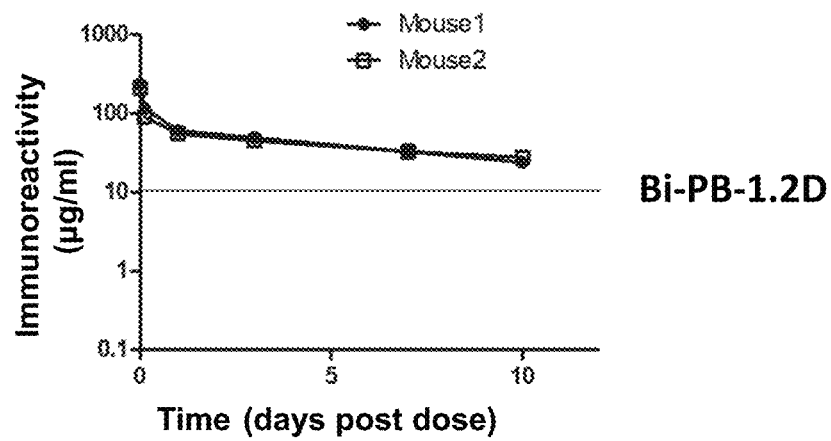
Figure 52A:
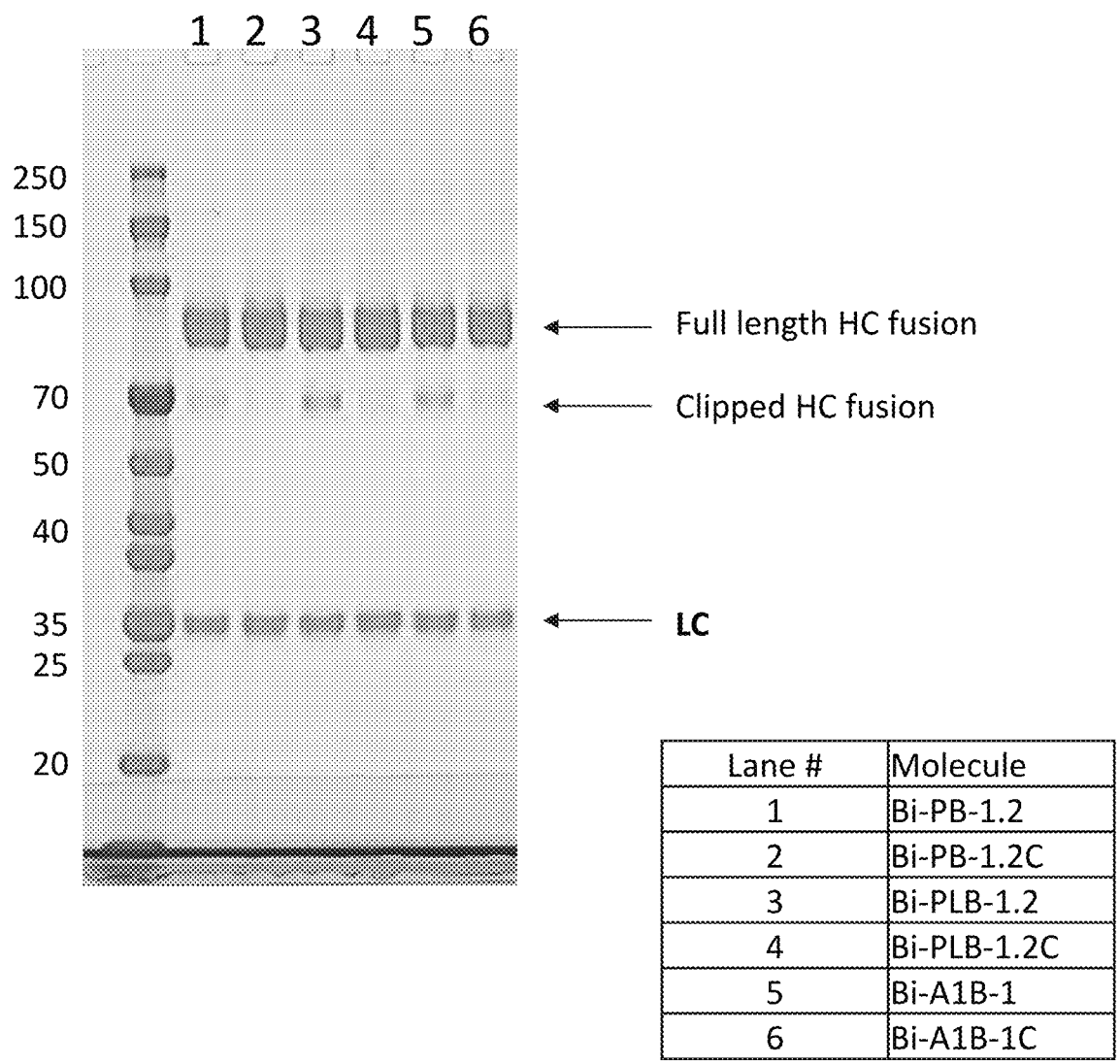
FIG. 52 shows FIGS. 52A & 52B a reducing polyacrylamide gel (PAGE) analysis showing reduced levels of clipped fragments from the C variants compared to the parental wild-type Bi-PB-1.2, Bi-PLB-1.2 and Bi-A1B-1.
Figure 52B:
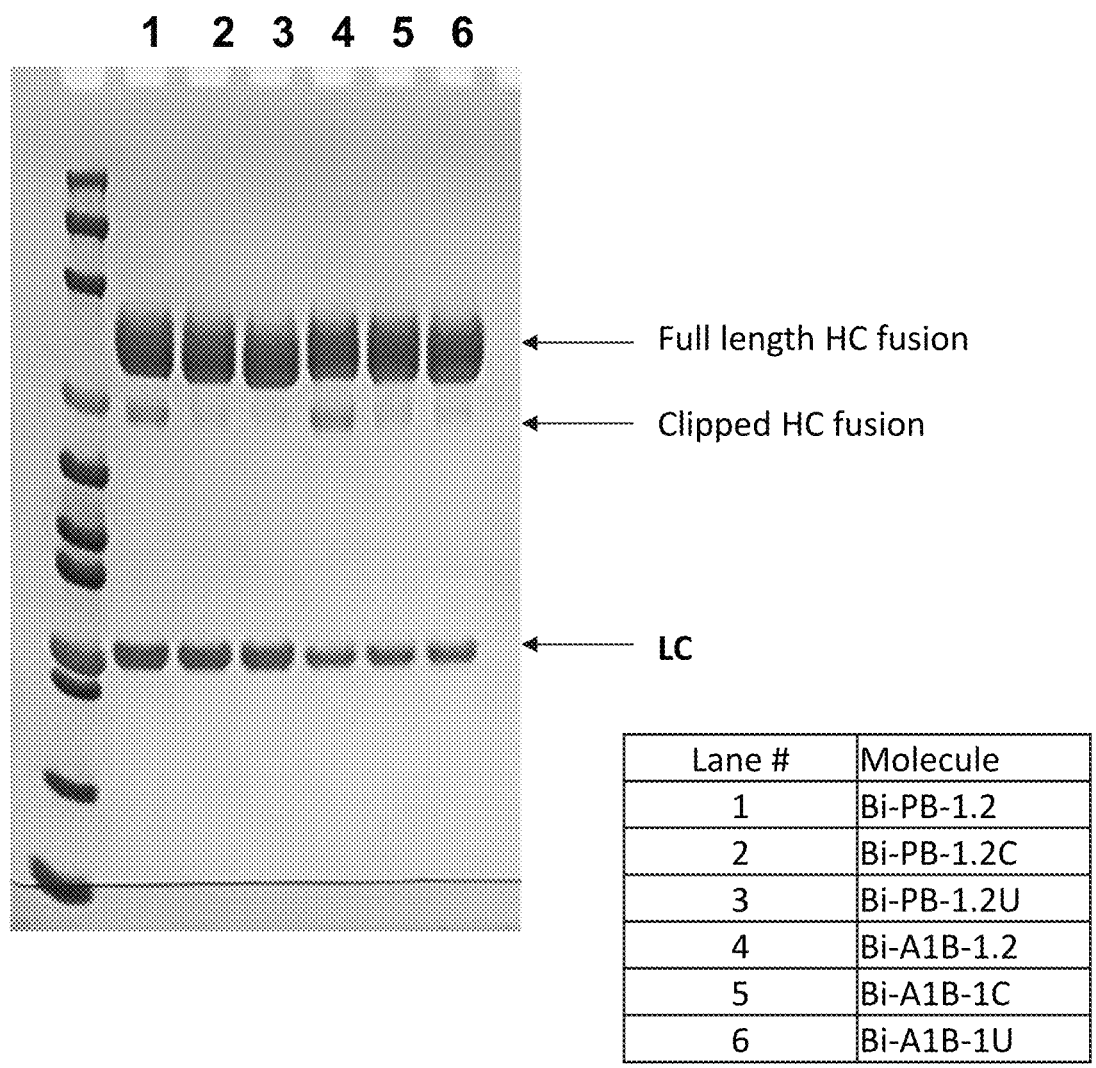

To further examine the specific nature of the cleavage(s), the Bi-PB-1.2 antagonist was expressed in CHO-K1 cells and subjected to cation-exchange chromatography (CEX) in order to generate fractions for further analysis by liquid chromatography-mass spectrometry (LC-MS) to identify site(s) associated with clipping (FIG. 38). The same analysis was extended to Bi-A1B-1 (data not shown). For the LC-MS analysis, samples were enzymatically deglycosylated using PNGase F. The reduced intact proteins were then separated by reversed phase ultra-high performance liquid chromatography (RP-UPLC) using TSKgel Phenyl-5PW. Mobile phase A (MPA) and mobile phase B (MPB) were 0.05% formic acid in water, and 0.05% formic acid in acetonitrile, accordingly. The column effluent was directed through an in-line UV detector and then into the ESI source of an ESI-TOF (Time-of-flight) mass spectrometer. Data was deconvoluted using Waters Masslynx software. For sequence accuracy confirmation, the experimental masses of the reduced deglycosylated molecules were compared with theoretical masses calculated from the primary amino acid sequence.

The results from LC-MS (data not shown) identified several proteolytic cleavage fragments (FIG. 39). More particularly, the results of these analyses showed that Bi-PB-1.2 and Bi-AB-1 have similar cleavage sites in their respective heavy chains as further shown in FIGS. 40A and 40B, respectively.

Example 10: Characterization of TGFβ1 RII ECD Mutants to Reduce Clipping

In order to develop TGFβ1 RII ECD-containing variant molecules exhibiting reduced clipping, various ECD mutants were designed as shown in FIG. 41A-41C. The mutants were designed to target the proposed clipping sites. FIGS. 42A-42H, 43, and 44A-44D show the heavy chain sequences of Bi-PB-1.2, Bi-PLB-1.2, and Bi-A1B-1 variants, respectively, containing the different ECD mutants described in FIGS. 41A-41C, which were generated and expressed. FIG. 45 highlights specific amino acid deletion mutants without additional substitutions (variants Δ7, Δ12, Δ13) and with additional substitutions (variants B, C, I-B1), as well as substitution mutants in the full length molecule (variants D-H) targeting the proposed clipping sites.

The resulting molecules were transiently expressed in CHO cells and protein A affinity purified. In FIGS. 46A-46C, reduced PAGE analysis of the expressed products in FIGS. 42A-42H indicates a reduction of clipping in the variant molecules. Consistent with this result, SEC profiles of the expressed products shown in FIGS. 47A and 47B are not accompanied by "shoulders" and secondary peaks seen in Bi-PB-1.2 or as observed in FIG. 37. In FIG. 48, peaks in the SEC profiles are quantified and show that the variants exhibit low percentages of high molecular forms compared to the parental molecule.

Example 11: Functional Activity of TGFβ1 RII ECD Mutants

To confirm that that reduced clipping in the variants is not at the expense functional activity, a cell-based assay was conducted to evaluate the functional activity of the ECD variants (FIG. 49). Briefly, serial dilutions of Bi-PB-1.2 and the various TGFβ1 RII ECD variants that were produced in HEK293 cells were made and tested (along with a negative control antibody) to see whether the antagonists block the ability of TGF-β1 to activate luciferase expression under the control of a SMAD response element as described above. Bioactivity was determined by a decrease in the amount of luciferase-mediated luminescence. The IC50 results of this analysis are summarized in FIG. 50, and show that all of the variants retain bioactivities similar to the parental Bi-PB-1.2 and Bi-A1B-1 molecules, except Bi-A1B-1W, Bi-PB-1.2Δ15 and Bi-PB-1.2Δ20.

Example 12: Pharmacokinetics of Bi-PB-1C and Bi-PB-1D

To evaluate the pharmacokinetic properties of Bi-PB-1.2C and Bi-PB-1.2D relative to Bi-PB-1.2 (wt) in vivo, pharmacokinetic profiles were generated. Briefly, 10 mg/kg of each antagonist was intravenously injected into the tail vein of 6-10 week old female CD1 mice (n=2 mice per molecule). Serum was harvested at 3 minutes, 3 hours, 1 day, 3 days, 7 days and 10 days post injection. To detect the antibodies in the serum, 96 well ELISA plates were coated with 5 μg/ml goat anti-human IgG F(ab')2 fragment (Sigma, #SAB3701274) and then blocked with 5% milk in PBS. Serially diluted mouse serum in 5% milk and serially diluted purified protein molecule as standard were added to the plates. Following incubation with Peroxidase AffiniPure Mouse Anti-Human IgG, Fcγ Fragment Specific (Jackson ImmunoResearch, #209-035-098) and further washes, Bi-PB-1.2 (FIG. 51A), Bi-PB-1.2C (FIG. 51B), and Bi-PB-1.2D (FIG. 51C) antagonists were detected following incubation with TMB-ELISA Substrate Solution (Thermo-Fisher, #34029), and quantified by OD650 signal with a Perkin Elmer multimode plate reader. The results of this analysis show pharmacokinetic profiles in mice for Bi-PB-1.2C and Bi-PB-1.2D are comparable to Bi-PB-1.2, exhibiting an in vivo half-life ($T_{1/2}$) of about 5-8 days.

Example 13: Production from Stable CHO Cell Pools

The C variant molecules corresponding to parental Bi-PB-1.2, Bi-PLB-1, and Bi-A1B-1 molecules and the U variants of Bi-PB-1.2 and Bi-A1B-1 molecules were produced from CHO-KI stable cell pools and their degree of clipping was compared with their wild-type counterparts and/or with the C variant counterparts. The CHO-K1 stable cell pools were grown under fed-batch conditions for 14 days and purified by protein A chromatography. Clipping was assessed by reducing PAGE analysis of the purified mutant and variant proteins. The results of this analysis showed significant reduction of clipping with the C and U variants as compared to the parental wild type molecules (FIGS. 52A-52B).

The above description is for the purpose of teaching a person of ordinary skill in the art how to practice the present invention and is not intended to detail all those obvious modifications and variations which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A protein comprising:
   a first targeting domain comprising a mutated TGF-β1 RII extracellular domain (mutated ECD), wherein the mutated ECD comprises SEQ ID NO:89 with one or more substitutions and/or deletions that reduce proteolytic degradation or clipping; and
   an immunoglobulin scaffold having an amino terminus and a carboxy terminus, and
   wherein the mutated ECD comprises an amino acid sequence selected from the group consisting of SEQ ID NOS: 114-123 and 251-270.

2. The protein of claim 1, wherein the first targeting domain is linked to the immunoglobulin scaffold via a peptide linker.

3. The protein of claim 1, further comprising a second targeting domain that comprises an immune checkpoint regulator antagonist, a VEGF pathway antagonist, or a Tie2 tyrosine kinase receptor antagonist.

4. The protein of claim 3, wherein the second targeting domain comprises an immune checkpoint regulator antagonist.

5. The protein claim 4, wherein the second targeting domain specifically binds to PD-1.

6. The protein claim 4, wherein the second targeting domain specifically binds to PD-L1.

7. The protein claim 4, wherein the second targeting domain specifically binds to TIGIT.

8. The protein claim 4, wherein the second targeting domain specifically binds to LAG-3.

9. The protein of claim 3, wherein the second targeting domain comprises a VEGF pathway antagonist.

10. The protein of claim 9, wherein the VEGF pathway antagonist specifically binds to VEGF-A.

11. The protein of claim 9, wherein the VEGF pathway antagonist comprises VEGFR ECD.

12. The protein of claim 3, wherein the second targeting domain comprises a Tie2 tyrosine kinase receptor antagonist.

13. The protein of claim 2, wherein the second targeting domain comprises a SEQ ID NO: 157, 158, 167, 168 or 169.

14. The protein of claim 1, wherein the immunoglobulin scaffold is an IgG1, IgG2 or IgG4 scaffold.

15. The protein of claim 14, wherein the immunoglobulin scaffold containing an N297A mutation, a K447A mutation, or both.

16. The protein of claim 14, wherein the immunoglobulin scaffold comprises an amino acid sequence selected from the group consisting of SEQ ID NOS: 100, 159-166 and 173-175.

17. The protein of claim 1, wherein the mutated ECD comprises the amino acid sequence of SEQ ID NO: 263.

18. The protein of claim 1, wherein the mutated ECD comprises the amino acid sequence of SEQ ID NO: 116.

19. A pharmaceutical composition comprising:
    the protein of claim 1; and
    a pharmaceutically acceptable carrier.

20. An expression vector comprising a nucleotide sequence encoding the protein of claim 1.

21. A cell line that expressed the protein of claim 1.

22. A method of treating a cell proliferative disorder in a subject, comprising:
    administering to a subject in need thereof an effective amount of the protein of claim 1.

* * * * *